US010758609B2

United States Patent
Yamamoto

(10) Patent No.: US 10,758,609 B2
(45) Date of Patent: Sep. 1, 2020

(54) CROSS-REACTIVE T-CELL EPITOPES OF HIV, SIV, AND FIV FOR VACCINES IN HUMANS AND CATS

(71) Applicant: UNIVERSITY OF FLORIDA RESEARCH FOUNDATION, INC., Gainesville, FL (US)

(72) Inventor: Janet K. Yamamoto, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 182 days.

(21) Appl. No.: 15/762,108

(22) PCT Filed: Sep. 25, 2016

(86) PCT No.: PCT/US2016/053624
§ 371 (c)(1),
(2) Date: Jul. 31, 2018

(87) PCT Pub. No.: WO2017/053918
PCT Pub. Date: Mar. 30, 2017

(65) Prior Publication Data
US 2018/0333481 A1 Nov. 22, 2018

Related U.S. Application Data

(60) Provisional application No. 62/290,297, filed on Feb. 2, 2016, provisional application No. 62/233,072, filed on Sep. 25, 2015.

(51) Int. Cl.
| *A61K 39/21* | (2006.01) |
| *A61K 39/12* | (2006.01) |
| *A61K 39/00* | (2006.01) |
| *C07K 14/005* | (2006.01) |
| *C12N 15/00* | (2006.01) |
| *A61P 31/14* | (2006.01) |
| *A61P 31/18* | (2006.01) |
| *A61K 9/00* | (2006.01) |

(52) U.S. Cl.
CPC ............ *A61K 39/21* (2013.01); *A61K 9/0019* (2013.01); *A61K 39/12* (2013.01); *A61P 31/14* (2018.01); *A61P 31/18* (2018.01); *C07K 14/005* (2013.01); *A61K 2039/5252* (2013.01); *A61K 2039/54* (2013.01); *A61K 2039/545* (2013.01); *A61K 2039/552* (2013.01); *A61K 2039/572* (2013.01); *A61K 2039/575* (2013.01); *A61K 2039/645* (2013.01); *C12N 2740/15034* (2013.01); *C12N 2740/15071* (2013.01); *C12N 2740/16134* (2013.01); *C12N 2740/16171* (2013.01); *C12N 2740/16234* (2013.01); *C12N 2740/16271* (2013.01); *C12N 2740/16334* (2013.01); *C12N 2740/16371* (2013.01)

(58) Field of Classification Search
CPC .. C07K 14/005; A61K 39/00; A61K 2039/53; A61K 39/12; C12N 2740/16122
See application file for complete search history.

(56) References Cited

U.S. PATENT DOCUMENTS

| 5,756,666 A | 5/1998 | Takiguchi et al. |
| 2009/0274725 A1 | 11/2009 | Yamamoto et al. |
| 2015/0231230 A1* | 8/2015 | Yamamoto ............ A61K 39/21 424/188.1 |

OTHER PUBLICATIONS

Abbott, J.R. et al. "Utilization of feline ELISPOT for mapping vaccine epitopes," *Methods Mol. Biol.*, 2012, pp. 47-63, vol. 792.
Abbott, J.R. et al. "Evolutionarily conserved T-cell epitopes on FIV for designing an HIV/AIDS vaccine," *Vet. Immunol. Immunopathol.*, 2011, pp. 246-254, vol. 143.
Ackley, C.D. et al. "Immunologic abnormalities in pathogen-free cats experimentally infected with feline immunodeficiency virus," *J. Virol.*, 1990, pp. 5652-5655, vol. 64.
Ali R. et al. "Multiple antigen peptide containing B and T cell epitopes of F1 antigen of *Yersinia pestis* showed enhanced Th1 immune response in murine model," *Scand J Immunol*, 2013, pp. 361-371, vol. 77.
Allele Frequency Net Database, allelefrequencies.net.
Almeida, J.R. et al. "Superior control of HIV-1 replication by CD8+ T cells is reflected by their avidity, polyfunctionality, and clonal turnover," *The Journal of experimental medicine*, 2007, pp. 2473-2485, vol. 204, No. 10.
Aranyos, A.M. et al. "An initial examination of the potential role of T-cell immunity in protection against feline immunodeficiency virus (FIV) infection," *Vaccine*, 2016, pp. 1480-1488, vol. 34, No. 12, doi: 10.1016/j.vaccine.2016.01.017. Epub Jan. 21, 2016.
Ardito, M. et al. "An integrated genomic and immunoinformatic approach to H. pylori vaccine design," *Immunome Res*, 2011, pp. 1-12, vol. 7, No. 2.
Balla-Jhagjhoorsingh, S.S. et al. 1999. "Conserved CTL epitopes shared between HIV-infected human long-term survivors and chimpanzees," *J. Immunol.*, 1999, pp. 2308-2314, vol. 162.
Barouch, D.H. et al. "Mosaic HIV-1 vaccines expand the breadth and depth of cellular immune responses in rhesus monkeys," *Nat Med*, 2010, pp. 319-323, vol. 16, No. 3.

(Continued)

*Primary Examiner* — Barry A Chestnut
(74) *Attorney, Agent, or Firm* — Saliwanchik, Lloyd & Eisenschenk

(57) ABSTRACT

The subject invention concerns methods and materials for inducing an immune response in an animal or person against an immunodeficiency virus, such as HIV, SIV, or FIV. In one embodiment, a method of the invention comprises administering one or more antigens and/or immunogens to the person or animal wherein the antigen and/or immunogen comprises one or more evolutionarily conserved epitopes of immunodeficiency viruses. In one embodiment, the epitope is one that is conserved between HIV and FIV.

20 Claims, 33 Drawing Sheets
Specification includes a Sequence Listing.

(56) References Cited

OTHER PUBLICATIONS

Belyakov, I.M. et al. "Mucosal immunity and HIV-1 infection: applications for mucosal AIDS vaccine development," *Curr Top Microbiol Immunol*, 2012, pp. 157-179, vol. 354.
Benmohamed L. et al. "Lipopeptide vaccines—yesterday, today, and tomorrow," *Lancet Infect Dis*, 2002, pp. 425-431, vol. 2.
Betts, M.R. et al. "Human immunodeficiency virus type 1-specific cytotoxic T lymphocyte activity is inversely correlated with HIV type 1 viral load in HIV type 1-infected long-term survivors," *AIDS Res. Hum. Retroviruses*, 1999, pp. 1219-1228, vol. 15, No. 13.
Betts, M.R. et al. "HIV nonprogressors preferentially maintain highly functional HIV-specific $CD8^+T$ cells," *Blood*, 2006, pp. 4781-4789, vol. 107, No. 12.
Bhasin, M. et al. "Prediction of CTL epitopes using QM, SVM and ANN techniques," *Vaccine*, 2004; pp. 3195-3201, vol. 22.
Brown, D.M. "Cytolytic CD4 cells: Direct mediators in infectious disease and malignancy," *Cell Immunol.*, 2010, pp. 89-95, vol. 262, No. 2, Epub Feb. 24, 2010.
Buchbinder, S.P. et al. "Efficacy assessment of a cell-mediated immunity HIV-1 vaccine (the Step Study): a double-blind, randomised, placebo-controlled, test-of-concept trial," *Lancet*, 2008, pp. 1881-1893, vol. 372.
Caligiuri, M.A. "Human natural killer cells," *Blood*, 2008, pp. 461-469, vol. 112, No. 3.
Cao, H. et al. "Cytotoxic T-lymphocyte cross-reactivity among different human immunodeficiency virus type 1 clades: implications for vaccine development," *J Virol*, 1997, pp. 8615-8623, vol. 71, No. 11.
Carlson, J.M. et al. "Widespread impact of HLA restriction on immune control and escape pathways of HIV-1," *Journal of Virology*, 2012, pp. 5230-5243, vol. 86, No. 9, doi: 10.1128/JVI.06728-11.
Cassidy, S.A. et al. "Effects of peptide on NK cell-mediated MHC I recognition," *Front Immunol*, 2014, p. 133, vol. 5.
Cebere, I. et al. "Phase I clinical trial safety of DNA- and modified virus Ankara-vectored human immunodeficiency virus type 1 (HIV-1) vaccines administered alone and in a prime-boost regime to healthy HIV-1-uninfected volunteers," *Vaccine*, 2006, pp. 417-425, vol. 24.
Cohen, N.R. et al. "Antigen Presentation by CD1 Lipids, T Cells, and NKT Cells in Microbial Immunity," *Adv Immunol*, 2009, pp. 1-94, vol. 102, Abstract.
Coleman, J.K. et al. "HIV-1 p24 vaccine protects cats against FIV," *AIDS*, 2005, pp. 1457-1466, vol. 19, No. 14.
Coleman, J.K. et al. "Feline immunodeficiency virus (FIV) vaccine efficacy and FIV neutralizing antibodies," *Vaccine*, 2014, pp. 746-754, vol. 32, No. 6.
Corey. L. et al. "HIV vaccines: mosaic approach to virus diversity," *Nat. Med.*, 2010, pp. 268-270, vol. 16, No. 3.
Cruz, L.J. et al. "Enhanced immunogenicity and cross-reactivity of HIV-1 V3-peptide and multiple antigen peptides conjugated to distinct carrier proteins," *Int immunopharmacol*, 2009, pp. 1452-1459, vol. 9.
De Groot, A.S. et al. "Identification of immunogenic HLA-B7 "Achilles' heel" epitopes within highly conserved regions of HIV," *Vaccine*, 2008, pp. 3059-3071, vol. 26, No. 24.
De Souza, M.S. et al. "The Thai phase III trial (RV144) vaccine regimen induces T cell responses that preferentially target epitopes within the V2 region of HIV-1 envelope," *J Immunol.*, 2012, pp. 5166-5176, vol. 188, No. 10.
Elder, J.H. et al. "Feline immunodeficiency virus (FIV) as a model for study of lentivirus infections: parallels with HIV," *Curr HIV Res*, 2010, pp. 73-80, vol. 8, No. 1.
Flynn, N.M., et al. "Placebo-controlled phase 3 trial of a recombinant glycoprotein 120 vaccine to prevent HIV-1 infection," *J. Infect. Dis.*, 2005, pp. 654-665, vol. 191.
Fujii, S. et al. "Adjuvant activity mediated by iNKT cells," *Semin Immunol*, 2010, pp. 97-102, vol. 22.

Fujita, Y. et al. "Current status of multiple antigen-presenting peptide vaccine systems: Application of organic and inorganic nanoparticles," *Chem Cent J*, 2011, p. 1-8, vol. 5, No. 48.
Fust, G. "Enhancing antibodies in HIV infection," *Parasitology*, 1997, 115 Suppl: S127-140, Abstract.
Galin, F. et al. "Possible therapeutic vaccines for canine myasthenia gravis: implications for the human disease and associated fatigue," *Brain Behav Immun*, 2007, pp. 323-331, vol. 21.
Gartland, A.J. et al. "Analysis of HLA A*02 Association with Vaccine Efficacy in the RV144 HIV-1 Vaccine Trial," *Journal of Virology*, 2014, pp. 8242-8255, vol. 88, No. 15.
Gengozian, N. et al. "Fractionation of feline bone marrow with the soybean agglutinin lectin yields populations enriched for erythroid and myeloid elements: transplantation of soybean agglutinin-negative cells into lethally irradiated recipients," Transplantation, 1997, pp. 510-518, vol. 64, Abstract.
Goepfert, P.A. et al. "Specificity and 6-month durability of immune responses induced by DNA and recombinant modified vaccinia Ankara vaccines expressing HIV-1 virus-like particles," *J Infect Dis*, 2014, pp. 99-110, vol. 210.
Gonzalez-Galarza, F.F. et al. "Allele frequency net: a database and online repository for immune gene frequencies in worldwide populations," *Nucleic acids research*, 2011, pp. D913-D919, vol. 30. doi: 10.1093/ nar/gkq1128.
Goonetilleke, N. et al. "Induction of multifunctional human immunodeficiency virus type 1 (HIV-1)-specific T cells capable of proliferation in healthy subjects by using a prime-boost regimen of DNA- and modified vaccinia virus Ankara-vectored vaccines expressing HIV-1 Gag coupled to $CD8^+$T-cell epitopes," *J Virol*, 2006, pp. 4717-4728, vol. 80.
Gorse, G.J. et al. "Safety and immunogenicity of cytotoxic T-lymphocyte poly-epitope, DNA plasmid (EP HIV-1090) vaccine in healthy, human immunodeficiency virus type 1 (HIV-1)-uninfected adults," *Vaccine*, 2008, pp. 215-223, vol. 26.
Goulder, P.J. et al. "Impact of MHC class I diversity on immune control of immunodeficiency virus replication," *Nat. Rev. Immunol.*, 2008, pp. 619-630, vol. 8.
Goulder, P.J. et al. "HIV and HLA class I: an evolving relationship," *Immunity*, 2012, pp. 426-440, vol. 37. doi: 10.1016/j.immuni.2012.09.005.
Hanke T. et al. "Clinical experience with plasmid DNA- and modified vaccinia virus Ankara-vectored human immunodeficiency virus type 1 clade A vaccine focusing on T-cell induction," *J. Gen. Virol.*, 2007, pp. 1-12, vol. 8.
Haynes, B.F. et al. "Immune-correlates analysis of an HIV-1 vaccine efficacy trial," *N Engl J Med*, 2012, pp. 1275-1286, vol. 366.
Heegaard, P.M.H., et al. "Dendrimers for vaccine and immunostimulatory uses. A review," *Bioconjug Chem*, 2010, pp. 405-418, vol. 21.
Horton' H. et al. "Optimization and validation of an 8-color intracellular cytokine staining (ICS) assay to quantify antigen-specific T cells induced by vaccination," *J Immunol.*, 2007, pp. 39-54, vol. 323.
Hosie, M.J. et al. "Serological responses of cats to feline immunodeficiency virus," *AIDS*, 1990, pp. 215-220, vol. 4.
IPP H. et al. "The paradox of the immune response in HIV infection: when inflammation becomes harmful," *Clin Chim Acta*, 2013, pp. 96-99, vol. 416.
Jacobs, E.S. et al. "A CD4+ T cell antagonist epitope down-regulates activating signaling proteins, up-regulates inhibitory signaling proteins and abrogates HIV-specific T cell function," *Retrovirology*, 2014, p. 57, vol. 11.
Jaoko W. et al. "Safety and immunogenicity of recombinant low-dosage HIV-1 A vaccine candidates vectored by plasmid pTHr DNA or modified vaccinia virus Ankara (MVA) in humans in East Africa," *Vaccine*, 2008, pp. 2788-2795, vol. 26.
Jenner, E. "An inquiry into the causes and effects of the Variolae Vaccinae, a disease discovered in some of the western counties of England, particularly Gloucestershire, and known by the name of the cow-pox," *London: Printed by Sampson Low*, 1798.
Johnson, R.P. et al. "HIV-1 gag-specific cytotoxic T lymphocytes recognize multiple highly conserved epitopes. Fine specificity of the gag-specific response defined by using unstimulated peripheral blood mononuclear cells and cloned effector cells," *J Immunol*, 1991, 147: 1512-21.

(56) References Cited

OTHER PUBLICATIONS

Kakinuma, S. et al. "Nucleotide Sequence of Feline Immunodeficiency Virus: Classification of Japanese Isolates into Two Subtypes Which Are Distinct from Non-Japanese Subtypes," *J. Virol.*, 1995, 69(6):3639-3646.
Kiepiela P. et al. "CD8+T-cell responses to different HIV proteins have discordant associations with viral load," *Nature Med*, 2007, 13: 46-53.
Kim, J.H. et al. "HIV vaccines: lessons learned and the way forward," *Curr Opin HIV AIDS*, 2010, 5:428-434.
Klenerman, P. et al. "Cytotoxic T-cell activity antagonized by naturally occurring HIV-1 Gag variants," *Nature*, 1994, 369:403-407.
Koff, W.C. "HIV vaccine development: Challenges and opportunities towards solving the HIV vaccine-neutralizing antibody problem," *Vaccine*, 2010, 30:4310-5.
Korber, B.T. et al. "T-cell vaccine strategies for human immunodeficiency virus, the virus with a thousand faces," *J Virol*, 2009; 83: 8300-8314.
Kotterman, M.A. et al. "Engineering adeno-associated viruses for clinical gene therapy," *Nat Rev Gene*, 2014, 15:445-51. Review.
Kowalczyk W. et al. "Strategies and limitations in dendrimeric immunogen synthesis. The influenza virus M2e epitope as a case study," Bioconjug Chem, 2010, 21:102-110.
Kowalczyk, W. et al. "Synthesis of multiple antigenic peptides (MAPs)—strategies and limitations," *J. Pept Sci.*, 2011, 17:247-251 (published online Nov. 30, 2010).
La Cava, A. "Modulation of autoimmunity with artificial peptides," *Autoimmun Rev*, 2010, 10:18-21.
Lane, H.C. "Pathogenesis of HIV infection: total CD4+T-cell pool, immune activation, and inflammation," *Top HIV Med*, 2010; 18:2-6.
Larsen, M.V. et al. "Large-scale validation of methods for cytotoxic T-lymphocyte epitope prediction," *BMC Bioinform*, 2007, 8:424.
Leeansyah, E. et al. "Soluble biomarkers of HIV transmission, disease progression and comorbidities," *Curr Opin HIV AIDS*, 2013, 8:117-124.
Leslie, A.J. et al. "HIV evolution: CTL escape mutation and reversion after transmission," *Nat. Med.*, 2004, 10:282-9.
Leslie, A. et al. "Additive contribution of HLA class I alleles in the immune control of HIV-1 infection," *Journal of Virology*, 2010, 84, 9879-9888. doi: 10.1128/JVI.00320-10.
Lettau M. et al. "Secretory lysosomes and their cargo in T and NK cells," Immunol Lett, 2007, 108:10-19.
Li, F. et al. "Mapping HIV-1 vaccine induced T-cell responses: bias towards less-conserved regions and potential impact on vaccine efficacy in the Step study," PloS One., 2011, 6:e20479. doi:10.1371/journal.pone.0020479.
Li, F. et al. "HIV-1 CTL-based vaccine immunogen selection: antigen diversity and cellular response features," *Curr HIV Res*, 2007, 5: 97-107.
Lichterfeld, M. "Loss of HIV-1-specific CD8+T cell proliferation after acute HIV-1 infection and restoration by vaccine-induced HIV-1-specific CD4+ T cells," *J. Exp. Med.*, 2004, 200:701-12.
Liu, C. et al. "Association of polymorphisms in human leukocyte antigen class I and transporter associated with antigen processing genes with resistance to human immunodeficiency virus type 1 infection," *J. Infectious Dis.*, 2003, 187, 1404-1410.
Llano, A. "How to optimally define optimal cytotoxic T lymphocyte epitopes in HIV infection?," In Yusim K (ed), *HIV Molecular Immunology*, 2009. Los Alamos National Laboratory, Los Alamos, NM.
Los Alamos National Laboratory. HIV molecular immunology database: Best-defined CTL/CD8+Epitope Summary: (hiv.lanl.gov/content/immunology/tables/optimal_ctl_summary.html), data last updated on Sep. 19, 2016.
Louwagie, J. et al. "Phylogenetic analysis of gag genes from 70 international HIV-1 isolates provides evidence for multiple genotypes," *AIDS*, 1993, 7:769-780.
Lu, J. et al. "Multi epitope Trojan antigen peptide vaccines for the induction of antitumor CTL and Th immune responses," *J lmmunol*, 2004, 172:4575-4582.
Lu, J. et al. "TAP-independent presentation of CTL epitopes by Trojan antigens," *J lmmunol*, 2001, 166:7063-7071.
Lundegaard, C. et al. "NetMHC-3.0: Accurate web accessible predictions of Human, Mouse, and Monkey MHC class I affinities for peptides of length 8-11," *NAR*, 2008; 36: 50912.
Macdonald, K.S. et al. "The HLA A2/6802 supertype is associated with reduced risk of perinatal human immunodeficiency virus type 1 transmission," *The Journal of infectious diseases*, 2001, 183:503-506.
Macdonald, K.S. et al. "Human leucocyte antigen supertypes and immune susceptibility to HIV-1, implications for vaccine design," *Immunology letters*, 2001, 79:151-157.
Mahajan, B. et al. "Multiple antigen peptide vaccines against Plasmodium falciparum malaria," *Infect Immun*, 2010, 78:4613-4624.
Mcdermott, A.B. et al. "CD8+ T cells in preventing HIV infection and disease" *AIDS*, 2012, 26:1281-92.
Mckinnon, L.R. et al. "HIV-specific CD8+ T-cell proliferation is prospectively associated with delayed disease progression," *lmmunol. Cell Biol*, 2012, 90:346-51.
Mcllroy, D. "Do HIV-specific CTL continue to have an antiviral function during antiretroviral therapy? If not, why not, and what can be done about it?" *Front. lmmunol. vol. 4, article 52*, online on Mar. 2013, doi: 10.3389/FIMMU.2013.00052.
Moss, S.F. et al. "HelicoVax: epitope-based therapeutic Helicobacter pylori vaccination in a mouse model," *Vaccine*, 2011, 29:2085-91.
Mothe, B. et al. "Definition of the viral targets of protective HIV-1-specific T cell responses," *J. Transl. Med*, 2011, 9:208.
Mwau, M.I. et al. "A human immunodeficiency virus 1 (HIV-1) clade A vaccine in clinical trials: stimulation of HIV-specific T-cell responses by DNA and recombinant modified vaccinia virus Ankara (MVA) vaccines in humans," *J Gen Virol*, 2004, 85: 911-9.
Nakayama, K. "Furin: a mammalian subtilisin/Kex2p-like endoprotease involved in processing of a wide variety of precursor proteins," *Biochem J*, 1997, 327:625-35.
Nardelli, B. et al. "Cellular immune-responses Induced by in-vivo priming with a lipid-conjugated multimeric antigen peptide," *Immunology*, 1993, 79:355-361.
Nishimura, Y. et al. "Down-modulation of CD3epsilon expression in CD8alpha+beta—T cells of feline immunodeficiency virus-infected cats" *J Gen Virol*, 2004, 85:2585-2589.
Ogg, G.S. et al. "Quantitation of HIV-1-specific cytotoxic T lymphocytes and plasma load of viral RNA," *Science*, 1998, 279:2103-6.
Oka, Y. et al. "WT1 Peptide Vaccine as a Paradigm for "Cancer Antigen-Derived Peptide"—Based Immunotherapy for Malignancies: Successful Induction of Anti-Cancer Effect by Vaccination with a Single Kind of WT1 Peptide," *Anti-Cancer Agent Med Chem*, 2009, 9:787-797, Abstract.
Olmsted, R.A. et al. "Molecular cloning of feline immunodeficiency virus," *Proc. Nat. Acad. Sci. USA*, 1989, 86:2448-2452.
Olmsted, R.A. et al. "Nucleotide sequence analysis of feline immunodeficiency virus: Genome organization and relationship to other lentivirus," *Proc. Natl. Acad. Sci. USA*, 1989, 86:8088-8092.
Omori, M. et al. "Cellular immune responses to feline immunodeficiency virus (FIV) induced by dual-subtype FIV vaccine," *Vaccine*, 2004, 23:386-398.
Pattacini, L. et al. "A novel HIV vaccine adjuvanted by IC31 induces robust and persistent humoral and cellular immunity," *PloS one 7*, 2012, e42163. doi:10.1371/journal.pone.0042163.
Pedersen, N.C. et al. "Isolation of a T-lymphotropic virus from domestic cats with an immunodeficiency-like syndrome," *Science*, 1987, 235:790-793.
Pitisuttithum, P. et al. "Randomized, double-blind, placebo-controlled efficacy trial of a bivalent recombinant glycoprotein 120 HIV-1 vaccine among injection drug users in Bangkok, Thailand," *J. Infect. Dis.*, 2006, 194:1661-71.
Plotkin, S.A. "Vaccines: correlates of vaccine-induced immunity," *Clin. Infect. Dis.*, 2008, 47:401-09.

(56) References Cited

OTHER PUBLICATIONS

Posnett, D.N. et al. "A Novel Method for Producing Anti-peptide Antibodies," *J. Biol. Chem.*, 1988, 263(4):1719-1725.
Pu, R. et al. "Dual-subtype FIV vaccine protects cats against in vivo swarms of both homologous and heterologous subtype FIV isolates," *AIDS*, 2001, 15:1225-1237.
Pu, R. et al. "Protection of neonatal kittens against feline immunodeficiency virus infection with passive maternal antiviral antibodies," *AIDS*, 1995, 9:235-242.
Pu, R. et al. "MHC-restricted protection of cats against FIV infection by adoptive transfer of immune cells from FIV-vaccinated donors," *Cell Immunol*, 1999, 198:30-43.
Rerks-Ngarm, S. et al. "Vaccination with ALVAC and AIDSVAX to prevent HIV-1 infection in Thailand," *N. Engl. J. Med.*, 2009, 361:2209-20.
Richmond, M. et al. "Epitope mapping of HIV-specific CD8+ T cell responses by multiple immunological readouts reveals distinct specificities defined by function," *J Virol*, 2011, 85:1275-86.
Rigby, M.A. et al. "Evolution of structural proteins of feline immunodeficiency virus: molecular epidemiology and evidence of selection for change," *J. Gen. Virol.*, 1993, 74:425-436.
Roff, S.R. et al. "The significance of interferon-γ in HIV-1 pathogenesis, therapy, and prophylaxis," Front. Immunol. vol. 4, article 498, online on Jan. 13, 2014; doi: 10.3389/fimmu.2013.00498.
Rolland, M. et al. "Hiv-1 Group M Conserved Elements Vaccine," *PLoS Pathog.*, 2007, 3:e157. doi:10.1371/journal.ppat.0030157.
Rowland-Jones, S.L. et al. "Cytotoxic T cell responses to multiple conserved HIV epitopes in HIV-resistant prostitutes in Nairobi," *J Clin Invest*, 1998, 102: 1758-65.
Rowland-Jones, S. et al. "HIV-specific cytotoxic T-cells in HIV-exposed but uninfected Gambian women," *Nat. Med.*, 1995, 1:59-64.
Salmon-Ceron, D et al. "Immunogenicity and safety of an HIV-1 lipopeptide vaccine in healthy adults: a phase 2 placebo-controlled ANRS trial," *AIDS*, 2010, 24:2211-23.
Sanou, M.P. et al. "HIV-1 Vaccine Trials: Evolving Concepts and Designs," *The Open AIDS Journal 6*, 2012, 274-288.
Santra, S. et al. "Mosaic vaccines elicit CD8$^+$T lymphocyte responses that confer enhanced immune coverage of diverse HIV strains in monkeys," *Nat Med*, 2010, 16: 324-8.
Santra, S. et al. "Breadth of cellular and humoral immune responses elicited in rhesus monkeys by multi-valent mosaic and consensus immunogens," *Virology*, 2012, 428:121-7.
Saunders, K.O. et al. "The design and evaluation of HIV-1 vaccines," *AIDS*, 2012, 26:1293-1302.
Shan, L. et al. "Stimulation of HIV-1-specific cytolytic T lymphocytes facilitates elimination of latent viral reservoir after virus reactivation," *Immunity*, 2012, 36:491-501.
Shimojima, M. et al. "Use of CD134 as a primary receptor by the feline immunodeficiency virus," *Science*, 2004, 303:1192-5.
Sidney, J. et al. "HLA class I supertypes: a revised and updated classification," *BMC Immunol*, Jan. 22, 2008;9:1. doi: 10.1186/1471-2172-9-1.
Smith, S.M. "HIV CTL escape: at what cost?" *Retrovirology*, 2004; 1: 8.
Sodora, D.L. et al. "Identification of three feline immunodeficiency virus (FIV) env gene subtype and comparison of the FIV and human immunodeficiency virus type 1 evolutionary patterns," *J. Virol.*, 1994, 68:2230-2238.
Soghoian, D.Z. et al. "HIV-specific cytolytic CD4 T cell responses during acute HIV infection predict disease outcome." *Sci. Transl. Med.*, 2012, 4:123ra25. doi:10.1126/scitranslmed.3003165.
Spearman, P. et al. "Safety and immunogenicity of a CTL multiepitope peptide vaccine for HIV with or without GM-CSF in a phase I trial," *Vaccine*, 2009, 27: 243-9.
Spina, C.A., et al. "Preferential replication of HIV-1 in the CD45RO memory cell subset of primary CD4 lymphocytes in vitro," *J. Clin. Invest*. 99, 1997, 1774-1785.
Stamatatos, L. "HIV vaccine design: the neutralizing antibody conundrum," *Curr. Opin. Immunol.*, 2012, 24:316-23.

Stevenson, M. et al. "HIV-1 replication is controlled at the level of T cell activation and proviral integration," *The EMBO journal 9*, 1990, 1551-1560.
Stranzl, T. et al. "NetCTLpan: pan-specific MHC class I pathway epitope predictions," *Immunogenetics*, 2010; 62: 357-68.
Talbott, R.L. et al. "Nucleotide sequence and genomic organization of feline immunodeficiency virus," *Proc. Natl. Acad. Sci. USA*, 1989, 86:5743-5747.
Tam, J.P. "Synthetic Peptide Vaccine Design: Synthesis and Properties of a High-Density Multiple Antigenic Peptide System," *Proc. Nat. Acad. Sci. USA*, 1988, 85(15):5409-5413.
Tanabe, T. et al. "Feline immunodeficiency virus lacks sensitivity to the antiviral activity of feline IFN-gamma," *J Interferon Cytokine Res*, 2001, 21:1039-46.
Tang, J. et al. "Human leukocyte antigen variants B*44 and B*57 are consistently favorable during two distinct phases of primary HIV-1 infection in sub-Saharan Africans with several viral subtypes," *Journal of Virology*, 2011, 85, 8894-8902.
Taylor, B.S. et al. "The challenge of HIV-1 subtype diversity," *N Engl J Med*, Apr. 10, 2008;358(15):1590-602.
Tellier, M.C. et al. Efficacy evaluation of prime-boost protocol: canarypoxvirus-based feline immunodeficiency virus (FIV) vaccine and inactivated FIV-infected cell vaccine against heterologous FIV challenge in cats, AIDS, 1998, 12:11-18.
Troyer, R.M. et al. "Variable fitness impact of HIV-1 escape mutations to cytotoxic T lymphocyte (CTL) response," *PLoS Pathog*, 2009, 5:e1000365.
Uhl, E.W. et al. "FIV vaccine development and its importance to veterinary and human medicine: a review FIV vaccine 2002 update and review," *Vet Immunol Immunopathol.*, 2002, 90(3-4):113-32.
Uhl, E.W. et al. "Advances in FIV vaccine technology," *Vet Immunol Immunopathol*, 2008, 123:65-80.
Vaccari, M. et al. "Phase III HIV vaccine trial in Thailand: a step toward a protective vaccine for HIV," *Expert Rev Vaccines*, 2010, 9:997-1005, Abstract.
Vogel, T.U. et al. "Induction of anti-simian immunodeficiency virus cellular and humoral immune responses in rhesus macaques by peptide immunogens: correlation of CTL activity and reduction of cell-associated but not plasma virus load following challenge," *J Gen Virol*, 2002, 83:81-91.
Voronin, Y. et al. "The future of HIV vaccine research and the role of the Global HIV Vaccine Enterprise," *Curr Opin HIV AIDS*, 2010, 5:414-420.
Walker, B.D. et al. "HIV-1 reverse transcriptase is a target for cytotoxic T lymphocytes in infected individuals," *Science*, 1988, 240:64-6.
Walther-Jallow, L. et al. "Cross-protection against mucosal simian immunodeficiency virus (SIVsm) challenge in human immunodeficiency virus type 2-vaccinated cynomolgus monkeys," *J. Gen. Virol*, 2001, 82:1601-12.
Wang, G.Z. et al. "Multiple Antigenic Peptides of Human Heparanase Elicit a Much More Potent Immune Response against Tumors," *Cancer Prev Res*, 2011, 4:1285-1295.
Wang, Y.E. et al. "Protective HLA class I alleles that restrict acute-phase CD8$^+$T-cell responses are associated with viral escape mutations located in highly conserved regions of human immunodeficiency virus type-1," *J Virol*, 2009; 83: 1845-55.
Weinberg, A.D. "OX40: targeted immunotherapy—implications for tempering autoimmunity and enhancing vaccines," *Trends Immunol.*, 2002, 23:102-109.
Yamamoto, J.K. et al. "Experimental vaccine protection against homologous and heterologous strains of feline immunodeficiency virus," *J. Virol*, 1993, 67(1):601-605.
Yamamoto, J.K. et al. "T. Feline immunodeficiency virus pathogenesis and development of a dual-subtype feline-immunodeficiency-virus vaccine," *AIDS*, 2007; 21: 547-63.
Yamamoto, J.K. et al. "Feline immunodeficiency virus model for designing HIV/AIDS vaccines," *Curr HIV Res*, 2010; 8:14-25.
Yamamoto, J.K. "Bovine and feline immunodeficiency viruses," In: Encyclopedia of Virology. 3rd Ed. B. Hahy and M Van Regenmortel (Eds), Elsevier Ltd, Oxford, UK, pp. 347-354, 2008.
Yamamoto, J.K. "Evolving perspectives on FIV vaccines," *Practitioner's Update: Feline Retrovirus Disease*, 2010, 1:4-7.

(56) References Cited

OTHER PUBLICATIONS

Yamamoto, J.K. et al. "Development of the dual-subtype FIV vaccine," *AIDScience*, Apr. 2002, 2(8).

Yamamoto, J.K. et al. "Human alpha- and beta-interferon but not gamma-suppress the in vitro replication of LAV, HTLV-III, and ARV-2," *Journal of interferon research 6*, 1986, 143-152.

Yamamoto, J.K et al. "Pathogenesis of experimentally induced feline immunodeficiency virus infection in cats," *Am. J. Vet. Res.*, 1988, 49:1246-1258.

Yamamoto, J.K. et al. "Feline immunodeficiency syndrome—a comparison between feline T-lymphotropic lentivirus and feline leukemia virus," *Leukemia*, 1988, December Supplement 2:204S-215S.

Yongqun, H. et al. "Emerging Vaccine Informatics," *J Biomed Biotechnol*, 2010; 2010: 218590.

Yusim, K. et al. "Clustering patterns of cytotoxic T-lymphocyte epitopes in human immunodeficiency virus type 1 (HIV-1) proteins reveal imprints of immune evasion on HIV-1 global variation," *J Virol*, 2002; 76:8757-68.

Zhang, X. et al. "HLA-B*44 is associated with a lower viral set point and slow CD4 decline in a cohort of Chinese homosexual men acutely infected with HIV-1," *Clinical and vaccine immunology: CVI 20*, 1048-1054.

Zorko, M. et al. "Cell-penetrating peptides: mechanism and kinetics of cargo delivery," *Adv Drug Deliv Rev*, 2005, 57:529-545.

Kulkosky, J. et al. "Expression of Latent HAART-Persistent HIV Type I Induced by Novel Cellular Activating Agents," *AIDS Research and Human Retroviruses*, 2004, 20(5):497-505.

Deng, K. et al. "Broad CTL response is required to clear latent HIV-1 due to dominance of escape mutations," *Nature*, Jan. 15, 2015, 517(7534):381-396.

Marsden, M.D. et al. "Experimental Approaches for Eliminating Latent HIV," *For Immunopathol Dis Therap.*, 2015, 6(1-2):91-99.

Sahay, B. et al. "Immunogenicity and Efficacy of a Novel Multi-Antigenic Peptide Vaccine Based on Cross-Reactivity between Feline and Human Immunodeficiency Viruses," *Viruses*, 2019, 11(2):136, pp. 1-25.

Siliciano, J.D. et al. "Enhanced Culture Assay for Detection and Quantitation of Latently Infected, Resting CD4$^+$T-Cells Carrying Replication-Competent Virus in HIV-1-Infected Individuals," *Methods in Molecular Biology*, 2005, 304:3-15.

Roff, S. et al. "T-cell Based Lentiviral Vaccines" Abstract presented at the 17th Annual International Meeting of the Institute of Human Virology, Baltimore, Maryland, Sep. 2015.

Yamamoto, J. "A need for T-cell based vaccines against AIDS lentiviruses" Abstract presented at Vaccines 2015 Conference, San Francisco, Nov. 30-Dec. 2, 2015.

Roff, S. et al. "Conserved epitopes on HIV-1, FIV and SIV p24 proteins are recognized by HIV-1 infected subjects" *Human Vacc. Immunotherap.*, Jun. 2015, 11:1540-1556.

Sanou, M. et al. "Evolutionarily conserved epitopes on human immunodeficiency virus type 1 (HIV-1) and feline immunodeficiency virus reverse transcriptases detected by HIV-1-infected subjects" *Journal of Virology*, 2013, vol. 87, No. 18, pp. 10004-10015.

\* cited by examiner

Distribution of Cats in Vaccine and Control Groups

Vaccine Group 1 – Subcutaneous / No IL12  (n=7)  – ID Code: HOC, RL2, RM4, RO1, RO7, RP4, RQ1
Vaccine Group 2 – Intradermal / With IL12  (n=7)  – ID Code: HOB, RL1, RL4, RM3, RO2, RP3, RQ5
Control Group 3a – Subcutaneous / No IL12  (n=3)  – ID Code: RO3, RP2, RQ7
Control Group 3b – Intradermal / With IL12  (n=3)  – ID Code: HOD, RO5, RQ2
Control Group 3c – SC+ID PBS  (n=3)  – ID Code: RO6, RP1, RQ4
Control Group 3d – None  (n=1)  – ID Code: HO1

FIG. 6B

CROSS-REACTIVE T-CELL EPITOPES OF HIV, SIV, AND FIV FOR VACCINES IN HUMANS AND CATS

CROSS-REFERENCE TO RELATED APPLICATIONS

The present application is the National Stage of International Application No. PCT/US2016/053624, filed Sep. 25, 2016, which claims the benefit of U.S. Provisional Application Serial Nos. 62/290,297, filed Feb. 2, 2016, and 62/233,072, filed Sep. 25, 2015, each of which is hereby incorporated by reference herein in its entirety, including any figures, tables, nucleic acid sequences, amino acid sequences, or drawings.

GOVERNMENT SUPPORT

This invention was made with government support under grant numbers R01-AI065276 and R01-AI030904 awarded by the National Institutes of Health. The government has certain rights in the invention.

SEQUENCE LISTING

The Sequence Listing for this application is labeled "2OF1602.TXT" which was created on Jul. 11, 2019 and is 25 KB. The entire contents of the sequence listing is incorporated herein by reference in its entirety.

BACKGROUND OF THE INVENTION

An effective prophylactic HIV-1 vaccine is needed to eradicate the HIV/AIDS pandemic but designing such a vaccine is a challenge. Despite many advances in vaccine technology and approaches to generate both humoral and cellular immune responses, major phase-II and -III vaccine trials against HIV/AIDS have resulted in only moderate successes. The modest achievement of the phase-III RV144 prime-boost trial in Thailand re-emphasized the importance of generating robust humoral and cellular responses against HIV. While antibody-directed approaches are being pursued by some groups, others are attempting to develop vaccines targeting cell-mediated immunity, since evidence show CTLs to be important for the control of HIV replication. Phase-I and -IIa multi-epitope vaccine trials have already been conducted with vaccine immunogens consisting of known CTL epitopes conserved across HIV subtypes, but have so far fallen short of inducing robust and consistent anti-HIV CTL responses. Thus, a need remains in the art for an effective vaccine against HIV.

Domestic cats are subject to infection by several retroviruses, including feline leukemia virus (FeLV), feline sarcoma virus (FeSV), endogenous type C oncoronavirus (RD-114), and feline syncytia-forming virus (FeSFV). Of these, FeLV is the most significant pathogen, causing diverse symptoms including lymphoreticular and myeloid neoplasms, anemias, immune-mediated disorders, and an immunodeficiency syndrome that is similar to human acquired immune deficiency syndrome (AIDS). Recently, a particular replication-defective FeLV mutant, designated FeLV-AIDS, has been more particularly associated with immunosuppressive properties.

The discovery of feline T-lymphotropic lentivirus (now designated as feline immunodeficiency virus, FIV) was first reported in Pedersen et al. (1987). Characteristics of FIV have been reported in Yamamoto et al. (1988a); Yamamoto et al. (1988b); and Ackley et al. (1990). Seroepidemiologic data have shown that infection by FIV is indigenous to domestic and wild felines throughout the world. A wide variety of symptoms are associated with infection by FIV, including abortion, alopecia, anemia, conjunctivitis, chronic rhinitis, enteritis, gingivitis, hematochezia, neurologic abnormalities, periodontitis, and seborrheic dermatitis. The immunologic hallmark of domestic cats infected with FIV is a chronic and progressive depletion of feline $CD4^+$ peripheral blood lymphocytes, a reduction in the CD4:CD8 cell ratio and, in some cases, an increase in CD8-bearing lymphocytes.

Cloning and sequence analysis of FIV has been reported in Olmsted et al. (1989a); Olmsted et al. (1989b); and Talbott et al. (1989). Hosie and Jarrett (1990) described the serological response of cats infected with FIV. FIV virus subtypes can be classified according to immunotype based on the level of cross-neutralizing antibodies elicited by each strain (Murphy and Kingsbury, 1990). Recently, viruses have been classified into subtypes according to genotype based on nucleotide sequence homology. Although HIV and FIV subtyping is based on genotype (Sodora et al., 1994; Rigby et al., 1993; and Louwagie et al., 1993), little is known about the correlation between the genotype and immunotype of subtypes. FIV viral isolates have been classified into five FIV subtypes: A, B, C, D, and E (Kakinuma et al., 1995; Yamamoto et al., 2007; Yamamoto et al., 2010). Infectious isolates and infectious molecular clones have been described for all FIV subtypes except for subtypes C and E (Sodora et al., 1994). Subtype C FIV has originally been identified from cellular DNA of cats from Canada (Sodora et al., 1994; Rigby et al., 1993; Kakinuma et al., 1995). Examples of FIV strains identified in the art include (subtype of the strain is shown in parenthesis) Petaluma (A), Dixon (A), UK8 (A), Dutch113 (A), Dutch19K (A), UK2 (A), SwissZ2 (A), Sendai-1 (A), USCAzepy01A (A), USCAhnky11A (A), USCAtt-10A (A), USCAlemyOl (A), USCAsam-01A (A), PPR (A), FranceWo, Netherlands, Bangston (A/B), Aomori-1 (B), Aomori-2 (B), USILbrny03B (B), TM2 (B), Sendai-2 (B), USCKlgri02B (B), Yokohama (B), USMAsboy03B (B), USTXmtex03B (B), USMCglwd03B (B), CABCpbar03C (C), CABCpbar07C (C), CABCpady02C (C), Shizuoka (D), Fukuoka (D), LP3 (E), LP20 (E), and LP24 (E).

The commercial release of an effective HIV-1 vaccine is not imminent even after completion of four major phase IIB-III vaccine trials against HIV/AIDS (Saunders et al. (2012)). Our limited understanding about the mechanisms of vaccine protection (Plotkin (2008)) and the identity of the protective viral epitopes (Mothe et al. (2011); Koff (2010)) further hampers the development of an effective vaccine. Initial studies focused on antibody-based vaccine designs with an emphasis on generating broadly virus neutralizing antibodies (bNAbs) (Stamatatos (2012)). However, two phase-III vaccine trials using envelope (Env) immunogens failed (Flynn et al. (2005); Pitisuttithum et al. (2006)). Subsequent focus was placed on the T-cell-based vaccines that generate protective cell-mediated immunity (CMI) against global HIV-1 isolates (Buchbinder et al. (2008)). The CMI responses, essential for an effective vaccine, most likely include cytotoxic T lymphocyte (CTL) activities that specifically target HIV-1 infected cells (Ogg et al. (1998); Walker et al. (1988); Belyakov et al. (2012)). Unlike NAb epitopes which reside exclusively on the Env proteins, the selection of specific vaccine epitopes for the development of T-cell-based vaccines is more difficult to achieve. A vast number of CTL-associated epitopes can be found to span the whole length of most HIV proteins (Los Alamos National Laboratory (LANL) database, hiv-web.lanl.gov/content/immunology/maps/maps.html) (Llano et al. (2009)). The goal to develop T-cell-based vaccines is challenged by the capacity of the virus to evade antiviral immunity through mutation(s) for resistance (Li et al. (2011); Leslie et al. (2004)).

A recent phase III trial consisting of priming with a gag-pr-gp41-gp120 canarypox vectored vaccine and boosting with Env gp120 induced both humoral immunity and CMI and conferred a modest overall efficacy (Rerks-Ngarm et al. (2009)). However, phase I and II vaccine trials consisting of cross-subtype conserved CTL-associated peptide epitopes have shown minimal CMI responses (Sanou et al. (2012a); Hanke et al. (2007); Salmon-Ceron et al. (2010)). Therefore, a thorough selection of potent anti-HIV T cell-associated epitopes, which are conserved among HIV-1 subtypes and do not mutate without negatively affecting viral fitness (Troyer et al. (2009); Goulder et al. (2008); Rolland et al. (2007)), would be valuable for an effective HIV-1 vaccine. One approach is to select conserved, non-mutable CTL epitopes on essential viral structural proteins or enzymes that also persist on the older subgenuses of the lentivirinae which have survived evolutionary pressure (Yamamoto et al. (2010)). Such an approach was successfully used in the development of the initial smallpox vaccines (Jenner (1798)). In line with this strategy, the recognition of conserved epitopes on other lentivirus species has been made by the PBMC from HIV-1 positive (HIV+) humans (Balla-Jhagjhoorsingh et al. (1999)), HIV-2 vaccinated and SIV-challenged non-human primates (Walther-Jallow et al. (2001)), and HIV-1 p24-vaccinated and FIV-challenged cats (Abbott et al. (2011); Coleman et al. (2005)).

The viral enzyme, reverse transcriptase (RT), is one of the most conserved viral proteins by possessing the lowest entropy value among the HIV-1 proteins from various subtypes (Yusim et al. (2002)) and contains many CTL-associated epitopes (Walker et al. (1988)). The RT proteins of HIV-1 and FIV also share the highest degree of identity in their amino acid (aa) sequences (Yamamoto et al. (2010)). The current studies were undertaken to identify the conserved CTL-associated epitopes on FIV and HIV-1 RT proteins. The major objective of such studies is to identify evolutionarily-conserved CMI epitopes that may be more resistant to mutation, and thus useful in the development of an effective, T-cell-based HIV-1 vaccine.

BRIEF SUMMARY OF THE INVENTION

The subject invention concerns methods and materials for inducing an immune response in an animal or person against an immunodeficiency virus, such as HIV, SIV, or FIV. In one embodiment, a method of the invention comprises administering one or more antigens and/or immunogens to the person or animal wherein the antigen and/or immunogen comprises one or more evolutionarily conserved epitopes of immunodeficiency viruses. In one embodiment, the epitope is one that is conserved between HIV and FIV. In another embodiment, the epitope is one that is conserved between HIV, SIV, and FIV. In one embodiment, the epitope is a T-cell epitope. In a specific embodiment, the T-cell epitope is a cytotoxic T lymphocyte (CTL) and T-helper (Th) epitope. In one embodiment, an epitope of the invention comprises the amino acid sequence shown in one or more of SEQ ID NOs: 1 to 35.

The subject invention also concerns evolutionarily conserved epitopes of immunodeficiency viruses. In one embodiment, the epitope is one that is conserved between HIV and FIV. In another embodiment, the epitope is one that is conserved between HIV, SIV, and FIV. In one embodiment, the epitope is a T-cell epitope. In a specific embodiment, the T-cell epitope is a cytotoxic T lymphocyte (CTL) and T-helper (Th) epitope.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

Seven peptides were used to develop seven multiple antigenic peptide (MAP) immunogens consisting of MAP2, MAP2v, MAP3, MAP4, MAP5, MAP9, and MAP11. MAP2 (extra-leucine peptides FRT3-3 and FRT3-4), MAP2v (viral sequence peptides FRT3-3 and FRT3-4v), MAP3 (peptides Fp14-3 and Fp14-4), and MAP5 (peptides FRT7-1 and FRT7-2) contained at least two peptide epitopes as shown in the parenthesis. MAP4 (peptide Fp9-3), MAP9 (peptide FTM8) and MAP11 (peptide FMA2) contained single peptide. The peptide in MAP2 differs from the peptide in MAP2v by having additional "L (leucine in red)". The peptide sequence of MAP2v is the actual viral sequence. The FIV peptides derived from p24 and reverse transcriptase were first described in Roff et al. (2015) and Sanou et al. (2013), respectively.

Figure 1:
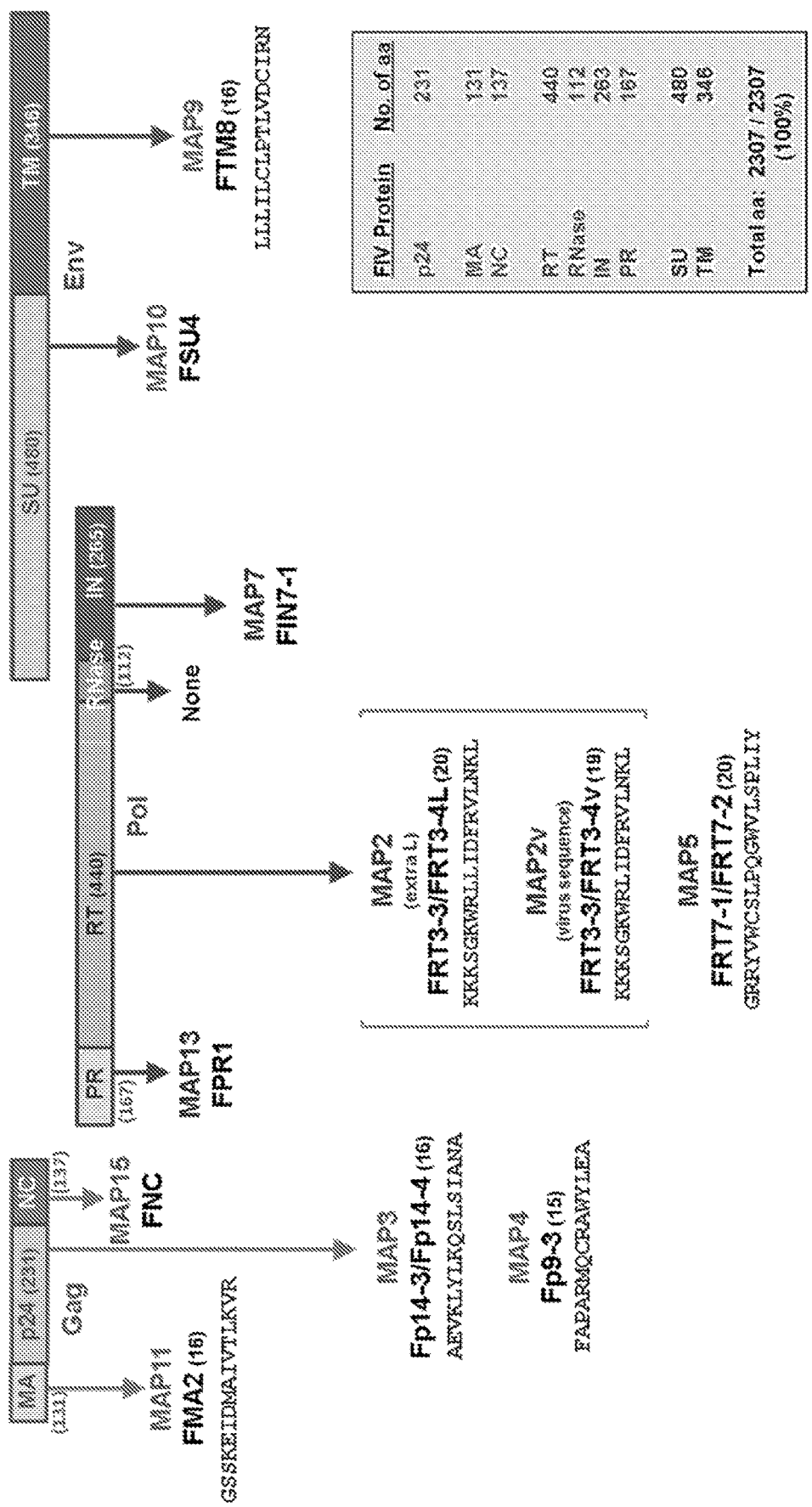
FIG. 1. Amino acid (aa) sequence and nomenclature of FIV MAP and peptide(s) used for the MAP Vaccine Trial 1. Overlapping peptide analyses for immunogenicity were performed on FIV p24, reverse transcriptase (RT), RNAse, integrase (IN), and transmembrane envelope (TM Env) to identify vaccine immunogens. In contrast, FIV matrix (MA), nucleocapsid (NC), and surface (SU) Env were evaluated for sequence similarity followed by an evaluation of immunogenicity on those with high aa sequence similarity to HIV-1. Immunogenicity analyses were performed using peripheral blood mononuclear cells (PBMC) and T cells from HIV-positive human subjects and FIV-vaccinated laboratory cats. In summary, all FIV structural proteins and FIV enzymes were analyzed as shown in the box insert.

```
FIG. 1 sequences:
                                    (SEQ ID NO: 65)
GSSKEIDMAIVTLKVR;

(SEQ ID NO: 26)
AEVKLYLKQSLSIANA;

(SEQ ID NO: 20)
FAPARMQCRAWYLEA;

(SEQ ID NO: 31)
KKKSGKWRLLIDFRVLNKL;

(SEQ ID NO: 30)
KKKSGKWRLIDFRVLNKL;

(SEQ ID NO: 35)
GRRYVWCSLPQGWVLSPLIY;

(SEQ ID NO: 16)
LLLILCLPTLVDCIRN.
```

Figure 2A:
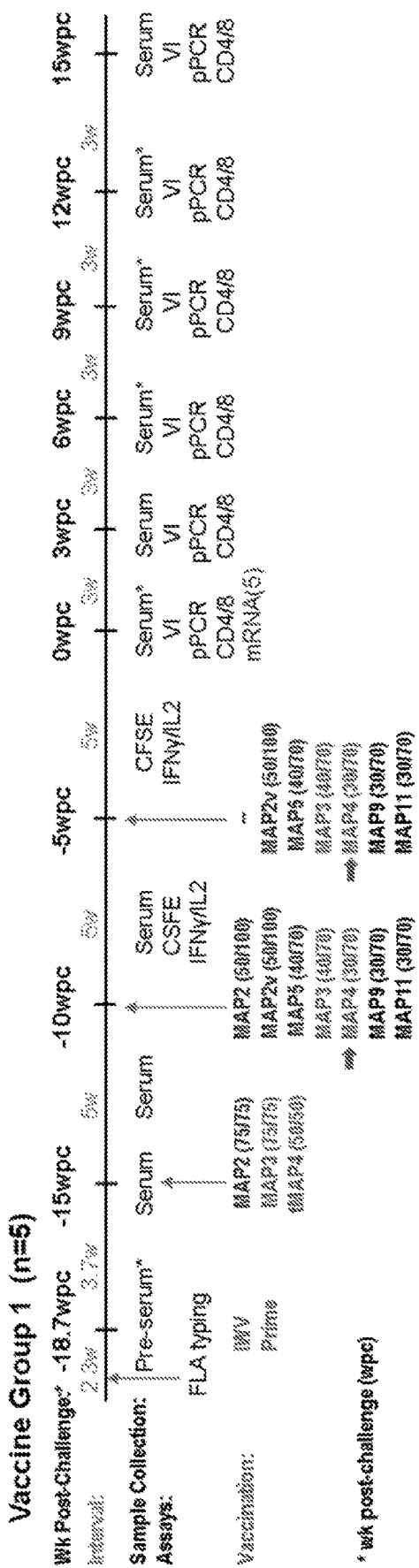
Figure 2B:
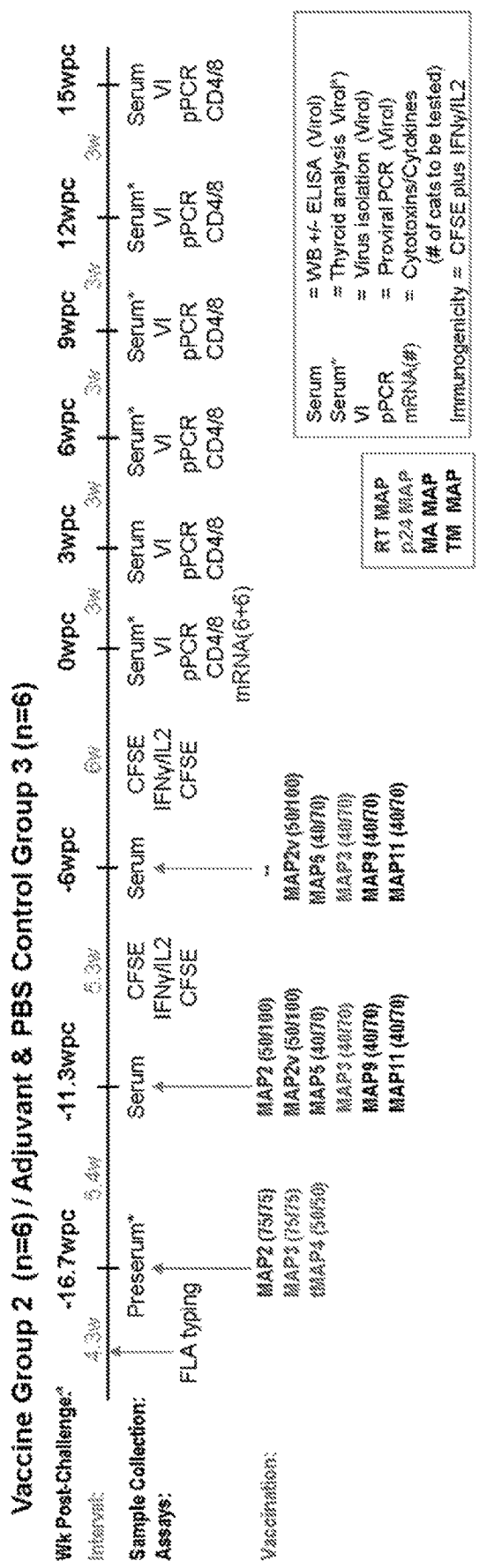
Figure 3A:
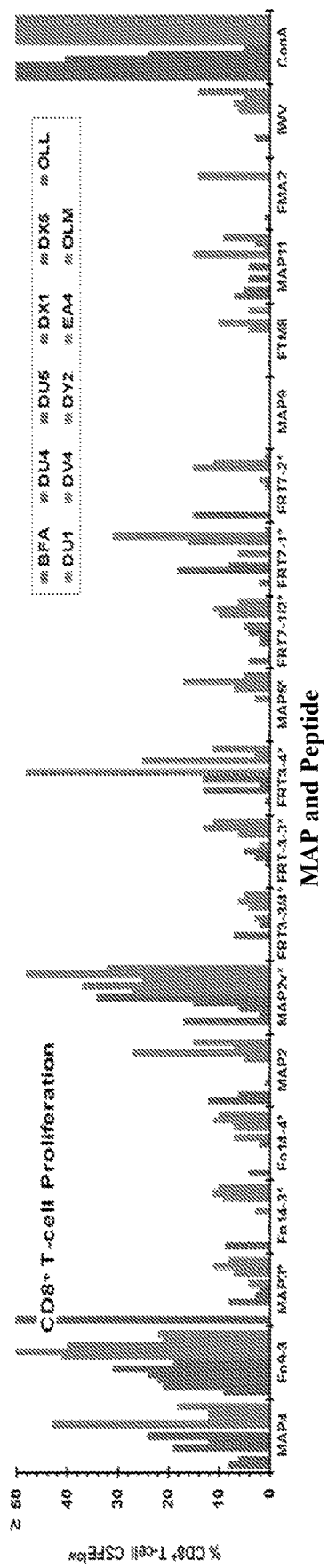
Figure 3B:
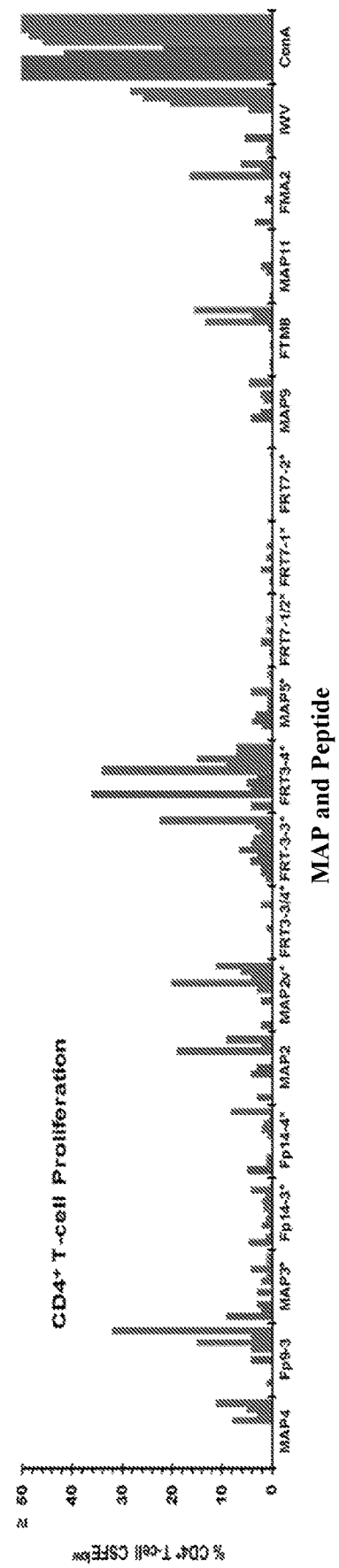
Figure 3C:
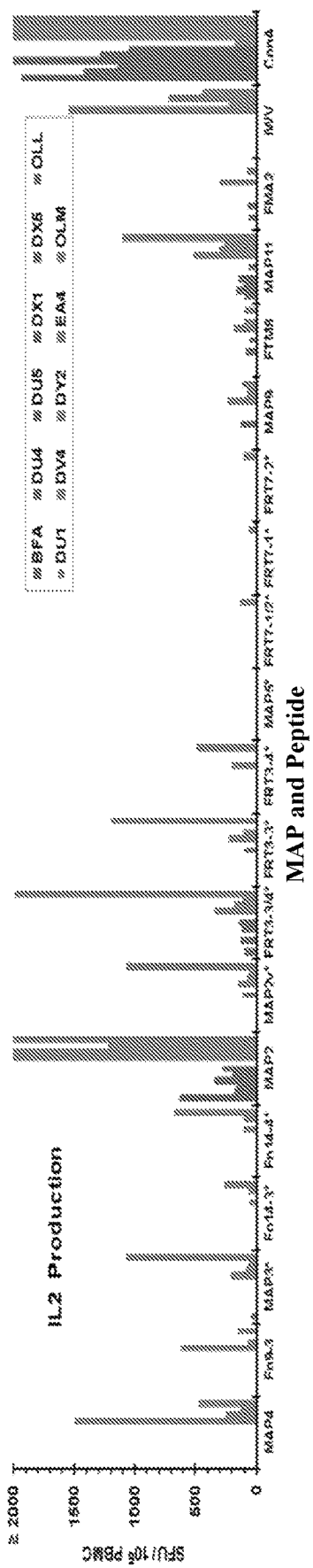
Figure 3D:
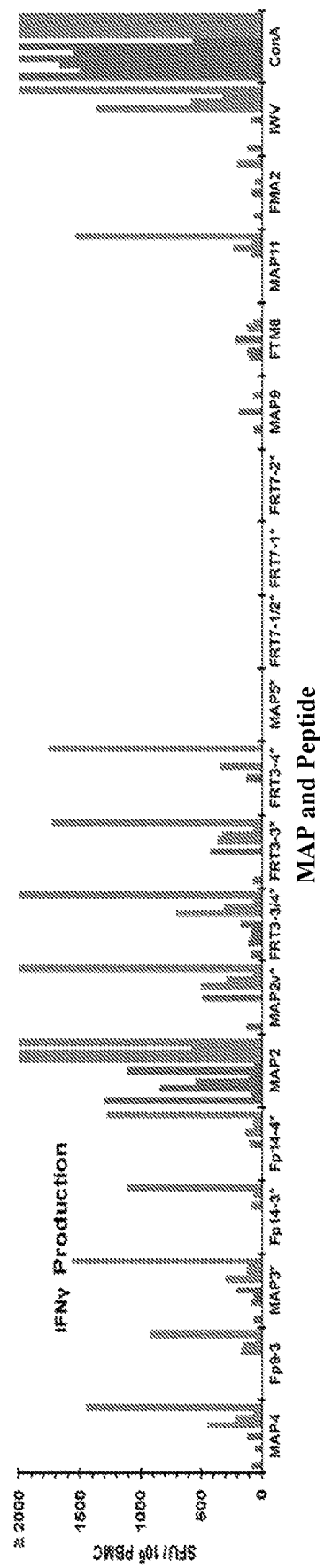

FIGS. 2A-2B. The schedule of the ongoing MAP Vaccine Trial I. Group 1 (n=5) (FIG. 2A) received single priming with inactivated dual-subtype whole virus vaccine (IWV) followed 3.7 weeks (w or wk) later with MAP vaccination and subsequently two more MAP vaccinations at 5 wk intervals. Group 2 (n=6) (FIG. 2B) received three MAP vaccinations at intervals of 5.3-5.4 wk. The individual MAP used per vaccination and its subcutaneous dose/intradermal dose in parenthesis are shown under each of the three MAP vaccinations. Control Group 3 received either adjuvant plus feline IL12 (FeIL12) (n=3) or PBS alone (n=3) at an immunization schedule identical to Group 2. The blue arrow next to MAP4 in Group 1 schedule indicates that MAP4 was included in all three vaccinations whereas Group 2 received no MAP4 vaccination in the 2nd and the 3rd vaccinations. MAPs in red, blue and black contain RT, p24, and MA/TM peptides, respectively. Immunological parameters measured were FIV MAP-specific and peptide-specific CD4$^+$ and CD8$^+$ T-cell proliferation (CSFE), production of IFNγ and IL2, and production of cytotoxins/cytolysin and cytokine mRNAs, as well as vaccine-induced antibodies using FIV-antigen Western blot (WB) and ELISA. The virological analyses performed were FIV virus isolation (VI) including analysis of viral set-point load, proviral PCR (pPCR), CD4/CD8 T-cell counts for decline in CD4$^+$ T cells upon infection, and infection-induced FIV antibodies using WB.

FIGS. 3A-3D. T-cell proliferation and cytokine production to MAPs and their peptides at 3-6 wk post-challenge. The CD8$^+$ T-cell proliferation (FIG. 3A), CD4$^+$ T-cell proliferation (FIG. 3B), IL2 production of PBMC (FIG. 3C), and IFNγ production of PBMC (FIG. 3D) in response to in vitro stimulation with either MAP or its peptide(s) shown immediately after are presented. Each bar represents a response from a single cat with the prime-boost Group 1 in red bars and only MAP-vaccination Group 2 in blue bars. Cats in Group 2 received one vaccination of MAP4 containing peptide Fp9-3 as shown as (1× over blue bars). MAP3 and MAP2 in combination with MAP2v were vaccinated 3×, while MAP3, MAP9, and MAP11 were vaccinated 2× as shown under the MAP/peptide designations. The T-cell mitogen concanavalin A (ConA) was used as non-specific positive stimulant.

The majority of the MAPs and their corresponding peptide(s) in Groups 1 and 2 induced high CD8$^+$ T-cell proliferation after 3×MAP vaccinations. However, those MAPs with only 2× vaccinations generally induced low responses except for the reasonably high CD8$^+$ T-cell proliferation induced by MAP5 and its peptide FRT7-1. MAP2v induced less IFNγ and IL2 productions than MAP2 and maybe a better vaccine immunogen. Results from our previous conventional FIV vaccine trials performed under corporate contracts showed a correlation of high IFNγ responses with no protection (Pu and Yamamoto, personal communique). Note that cat OLM from Group 1 (fifth red bar for each stimulant) induced the most IFNγ and IL2 productions to MAPs and their peptide(s), and it was one of the first two cats to be FIV infected along with the 4 of 6 non-vaccinated control cats.

When the individual cats in Group 1 were evaluated for % CD8$^+$ T-cell CFSE$^{low}$ over % CD4$^+$ T-cell CFSE$^{low}$ ratio, peptide Fp9-3 induced the highest CD8/CD4 response ratio of 111.75 followed by FRT7-1/FRT7-2 (ratio of 11), FRT3-3/FRT3-4 (ratio of 9), and Fp14-3/Fp14-4 (ratio of 4.8). Moreover, Fp9-3 and FRT7-1/7-2 induced no IFNγ response, whereas FRT3-3/FRT3-4 (531 SFU/10$^6$ PBMC) followed by Fp14-3/Fp14-4 (96 SFU/10$^6$ PBMC) induced the most IFNγ production. The high CD8/CD4 T-cell response ratio may indicate higher CD8$^+$ CTL with minimal-to-no induction of CD4$^+$ T-cell activation. Activated CD4$^+$ T cells have higher levels of activation marker CD134 which is the cellular receptor for FIV (Weinberg, 2002; Shimojima et al., 2004). Activated CD4$^+$ T cells will allow proviral integration which is required for lentiviral replication (Yamamoto, 2008; Levy, 2007). Furthermore, IFNγ can enhance in vitro and in vivo FIV or AIDS virus replication (Tanabe and Yamamoto, 2001; Yamamoto et al., 1986; Yamamoto, 2009). Thus, an FIV peptide that induces potent anti-FIV CD8 CTLs, low-to-nil CD4$^+$ T-cell proliferation, and minimal IFNγ production will be an ideal vaccine peptide. Based on these data shown and described here, MAP4 with peptide Fp9-3 is the best vaccine immunogen followed by MAP5 (FRT7-1/FRT7-2) and then MAP3 (Fp14-3/Fp14-4) and MAP2v (FRT3-3/FRT3-4).

Figures 1, 4A:
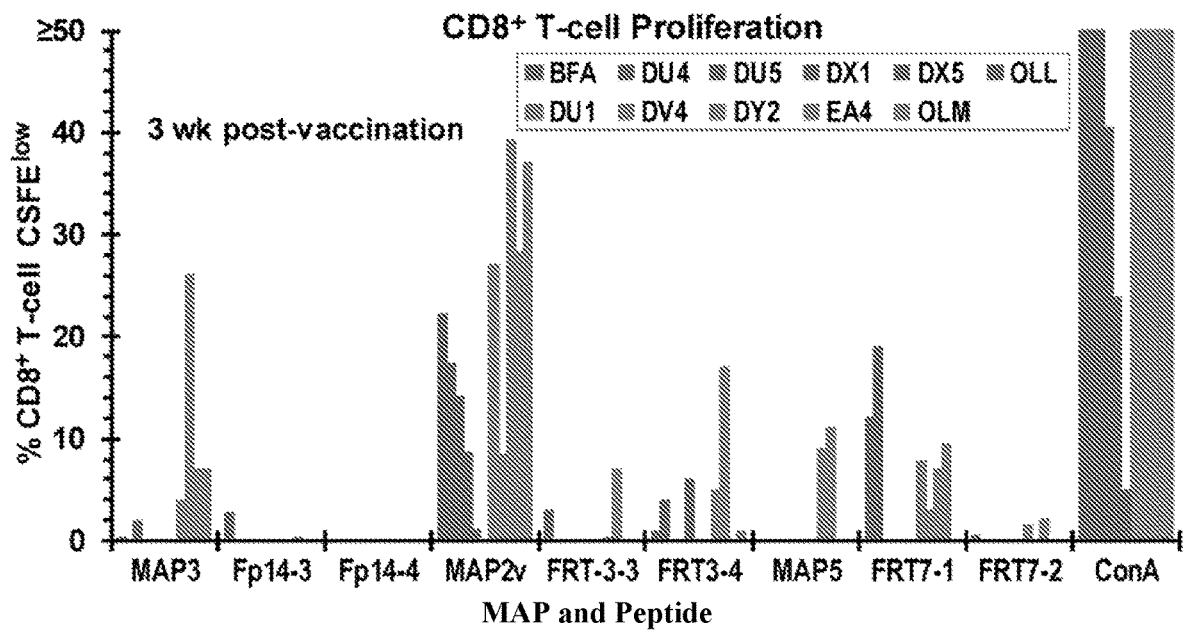

FIGS. 4A-1, 4A-2, 4B-1, and 4B-2. Comparison of FIV Peptide-specific immunity at 3 versus 6 wk post-final vaccination. The CD8$^+$ (FIGS. 4A-1 and 4A-2) and CD4$^+$ (FIGS. 4B-1 and 4B-2) T-cell proliferation responses at 3 wk post-final vaccination (FIGS. 4A-1 and 4B-1) were compared to those at 6 wk post-final vaccination (FIGS. 4A-2 and 4B-2) for MAP3 (peptides Fp14-3 & Fp14-4), MAP2v (peptides FRT3-3 & FRT3-4) and MAP5 (peptides FRT7-1 & FRT7-2). Each bar represents a response from a single cat as shown in FIG. 4A-1 insert. The prime-boost Group 1 is in red bars and Group 2 with only MAP vaccinations is in blue bars. The CD8$^+$ T-cell proliferation responses are more elevated at 6 wk than at 3 wk post-final vaccination, whereas the CD4$^+$ T-cell proliferation have higher magnitudes at 3 wk than 6 wk and only low levels remain in 6 wk. Thus, future vaccinations should be performed at intervals of 6 wk, and the challenge should be administered after 6 wk post-final vaccination when CD8$^+$ T-cell proliferation is more robust than CD4$^+$ T-cell proliferation.

Figures 2, 4A:
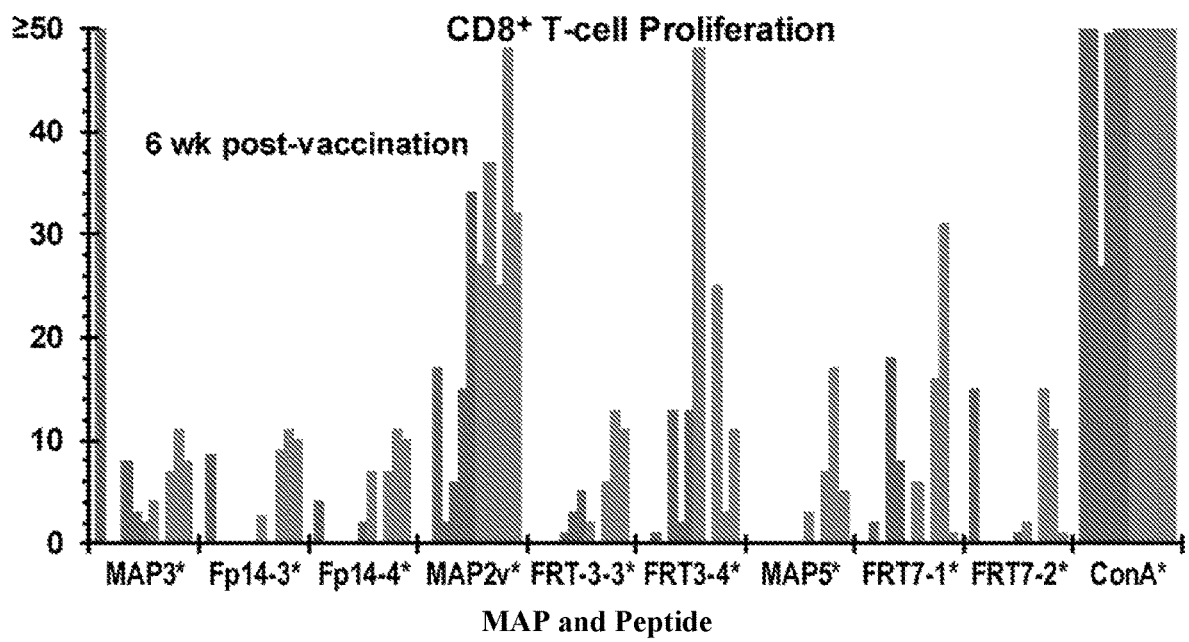
Figures 1, 4B:
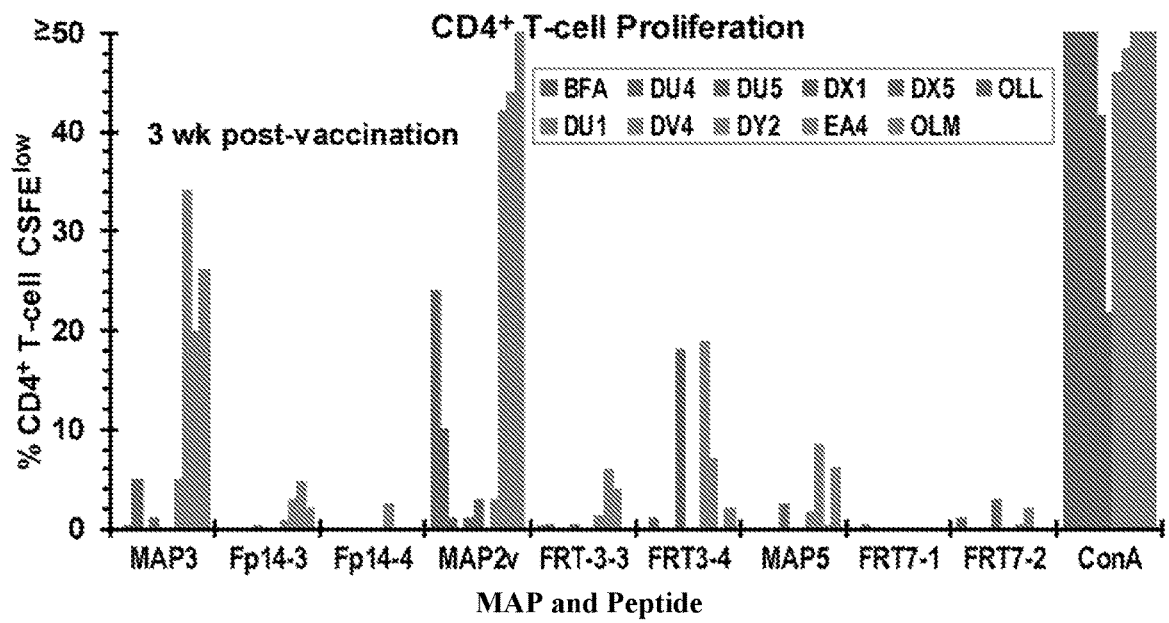
Figures 2, 4B:
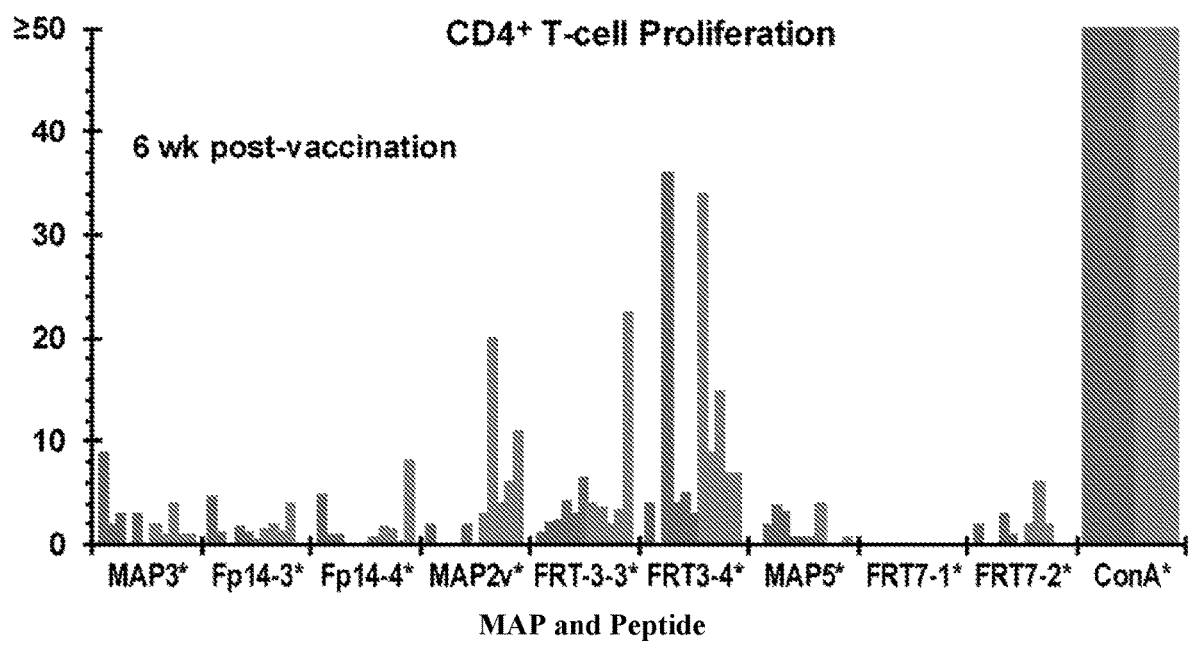
Figure 5:
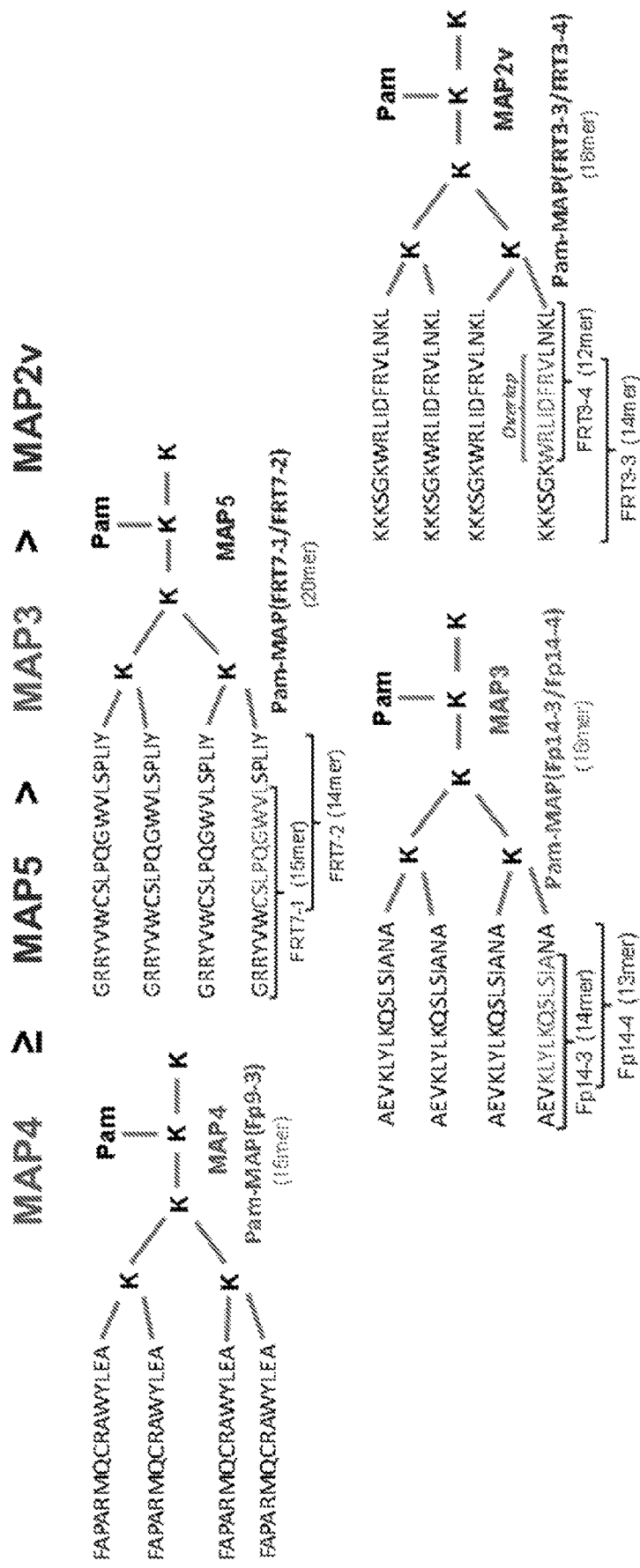

FIG. 5. Vaccine Efficacy of Individual MAPs. Based on the immunogenicity described in FIG. 4 legend and current efficacy results, MAP4 (Fp9-3) is the best vaccine immunogen followed by MAP5 (FRT7-1/7-2) and then MAP3 (Fp14-3/Fp14-4) and MAP2v (FRT3-3/FRT3-4). The structure of the best four MAPs is shown below the efficacy results.

```
FIG. 5 sequences:
                                  (SEQ ID NO: 20)
     FAPARMQCRAWYLEA;

(SEQ ID NO: 35)
     GRRYVWCSLPQGWVLSPLIY;

(SEQ ID NO: 26)
     AEVKLYLKQSLSIANA;

(SEQ ID NO: 30)
     KKKSGKWRLIDFRVLNKL.
```

Figure 6A:
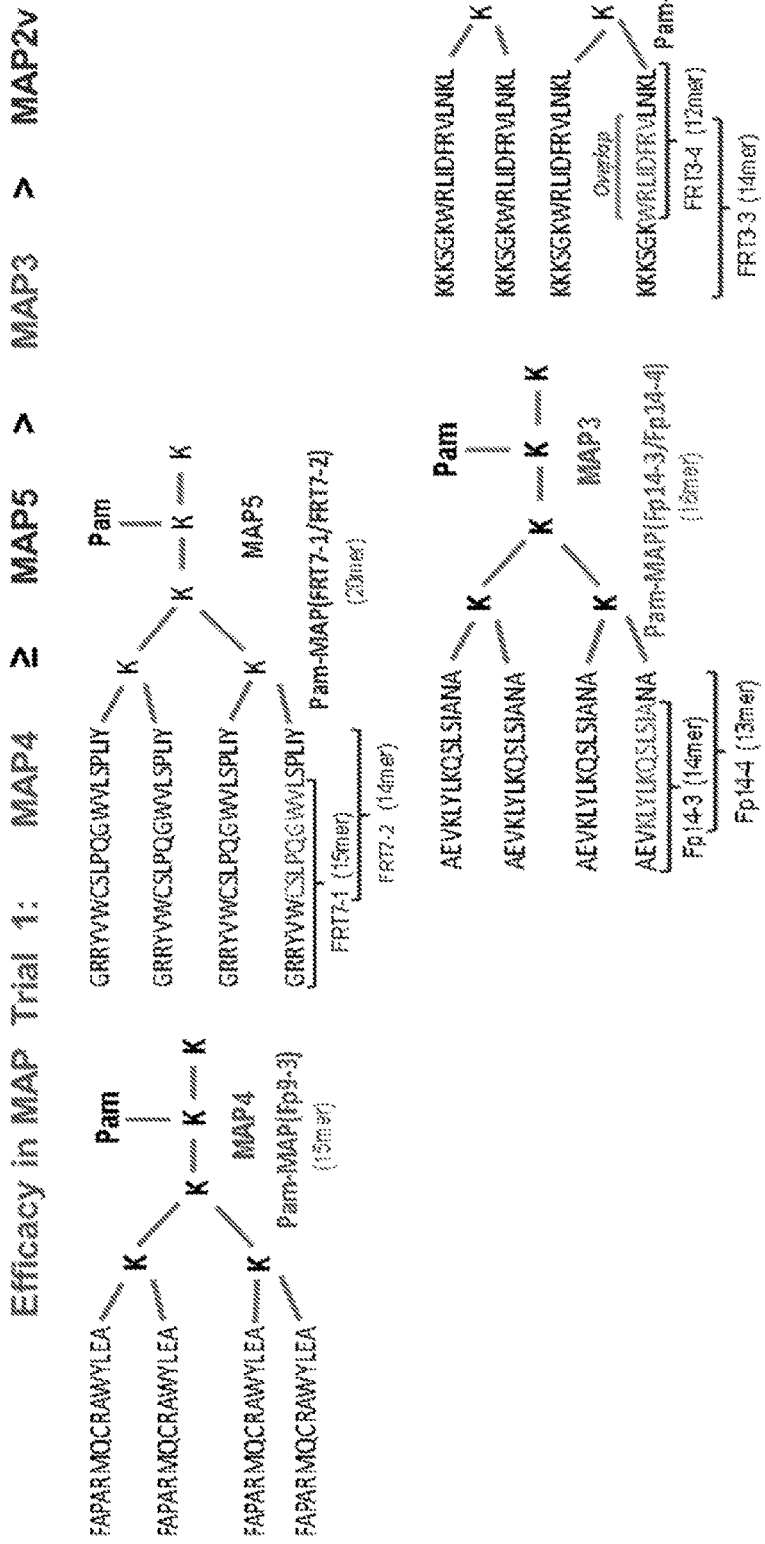

FIGS. 6A-6B. FIG. 6A shows MAP5 used in MAP Trial 2. FIG. 6B shows distribution of cats in vaccine and control groups.

```
FIG. 6A sequences:
                                  (SEQ ID NO: 20)
     FAPARMQCRAWYLEA;

(SEQ ID NO: 35)
     GRRYVWCSLPQGWVLSPLIY;

(SEQ ID NO: 26)
     AEVKLYLKQSLSIANA;

(SEQ ID NO: 30)
     KKKSGKWRLIDFRVLNKL.
```

Figures 1, 7A:
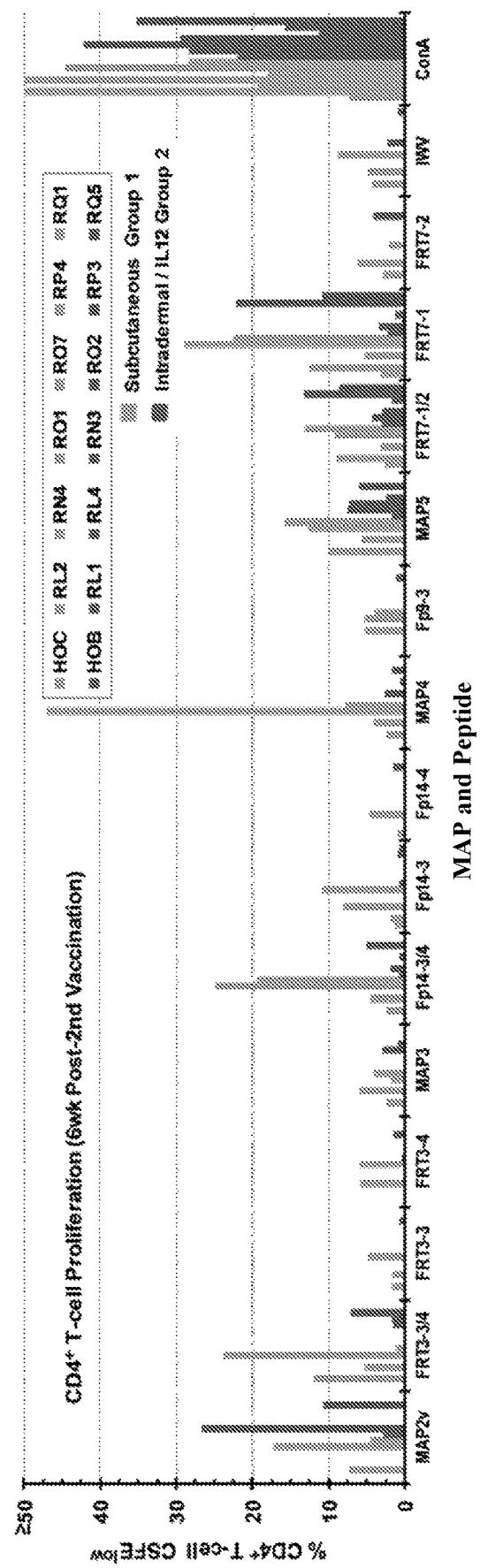
Figures 2, 7A:
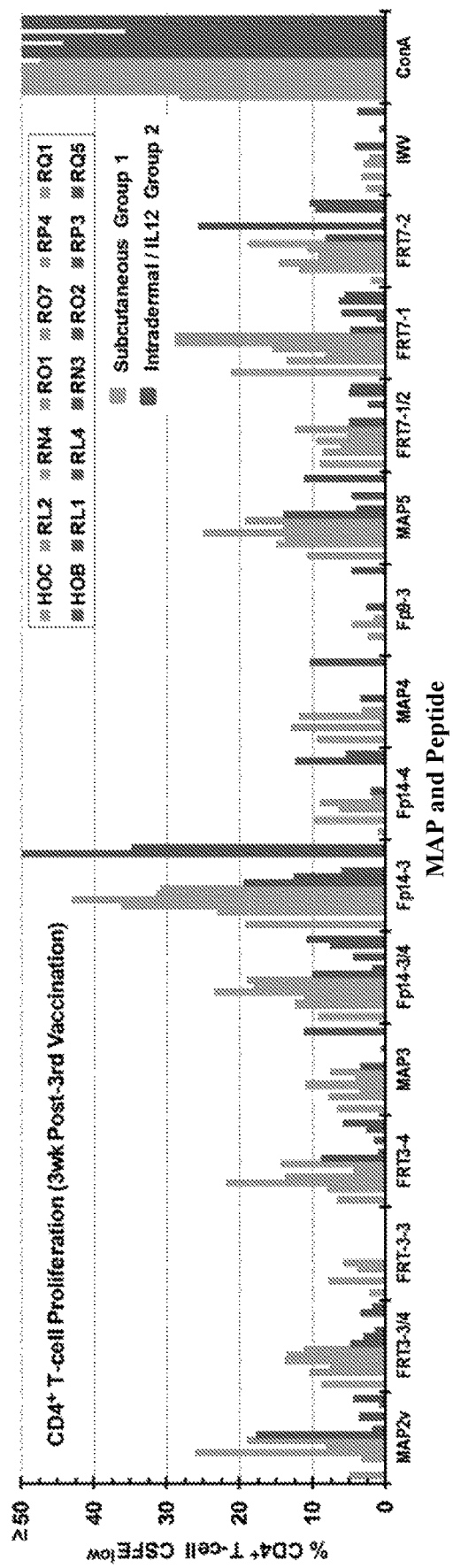
Figures 3, 7A:
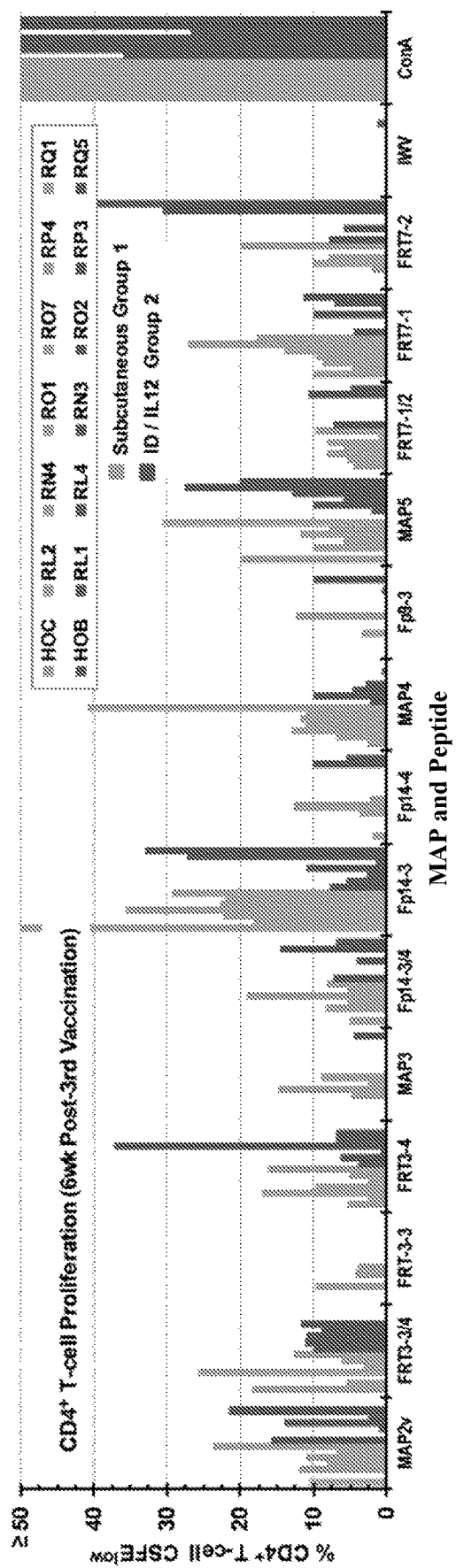
Figures 1, 7B:
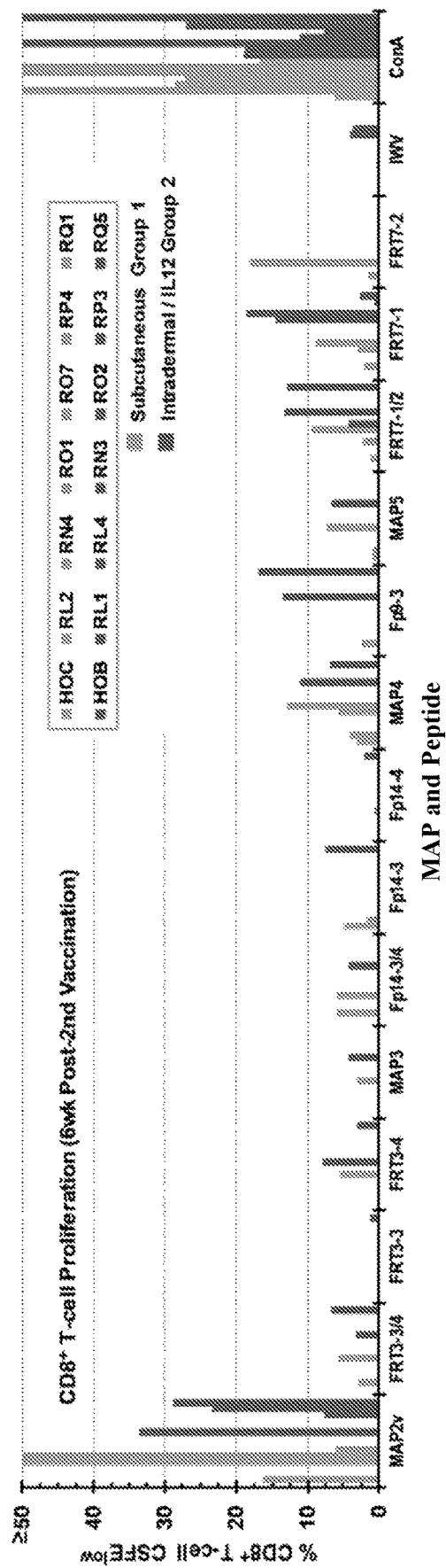
Figures 2, 7B:
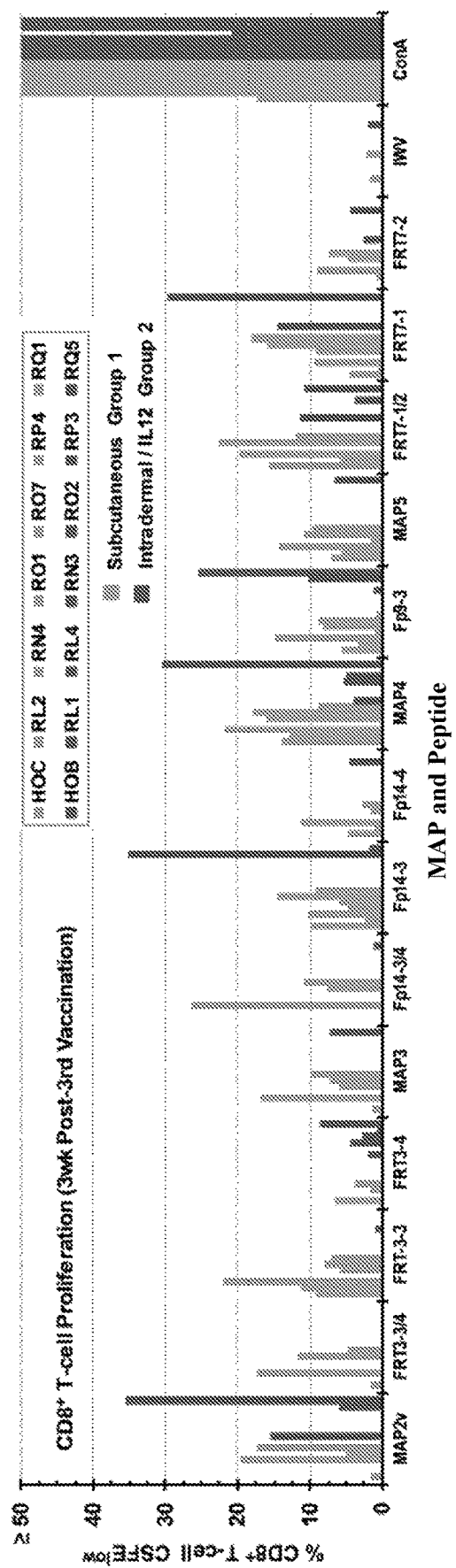
Figures 3, 7B:
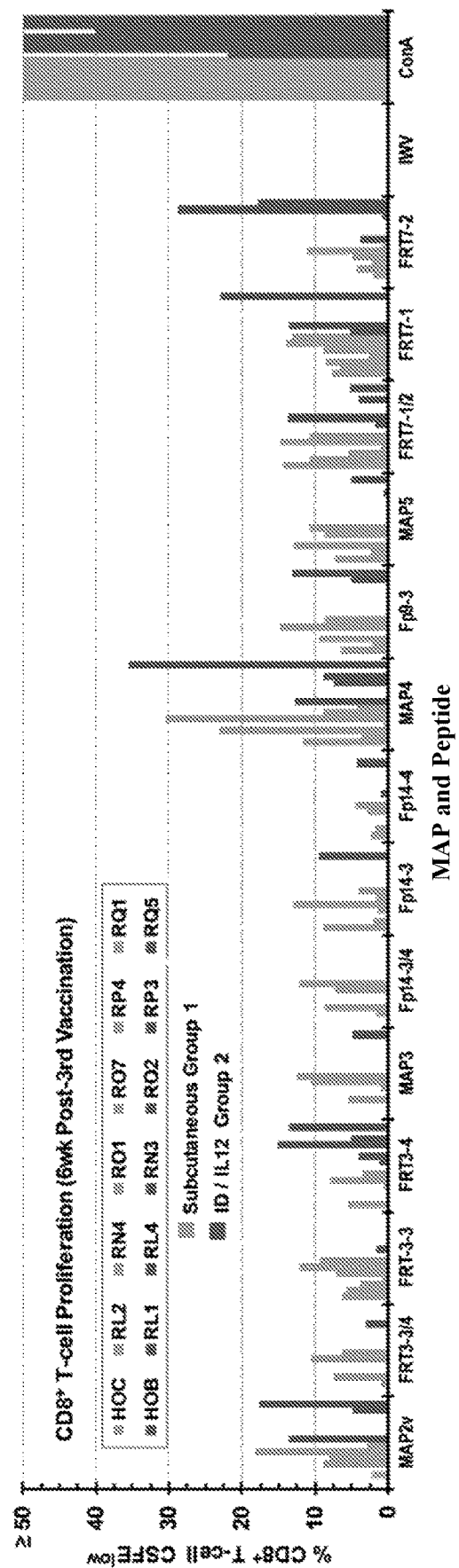

FIGS. 7A-1, 7A-2, 7A-3, 7B-1, 7B-2, 7B-3. FIG. 7A-1 shows CD4$^+$ T-cell proliferation (6 week post-2$^{nd}$ vaccination). FIG. 7B-1 shows CD8+ T-cell proliferation (6 week post-2$^{nd}$ vaccination). FIG. 7A-2 shows CD4+ T-cell proliferation (3 week post-3$^{rd}$ vaccination). FIG. 7B-2 shows CD8+ T-cell proliferation (3 week post-3$^{rd}$ vaccination). FIG. 7A-3 shows CD4+ T-cell proliferation (6 week post-3$^r$ vaccination). FIG. 7B-3 shows CD8+ T-cell proliferation (6 week post-3$^r$ vaccination).

Figures 1, 8A:
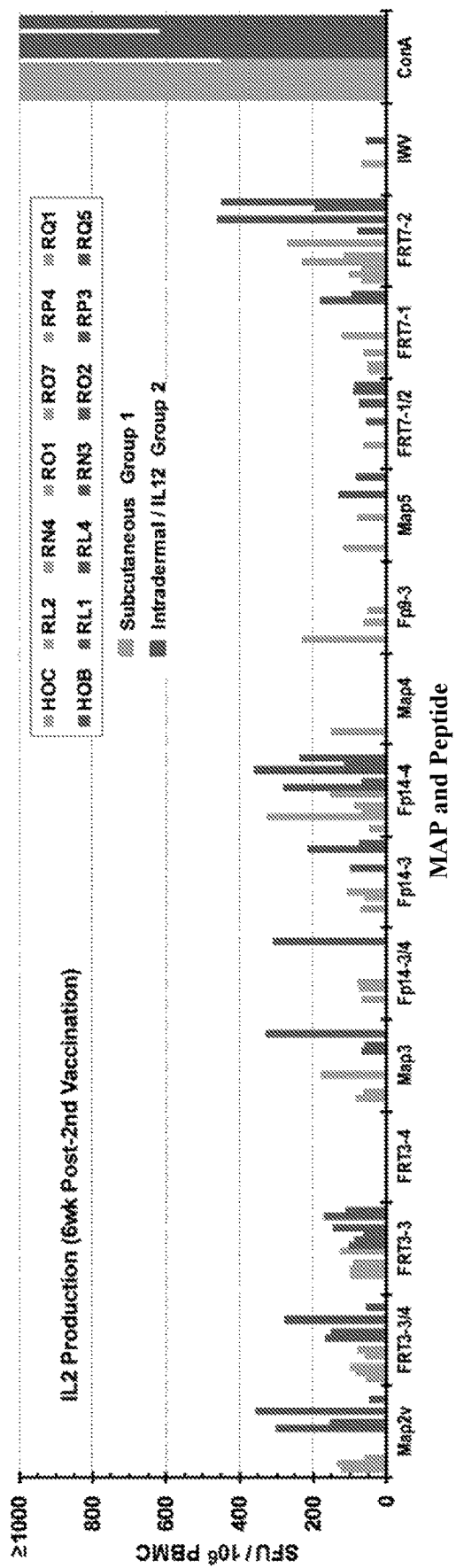
Figures 2, 8A:
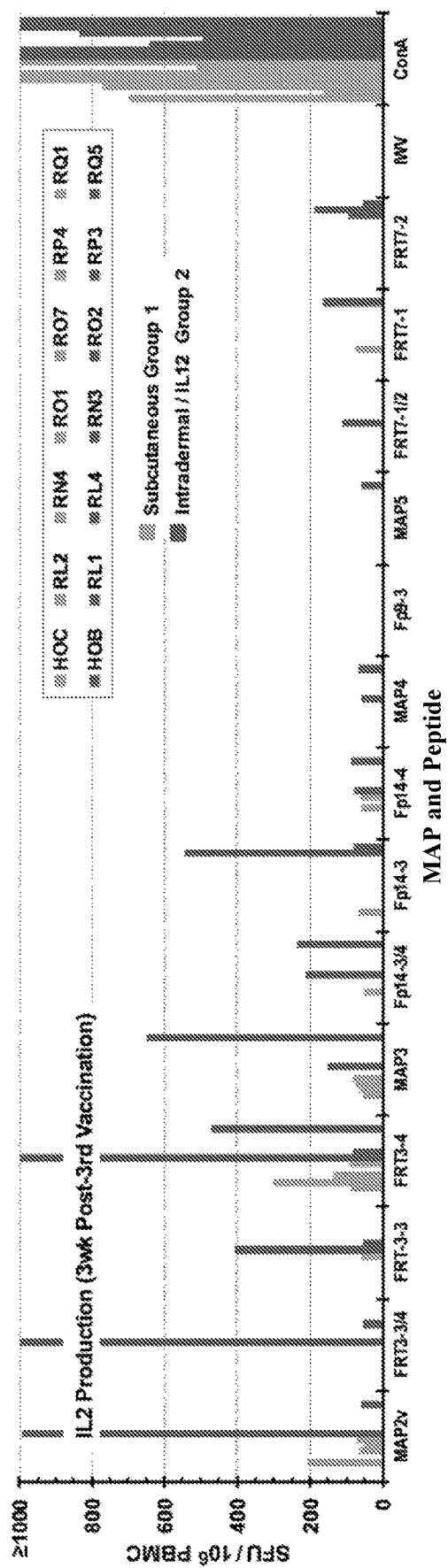
Figures 3, 8A:
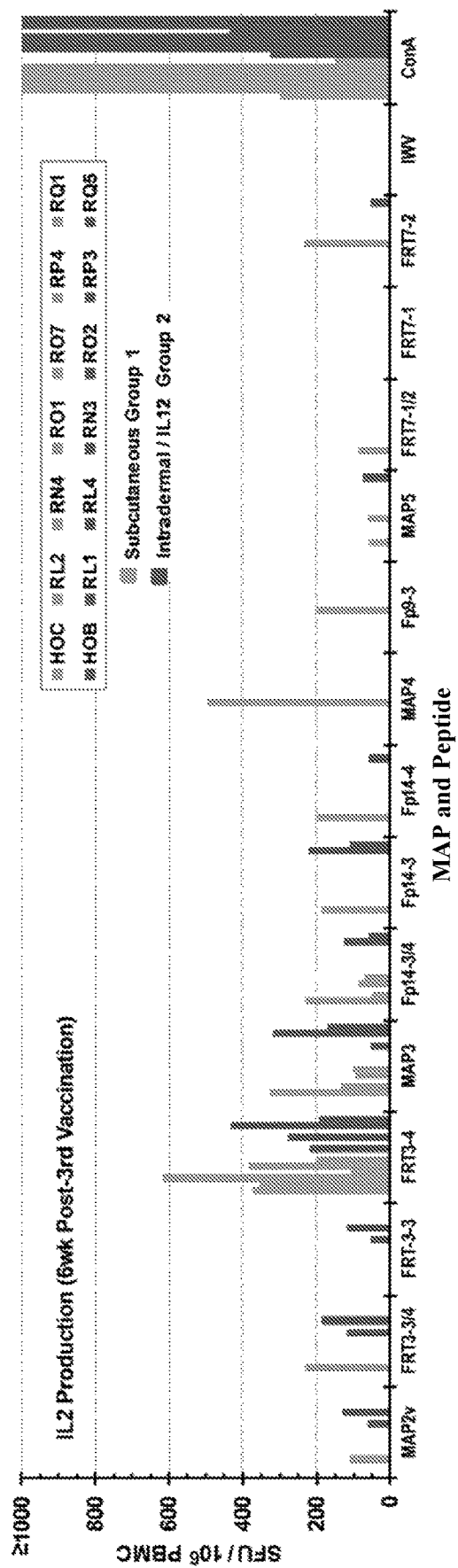
Figures 1, 8B:
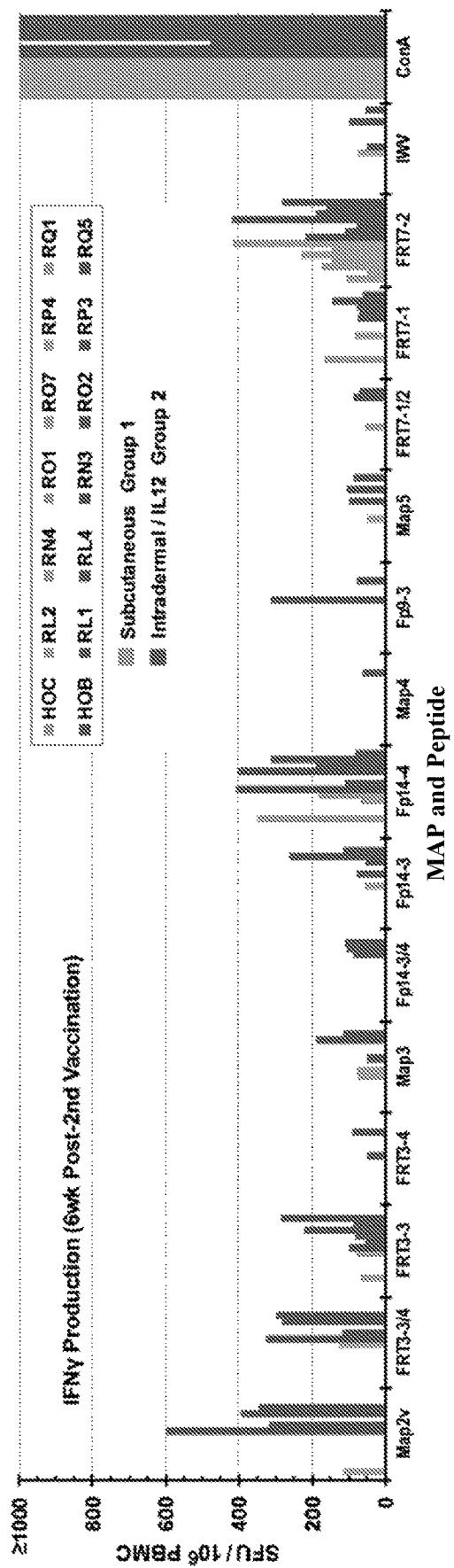
Figures 2, 8B:
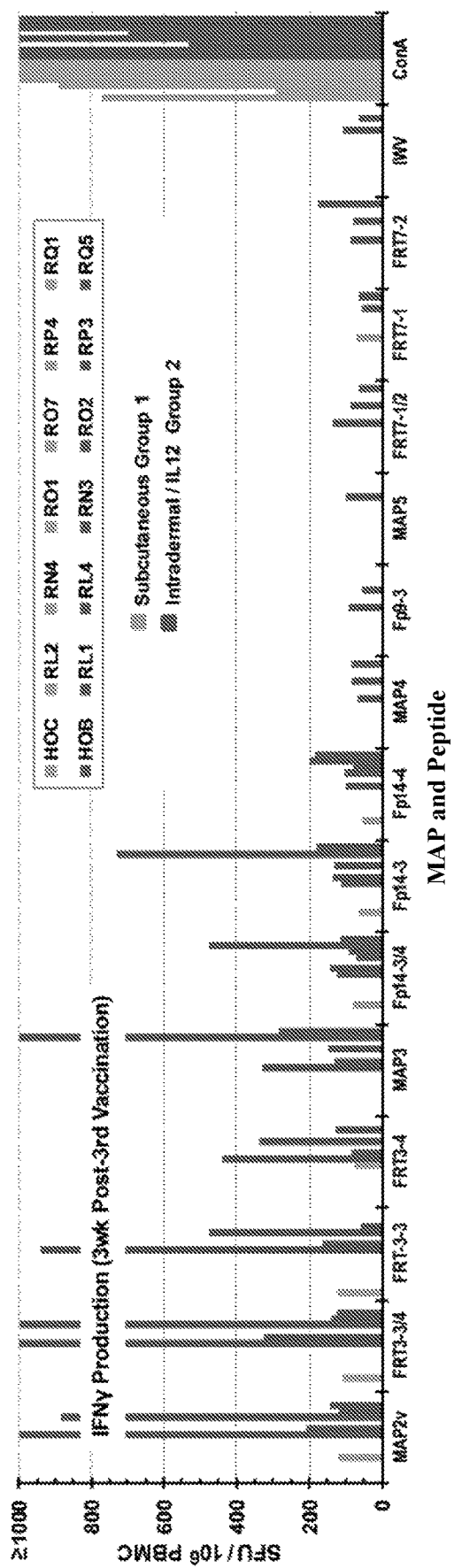
Figures 3, 8B:
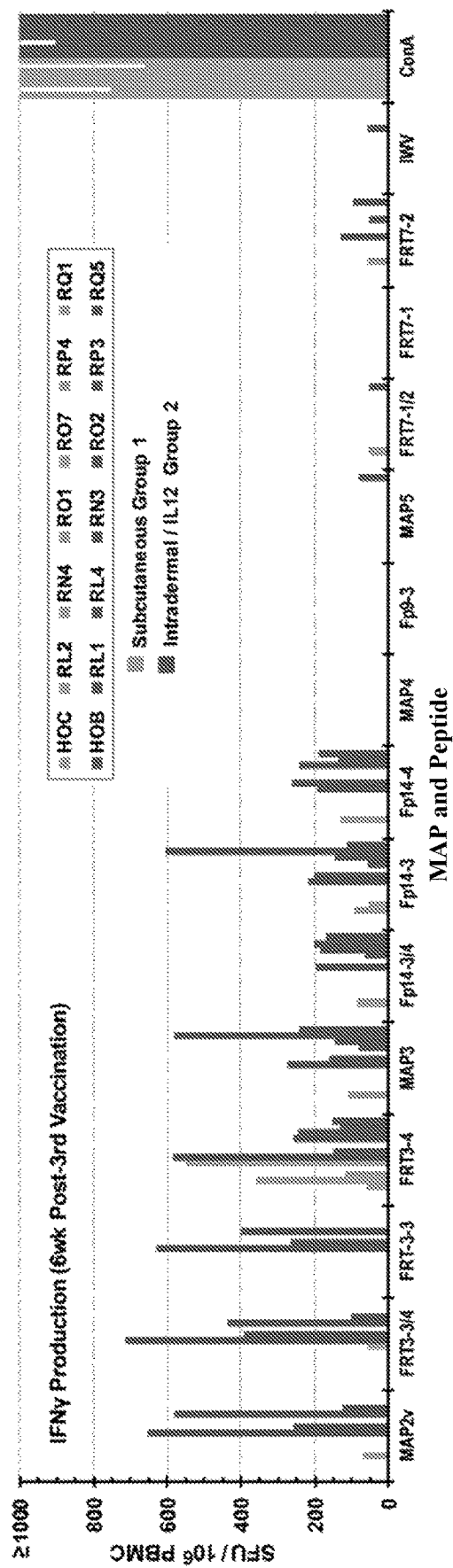

FIGS. 8A-1, 8A-2, 8A-3, 8B-1, 8B-2, 8B-3. FIG. 8A-1 shows IL2 production (6 week post-2$^{nd}$ vaccination). FIG. 8B-1 shows IFNγ production (6 week post-2$^{nd}$ vaccination). FIG. 8A-2 shows IL2 production (3 week post-3$^r$ vaccination). FIG. 8B-2 shows IFNγ production (3 week post-3$^{rd}$ vaccination). FIG. 8A-3 shows IL2 production (6 week post-3$^{rd}$ vaccination). FIG. 8B-3 shows IFNγ production (6 week post-3$^{rd}$ vaccination).

Figure 9A:
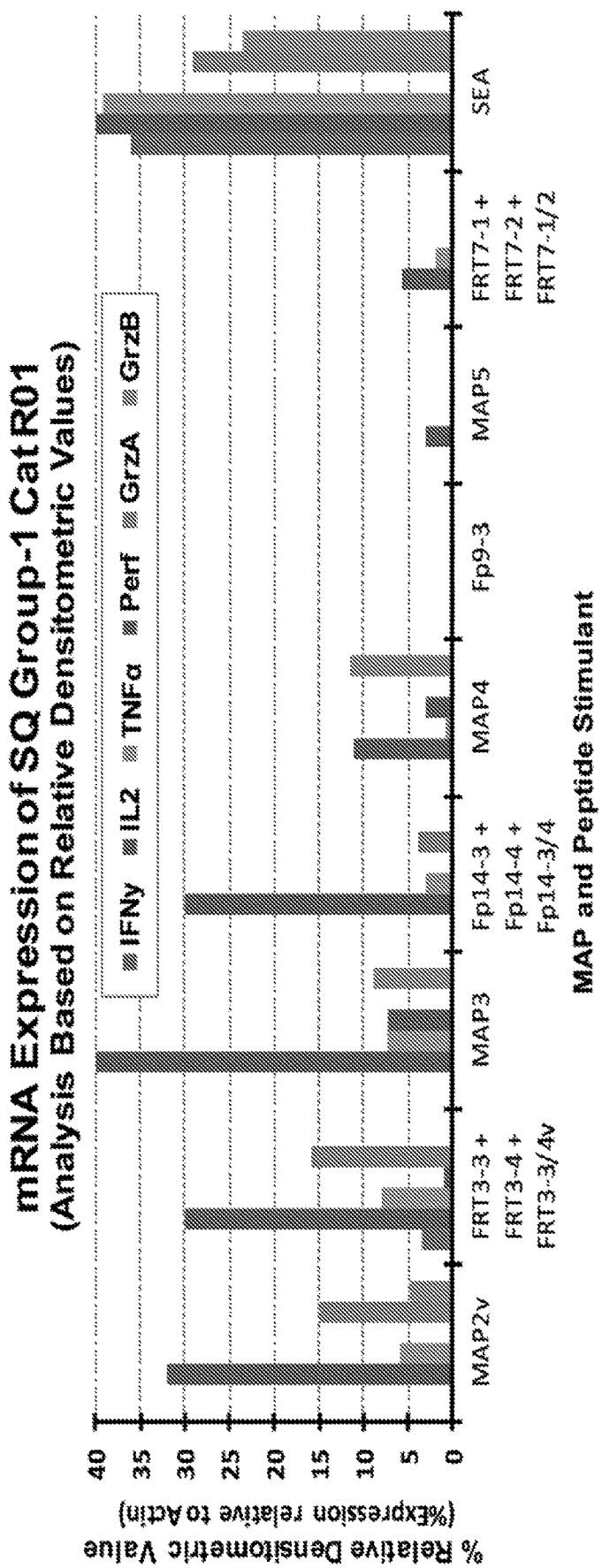
Figure 9B:
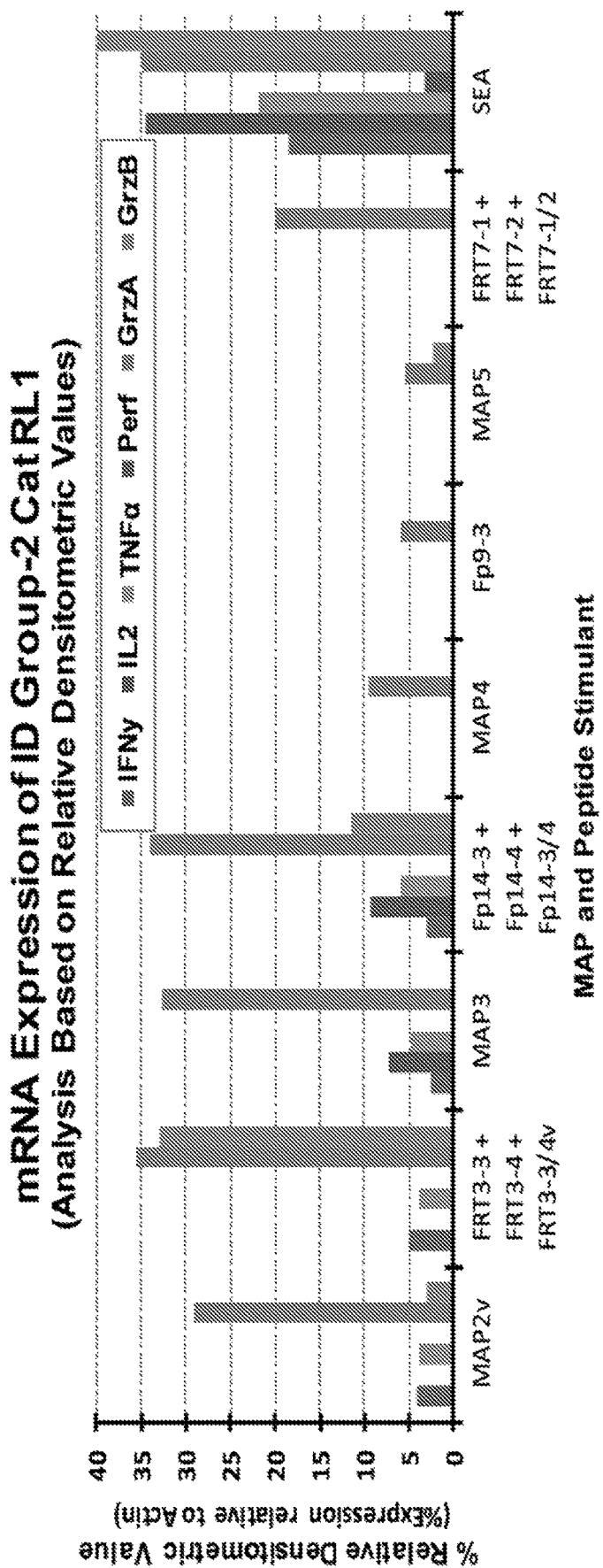

FIGS. 9A-9B. FIG. 9A shows mRNA expression of SQ Group-1 Cat R01. FIG. 9B shows mRNA expression of ID Group-2 Cat RL1.

Figure 10A:
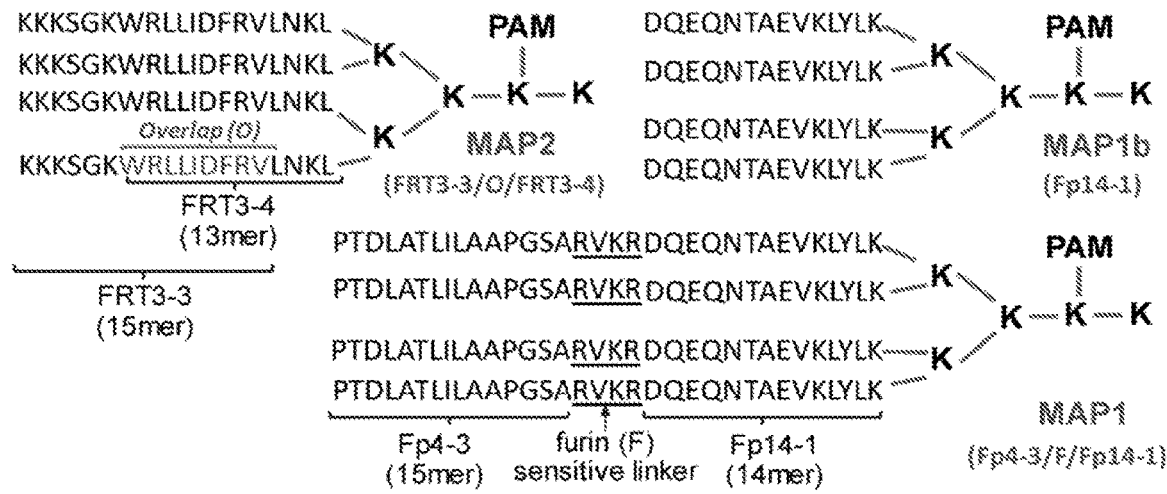
Figure 10B:
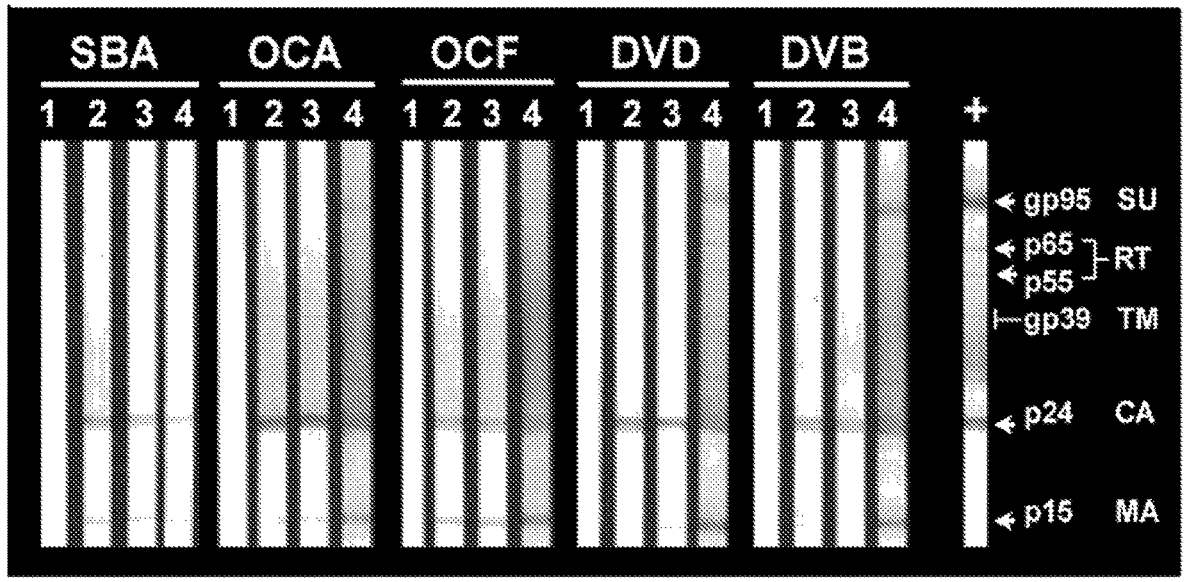

FIGS. 10A-10F. Vaccine immunogens and pre-challenge vaccine immunogenicity. MAP immunogens used for vaccination are shown with the individual peptides linked with lysine (K) branch containing palmitic acid at the second-to-last lysine residue from the carboxyl end (FIG. 10A). FIG. 10B: Serum IgG immunoblot results of cats from Group 1 (SBA, OCA, OCF) and Group 2 (DVD,DVB) before priming (lane 1), at least 3 wk post-prime but before boost (lane 2), 1 week before challenge (lane 3), and at termination (lane 4). Serum from cat SBA in lane 4 is at 61 wpc or 14 wk post-challenge boost. Serum for positive control (+) is from an FIV infected cat. CD3+CD8+ T-cell proliferation (FIG. 10C), CD3+CD4+ T-cell proliferation (FIG. 10D), IFN ELISpot (FIG. 10E), and IL2 ELISpot (FIG. 10F) responses were stimulated in vitro with peptide pools Fp4, Fp14, FRT3; individual peptides (Pept) Fp4-3, Fp14-1, FRT3-3, FRT3-4; MAP1c, MAP1b, MAP1, MAP2; or concanavalin A (ConA). Note MAP1c not shown in (FIG. 10A) contains four copies of the peptide Fp4-3. Bars are color coded for Group 1 (blue or light blue) and Group 2 (red or pink). Each vaccinated cat with the corresponding color is shown in the inset in FIG. 10C. The light blue and pink bars represent cats that displayed no partial or full

```
FIG. 10 sequences:              (SEQ ID NO: 31)
KKKSGKWRLLIDFRVLNKL;
                                (SEQ ID NO: 24)
DQEQNTAEVKLYLK;
                                (SEQ ID NO: 102)
PTDLATLILAAPGSARVKRDQEQNTAEVKLYLK.
```

Figure 11A:
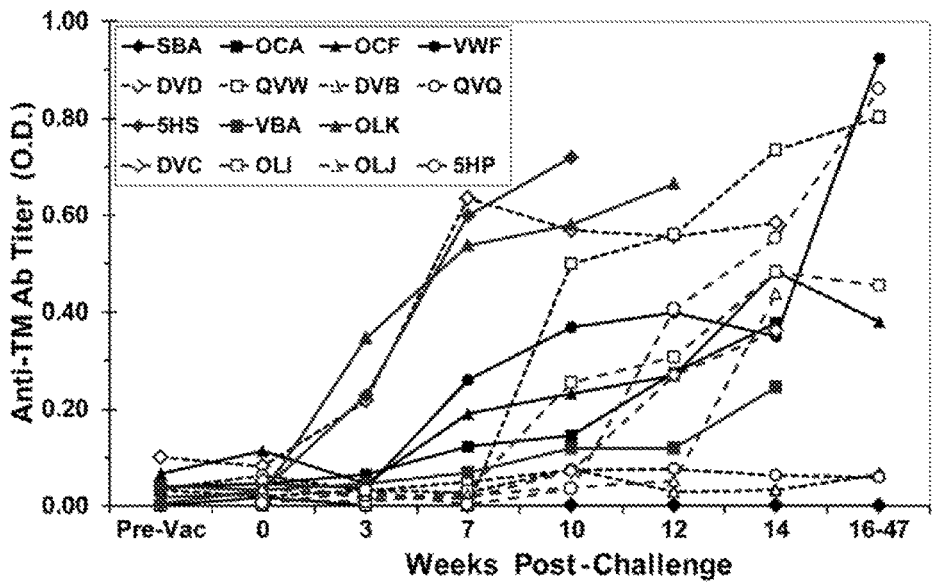
Figure 11B:
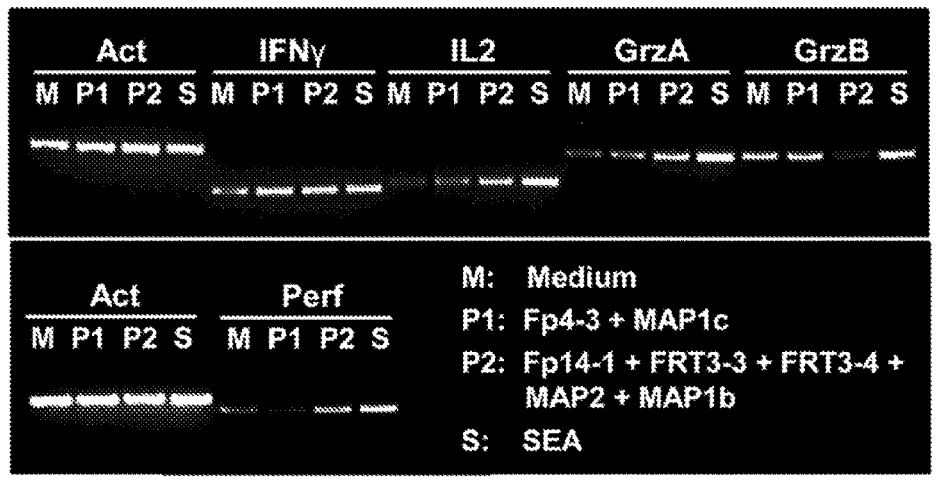
Figure 11C:
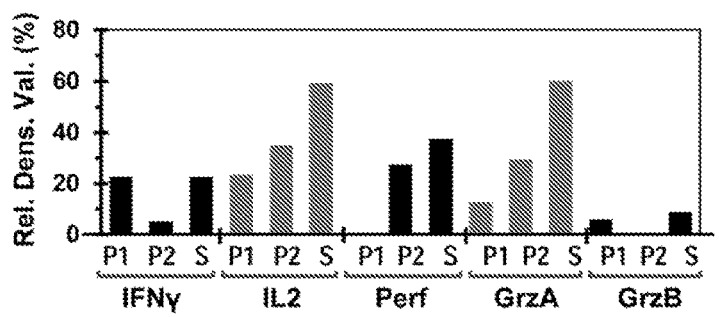
Figure 11D:
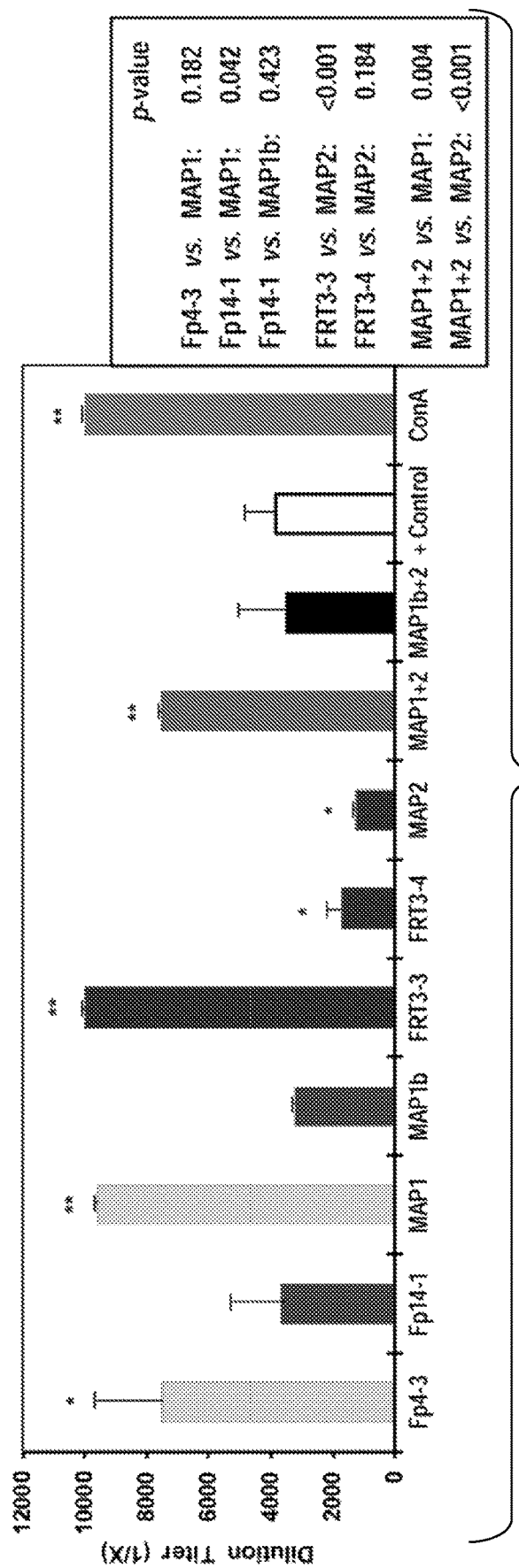

FIGS. 11A-11D. FIV challenge induced virus-specific antibodies and immunity after post-challenge vaccine boost. Antibodies to FIV the transmembrane (TM) region were monitored over 14 weeks post-challenge (wpc) or until termination (16-47 wpc) (FIG. 11A) except for cats 5HS (terminated 10 wpc) and OLK (terminated 12 wpc). MAP-vaccinated Group 1 (black line, closed symbols), MAP-vaccinated Group 2 (black dotted line, open symbols), 1×-prime Group 3 (red line, closed symbols), and control Group 4 (red dashed line, open symbols) are shown. Cat SBA received a MAP1/MAP2 boost at 47 wpc and tested for IFNγ, IL2, perforin (Perf), GrzA, and GrzB mRNA expression at 14 wk post-challenge boost (FIG. 11B). Each lane consists of PBMC cultured with a combination of Fp4-3 and MAP1c (P1); a combination of Fp14-1, FRT3-3, FRT3-4, MAP2, and MAP1b (P2); mitogen staphylococcal enterotoxin A (SEA) (S); and media control (M). Relative densitomitric values of each band are compared to the corresponding β-actin housekeeping gene band as depicted in (FIG. 11C). Direct enhancement or suppression of in vitro FIV infection with peptide antigens and MAP immunogens was tested (FIG. 11D). MAP1 and MAP1b consist of peptides Fp4-3 plus Fp14-1 and Fp14-1 respectively (blue bars). MAP2 is an overlapping sequence containing FRT3-3 and FRT3-4 (red bar). The combination of MAP1 plus MAP2 (MAP1+2, brown bar) and MAP1b plus MAP2 (MAP1b+2, black bar) are also compared to FIV virus control (+ Control or baseline, white bar) and mitogen ConA control (grey bar) as the viral enhancement control. Significant differences between the virus control group and peptide or MAP stimulant group are shown as (*) for p<0.05 or (**) for p<0.001 above the bar. Additional comparisons with corresponding p values are shown in a chart.

Figure 12:
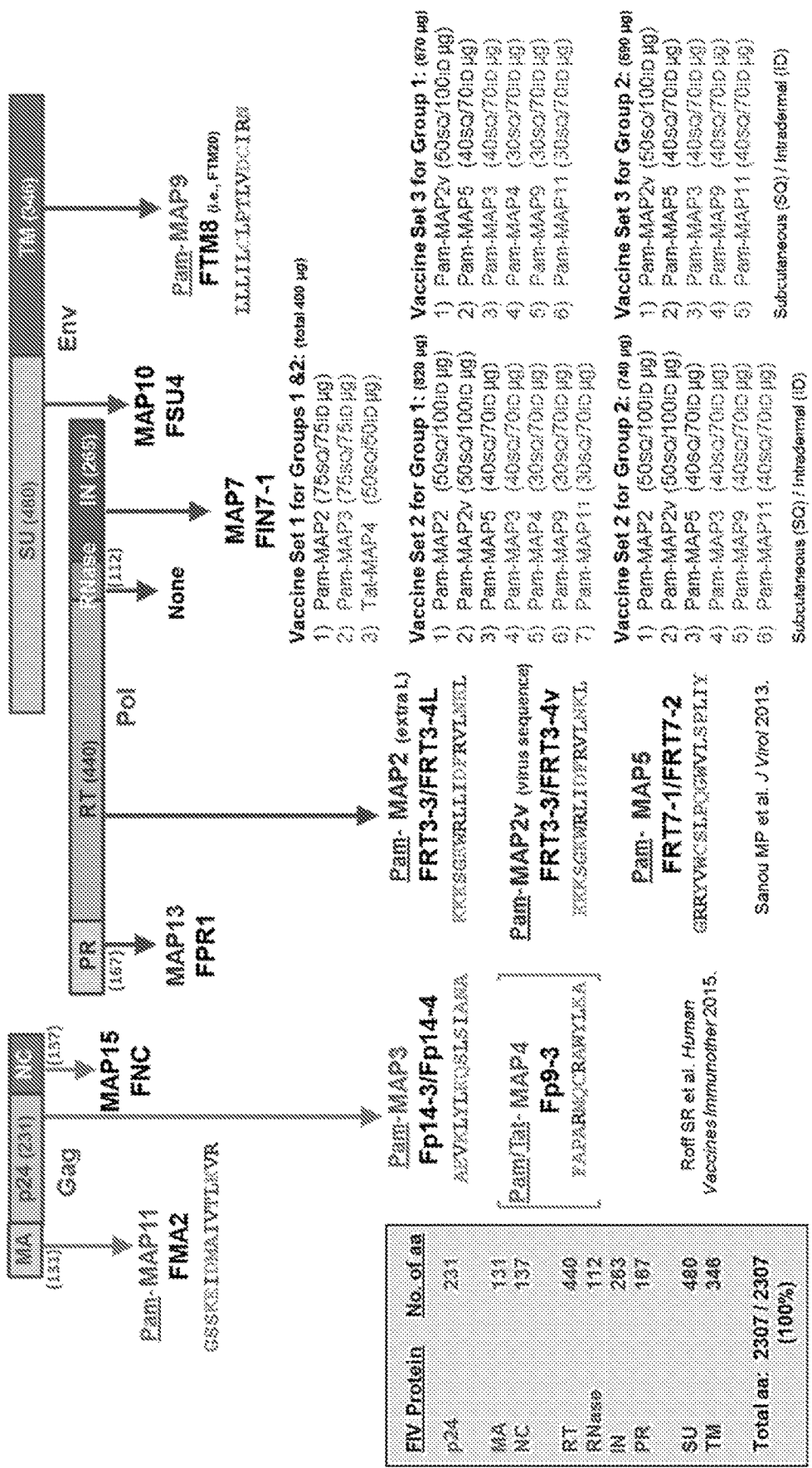

FIG. 12. Conserved T-cell epitopes selected from specific FIV proteins. Except for the FIV RNAse, conserved T-cell epitopes were detected in all of the FIV structural or enzyme proteins. Structural protein Gag (green) consists of matrix (MA), capsid p24, and nucleocapsid (NC). The other structural proteins are the glycosylated envelope proteins (blue) and consist of surface envelope (SU) and transmembrane envelope (TM). The viral enzymes (red) tested are protease (PR), reverse transcriptase (RT), RNase, and integrase (IN). The peptide sequences of the MAPs are shown below the MAP and peptide codes. Note that MAP2 has an extra leucine (L) in the peptide sequence, whereas MAP2v is the exact sequence of the virus. The doses of the MAPs used for subcutaneous (SC) and intradermal (ID) immunizations are also shown for each vaccination groups (list on the lower right). The insert in left bottom shows the numbers of amino acids present in each FIV protein tested.

```
FIG. 12 sequences:              (SEQ ID NO:65)
GSSKEIDMAIVTLKVR;
                                (SEQ ID NO: 26)
AEVKLYLKQSLSIANA;
                                (SEQ ID NO: 20)
FAPARMQCRAWYLEA;
                                (SEQ ID NO: 31)
KKKSGKWRLLIDFRVLNKL;
                                (SEQ ID NO: 30)
KKKSGKWRLIDFRVLNKL;
                                (SEQ ID NO: 35)
GRRYVWCSLPQGWVLSPLIY;
                                (SEQ ID NO: 16)
LLL1LCLPTLVDCIRN.
```

Figure 13A:
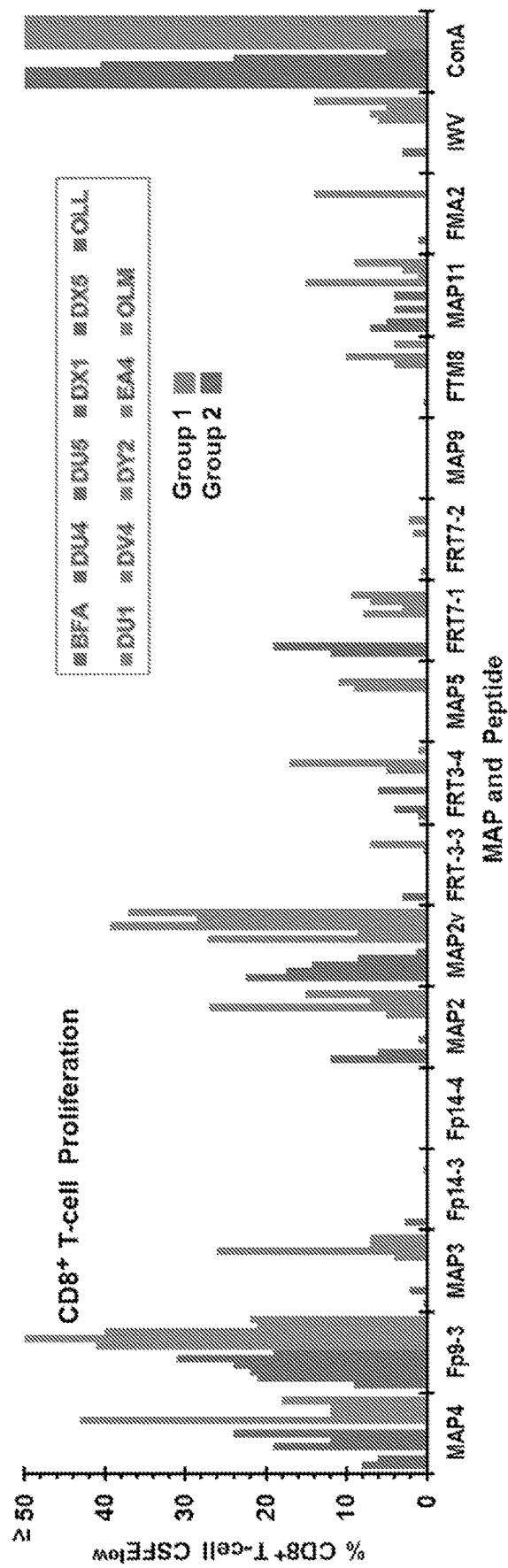
Figure 13B:
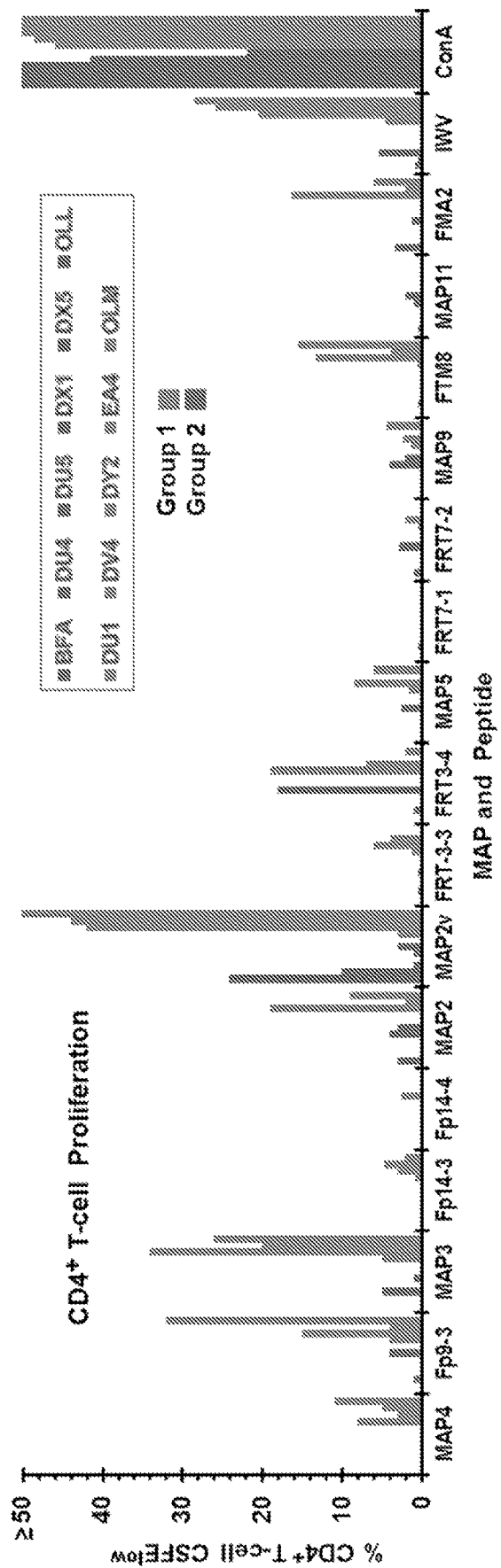

FIGS. 13A-13B. Pre-challenge T-cell proliferation responses. Each vaccinated cats at post-last vaccination before challenge were analyzed for CD3+CD8+ T-cell proliferation (FIG. 13A) and CD3+CD4+ T-cell proliferation (FIG. 13B) upon stimulation in vitro with MAPs, their individual peptides, inactivated whole FIV virus antigen (IWV), and concanavalin A (ConA). The number of vaccination, the MAP code, and its individual peptide(s) are 1×-3×MAP4 (Fp9-3); 3×MAP3 (Fp14-3 & Fp14-4); 2×MAP2 and 2×MAP2v (FRT3-3 & FRT3-4); 2×MAP5 (FRT7-1 & FRT7-2); 2×MAP9 (FTM8); and 2×MAP11 (FMA2). MAP2 has an extra leucine (L), whereas MAP2v is the exact sequence of the virus. The proliferation responses are described as carboxyfluorescein diacetate succinimide ester (CFSE)-proliferation determined by FACS. Red bars represent responses from Group 1 (n=5) and blue bars represent responses from Group 2 (n=6). Each vaccinated cat with the corresponding color is shown in the inset in panel A. The responses to each stimulant from the control Group 3 were averaged. The average proliferation value of the control group was subtracted from the proliferation response of each vaccinated cat from Groups 1 and 2.

Figure 14A:
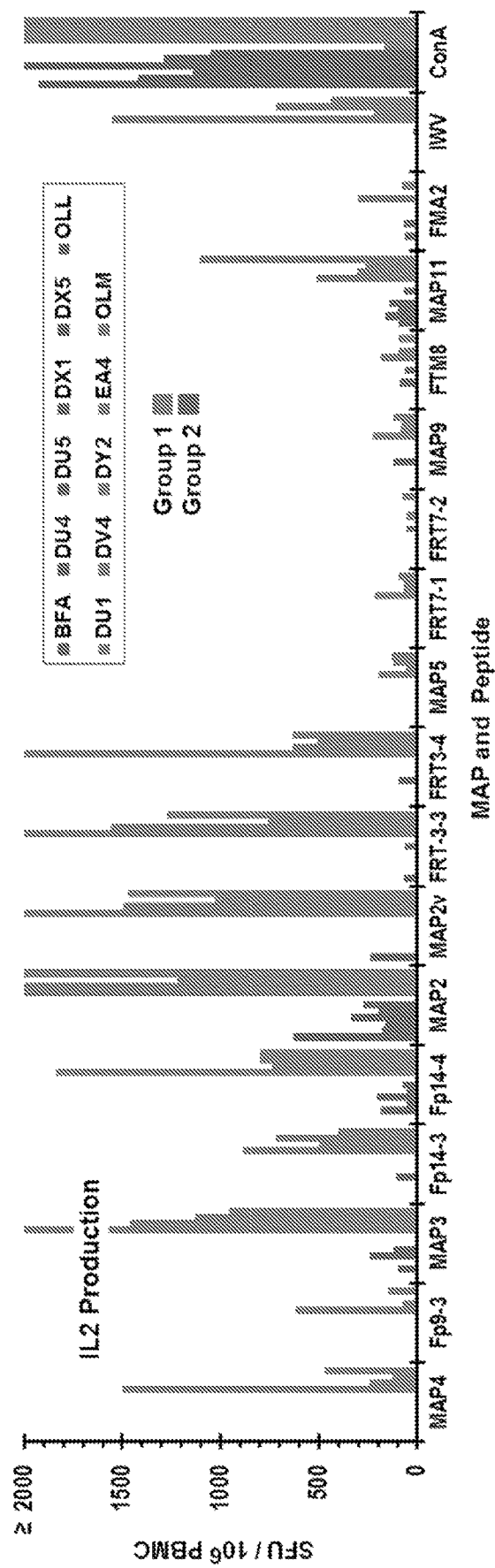
Figure 14B:
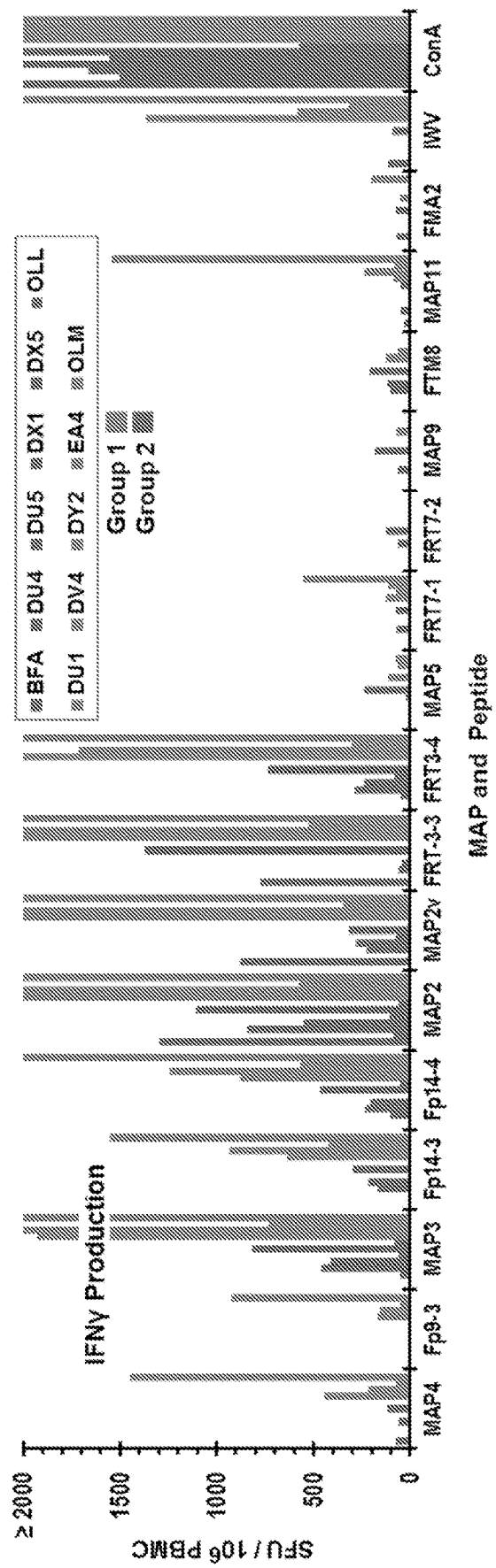

FIGS. 14A-14B. Pre-challenge cytokine production. Each vaccinated cats at post-last vaccination before challenge were analyzed for IL2 ELISpot (FIG. 14A) and IFNγ ELISpot (FIG. 14B) responses upon in vitro stimulation with MAPs and their individual peptides as described in FIG. 4 legend. Bars are color coded for Group 1 (red) and Group 2 (blue). The bar results for cats in Groups 1 and 2 are after the subtraction of 50 spot forming unit (SFU)/10⁶ PBMC. The average value to each stimulant from Group 3 were <50 SFU.

BRIEF DESCRIPTION OF THE SEQUENCES

SEQ ID NOs:1-35 and 39-101 are epitopes contemplated within the scope of the invention.

```
SEQ ID NO: 36 is FRT3-3 peptide (KKKSGKWRLIDFRV).

SEQ ID NO: 37 is FRT3-4 peptide (WRLIDFRVLNKL).
```

SEQ ID NO:38 is an example of a linker sequence that can be used to link peptides of the present invention (RVKR).

DETAILED DESCRIPTION OF THE INVENTION

The subject invention concerns methods and materials for providing an immune response in an animal or person against an immunodeficiency virus, such as HIV, SIV, or FIV. In one embodiment, a method of the invention comprises administering one or more antigens and/or immunogens to the person or animal wherein the antigen or immunogen comprises one or more epitopes evolutionarily conserved between different immunodeficiency viruses. In one embodiment, the epitope is one that is conserved between HIV and FIV, or between HIV and SIV. In another embodiment, the epitope is one that is conserved between HIV, SIV, and FIV. In one embodiment, where a human is administered the antigen and/or immunogen, the antigen or immunogen is from an FIV or HIV, and the epitope is evolutionarily conserved between HIV and FIV. In one embodiment, where the animal is a feline animal, the antigen and/or immunogen is from an HIV or FIV, and the epitope is evolutionarily conserved between HIV and FIV. In one embodiment of a method of the present invention, the epitope is a T-cell epitope; i.e., an epitope that is recognized by a T cell and that can stimulate the T cell to exert its effector activity. In a specific embodiment, the epitope induces one or more T cell responses, such as production and/or release of cytotoxins (e.g., granzymes, and/or granulysin), cytolysins (e.g., perforin), and/or cytokines (IFNγ, TNF-α, IL-2, IL-4, IL-5, IL-9, IL-10, IL-13, etc.). In a specific embodiment, the T-cell epitope is a cytotoxic T lymphocyte (CTL), polyfunctional T cell epitope, and/or T-helper (Th) epitope. Antigens and immunogens of the invention include peptides and/or proteins that comprise one or more evolutionarily conserved epitopes of the invention.

Epitopes contemplated within the scope of the invention include peptides or proteins comprising the amino acid sequence shown in any of SEQ ID NOs:1 to 37 or SEQ ID NOs:39 to 101, independently or any possible combination thereof (including overlapping sequences), or an amino acid sequence shown in any of the examples, figures or tables of the subject application, or an immunogenic fragment or variant of the amino acid sequence. In a specific embodiment, a peptide or protein of the invention comprises the amino acid sequence shown in any of SEQ ID NOs: 1, 3, 4, 5, 6, 8, 10, 12, 14, 15, 16, 17, 19-23, 26, 29-37, 52, 53, and 66, or an immunogenic fragment or variant thereof. In one embodiment, a plurality of peptides and/or proteins comprising an epitope of the invention are administered to the person or animal. For example, in one embodiment, two or more peptides or proteins comprising the amino acid sequence of any of SEQ ID NOs:1 to 37 or SEQ ID NOs:39 to 101, or an immunogenic fragment or variant thereof, are administered. For example, a first peptide comprising SEQ ID NO:1 and a second peptide comprising SEQ ID NO:2 can be administered. In another embodiment, a peptide or protein comprising two or more epitopes of the present invention is administered to the person or animal. For example, a peptide or protein comprising the amino acid sequence of both SEQ ID NO:1 and SEQ ID NO:2 can be administered. In one embodiment, the peptide or protein can comprise two or more epitopes by linking two or more peptide sequences of the invention together, or by having a polynucleotide encode two or more peptide sequences together in a single protein, and expressing the polynucleotide to produce the protein. In one embodiment, a peptide or protein comprising two or more amino acid sequences shown in any of SEQ ID NOs: 1 to 37 or SEQ ID NOs:39 to 101, or an immunogenic fragment or variant thereof, is administered to the person or animal.

In one embodiment, the immune response induced by a method of the present invention is a T cell response, such as a CTL-associated immune response and/or a T helper cell response. In a specific embodiment, the immune response induced by a method of the present invention comprises CD4+ and/or CD8+ T cell responses, and/or gamma interferon (IFNγ) production. In one embodiment, cytotoxins (such as granzyme A, granzyme B, etc.), cytolysins (e.g., perforin), and/or cytokines (IFNγ, IL-4, IL-5, IL-9, IL-10, IL-13, etc.) are produced. In one embodiment, the immune response is a protective immune response that provides protection to the person or animal from infection by an immunodeficiency virus. In a specific embodiment, the immune response provides the person or animal with protection from infection by HIV or FIV. In one embodiment, the person or animal receiving the antigen or immunogen is already infected with an immunodeficiency virus. In another embodiment, the person or animal is not infected with an immunodeficiency virus prior to administration of the antigen or immunogen.

The subject invention also concerns evolutionarily conserved epitopes of immunodeficiency viruses. In one embodiment, the epitope is one that is conserved between HIV and SIV, or between HIV and FIV. In another embodiment, the epitope is one that is conserved between HIV, SIV, and FIV. In one embodiment, the epitope is a T-cell epitope. In a specific embodiment, the T-cell epitope is a cytotoxic T lymphocyte (CTL) epitope, polyfunctional T cell (CD3+CD4+ and CD3+CD8+ T cells that express multiple cytokines, cytotoxins, chemokines, and functional activities such as proliferation) epitope, and/or T-helper (Th) epitope. In one embodiment, the epitopes are from a matrix (MA) protein. In another embodiment, the epitopes are from a viral integrase protein. In another embodiment, the epitopes are from a viral nucleocapsid (NC) protein. In a further embodiment, the epitopes are from a viral protease (PR) protein. In yet a further embodiment, the epitopes are from a transmembrane (TM) or surface (SV) envelope protein. In another embodiment, the epitopes are from a p24 or reverse transcriptase (RT) protein. Antigens and immunogens of the invention can be peptides and/or proteins that comprise one or more evolutionarily conserved epitopes of the invention. Examples of epitopes contemplated within the scope of the invention include peptides or proteins comprising the amino acid sequence shown in any of SEQ ID NOs:1 to 37 or SEQ ID NOs:39 to 101, independently or any possible combination thereof, or an amino acid sequence shown in any of the examples, figures or tables of the subject application, or an immunogenic fragment or variant of the amino acid sequence. In a specific embodiment, an epitope of the invention comprises a peptide or protein comprising the amino acid sequence shown in any of SEQ ID NOs:1, 3, 4, 5, 6, 8, 10, 12, 14, 15, 16, 17, 19-23, 26, 29-37, 52, 53, and 66. In another embodiment, an epitope of the invention comprises a peptide or protein comprising two or more amino acid sequences of any of SEQ ID NOs:1 to 37 or SEQ ID NOs:39 to 101, or an immunogenic fragment or variant thereof. In a specific embodiment, an epitope of the invention comprises a peptide or protein comprising the amino acid sequence of SEQ ID NO:1, 3, 4, 5, 6, 8, 10, 12, 14, 15, 16, 17, 19-23, 26, 29-37, 52, 53, and 66. The subject invention also concerns polynucleotides encoding the amino acid sequence of epitopes of the invention.

The subject invention also concerns vaccines and immunogenic compositions comprising one or more antigens and/or immunogens that comprise or encode evolutionarily conserved epitopes of the present invention. The vaccine or immunogenic compositions of the subject invention also encompass recombinant viral vector-based or polynucleotide constructs that may comprise a nucleic acid encoding a peptide or protein comprising an evolutionarily conserved epitope of the present invention or encoding a chimeric polypeptide of the present invention. Examples of epitopes contemplated within the scope of the invention include peptides or proteins comprising the amino acid sequence shown in any of SEQ ID NOs:1 to 37 or SEQ ID NO:39 to 101, independently or any possible combination thereof, or an amino acid sequence shown in any of the examples, figures or tables of the subject application, or an immunogenic fragment or variant of the amino acid sequence. In a specific embodiment, a peptide or protein of the invention comprises the amino acid sequence shown in any of SEQ ID NOs:1, 3, 4, 5, 6, 8, 10, 12, 14, 15, 16, 17, 19-23, 26, 29-37, 52, 53, or 66. In another embodiment, a peptide or protein of the invention can comprise two or more amino acid sequences of any of SEQ ID NOs:1 to 37 or SEQ ID NOs:39 to 101, or an immunogenic fragment or variant thereof. Any suitable viral vector that can be used to prepare a recombinant vector/virus construct is contemplated for use with the subject invention. For example, viral vectors derived from adenovirus, avipox, herpesvirus, vaccinia, canarypox, entomopox, swinepox, West Nile virus and others known in the art can be used with the compositions and methods of the present invention. Recombinant polynucleotide vectors that encode and express components can be constructed using standard genetic engineering techniques known in the art. In addition, the various vaccine compositions described herein can be used separately and in combination with each other. For example, primary immunizations of an animal may use recombinant vector-based constructs, having single or multiple strain components, followed by secondary boosts with vaccine compositions comprising inactivated virus or inactivated virus-infected cell lines. Other immunization protocols with the vaccine compositions of the invention are apparent to persons skilled in the art and are contemplated within the scope of the present invention.

The subject invention also concerns compositions comprising epitopes and/or chimeric polypeptides of the invention, or polynucleotides encoding them. In one embodiment, a composition of the invention comprises a pharmaceutically or biologically acceptable carrier, diluent, and/or adjuvant.

The subject invention also concerns expression constructs comprising one or more polynucleotides of the invention. Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the immunogens of the invention. Chemical enhancers are cis-acting elements that increase gene transcription and can also be included in the expression construct. Chemical enhancer elements are known in the art, and include, but are not limited to, the cytomegalovirus (CMV) early promoter enhancer element and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides, vectors, and expression constructs of the invention can be introduced in vivo via lipofection (DNA transfection via liposomes prepared from synthetic cationic lipids) (Felgner et al., 1987). Synthetic cationic lipids (LIPOFECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced as naked DNA using methods known in the art, such as transfection, microinjection, electroporation, calcium phosphate precipitation, and by biolistic methods.

The subject invention also concerns methods for enhancing infection and/or activating latent infection of an immunodeficiency virus, such as FIV, SIV, or HIV, in a person or animal, or in cells obtained from a person or animal. In one embodiment, the person or animal has a latent infection of HIV or FIV. In another embodiment, the method comprises infecting or exposing the animal to the virus. In one embodiment, one or more peptides, or a composition or a MAP construct comprising the one or more peptides, of the invention that enhances viral infection is administered to the person or animal. In a specific embodiment, a peptide comprising the amino acid sequence of SEQ ID NO:28, 30, or 36 is administered to a feline animal that is infected with, or will subsequently be infected with FIV.

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the exemplified sequences. The polynucleotide includes both the sense and antisense strands as either individual strands or in the duplex.

The methods of the present invention contemplate a primary immunization with an antigen, immunogen, peptide, polypeptide, polynucleotide, vaccine, and/or composition of the invention. Subsequent or secondary immunizations are also contemplated within the scope of the subject methods. The antigen, immunogen, peptide, polypeptide, polynucleotide, vaccine, and/or composition used for secondary immunizations can be the same as or vary from that used for primary immunization. For example, primary immunizations of an animal may use recombinant vector-based HIV, FIV, or SIV constructs, having single or multiple strain components, followed by secondary boosts with compositions comprising HIV-, FIV-, or SIV-infected cell lines, or HIV, FIV, or SIV polypeptides, or cell free HIV or SIV virus, also having single or multiple strain components. Primary immunizations can also use an HIV, FIV, and/or SIV DNA vaccine. In one embodiment, a recombinant vector construct is used for the primary immunization, whereas a protein, or protein plus recombinant vector construct, subunit vaccine composition is used for secondary boosts. Other immunization protocols with the vaccine compositions of the invention are apparent to persons skilled in the art and are contemplated within the scope of the present invention.

The subject invention also concerns antibodies, or an antigen binding fragment thereof, that bind to epitopes of the invention. In one embodiment, an antibody of the invention is a monoclonal antibody. In one embodiment, an antibody of the invention binds specifically to an HIV protein, e.g., an HIV MA protein. In another embodiment, an antibody of the invention binds specifically to an FIV protein, e.g., an FIV MA protein. In a further embodiment, an antibody of the invention binds specifically to both an HIV and an FIV protein, i.e., the antibody cross-reacts with an epitope that is present on both an HIV and an FIV protein, such as a MA protein. The subject invention also concerns the epitopes recognized by an antibody of the invention.

The antibodies can be polyclonal or monoclonal in form. The antibodies can be derived from any animal capable of producing antibodies to the epitopes, and include, for example, human, ape, monkey, mouse, rat, goat, sheep, pig, cow, and feline animals. Also contemplated within the scope of the invention are non-human antibodies that have been "humanized" using standard procedures known in the art, such as those described in U.S. Pat. Nos. 5,530,101; 5,585,089; 5,693,762; 6,180,370; and 6,407,213.

An antibody that is contemplated for use in the present invention can be in any of a variety of forms, including a whole immunoglobulin, an antibody fragment such as Fv, Fab, and similar fragments, as well as a single chain antibody that includes the variable domain complementarity determining regions (CDR), and similar forms, all of which fall under the broad term "antibody," as used herein.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment of an antibody yields an F(ab')$_2$ fragment that has two antigen binding fragments, which are capable of cross-linking antigen, and a residual other fragment (which is termed pFc').

Additional fragments can include diabodies, linear antibodies, single-chain antibody molecules, and multispecific antibodies formed from antibody fragments. As used herein, "antigen binding fragment" with respect to antibodies, refers to, for example, Fv, F(ab) and F(ab')$_2$ fragments.

Antibody fragments can retain an ability to selectively bind with the antigen or analyte are contemplated within the scope of the invention and include:

(1) Fab is the fragment of an antibody that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain ($V_L$), the variable region of the heavy chain ($V_H$), linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. For a review of sFv fragments, see Pluckthun in The Pharmacology of Monoclonal Antibodies, vol. 113, Rosenburg and Moore eds. Springer-Verlag, N.Y., pp. 269 315 (1994).

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Antibodies to be used in the subject invention can be genus or species specific to a target cell. Antibodies of the invention can be prepared using standard techniques known in the art. Antibodies useful in the invention can be polyclonal or monoclonal antibodies. Monoclonal antibodies can be prepared using standard methods known in the art (Kohler et al., 1975).

The subject invention also concerns hybridomas that produce monoclonal antibodies of the present invention.

Peptide and/or polypeptide antigens and immunogens of the present invention can also be provided in the form of a multiple antigenic peptide (MAP) construct, with or without lypophylic attachment to each peptide string. The preparation of MAP constructs has been described in Tam (1988) and Kowalczyk et al. (2010). MAP constructs utilize a core matrix of lysine residues onto which multiple copies of an immunogen (e.g., a peptide) are synthesized (Posnett et al., 1988). In one embodiment, MAP constructs of the invention can comprise one or more fatty acids attached to the core matrix. The fatty acid can comprise from about 4 to about 48 or more carbon atoms, and can be saturated and/or unsaturated. In a specific embodiment, the fatty acid is palmitic acid (hexadecanoic acid). Multiple MAP constructs, each containing the same or different immunogens, can be prepared and administered in a vaccine composition in accordance with methods of the present invention. In one embodiment, the same or different peptides are linked end to end. The same or different peptides can be linked directly to each other (i.e., without a linker sequence) or they can be linked via a linker moiety such as a short amino acid sequence (e.g., a furin-sensitive linker), examples of which include, but are not limited to, peptides comprising SEQ ID NO:38. In one embodiment, a MAP construct is provided with and/or administered with one or more adjuvants. In one embodiment, a MAP of the invention comprises one or more peptides that comprise the amino acid sequences of one or more of SEQ ID NOs:1 to 37 or SEQ ID NOs:39 to 101, or an immunogenic fragment or variant thereof.

Natural, recombinant or synthetic peptides and polypeptides of immunodeficiency viral proteins, and peptide fragments thereof, can also be used as vaccine compositions according to the subject methods. Procedures for preparing peptides and polypeptides are well known in the art. For example, peptides and polypeptides can be synthesized using solid-phase synthesis methods (Merrifield, 1963). Peptides and polypeptides can also be produced using recombinant DNA techniques wherein a polynucleotide molecule encoding a protein or peptide is expressed in a host cell, such as bacteria, yeast, or mammalian cell lines, and the expressed protein or peptide purified using standard techniques of the art.

According to the methods of the subject invention, the antigenic, immunogenic, and vaccine compositions described herein can be administered to susceptible hosts in an effective amount and manner to induce an immune response and/or protective immunity against subsequent challenge or infection of the host by FIV, SIV, or HIV. The immunogens are typically administered parenterally, by injection, for example, either subcutaneously, intradermally, intraperitoneally, or intramuscularly, or by oral or nasal administration, or any combination of such routes of administration. Usually, the immunogens are administered to a host animal at least two times, with an interval of one or more weeks between each administration. However, other regimens for the initial and booster administrations of the immunogens are contemplated, and may depend on the judgment of the practitioner and the particular host animal being treated.

Antigens, immunogens, and vaccines that can be used in accordance with the present invention can be provided with a pharmaceutically-acceptable carrier or diluent. Compounds and compositions useful in the subject invention can be formulated according to known methods for preparing pharmaceutically useful compositions. Formulations are described in detail in a number of sources which are well known and readily available to those skilled in the art. For example, *Remington's Pharmaceutical Science* by E.W. Martin, Easton Pa., Mack Publishing Company, 19$^{th}$ ed., 1995, describes formulations which can be used in connection with the subject invention. In general, the compositions of the subject invention will be formulated such that an effective amount of an antigen, immunogen, or vaccine is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptidomimetics include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of an immunogen of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the antigen, antigens, immunogen or immunogens based on the weight of the total composition including carrier or diluent.

The antigenic, immunogenic, and vaccine compositions of the subject invention can be prepared by procedures well known in the art. For example, the antigens, immunogens, or vaccines are typically prepared as injectables, e.g., liquid solutions or suspensions. The antigens, immunogens, or vaccines are administered in a manner that is compatible with dosage formulation, and in such amount as will be therapeutically effective and immunogenic in the recipient. The optimal dosages and administration patterns for a particular antigen, immunogen, or vaccine formulation can be readily determined by a person skilled in the art.

Virus and cells in an antigenic, immunogenic, or vaccine formulation may be inactivated or attenuated using methods known in the art. The amount of cell-free whole or partial virus in a dose will usually be in the range from about 0.1 mg to about 5 mg, and more usually being from about 0.2 mg to about 2 mg. The dosage for formulations comprising virus-infected cell lines will usually contain from about $10^6$ to about $10^8$ cells per dose, and more usually from about $5 \times 10^6$ to about $7.5 \times 10^7$ cells per dose. The amount of protein or peptide immunogen in a dose for a feline animal can vary from about 0.1 μg to 10000 μg, or about 1 μg to 5000 g, or about 10 μg to 1000 μg, or about 25 μg to 750 μg, or about 50 μg to 500 μg, or 100 μg to 250 μg, depending upon the size, age, etc., of the animal receiving the dose.

In one embodiment, an antigen, immunogen, or vaccine of the invention is provided with one or more adjuvants that increase the person or animal's immune response against the antigen or immunogen. Antigen, immunogens, and vaccines of the invention can be provided with and/or administered with any suitable adjuvant or adjuvants known in the art. In one embodiment, the adjuvant is one that helps induce a strong cellular immune response. Adjuvants that can be used in the antigen and immunogen formulations of the invention include threonyl muramyl dipeptide (MDP) (Byars et al., 1987), Ribi adjuvant system components (Corixa Corp., Seattle, Wash.) including the cell wall skeleton (CWS) component, Freund's complete, and Freund's incomplete adjuvants, bacterial lipopolysaccharide (LPS), such as from *E. coli*, or a combination thereof. A variety of other adjuvants suitable for use with the methods and vaccines of the subject invention, such as alum, aluminum hydroxide, and saponin are well known in the art and are contemplated for use with the subject invention. Cytokines (γ-IFN, GM-CSF, CSF, etc.) and lymphokines and interleukins (IL-1, IL-2, IL-3, IL-4, IL-5, IL-6, IL-7, IL-8. IL-9, IL-10, IL-11, IL-12, IL-13, IL-14, IL-15, IL-16, IL-17, 11-18, 11-19, IL-20, IL-21, and 11-22) have also been used as adjuvants and/or supplements to vaccine compositions and are contemplated within the scope of the present invention. One or more different cytokines and lymphokines can be included in a composition comprising an antigen, immunogen, or vaccine of the invention. In one embodiment, an antigen, immunogen, or vaccine of the invention is administered to an animal in combination with the lymphokine interleukin-12 (IL-12) optionally in combination with another adjuvant. Also contemplated within the scope of the invention is the use of the lymphokine interleukin-18 (11-18) as part of an adjuvant composition. In one embodiment, an adjuvant composition used with the subject invention comprises a combination of 11-12 and IL-15, or IL-15 and 11-18, or IL-12 and IL-18, or 11-12, 11-15, and 11-18. The cytokine selected is of a species that has biological activity in the animal receiving the antigen or immunogen. For example, if the animal is a cat, then the cytokine can be a human cytokine or a feline cytokine, e.g., feline IL-12, feline IL-15, feline IL-18, etc.

Abbreviations of FIV strains used herein are shown below in Table 1:

| Strain (subtype) | Abbreviation | Strain (subtype) | Abbreviation |
|---|---|---|---|
| Petaluma (A) | $FIV_{Pet}$ | PPR (A) | $FIV_{PPR}$ |
| Dixon (A) | $FIV_{Dix}$ | FranceWo | $FIV_{Fra}$ |
| UK8 (A) | $FIV_{UK8}$ | Netherlands | $FIV_{Net}$ |
| Bangston (B) | $FIV_{Bang}$ | USILbrny03B (B) | $FIV_{USI03}$ |
| Aomori-1 (B) | $FIV_{Aom1}$ | TM2 (B) | $FIV_{TM2}$ |
| Aomori-2 (B) | $FIV_{Aom2}$ | USCKlgri02B (B) | $FIV_{USC02}$ |
| FC1 (B) | $FIV_{FC1}$ | Yokohama (B) | $FIV_{Yok}$ |
| Shizuoka (D) | $FIV_{Shi}$ | USMAsboy03B (B) | $FIV_{USMA03}$ |
| Dutch113 (A) | $FIV_{Dut113}$ | USTXmtex03B (B) | $FIV_{UST03}$ |
| Dutch19K (A) | $FIV_{Dut19}$ | USMCglwd03B (B) | $FIV_{USMC03}$ |
| UK2 (A) | $FIV_{UK2}$ | CABCpbar03C (C) | $FIV_{CAB03}$ |
| SwissZ2 (A) | $FIV_{SwiZ2}$ | CABCpbar07C (C) | $FIV_{CAB07}$ |
| Sendai-1 (A) | $FIV_{Sen1}$ | CABCpady02C (C) | $FIV_{CAB02}$ |
| Sendai-2 (B) | $FIV_{Sen2}$ | Fukuoka (D) | $FIV_{Fuku}$ |
| USCAzepy01A (A) | FIV | | |
| USCAhnky11A (A) | $FIV_{USC11}$ | | |
| USCAtt-10A (A) | $FIV_{USC10}$ | | |
| USCAlemy01 (A) | FIV | | |
| USCAsam-01A (A) | FIV | | |

Antigens, immunogens, and vaccines of the invention are typically administered parenterally, by injection, for example, either subcutaneously, intradermally, intraperitoneally, or intramuscularly. Other suitable modes of administration include oral or nasal administration. Usually, the antigens, immunogens, and vaccines are administered to a human or animal at least two times, with an interval of one or more weeks between each administration. However, other regimens for the initial and booster administrations of the antigens, immunogens, and vaccines are contemplated, and may depend on the judgment of the practitioner and the patient being treated.

Antigenic, immunogenic, and vaccine compositions of the subject invention can be prepared by procedures well known in the art. For example, the antigens, immunogens, and vaccines are typically prepared as injectables, e.g., liquid solutions or suspensions. The antigens, immunogens, and vaccines are administered in a manner that is compatible with dosage formulation, and in such amount as will be therapeutically effective and immunogenic in the recipient. The optimal dosages and administration patterns for a particular antigen, immunogen, and vaccine formulation can be readily determined by a person skilled in the art.

Antigens, immunogens, and vaccines that can be used in accordance with the present invention can be provided with a pharmaceutically-acceptable carrier or diluent. In one embodiment, an antigen, immunogen, or vaccine of the invention is provided with one or more adjuvants that increase the human or animal's immune response against the antigen or immunogen. Antigens, immunogens, and vaccines of the invention can be provided with and/or administered with any suitable adjuvant or adjuvants known in the art.

The peptides contemplated in the subject invention include the specific peptides exemplified herein as well as equivalent peptides which may be, for example, somewhat longer or shorter than the peptides exemplified herein. For example, using the teachings provided herein, a person skilled in the art could readily make peptides having from 1 to about 15 or more amino acids added to, or 1 to 10 amino acids removed from, either or both ends of the disclosed peptides using standard techniques known in the art. Any added amino acids can be different or the same as the corresponding amino acids of the full-length protein from which the peptide is derived. The skilled artisan, having the benefit of the teachings disclosed in the subject application, could easily determine whether a longer or shorter peptide retained the immunogenic activity of the specific peptides exemplified herein.

Substitution of amino acids other than those specifically exemplified or naturally present in a peptide of the invention are also contemplated within the scope of the present invention. For example, non-natural amino acids can be substituted for the amino acids of a peptide, so long as the peptide having the substituted amino acids retains substantially the same immunogenic activity as the peptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a peptide of the present invention having an amino acid of one class is replaced with another amino acid of the same class fall within the scope of the subject invention so long as the peptide having the substitution still retains substantially the same antigenic or immunogenic activity as the peptide that does not have the substitution. Table 2 below provides a listing of examples of amino acids belonging to each class.

TABLE 2

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |

TABLE 2-continued

| Class of Amino Acid | Examples of Amino Acids |
| --- | --- |
| Acidic | Asp, Glu |
| Basic | Lys, Arg, His |

Polynucleotides encoding a specifically exemplified peptide or polypeptide of the invention, or a shorter or longer peptide or polypeptide, or a peptide having one or more amino acid substitutions in the sequence are contemplated within the scope of the present invention. The subject invention also concerns variants of the polynucleotides of the present invention that encode a peptide of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of a peptide or a polypeptide of the present invention can be generated as described herein and tested for the presence of immunogenic activity using standard techniques known in the art.

Polynucleotides, peptides, and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See Worldwide Website: ncbi.nlm.nih.gov.

Factors affecting the preferred dosage regimen may include, for example, the age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art using conventional means. It should further be noted that live attenuated viruses are generally self-propagating; thus, the specific amount of such a virus administered is not necessarily critical.

It is contemplated that an antigen, immunogen, or vaccine of the invention may be administered to the patient a single time; or, alternatively, two or more times over days, weeks, months, or years. In some embodiments, the vaccine is administered at least two times. In some such embodiments, for example, the vaccine is administered twice, with the second dose (e.g., the booster) being administered at least about 2 weeks after the first. In some embodiments, the vaccine is administered twice, with the second dose being administered no greater than 8 weeks after the first. In some embodiments, the second dose is administered at from about 2 weeks to about 4 years after the first dose, from about 2 to about 8 weeks after the first dose, or from about 3 to about 4 weeks after the first dose. In some embodiments, the second dose is administered about 4 weeks after the first dose. In the above embodiments, the first and subsequent dosages may vary, such as, for example, in amount and/or form. Often, however, the dosages are the same as to amount and form. When only a single dose is administered, the amount of antigen, immunogen, or vaccine in that dose alone generally comprises a therapeutically effective amount of the antigen, immunogen, or vaccine. When, however, more than one dose is administered, the amounts of antigen, immunogen, or vaccine in those doses together may constitute a therapeutically effective amount.

In some embodiments, the antigen, immunogen, or vaccine is administered before the recipient is infected with virus. In such embodiments, the antigen, immunogen, or vaccine may, for example, be administered to prevent, reduce the risk of, or delay the onset of one or more (typically two or more) clinical symptoms.

In some embodiments, the antigen, immunogen, or vaccine is administered after the recipient is infected with virus. In such embodiments, the antigen, immunogen, or vaccine may, for example, ameliorate, suppress, or eradicate the virus or one or more (typically two or more) clinical symptoms.

It is contemplated that the antigen, immunogen, or vaccine may be administered via the patient's drinking water and/or food. It is further contemplated that the antigen, immunogen, or vaccine may be administered in the form of a treat or toy.

"Parenteral administration" includes subcutaneous injections, submucosal injections, intravenous injections, intramuscular injections, intrasternal injections, transcutaneous injections, and infusion. Injectable preparations (e.g., sterile injectable aqueous or oleaginous suspensions) can be formulated according to the known art using suitable excipients, such as vehicles, solvents, dispersing, wetting agents, emulsifying agents, and/or suspending agents. These typically include, for example, water, saline, dextrose, glycerol, ethanol, corn oil, cottonseed oil, peanut oil, sesame oil, benzyl alcohol, benzyl alcohol, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), propylene glycol, and/or polyethylene glycols. Excipients also may include small amounts of other auxiliary substances, such as pH buffering agents.

The antigen, immunogen, or vaccine may include one or more excipients that enhance a patient's immune response (which may include an antibody response, cellular response, or both), thereby increasing the effectiveness of the vaccine. Use of such excipients (or "adjuvants") may be particularly beneficial when using an inactivated vaccine. The adjuvant(s) may be a substance that has a direct (e.g., cytokine or Bacille Calmette-Guerin ("BCG")) or indirect effect (liposomes) on cells of the patient's immune system. Examples of often suitable adjuvants include oils (e.g., mineral oils), metallic salts (e.g., aluminum hydroxide or aluminum phosphate), bacterial components (e.g., bacterial liposaccharides, Freund's adjuvants, and/or MDP), plant components (e.g., Quil A), and/or one or more substances that have a carrier effect (e.g., bentonite, latex particles, liposomes, and/or Quil A, ISCOM). It should be recognized that this invention encompasses antigens, immunogens, and vaccines that comprise an adjuvant(s), as well as antigens, immunogens, and vaccines that do not comprise any adjuvant.

It is contemplated that the antigen, immunogen, or vaccine may be freeze-dried (or otherwise reduced in liquid volume) for storage, and then reconstituted in a liquid before or at the time of administration. Such reconstitution may be achieved using, for example, vaccine-grade water.

The present invention further comprises kits that are suitable for use in performing the methods described above. The kit comprises a dosage form comprising an antigen, immunogen, or vaccine described above. The kit also comprises at least one additional component, and, typically, instructions for using the antigen, immunogen, or vaccine with the additional component(s). The additional component(s) may, for example, be one or more additional ingredients (such as, for example, one or more of the excipients discussed above, food, and/or a treat) that can be mixed with the antigen, immunogen, or vaccine before or during administration. The additional component(s) may alternatively (or additionally) comprise one or more apparatuses for administering the antigen, immunogen, or vaccine to the patient. Such an apparatus may be, for example, a syringe, inhaler, nebulizer, pipette, forceps, or any medically acceptable delivery vehicle. In some embodiments, the apparatus is suitable for subcutaneous administration of the antigen, immunogen, or vaccine. In some embodiments, the apparatus is suitable for intranasal administration of the antigen, immunogen, or vaccine.

Other excipients and modes of administration known in the pharmaceutical or biologics arts also may be used.

The subject invention also concerns methods for determining whether an animal, such as a feline animal, has been vaccinated against FIV with an FIV vaccine of the present invention, or is infected by FIV or has been infected by FIV. In one embodiment, a biological sample, such as a blood or serum sample, is obtained from a feline animal, and the sample is assayed to determine whether the animal has antibodies that bind specifically to HIV antigens. Epitopes of an HIV protein that are only recognized by HIV antibodies and that are not recognized by FIV antibodies can be used in the subject invention.

TABLE 3

Matrix (MA) epitope peptides

| | | | |
|---|---|---|---|
| HMA1 | KIRLRPGGK-KKY | | SEQ ID NO: 1 |
| FMA1 | NVAVGVGGKSKKF | (MAP12) | SEQ ID NO: 2 |
| HMA2 | GSEELRSLYNTVATL | | SEQ ID NO: 3 |
| FMA2 | GSSKEIDMAIVTLKV | (MAP 11) | SEQ ID NO: 4 |

TABLE 3-continued

| | Nucleocapsid (NC) epitope peptides | | |
|---|---|---|---|
| HNC2 | TAPPEESFRSGVETTT | | SEQ ID NO: 5 |
| FNC2 | AAAPVNQMQQAVMPSA | (MAP 15) | SEQ ID NO: 6 |
| | Integrase (IN) epitope peptides | | |
| HIN7-1 | GERIVDIIATDIQTK | | SEQ ID NO: 7 |
| FIN7-1 | YELYMQQESLRIQDR | (MAP7) | SEQ ID NO: 8 |
| | Protease (PR) epitope peptides | | |
| HPR1 | TLWQRPLVTIKIGG | | SEQ ID NO: 9 |
| FPR1 | TLEKRPEILIFVNG | (MAP13) | SEQ ID NO: 10 |
| HPR2 | EALLDTGADDTVLE | | SEQ ID NO: 11 |
| FPR2 | KFLLDTGADITILN | (MAP14) | SEQ ID NO: 12 |
| | Transmembrane (TM) envelope epitope peptides | | |
| HTM4-3 | YLKDQQLLGIWGC | | SEQ ID NO: 13 |
| FTM4-3 | KFLYTAFAMQELR | (MAP 8) | SEQ ID NO: 14 |
| HTM8 | LRIVFAVLSIVNRVRQ | | SEQ ID NO: 15 |
| FTM8 | LLLILCLPTLVDCIRN | (MAP 9) | SEQ ID NO: 16 |
| | Surface (SU) envelope epitope peptides | | |
| HSU4 | DNWRSELYKYKVVKI | | SEQ ID NO: 17 |
| FSU4 | AGLRQSLEQYQVVKQ | (MAP10) | SEQ ID NO: 18 |

TABLE 4

| | p24 epitope peptides | | |
|---|---|---|---|
| Hp10-3 | IPVGEIYKR-WIILG | | SEQ ID NO: 19 |
| Fp9-3 | FAPARMQCRAWYLEA | (MAP4) | SEQ ID NO: 20 |
| Hp11-2/11-3 | R-WIILGLNKI--VRMY | | SEQ ID NO: 21 |
| Fp10-2/10-3 | RAWYLEALGKLAAIKAK | (MAP6) | SEQ ID NO: 22 |
| Hp15-1 | RAEQASQEVKNWMT | | SEQ ID NO: 23 |
| Fp14-1 | DQEQNTAEVKLYLK | (MAP1b) | SEQ ID NO: 24 |
| Hp15-2/Hp15-3 | QEVKNWMTETLLVQNA | | SEQ ID NO: 25 |
| Fp14-3/Fp14-4 | AEVKLYLKQSLSIANA | (MAP3) | SEQ ID NO: 26 |
| Hp4-3 | PQDLNTMLNTVGGHQ | | SEQ ID NO: 27 |
| Fp4-3 real | PTDMATLIMAAPGCA | FIV enhancing | SEQ ID NO: 28 |
| | Reverse transcriptase (RT) epitope peptides | | |
| HRT3-3/HRT3-4 | KKKDSTKWRKLVDFRELNKR | | SEQ ID NO: 29 |
| FRT3-3/FRT3-4 | KKKSGKWRLIDFRVLNKL | (MAP2v) FRT3-3 enhance/ FRT3-4 suppress | SEQ ID NO: 30 |
| FRT3-3L/FRT3-4 | KKK SGKWRLLIDFRVLNKL | (MAP2) | SEQ ID NO: 31 |
| HRT3-4/HRT3-5 | WRKLVDFRELNKRTQDFW | | SEQ ID NO: 32 |
| FRT3-4/FRT3-5 | WRMLIDFRVLNKLTDKGA | (MAP2B) | SEQ ID NO: 33 |
| HRT7-1/HRT7-2 | GIRYQYNVLPQGWKGSPAIF | | SEQ ID NO: 34 |
| FRT7-1/FRT7-2 | GRRYVWCSLPQGWVLSPLIY | (MAP5) | SEQ ID NO: 35 |

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Immunogenicity and Protective Efficacy of Multiple Antigenic Peptides Against Feline Immunodeficiency Virus Although recent developments in vaccine prophylaxis against HIV/AIDS have advanced our knowledge of protective immunity [1-3], the introduction of a safe and effective vaccine for worldwide distribution is not imminent. Research in vaccine development has been prolific, however only three candidates to date have reached large scale Phase III clinical trials (IAVI Clinical Trial Database; see Worldwide Website: iavireport.org/Trials-Database/Pages/default.aspx, accessed 29 Feb. 2015). The most successful Phase-III trial, RV144, reduced the risk of HIV infection by 31.2% overall with minimal protection of 3.7% in the high-risk group [4]. The vaccinated subjects who were negative for HIV had higher levels of IgG antibodies to HIV-1 envelope protein (Env) region at the V1V2 loop but not IgA antibodies to Env or HIV-1 neutralizing antibodies [5]. Polyfunctional $CD4^+$ T-cell and $CD4^+$ cytotoxic T lymphocyte (CTL)-like activities to the V2 region of the envelope were also detected in the vaccinees [6].

The continuously evolving viral antigens and the overwhelming antigenic variation in the HIV Env may require vaccine approach that would activate both humoral and cell-mediated immune (CMI) responses [4-10] as well as a novel method to selectively target antigenic regions of the virus. These regions must be conserved between viral subtypes, more resistant to mutations, and induce potent antiviral immunity. Functional studies have confirmed the presence of conserved lentiviral $CD8^+$ CTL and $CD4^+$ T helper (TH) cell epitopes within feline immunodeficiency virus (FIV) and HIV reverse transcriptase (RT) [11] and core protein p24 [12]. These epitopes are recognized by the peripheral blood mononuclear cells (PBMCs) and T cells from HIV-1 positive ($HIV^+$) human subjects (RT and p24) and FIV-vaccinated cats (p24). Rather than focusing only on HIV subtypes, these promising results support a strategic paradigm for the discovery of functionally crucial epitopes that are present within lentiviruses of different species which can induce potent and persistent antiviral immune responses.

The importance of inducing T-cell immunity in a lentiviral vaccine is demonstrated by the development of the commercially available dual-subtype FIV vaccine (Fel-O-Vax® FIV) that was released in 2002 [13]. Similar to HIV, FIV is a lentivirus that infects CD4+ T cells and causes immunodeficiency disease in its natural host [13,14]. As a result, FIV infection and disease progression in domestic cats, the natural host, is an important animal model for the development of a HIV vaccine [14]. Both commercial and prototype FIV vaccines confer protection against homologous and closely-related strains (tier-1 and some tier-2) by vaccine-induced FIV neutralizing antibodies (NAb) and anti-FIV T-cell immunity [13,15]. However, the prototype vaccine confers greater protection against heterologous tier-2 and tier-3 viruses correlating to greater anti-FIV T-cell immunity than the commercial vaccine [13,15]. The broad efficacy of the anti-FIV T-cell immunity observed with prototype vaccine [13,15,16] and the correlation of CD4+ T-cell activity to Env V2 peptides to HIV protected individuals from the HIV vaccine RV144 trial [5] further underscores the importance of developing T cell-based HIV and FIV vaccines [6,13].

Developing modalities capable of targeting specific regions of viruses is becoming increasingly important in lentiviral vaccinology [17-20]. Synthetic oligomeric peptides presented in branched chain configuration as dendrimers or multiple antigenic peptides (MAP) have been used to selectively and effectively target epitopes for cancer [21,22], infectious disease [23,24], autoimmune disease [25,26], and have more recently been utilized to refine NAb-based HIV and SIV vaccines [27,28]. In order to develop a T cell-based vaccine, MAPs targeting previously identified antigenic regions of p24 [12] and RT [11] were evaluated in specific pathogen free (SPF) cats primed once with prototype FIV vaccine and boosted four to six times with lentiviral MAPs. The immunogenicity, safety, and efficacy of MAP-based FIV vaccines were evaluated using the FIV-cat model.

Materials and Methods

Animals.

15 SPF cats were bred by the Laboratory of Comparative Immunology & Retrovirology in collaboration with Animal Care Services at the University of Florida. Age-matched cats of both sexes were distributed into four groups (Table 5). The animal work was performed according to the policy and protocols approved by IACUC.

Prime-Boost Vaccines.

A prototype dual-subtype FIV was administered one time as a priming dose. The prototype vaccine, modeled after the commercial dual-subtype FIV vaccine (Fel-O-Vax® FIV) [13], consists of 300 μg each of inactivated whole virus (IWV) FIV-Petaluma and IWV FIV-Shizuoka (600 μg IWV total) formulated in 1.20 mL of FD-1 (oil-in-water) adjuvant with 4 μg of recombinant feline IL12 (rFeIL12) (R&D Systems, Minneapolis, Minn.). MAPs were produced by LifeTein LLC (Hillsborough, N.J.). MAPs were formulated on a lysine backbone with four identical branches of either FIV p24 (Fp) or RT (FRT) peptide(s) on the first lysine backbone on the amino-end and contain palmitic acid ($CH_3(CH_2)_{14}COOH$) third lysine on the carboxyl-end (FIG. 10A). MAP1 consisted of branched chains of p24 peptides Fp4-3 and Fp14-1 linked with a furin sensitive linker (sensitive to cleavage in the trans-Golgi network) [29,30]. MAP1b contained four copies of peptide Fp14-1, and MAP2 contained four copies of overlapping sequence of peptides FRT3-3 and FRT3-4 without a furin linker. Each individual MAP or MAP combination was formulated in a final volume of 1 mL of FD-1 adjuvant with 4 μg of rFeIL12.

Immunization and Challenge.

Eight SPF cats were primed 1× with prototype dual-subtype FIV vaccine (IWV) [13] and boosted with a combination of MAP1 (peptides Fp4-3/Fp14-1), MAP1b (peptide Fp14-1), and/or MAP2 (peptides FRT3-3/FRT3-4) (Groups 1 and 2, Table 5). Immunizations consisted of 1× priming using subcutaneous (SC, 500 μg IWV) and intradermal (ID, 100 μg IWV) routes followed 4-6 wk later with 4×-6× boosts using MAPs (150 μg per MAP SC plus 50 μg per MAP ID) at 3-12 wk intervals. SC immunization volume consisted of 1 mL (500 μg) of IWV for priming and 0.75 mL MAP (150 μg single MAP or 300 μg MAP1+2) for boosting, with ID immunization consisting of 0.1 mL/site (50 μg/site IWV) or 0.125 mL/site (25 μg/site single MAP or 50 μg MAP1+2) immunized at two sites. Cats were challenged intravenously at 6 wk post last boost with 15×50% cat infectious dose (15 $CID_{50}$) of in vivo-derived subtype-B pathogenic $FIV_{FC1}$ [13]. Three IWV-primed cats (Group 3) and four PBS-immunized cats (Group 4) were used as controls (Table 5).

IFNγ and IL2 ELISpot Analyses.

IFNγ and IL2 ELISpot analyses were performed using feline IFNγ ELISpot and feline IL2 ELISpot kits (R&D Systems, Cat# SEL764 and SEL1890) as described [31]. The threshold is defined as ≥50 spot forming units (SFU) per 1×10⁶ PBMC when counted with MVS ELISpot Reader (MVS Pacific, LLC). Each result is an average of the duplicate samples after subtraction of the average value of the media controls.

T-Cell Proliferation and CD4/CD8 Phenotype Analyses.

Carboxyfluorescein diacetate succinimide ester (CFSE)-proliferation was performed according to the manufacturer's protocol (Invitrogen, Grand Island, N.Y.) and processed using a previously described modification [11,12]. The modification consisted of 2.5×10⁵ CFSE-labeled feline PBMC stimulated for 5 days (37° C., 5% $CO_2$) with 4 μg/mL peptide in culture media (RPMI medium 25 g/mL gentamycin, and 10% heat-inactivated fetal bovine serum (FBS)). Peptide pools consisted of 3-5 overlapping peptides of 4 μg/mL each. The antibodies used for flow cytometry based proliferation analysis consisted of murine anti-feline (Fe) CD3 monoclonal antibody (MAb clone kindly provided by Drs. Yorihiro Nishimura and Takayuki Miyazawa; described in [32]) combined with secondary goat anti-mouse IgG3-APC/CY7 MAb (SouthernBiotech, Birmingham, Ala.; Cat#1100-19); and murine anti-FeCD4-PE MAb (Southern-Biotech, Cat#8130-09); and murine anti-FeCD8 MAb (MAb clone kindly provided by Dr. Nazareth Gengozian, described in [33]) with secondary goat anti-mouse IgG2a-PE/CY7 (Southern Biotech, Cat#1080-17). The murine anti-B220-APC MAb for detecting feline B cells (SouthernBiotech, Cat#1665-11) and previously described MAbs for CFSE were used for FACS phenotyping. Both FACS phenotyping and CFSE-proliferation analyses were performed with BD LSRII and FACSDiva™ Software (BD Biosciences, San Jose, Calif.). The final value for each sample was derived after subtraction of the average value of the media controls using a positive threshold of ≥1 $CFSE^{low}$.

Monitoring of FIV Infection and Anti-FIV Antibodies.

FIV infection was determined by virus isolation from PBMC collected during the study and at study termination. Bone marrow (BM) and lymph nodes (LN) were collected at the termination of the study. BM aspiration and LN biopsy were collected for the protected cat (SBA) for continuous monitoring. FIV infection was detected by RT assay of the culture fluid harvested 2× per wk for 4 wk as well as env-specific proviral PCR of cultured tissue (PBMC, BM and LN) [13,34]. PBMC virus load was monitored from 14 weeks post-challenge (wpc) to 47 wpc and was determined from 2-4 time-points. Virus load assay consisted of $10^1$, $10^2$, $10^3$, $10^4$, $10^5$, and $10^6$ PBMC from each challenged cat co-cultured in quadruplicate with 2.5×$10^5$ feeder PBMC from an uninfected SPF cat for 2 wk in 1 mL total of culture media (37° C., 5% $CO_2$). The PBMC were resuspended in fresh culture media every 3-4 days over 2 wk and the collected fluid evaluated for FIV titer by RT assay. Four cats (OCA, OCF, 5HS, DVC) were terminated at 9-14 wpc to evaluate their tissues for pathogenic $FIV_{FC1}$-induced pathology during early infection and at a time point too early to determine viral set point.

To avoid detection of vaccine antibodies to p24 and RT, post-challenge sera were evaluated for infection-induced FIV antibodies by ELISA using 200 ng/well of transmembrane peptide (TM, aa 694-705: QELGCNQNQFFC (SEQ ID NO:68)) as previously described [36,37]. The positive threshold for anti-TM antibodies was set at 0.2 O.D. The post-vaccination sera immediately before challenge were evaluated for NAb titer to $FIV_{Pet}$ and $FIV_{FC1}$ by NAb assay as previously described [13]. The post-vaccination/pre-challenge sera were tested for antibodies to vaccine peptides by ELISA using each peptide as substrate and by FIV immunoblot with mini-blot modification as previously described [36]. All ELISA thresholds were set at twice the average of the individual serum from 15-20 SPF cats.

Cytokine and Cytoxin mRNAs of Cat SBA.

The PBMC from cat SBA at 61 wpc or 14 wk after post-challenge MAP1/MAP2 boost, and SPF cats were incubated for 7-8 hours (37° C., 5% $CO_2$) in the presence of each individual peptide or MAP before harvesting for RT-PCR. Tested peptides and MAPs consisted of: peptide/MAP combination 1 (P1: 5 µg/mL each of Fp4-3 plus MAP1c), peptide/MAP combination 2 (P2: 5 µg/mL each Fp14-1, FRT3-3, FRT3-4, MAP1b, plus MAP2), and T-cell mitogen staphylococcal enterotoxin A (SEA, 0.2 µg/mL) in culture media with 5% FBS and 2.5×$10^6$ PBMC/mL. The mRNA levels of feline IFNγ, IL2, perforin, granzyme A (GrzA), and GrzB were determined by RT-PCR as previously described [16]. The sequences of the primer set for the feline cytokines and cytotoxins are shown in Table 6 with respective accession number(s) of the complete or partial sequence from which they were derived. Multiple accession numbers represent 100% conservation observed at the primer pair sequences and in the size of the amplified product. The amplified sequences were sequenced by Eruofins MWG Operon LLC (Louiville, Ky.) and determined to be the correct sequence for the corresponding cytokine or cytotoxin.

FIV Enhancement and Suppression Analysis.

FIV viral enhancement or suppression was determined using a 48-well modification of the method described for detecting FIV enhancing activity of IFNγ and FIV suppressive activity of IFNα [37]. Briefly, 0.25-0.5×$10^6$ unstimulated PBMC from an uninfected SPF donor was cultured with 7 µg/mL of MAP1, MAP2, MAP1c, MAP1b, MAP1+ MAP2 (14 µg/mL total) or the peptides Fp4-3, Fp14-1, FRT3-3, FRT3-4, or negative control peptide Hp15-1 in a final volume of 1 mL/well. MAP1c contained four branched chains of peptide Fp4-3. T-cell mitogen concanavalin A (ConA) at 4 µg/mL was used as an infection enhancing control. Six hours after the culturing with peptide, MAP, or ConA, varying dilutions of $FIV_{FC1}$ were added to the wells. Seventy-two hours later the cells were re-cultured in fresh culture media with ConA-stimulated autologous PBMC (0.25-0.5×$10^6$) using the same amount of corresponding peptide, MAP, ConA or media. On Day 7, 10, and 13 of culture, 0.5 mL of culture fluid was collected and 0.5 mL of fresh media added to maintain a consistent volume. The harvested culture samples were analyzed for FIV titer using the previously described RT assay [13,34]. The results are shown as the end-point dilution titer from two studies using PBMC from different SPF donors.

Statistical analysis. The statistically significant differences between the end-point dilution titers of the peptide or MAP culture samples and either the virus control samples or specific MAP culture samples were calculated using a paired Student t-test with a two-tailed distribution (SigmaPlot version 11.0). Statistical comparisons between pre and post-vaccination(s) were similarly performed. The comparison was considered statistically significant when $p<0.05$.

Results

Humoral Immunogenicity of MAP Boosts.

Three weeks post IWV priming, antibody responses were detected against p24 but not RT (FIG. 10B, lane 2). Serum from all five IWV/MAP-vaccinated cats tested maintained or decreased antibody levels to p24 at 5 wk after the last MAP boost and before challenge (FIG. 10B, lane 3). The 1×IWV prime did not induce SU or TM antibodies. Individual peptide-specific ELISA analyses were performed to differentiate antibodies induced by IWV prime from those induced by the individual peptides in the MAPs. No specific antibodies to peptides Fp4-3, Fp14-1, FRT3-3, and FRT3-4 were detected throughout the vaccination (data not shown). As expected (from the lack of antibodies to SU or TM after priming), no FIV virus NAb were detected in any vaccinated cats prior to challenge (data not shown).

CMI and T-Cell Immunogenicity of MAP Boosts.

Figures 10C, 10D, 10E, 10F:
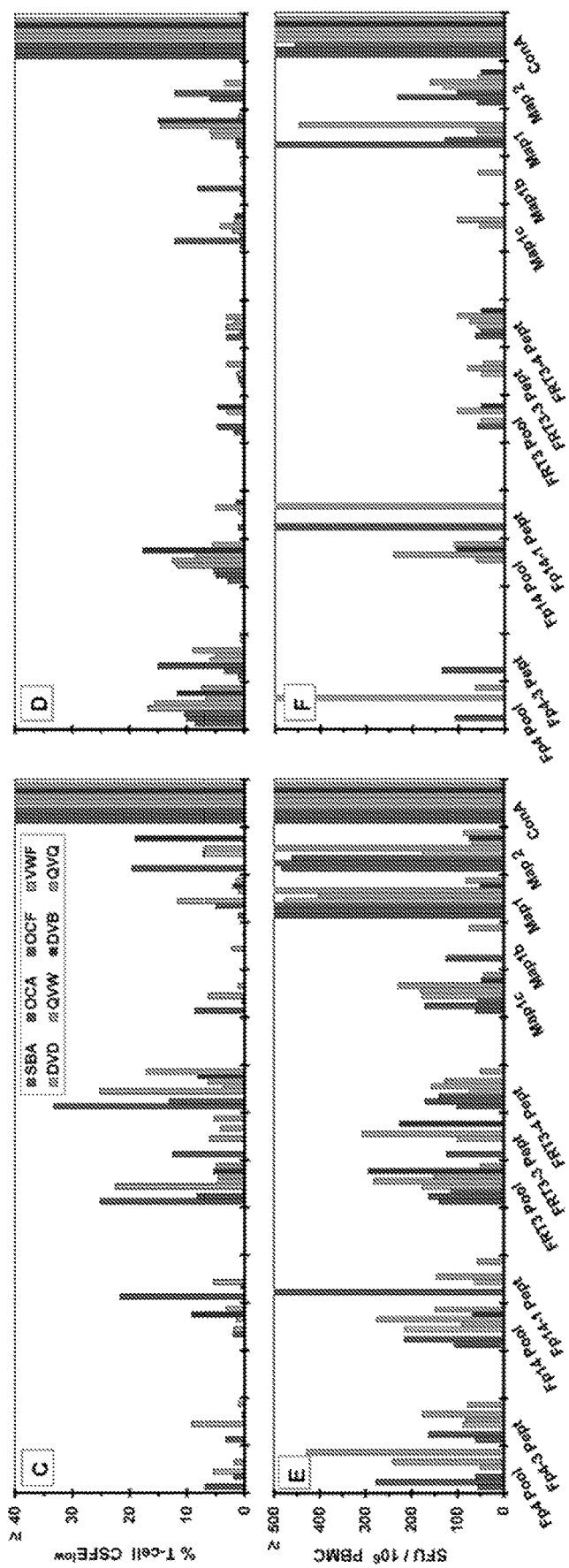

Strong T-cell proliferation (FIGS. 10C, 10D) and IFNγ production (FIG. 10C), but moderate IL2 production (FIG. 10D), to the FIV p24 and RT peptides and their peptide pools were observed in the T cells and PBMC of the MAP-vaccinated cats from Groups 1 and 2 at 4 wk post last boost and before challenge. Peptide pools Fp4, Fp14, and FRT3 contained Fp4-3, Fp14-1, and FRT3-3/FRT3-4 peptides respectively as well as 2-3 overlapping and/or adjacent peptides as previously described [11,12]. Notably, $CD3^+$ $CD4^+$ T cells from vaccinated cats responded to peptide pool Fp4 and peptide Fp4-3 at higher levels and frequency than $CD3^+CD8^+$ T cells (FIGS. 10C, 10D). However, $CD3^+CD8^+$ T cells responded to peptide-pool FRT3 and peptides FRT3-3 and FRT3-4 at a greater frequency and magnitude than $CD3^+CD4^+$ T cells. The T-cell responses to pool Fp14 and peptide Fp14-1 were lower and less frequent than the $CD8^+$ T-cell responses to FRT3 pool and FRT3-3/FRT3-4 peptides and the $CD4^+$ T-cell responses to the Fp4 pool and Fp4-3 peptide. In general, stimulation with peptide pools had slightly higher frequency and higher magnitude than the individual peptides (FIGS. 10C-10F). The four non-vaccinated SPF cats and eight SPF cats before vaccination had minimal (i.e., cat DVC with 2 $CFSE^{low}$ to FRT3-3; cat OLI with 3 $CFSE^{low}$ to FRT3-4) to no responses to these peptide pools and peptides (data not shown). The peptide pools were included to determine the additive effect of the peptide(s) and associated segments in the adjacent overlapping peptides (Table 7). Any peptides in the pool with eight or more overlapping aa identical to the target peptide (i.e., those used for MAP vaccination) have a potential to stimulate T cells based on the pocket binding capacity of the MHC [38]. Hence, this results in the higher magnitude and frequency of responses to the peptide pools since there is a greater overall amount of these sequences in the pool compared to the individual peptides.

Between peptides Fp4-3 and Fp14-1, the highest magnitude and frequency of responses to peptide Fp4-3 were observed with CD4+ T-cell proliferation, whereas the highest magnitude but low frequency (37%) of responses were observed with CD8+ T-cell proliferation to peptide Fp14-1 (FIGS. 10C, 10D). The fact that different patterns of T-cell responses were observed with peptides Fp4-3 and Fp14-1 by MAP1-vaccinated cats suggest that these responses represented independent recognition of individually cleaved peptides. Therefore, peptides Fp14-1 and Fp4-3 were most likely cleaved by endoprotease furin at the furin-sensitive linker (RVKR) (SEQ ID NO:38) [29,30]. The magnitude and frequency of IFNγ production induced by each of these peptides by PBMC of MAP1-vaccinated cats further support this conclusion (FIG. 10E).

In general, all peptides induced substantial IFNγ responses at high magnitude and frequency (FIG. 10E). The PBMC from five unvaccinated SPF cats had <15 SFU. Except for cat OCA with substantial IFNγ production to peptide Fp4-3 (161 SFU), the common feature of the partially and fully protected cats (Group 1 and Group2b) was their decreased (SBA, 60 SFU) or absence (OCF, DVB) of IFNγ production to Fp4-3 even though they received Fp4-3 containing MAP1. Robust IFNγ responses to MAP1 and MAP2 (FIG. 10E) were observed in comparison to the moderate T-cell proliferation responses to all MAPs. This observation suggests that the MAP formulation is either presenting the peptides to the IFNγ producing cells more efficiently and/or recruiting more IFNγ inducing cells. Since the IFNγ responses were detected in PBMC, the MAP with lipophilic palmitate may be recognized by NKT cells along with NK cells and T cells which produce large amount of IFNγ, and are considered to have adjuvant activity [39,40]. Overall, both peptides and MAPs stimulated the PBMC and T cells from MAP-vaccinated cats (FIGS. 10C-10F) but not from non-vaccinated cats (data not shown). These results demonstrate that MAP vaccination induces robust peptide-specific CMI including CD4+ and CD8+ T cell and potentially NK immunity. Furthermore, all MAP-vaccinated cats showed no observable adverse clinical signs or observable injection site reaction from MAP vaccination.

Challenge Efficacy of Prime-Boost Immunization.

Upon challenge, 1 of 4 cats (SBA) in MAP-vaccinated Group 1 was FIV negative by virus isolation and proviral PCR and was negative for virus specific FIV antibodies (Table 5; FIG. 10A, lane 4; FIG. 11A). This cat displayed normal CD4+ T-cell counts throughout the study. Another two cats (OCA, OCF) in Group 1 showed partial protection with one cat showing a substantial delay in CD4+ T-cell loss (Table 5). Partial protection was defined as a delay in detection of infectious virus, a delay in CD4+ T-cell loss, and/or lower viral set point compared to the virus control (Group 4). In addition, 1 of 4 cats (DVB) in Group 2 with only a single MAP1 boost also demonstrated partial protection (Table 5). In addition, cat DVB was considerably below the threshold (0.2 O.D.) for anti-TM antibodies (FIG. 11A). Except for the fully protected cat (SBA), all cats were positive by virus isolation and proviral PCR in all tested tissues (PBMC, BM, LN) at the end of the study (Table 5).

Interestingly, post-challenge anti-TM antibodies showed enhanced TM antibody titers at 3 wpc in two Group-3 cats (5HS and OLK) and one Group-2 cat (DVD) (FIG. 11A). Initial comparison between Groups 1 and 2 suggested that the additional two boosts in Group 2 decreased protection (Table 5). Moreover, sub-Group 2b vaccinated with MAP1b instead of MAP1 had one partially protected cat, an overall lower viral set point, and lower anti-TM antibody titers than those in sub-Group 2a (Table 5, FIG. 11A). Since MAP1b contained only peptide Fp14-1, the presence of peptide Fp4-3 in MAP1 may be inhibiting the protective capability of MAP1.

The 1×-prime Group 3 showed a slight enhancement in virus isolation, early CD4+ T-cell loss, and high early anti-TM antibody titers in 2 of 3 cats by 3 wpc (Table 5, FIG. 11A). All cats in Group 3 were positive by proviral PCR by 3 wpc (Table 5). Although statistically not significant due to the small number of cats, the FIV enhancing trend in Group 3 may indicate that priming with excessively high dose of IWV may induce responses to non-protective and potentially enhancing epitopes on FIV p24. Nevertheless the 4× boosts with MAP1/MAP2 in Group 1 were able to overcome the potential adverse effect of the high antigen prime and resulted in a partial-to-full protection in 3 of 4 cats (Table 5).

The Effect of Vaccine Peptides in the Fully Protected Cat.

Ideally, the CTL-associated cytotoxin mRNA analysis would have been performed prior to FIV challenge in all cats and although a delay in infection and lower viral load in vaccinated cats were an anticipated outcome, we did not expect any cat to confer complete protection. Consequently, after performing peptide-specific T-cell proliferation and cytokine (IFNγ and IL2) production analyses, these cats were challenged and evaluated for infection and terminated for tissue. Only one protected cat SBA was not terminated and subsequently monitored over 1 year for infection and post-challenge boost immunity. To test the possibility of Fp4-3 peptide decreasing the protective potential of the other peptides, the fully protected cat was boosted at 47 wpc with MAP1 plus MAP2. At 14 wk post-challenge boost, PBMC were analyzed for cytokine (IFNγ and IL2) and cytotoxin (perforin, GrzA, GrzB) mRNA production to Fp4-3 and MAP1c combination and to a combination of Fp14-1/FRT3-3/FRT3-4 peptides, MAP1b and MAP2. The Fp4-3 stimulation induced high IFNγ mRNA levels to Fp4-3 that were comparable to SEA stimulation and low IL2 and GrzA mRNA levels but no detectable levels of Fp4-3-specific perforin or GrzB in the PBMC (FIGS. 11B, 11C).

In comparison, stimulation with the Fp14-1/FRT3-3/FRT3-4/MAP1b+2 combination induced high mRNA production of IL2 and CTL-cytotoxins perforin and GrzA but minimal production of IFNγ and no production of GrzB. Non-vaccinated SPF cats had no production of cytokines or cytotoxins upon stimulation with any peptide/MAP combination. More importantly, GrzB production to SEA stimulation is extremely low in cat SBA compared to those of SPF cats. Thus, current findings suggest that perforin and GrzA but not IFNγ, predominantly induced by the Fp14-1/FRT3-3/FRT3-4 combination and may have mediated CMI activity against FIV in the only protected cat SBA. In contrast, peptide Fp4-3 induced minimal CTL-associated cytotoxin production but induced mainly IFNγ which may be more broadly pro-inflammatory.

The Direct Effect of Vaccine Peptides in In Vitro FIV Infection.

The profile of the response of the protected cat as well as potential enhancement of infection in Group 3 prompted the evaluation of viral enhancing and suppressive effects of p24 and RT peptides on FIV infection. Peptide Fp4-3 and MAP1 significantly enhanced FIV infection but Fp14-1 and MAP1b had no effect (FIG. 11D). Peptide FRT3-4 and MAP2 significantly suppressed FIV infection (p<0.05) but significant enhancement was observed with peptide FRT3-3

(p<0.001). Most likely the natural overlap of FRT3-3 and FRT3-4 in MAP2 allowed cellular processing or cellular recognition of more FRT3-4 than FRT3-3 peptides resulting in a significant inhibition of infection.

Due to the minimal protection conferred by groups containing high levels of MAP1, particularly those containing Fp4-3, the stimulatory effect of various combinations of MAP1, MAP2, and MAP1b were evaluated using viral enhancement/suppression assays. Treatment with MAP1 plus MAP2 (MAP1+2) combination resulted in a significantly higher viral infection compared to the untreated control (p<0.001) and with an overall level of virus expressed between that of the individual MAP1 and MAP2 (FIG. 11D). This combination most likely significantly decreased the FIV suppressive effect of MAP2 (p<0.001) but also significantly decreased the FIV enhancing effect of MAP1 (p<0.01) resulting in an intermediate phenotype. Based on these in vitro observations, the immunization with combined MAP1+2 most likely decreased the FIV enhancing activity of peptide Fp4-3, while it augmented the CTL-like activity induced by the combination of Fp14-1 and FRT3-3/FRT3-4 as observed with cat SBA (FIG. 11B).

The combination of MAP2 plus MAP1b without peptide Fp4-3 had no FIV enhancing activity but also showed no FIV suppressive activity of MAP2. Palmitic acid was attached to all MAPs (Pam-MAPs) to enhance its adjuvant activity by stimulating toll like receptor (TLR) and to enhance the uptake of the MAP by antigen presenting cells [17]. Thus, the loss of suppressive activity may be the outcome of having too much TLR activation caused by the additive effect of palmitic acid on both MAP1b and MAP2 in the 1-mL culture system. The current in vitro observation may explain why 6×MAP boosts in Group 2 were less effective than 4×MAP boosts in Group 1. The over stimulation of TLR by palmitic acid may have resulted in more non-specific stimulation which decreased or negated the potential protective efficacy. Future studies will balance Pam-MAP with MAP alone or MAP conjugated to Tat that has only cell penetrating activity [41].

Discussion

To date, the best clinical vaccine trial (RV144) against HIV-1 used a prime-boost approach consisting of 2× canarypox virus (ALVAC) vectored HIV-1 gag/pr/env immunizations followed by 2×ALVAC-HIV immunizations in combination with recombinant Env-B/E (AIDSVAX) [4]. Using a similar prime-boost approach in FIV/cat model, 2× priming with ALVAC subtype-A $FIV_{Ville-Franche}$ gag/pr/env followed by 1× boost with inactivated subtype-A $FIV_{Pet}$-infected cell vaccine (ICV) conferred 100% protection against homologous challenge and 100% partial-to-full protection against heterologous challenge [42]. In current study, cats were primed with the prototype IWV and boosted with a combination of MAP vaccine formulations containing three T-cell epitope peptides conserved among lentiviruses in addition to another T-cell peptide (Fp4-3) conserved only among FIV subtypes. The prototype dual-subtype FIV vaccine (IWV) has been reported to induce more T-cell immunity and confer more protection against tier-2 and -3 viruses than the commercial FIV vaccine [13,15,16]. This pilot study was designed to generate and evaluate anti-FIV T-cell immunity using the prime boost model and to evaluate the safety of Pam-MAP and not expected to confer significant protection. However the vaccine designed proved efficacious with the limited peptide repertoire and conferred 75% partial-to-full protection in MAP-vaccine Group 1 (Table 5).

The most innovative feature of the current study was the use of selected FIV peptides in the MAP formulations. FIV p24 peptide Fp14-1 in MAP1 and RT peptides FRT3-3 and FRT3-4 in MAP2 are previously reported conserved lentiviral epitopes [11,12]. These epitopes were recognized by both FIV-vaccinated cats (Fp14-1) and HIV+ human subjects (FRT3-3, FRT3-4) [11,12] and have significant aa sequence conservation with other AIDS lentiviruses (Table 7). In studies with HIV+ subjects, these peptides and their peptide-pools (Fp14 and FRT3) induced moderate IFNγ responses and moderate-to-high production of CTL-like cytotoxins in both CD4+ and CD8+ T cells as well as strong CD8+ T-cell proliferation [11,12]. In prototype FIV-vaccinated cats, peptide Fp14-1 and the Fp14 pool induced high magnitude and frequency of proliferation in both CD8+ and CD4+ T cells, but peptides FRT3-3 and FRT3-4 induced only low magnitude and frequency of response (Pu and Yamamoto, pers. comm.). The low frequency of response to FRT3-3 and FRT3-4 was anticipated due to the low amount of FIV RT protein present in the IWV vaccine compared to the p24 protein [43]. In the current study, Map2 immunization with a high concentration of overlapping FRT3-3/FRT3-4 peptides resulted in a high magnitude and frequency of CD8+ T-cell proliferation and IFNγ production to both peptides (FIGS. 11A, 11C). In comparison, MAP1 immunization with Fp14-1 induced a low frequency of T-cell proliferation to Fp14-1 peptide but had more consistent CD4+ T-cell proliferation and IFNγ production to the Fp14 pool (FIGS. 10C, 10D). Thus, the high quantity of RT peptides in the MAP2 formulation induced responses to the RT peptides in vaccinated cats, and strong CD8+ T-cell responses to FRT3-3/FRT3-4 in MAP2 likely contributed to the partial-to-full protection observed in Group 1.

Besides peptide Fp14-1, MAP1 contained peptide Fp4-3 which may have contributed to the lower T-cell responses to Fp14-1 (FIG. 10C) and thus attenuated the protective immunity induced by the Fp14-1 peptide. In IWV-vaccinated cats, peptide Fp14-1 induced a high magnitude (7-14 $CFSE^{low}$) and frequency (75%) of CD4+ T-cell proliferation but only low frequency (33%) of CD8+ T-cell proliferation (Pu and Yamamoto, pers. comm.). MAP1 immunization with high concentration of Fp14-1 peptide should have resulted in more T-cell proliferation than those induced by prototype vaccine but only low CD4+ T-cell proliferation to peptide Fp14-1 was observed (FIG. 10D). Peptide Fp4-3 is the only peptide used in the formulations that lacks lentiviral conservation (Table 8). However, this epitope is highly conserved among FIV subtypes and raises a major concern with regard to vaccine design since this study demonstrates that Fp4-3 peptide enhances in vitro FIV infection and inhibits potential protection in cats. The current efficacy study showed no protection in Group 2a which received the highest amount of Fp4-3. Notably, the only fully protected cat SBA had substantially greater pre-challenge CD8+ T-cell proliferation and IFNγ production to peptides FRT3-3/FRT3-4 than to peptide Fp4-3 (FIGS. 10C, 10E). The low CD4+ T-cell proliferation and IFNγ response in cat SBA to Fp4-3 (FIGS. 10D, 10E) may be another indication of the negative effects of Fp4-3 on protective immunity. Furthermore, CD4+ T-cell proliferation to all tested FIV peptides in the protected cat was generally lower than those of other MAP-vaccinated cats (FIG. 10D). Thus, complete protection most likely required maximal immunity to peptide FRT3-3/3-4 and strong CD8+ T-cell proliferation but minimal responses to peptide Fp4-3 and low CD4+ T-cell proliferation.

Protection due to enhanced immunity against FRT3-3/3-4 and minimal response to Fp4-3 is supported by the post-challenge immunity of cat SBA after a single post-challenge MAP1/MAP2 boost. Fp4-3 stimulation induced high levels of IFNγ mRNA expression and moderate expression of IL2 and GrzA, whereas the Fp14-1, FRT3-3, and FRT3-4 combination induced high expression of Th1 cytokine IL2 and CTL-associated cytotoxins perforin and GrzA (FIG. 11B). Since NK cells do not generally-induce peptide-specific responses [44], the upregulation of multiple cytotoxins more likely represents the antigen-specific activity of CTLs [16]. Based on these observations, peptide Fp4-3 induced minimal protective CTL-like activity, whereas the Fp14-1/FRT3-3/FRT3-4 combination induced robust CTL-like activity against FIV which likely contributed to the full protection of cat SBA.

Peptide Fp4-3 predominantly induced IFNγ responses without a major production of CTL-associated cytotoxins. It has been reported that IFNγ response alone without cytotoxin production does not generate strong CTL activity against HIV-1 [45,46]. More importantly, IFNγ has been reported to be a key inflammatory cytokine produced during early stage of HIV-1 infection which can augment infection and result in a higher viral set point [47,48]. Furthermore, IFNγ has been reported to directly enhance the in vitro infection of both HIV-1 and FIV in primary PBMC from HIV$^-$ human subjects and FIV$^-$ cats [37,49]. Therefore, the in vitro enhancement of FIV infection with Fp4-3 stimulation (FIG. 11D) may be mediated by enhanced IFNγ production in the culture. Thus, a peptide such as Fp4-3 that predominantly induces IFNγ may be contra-indicated as a vaccine immunogen. More importantly, the current study suggests that the FIV-enhancing immune activation of peptide Fp4-3 in MAP1 blocked the protective immunity of FRT3-3/FRT3-4 in MAP2 for the majority of the MAP-vaccinated cats. Therefore selection of the T-cell epitope peptides for vaccines should not only be based on polyfunctional T-cell cytokine and CTL analyses but should also include assays that evaluate the FIV enhancer/suppressor potential of these peptides.

In addition to the use of conserved lentiviral T-cell epitope peptides, the protective efficacy observed in Group 1 may be attributed to the use of MAP with FD-1 adjuvant including rFeIL12. The addition of rFeIL12 to the prototype FIV vaccine has been reported to enhance the efficacy against heterologous FIV isolates more than vaccine formulated only in FD-1 adjuvant [13]. In addition, peptide presented using MAP has been reported to augment the immunity to the peptide more than an equivalent amount of the peptide alone in the same adjuvant [21,50]. Lipidation including palmitoylation of MAP has been reported to further enhance the peptide specific responses by triggering TLRs and transport of peptides into the cells [17,51-53] as well as decrease the toxicity of MAP caused by free amino groups [51]. MAPs using NAb epitope-targeted peptides induced high levels of NAbs against HIV-1 [26,27]. Also, a MAP targeting Th2 epitopes has been used in combination with a MAP targeting the V3 NAb epitope to augment NAb titers [27]. In contrast, T-cell epitope-based vaccine designs consisting of pDNA, modified vaccinia virus vector, and multiple chain peptides with or without lipidation have been tested in Phase-I trials without major success (reviewed in [54]). However, MAP based on T-cell epitopes of tumor antigens induced antitumor CTLs and showed therapeutic efficacy [22,55].

The agonist/antagonist activity of peptides inducing FIV-specific CTL activity was likely a significant factor in MAP1/MAP2-vaccinated cats. Anti-HIV agonist/antagonist peptides on HIV-1 matrix and p2$^4$ have been reported for HLA-B8 or HLA-B27 restricted CTLs respectively [19]. The p24 peptides included the agonist KRWIIMGLNK (SEQ ID NO:69) (KK10) with antagonist KRWIILGLNK (SEQ ID NO:70) [19]. HLA-DRB restricted CD4$^+$ T cells recognized p24 peptides such as agonist PEVIPMFSALSE-GATP (SEQ ID NO:71) (PP16) with antagonist PEVIPMF-SALSEG (SEQ ID NO:72) (PG13) [18]. (Note the bold aa(s) represent changes or COOH-end truncation.) The FIV counterpart of these defined agonist/antagonist peptides of anti-HIV CTLs do not overlap with the FIV enhancer (Fp4-3 and FRT3-3) or suppressor (FRT3-4) peptides in current study. FRT3-3/FRT3-4 are overlapping peptides recognized by HIV$^+$ subjects [11], whereas PP16/PG13 is an agonist/antagonist pair recognized by a CTL clone derived from an HIV$^+$ subject [18]. It is important to note however that both PP16/PG13 and FRT3-3/FRT3-4 pairs can be an outcome of differential cellular cleavage which should be considered in peptide selection and vaccine design.

Through careful selection and screening of conserved lentiviral epitopes, the current study is the first to demonstrate the use of a T-cell epitope based MAP to induce CTL-associated and polyfunctional T-cell activities that conferred partial-to-full protection against FIV.

TABLE 5

Summary of immunization and challenge efficacy

| Group No. | Cat Code | Immunization[a] | | | | | | | VI/PCR/(VS) of PBMC[ab] | |
|---|---|---|---|---|---|---|---|---|---|---|
| | | Prime | Boost-1 | Boost-2 | Boost-3 | Boost-4 | Boost-5 | Boost-6 | 3 wpc | 7 wpc |
| 1 | SBA | IWV | MAP1 | MAP1 + 2 | MAP2 | MAP1 + 2 | — | — | −/− | −/− |
| | OCA | IWV | MAP1 | MAP1 + 2 | MAP2 | MAP1 + 2 | — | — | −/− | −/− |
| | OCF | IWV | MAP1 | MAP1 + 2 | MAP2 | MAP1 + 2 | — | — | −/− | −/+ |
| | VWF | IWV | MAP1 | MAP1 + 2 | MAP2 | MAP1 + 2 | — | — | −/− | −/− |
| 2a | DVD | IWV | MAP1 | MAP1 | MAP1 | MAP2 | MAP2 | MAP1 + 2 | +/+ | −/− |
| | QVW | IWV | MAP1 | MAP1 | MAP1 | MAP2 | MAP2 | MAP1 + 2 | −/− | −/− |
| 2b | DVB | IWV | MAP1b | MAP1b | MAP1b | MAP2 | MAP2 | MAP1 + 2 | −/− | −/− |
| | QVQ | IWV | MAP1b | MAP1b | MAP1b | MAP2 | MAP2 | MAP1 + 2 | −/− | −/− |
| 3 | 5HS | IWV | — | — | — | — | — | — | −/+ | +/+ |
| | VBA | IWV | — | — | — | — | — | — | −/+ | +/+ |
| | OLK | IWV | — | — | — | — | — | — | −/+ | −/+ |
| 4 | DVC | PBS | PBS | PBS | PBS | PBS | — | — | −/− | −/− |
| | OLI | PBS | PBS | PBS | PBS | PBS | — | — | +/+ | −/+ |
| | OLJ | PBS | PBS | PBS | PBS | PBS | — | — | −/− | −/− |
| | 5HP | PBS | PBS | PBS | PBS | PBS | — | — | −/− | −/+ |

TABLE 5-continued

Summary of immunization and challenge efficacy

| Group No. | Cat Code | VI/PCR/(VS) of PBMC[ab] | | | VI/PCR (14-47 wpc)[a] | | CD4+ T Loss[ac] (wpc) | TM Ab[d] (wpc) | Partial-to-Full Protection[e] |
|---|---|---|---|---|---|---|---|---|---|
| | | 10 wpc | 12 wpc | 14-47 wpc | BM | LN | | | |
| 1 | SBA | −/− | −/− | −/−/− | −/− | −/− | —[c] | — | 3/4 |
| | OCA | −/− | −/+ | +/−/n[f] | +/+[f] | +/+[f] | 12 | 12 | |
| | OCF | −/− | −/+ | +/+/3 | +/+ | +/+ | 17 | 10 | |
| | VWF | +/+ | +/+ | +/+/4 | n/n | +/+ | 7 | 7 | |
| 2a | DVD | +/+ | +/+ | +/+/5 | +/+ | +/+ | 10 | 3 | 0/2 |
| | QVW | +/+ | −/+ | +/+/5 | +/+ | +/+ | 7 | 10 | |
| 2b | DVB | −/+ | −/+ | +/+/3 | +/+ | +/+ | 12 | — | 1/2 |
| | QVQ | +/+ | +/+ | +/+/4 | +/+ | +/+ | 10 | — | |
| 3 | 5HS | +/+ | n/n[e] | +/+/n[f] | +/+[f] | +/+[f] | 3 | 3 | 0/3 |
| | VBA | +/+ | +/+ | +/+/5 | +/+ | +/+ | 7 | 14 | |
| | OLK | +/+ | +/+ | +/+/5[f] | +/+[f] | +/+[f] | 3 | 3 | |
| 4 | DVC | +/− | +/+ | +/+/n[f] | +/+[f] | +/+[f] | 7 | 12 | 0/4 |
| | OLI | +/+ | +/+ | +/+/5 | +/+ | +/+ | 10 | 10 | |
| | OLJ | −/+ | +/+ | +/+/5 | +/+ | +/+ | 10 | 14 | |
| | 5HP | +/+ | +/+ | +/+/4 | +/+ | +/+ | 10 | 12 | |

Table 5 Footnotes:
[a] Abbreviations: prototype dual-subtype inactivated whole virus vaccine (IWV), MAP1 plus MAP2 (MAP1 + 2), virus isolation (VI), proviral PCR (PCR), viral set point (VS), not done (n), negative (−), bone marrow (BM), lymph node (LN), week post-challenge (wpc), anti-transmembrane Ab (TM Ab).
[b] Under 14-47 wpc, the last lane is the average of the viral set point at multiple time points from PBMC starting at 14 wpc.
[c] Number of weeks post-challenge when CD4+ T-cell loss of 60% was detected. CD4+ T-cell count and CD4+/CD8+ T-cell ratio of cat SBA were still normal at 61 wpc.
[d] First time-point with detectable TM Ab titers (threshold of 0.2 O.D. in FIG. 12A).
[e] Partial protection represents a delay in VI, delay in CD4+ T-cell loss, and/or lower viral set point compared to control group.
[f] Cat 5HS, cat OLK, and two more cats (OCA, DVC) were euthanized at 10 wpc, 12 wpc, and 14 wpc respectively. All tissues were tested for FIV at termination however the viral set point was only be determined in cat OLK due to the early time point.

TABLE 6

Feline cytokine and cytotoxin primer pairs

| Cytokine/ Cytotoxin (Product Size)[a] | Forward (F) and Reverse (R) Primer Sequence Pair[b] | NCBI Accession No.[c] |
|---|---|---|
| IFNγ (243 bp) | F: 5'-ATGGTGGGTCGCTTTTCGTA-3' (SEQ ID NO: 103) | AY878359.1 |
| | R: 5'-GCAGATCATTCACAGGGATTTGA-3' (SEQ ID NO: 104) | X86972.1 NM_001009873.1 |
| IL2 (263 bp) | F: 5'-CCAAGAAGGCCACAGAATTG-3' (SEQ ID NO: 105) | AY878358.1 |
| | R: 5'-GTCAGCGTTGAGAAGATGCT-3' (SEQ ID NO: 106) | NM_001043337.1 |
| Perf (327 bp) | F: 5'-TGCCACAACGTCCTGAAACA-3' (SEQ ID NO: 107) | AY524984.1 |
| | R: 5'-TACCAGGTGAGAGCTGTAGAA-3' (SEQ ID NO: 108) | NM_001101660.1 |
| GrzA (382 bp) | F: 5'-CCAAGAACGAGCCAGAAAAG-3' (SEQ ID NO: 109) | EU427305.1 |
| | R: 5'-CCAGAATCTCCATTGCACGA-3' (SEQ ID NO: 110) | |
| GrzB (382 bp) | F: 5'-GCCCACAACATCAAGAAGCA-3' (SEQ ID NO: 111) | EU153367.1 |
| | R: 5'-CAGAGTCCCCCTGAAAGGAA-3' (SEQ ID NO: 112) | |
| β-Actin (400 bp) | F: 5'-TGCTGTCTCTGTACGCTTCT-3' (SEQ ID NO: 113) | AB051104.1 |
| | R: 5'-CAGGACTCCATACCCAGGAA-3' (SEQ ID NO: 114) | |

Table 6 Footnotes:
[a] Interferon-γ (IFNγ), interleukin-2 (IL2), perforin (Perf), granzyme A (GrzA), granzyme B (GrzB).
[b] NCBI Genbank accession numbers of those sequences used to design forward and reverse primers.
[c] Each accession number represents the sequence determination from one animal.

TABLE 7

Alignment of the peptide pools Fp4, Fp14, and FRT3

| Peptide Pool & Peptide Code | No. of aa[a] | aa Sequence of Peptides[b] | SEQ ID NO. |
|---|---|---|---|
| Fp4-1 | 15 | AFSANLTPTDMATLI | 73 |
| Fp4-2 | 14 | NLTPTDMATLIMAA | 74 |
| Fp4-3 | 15 | PTDMATLIMAAPGCA | 28 |
| Fp14-1 | 14 | DQEQNTAEVKLYLK | 24 |
| Fp14-2 | 15 | EQNTAEVKLYLKQSL | 75 |
| Fp14-3 | 14 | AEVKLYLKQSLSIA | 52 |
| Fp14-4 | 13 | KLYLKQSLSIANA | 53 |
| FRT3-1 | 13 | NPWNTPVFAIKKK | 76 |
| FRT3-2 | 15 | TPVFAIKKKSGKWRM | 77 |
| FRT3-3 | 15 | KKKSGKWRMLIDFRV | 67 |
| FRT3-4 | 13 | WRMLIDFRVLNKL | 78 |
| FRT3-5 | 14 | IDFRVLNKLTDKGA | 79 |

Table 7 Footnotes:
[a]Amino acid (aa).
[b]Underlined sequence overlaps with the corresponding bolded peptide.

TABLE 8

Sequence of the MAP peptides and their comparison to HIV-1 and SIV sequences

| Virus (Subtype) Peptide Code | Peptide Sequence and Counterpart Sequence[a,b] | aa Identity (%)[c] | aa Similarity (%)[c] | SEQ ID NO. |
|---|---|---|---|---|
| FIV (A, C) Fp4-3 | PTDMATLIMAAPGCA <br> .*****:* | – | – | 28** |
| FIV (B, D) | STDMATLIMSAPGCA <br> * *: *:: :. * | 87% | 100% | 80 |
| HIV-1 (B, C, D) | PQDLNTMLNTVGGHQ <br> * *: :: . * | 27% | 60% | 27 |
| HIV-1 (A) | PQDLNMMLNIVGGHQ <br> * *: :: ... . | 30% | 47% | 81 |
| SIV mm251 | PYDINQMLNCVGDHQ | 13% | 53% | 82 |
| FIV (A, B, D) Fp14-1 | DQEQNTAEVKLYLK <br> ********** *** | – | – | 24 |
| FIV (C) | DQEQNTAEVKTYLK <br> ** * *** ::. | 93% | 93% | 83 |
| HIV-1 (A) | RAEQATQEVKGWMT <br> ** : *** ::. | 43% | 64% | 84 |
| HIV-1 (B) | RAEQASQEVKNWMT <br> ** * :** ::. | 36% | 64% | 23 |
| HIV-1 (C) | RAEQATQDVKNWMT <br> ** : :** ::. | 39% | 64% | 85 |
| HIV-1 (D) | RAEQASQDVKNWMT <br> **. * ** ::. | 29% | 64% | 86 |
| SIV mm251 | RAEQTDAAVKNWMT | 39% | 64% | 87 |
| FIV (B, D) RT3-3/RT3-4 | KKK-SGKWRMLIDFRVLNKL <br> * *******  | – | – | 88** |

TABLE 8-continued

Sequence of the MAP peptides and their comparison to HIV-1 and SIV sequences

| Virus (Subtype) Peptide Code | Peptide Sequence and Counterpart Sequence[a,b] | aa Identity (%)[c] | aa Similarity (%)[c] | SEQ ID NO. |
|---|---|---|---|---|
| FIV (A, C) | KKK-SGKWRMLIDFRELNKL<br>\*\*\* \* \*\*\* \*:\*\*\* \*\*\* | 95% | 95% | 89 |
| HIV-1 (A, B, C, D) | KKKDSTKWRKLVDFRELNKR<br>\*\*\* ..\*\*\*\*\*\*\*\*\* \*\*:: | 75% | 80% | 29 |
| SIV mm251 | KKKDKNKWRMLIDFRELNRV | 70% | 90% | 62 |

Table 8 Footnote:
[a]Sequences are compared to the bolded sequence above.
[b]Identical (\*), similar (:), and moderately similar (.) and dissimilar ( ) aa to the aa of the bolded sequence based on charge, polarity, acid/base, and hydrophobicity. Dashes (−) indicate a gap or deletion in the aa sequence.
[c]Amino acid (aa) sequence identity and similarity compared to the bolded sequence above.

Example 2—MAP Vaccine Study 1 and Ongoing MAP Vaccine Study 2 in Cats

All information regarding MAP Vaccine Study 1 is in the manuscript except for the specific information on the selection of the FIV peptide epitopes. The peptide selection is described below with summary data in Tables 9 and 10.
Selection of FIV Peptides with Epitopes Inducing T-Cell Activity The selection of the epitopes for HIV-1 and FIV vaccines were based on the ability of the T cells from both HIV-1 positive (HIV+) human subjects and FIV-vaccinated cats to recognize viral epitopes that are conserved between FIV and HIV-1. Note that peptide epitope is the smallest amino acid (aa) sequence that can stimulate T cells to exert their effector activities. In current study, the peptide-specific immunological activities of the CD3+CD4+ T cells and CD3+CD8+ T cells were evaluated to identify the CD4+ T-helper (TH), CD4+ cytotoxic T lymphocyte (CTL), polyfunctional CD4+ T-cell, polyfunctional CD8+ T-cell, and CD8+ CTL effector activities. Thus, the peptide epitopes that induce strong anti-HIV and anti-FIV effector activities are being selected as vaccine immunogens.

The overlapping peptide pools of FIV and HIV-1 structural and enzyme proteins were used to stimulate the peripheral blood lymphocytes (PBMC) and the T cells from HIV+ subjects as previously described for epitope mapping of HIV-1 and FIV p24 and reverse transcriptase (RT) (Sanou et al., 2013; Roff et al., 2015). The individual peptides in those peptide pools with positive responses to either interferon-γ (IFNγ) production and/or T-cell proliferation were determined with IFNγ ELISpot analysis and CFSE-based CD3+CD4+ and CD3+CD8+ T-cell proliferation analyses followed by the FACS-based intracellular staining (ICS) for cytolysin (perforin) and cytotoxin (granzyme A [GrzA] and GrzB) (Sanou et al., 2013; Roff et al., 2015). Besides viral p24 and RT proteins, the identical approach was used to identify anti-HIV/FIV T-cell epitopes on viral matrix (MA), nucleocapsid (NC), protease (PR), RNAase, integrase (IN), surface envelope (SU Env), and transmembrane envelope (TM Env) (FIG. 12). The first set of results from these in vitro analyses is shown in Table 9 for FIV peptides and Table 10 for HIV-1 peptides. These results are shown as the frequency of responders in percentage, which is the number of responders to the peptides over the total number of subjects who were tested with individual peptides.

Concurrently, the overlapping peptide pools of FIV structural/enzyme proteins were used to stimulate PBMC and T cells from FIV-vaccinated cats. These cats were vaccinated with prototype dual-subtype FIV vaccine which was the prototype to our commercial FIV vaccine (Coleman et al., 2014). The feline assays (Example 1) equivalent to those of human assays (Sanou et al., 2013; Roff et al., 2015) were used except for ICS analysis. In place of ICS for cytolysin/cytotoxins, IL2 ELISpot analysis was performed. Subsequently, the individual peptides in those peptide pools with positive responses were further tested with the same analyses system. The results for FIV-vaccinated cats included IFNγ and IL2 productions and CD3+CD4+ and CD3+CD8+ T-cell proliferation (Table 9, the second set of results).

Subsequently, the in silico human leukocyte antigen (HLA) analyses were performed on those peptides reactive to either T cells from HIV+ subjects and/or vaccinated cats. The algorithms used were NetMHC 3.2 server for HLA class I (HLA-A, -B, -C) [see Worldwide Website: cbs.dtu.dk/services/NetMHC/], NetMHCII 2.2 server for HLA class II (HLA-DRB1) [see Worldwide Website: cbs.dtu.dk/services/NetMHCII/], and NetCTL 1.2 server for HLA-A and -B associated with cytotoxic lymphocytes (CTL) [see Worldwide Website: cbs.dtu.dk/services/NetCTL/] (Table 9, the third set of results). These in silico analyses determined the reactivity of the selected FIV peptides to the peptide-binding pockets of the HLA and feline leukocyte antigen (FLA, feline counterpart of HLA) allelic proteins called allotypes. It is well established that CD4+ T cells recognize viral peptides in context to the HLA class II on antigen presenting cells or infected target cells such as macrophages and dendritic cells. In contrast, CD8+ T cells recognize viral peptides bound to the HLA class I on infected target cells such as CD4+ T cells, macrophages, and dendritic cells. Thus, the HLA/FLA alleles/allotypes expressed in the individual host will determine which viral peptide epitopes can be recognized by the host's immune system to eliminate the viral infection. Unless the host is homozygous at the allelic site, each individual will possess two different alleles each from HLA-A, HLA-B, HLA-C, and HLA-DRB1. The in silico algorithms for HLA class-II DQ and DP are still in infancy and will not be used or discussed in current study. Similar to humans, domestic cats have three FLA class-I loci with each locus providing two FLA alleles from each chromosomal strand. In contrast, cats have 2-3 loci of FLA class-II DRB1 but lack the gene for DQ or lack complete DP allele. Therefore, the viral epitopes, which are recognized by the most common HLA class-I and -II allotypes prevalent in the host population, are considered to be more effective at inducing effector activities against viral infection than the less common HLA alleles/allotypes.

Domestic cats use FLA alleles/allotypes that resemble HLA alleles/allotypes at peptide-binding pocket. Cats possess FLA alleles resembling supertype A3 (75% of 60 alleles evaluated) the most similar followed by B27 (53%), B7 (33%), B44 (33%), A24 (33%), A2 (13%), and A1 (6.7%). Remarkably, the cross-reactive conserved FIV peptides identified had epitopes reactive to supertypes (in order of most similarity): A3, B27, A24, and A2 followed by B44, B58, A1, and B7. Thus, FIV peptides with anti-FIV T-cell activities and resembling HLA supertypes A3 and B27 will protect more population of cats than those reacting to supertypes A1, A26, and B8.

Lastly, the selected FIV peptides were tested for their potential to enhance or suppress in vitro FIV infection. This assay is called enhancer/suppressor (E/S) analysis of FIV infection (Table 9, last set of results). This feline assay (Example 1) is similar to the human assay described for E/S of HIV-1 infection (Roff et al., 2015) and differs by the use of uninfected cat PBMC and FIV inoculum in place of human PBMC and HIV-1 inoculum.

Selection of FIV Peptides for MAP Vaccine Trials in Cats
  MAP Vaccine Study 1.

The Pilot MAP Vaccine Study 1 was predominantly based on the data from preliminary immune analyses of PBMC and T cells of FIV-vaccinated cats in manuscript (Example 1) and the two publications with similar data using human cells (Sanou et al., 2013; Roff et al., 2015). These publications show PBMC and T cells from HIV$^+$ subjects are cross-reactive to the selected FIV peptides.

Those FIV peptides with responder frequencies of >25% in the CD8$^+$ T-cell proliferation and in the cytolysin/cytotoxin or IL2 production, and with no FIV enhancing potential, were selected for vaccine study in laboratory cats. In addition, the FIV peptides with epitopes reactive to multiple or key HLA/FLA allotypes and common on both HIV-1 and FIV were further selected. The selected peptides were synthesized into a multiple antigenic peptide (MAP) formulation and used as vaccine immunogens in the ongoing MAP Vaccine Study 2 (FIG. 12).

MAP Vaccine Study 2.

The selection of vaccine peptides were also based on the results from MAP Vaccine Study 1 (see Example 1) which determined that peptide Fp4-3 was not beneficial as vaccine immunogen, and may in fact enhance FIV infection and negate the protective efficacy of overlapping FRT3-3/FRT3-4 peptides. The E/S assay also demonstrated the FIV enhancing activity of Fp4-3 (FIG. 11D). The MAP with peptide Fp14-1 appeared to have minimal efficacy in the MAP Vaccine Study 1 and thus was not included in the MAP Vaccine Study 2. Due to the fact that peptide FRT3-3 has in vitro FIV-enhancing activity, the MAP2 consisted of overlapping FRT3-3/FRT3-4 peptide. In form of an overlap, this peptide instead had FIV suppressive activity in vitro (FIG. 11D) and was used (FIG. 12).

In the cat Group 1 (n=5) with the largest number of MAPs, a total of six peptides (i.e., six MAPs) were used as vaccine immunogens with three of these peptides having natural overlap of two peptide epitopes (Fp14-3/Fp14-4, FRT3-3/FRT3-4, and FRT7-1/FRT7-2) (FIG. 12, those with aa sequence). Group 2 received a total of five peptides (i.e., five MAPs) which also had the same three peptides with two peptide epitopes. MAP4 has been excluded in the last two vaccinations of Group 2 (n=6). Another difference in vaccine composition between Groups 1 and 2 is that Group 1 received a vaccine prime with prototype dual-subtype FIV vaccine, whereas Group 2 received no priming before the three vaccinations with multiple MAP vaccine. Each vaccination consisted of intradermal (ID) and subcutaneous (SC) immunization with different ratio of immunogens (FIG. 12). The vaccination intervals were 4-6 weeks. Group 3 (n=6) consisted of placebo control group which either received PBS (n=3) or PBS with adjuvant (n=3). The ongoing Study 2 did not include a group with only prototype FIV vaccine based on the previous pilot vaccine study (Table 5) which showed no protection but enhancement of FIV infection with the single immunization of prototype FIV vaccine. Note that both prototype and commercial FIV vaccines confer 30-50% with two vaccinations (Yamamoto, personal communique) and confer >70% protection with three vaccinations depending on the heterogeneity of the challenge FIV strains (Coleman et al., 2014).

Summary of Pilot MAP Vaccine Study 1

In the pilot study, three FIV peptides were formulated into three MAP formulations mixed in FD-1 adjuvant (Fort Dodge Animal Health) (oil-in-water) (Coleman et al., 2014) and used as a combined MAP vaccine. One MAP contained single peptide epitope (Fp14-1). Each of the two remaining peptides or MAPs contained two clearly defined T-cell epitopes (FRT3-3/FRT3-4, Fp4-3/Fp14-1). In the in vitro analyses, peptide Fp4-3 induced predominantly CD4$^+$ T-cell proliferation and moderate IFNγ production with minimal IL2 production (Table 9). Similarly, peptide Fp14-1 had slightly more responder frequency in CD4$^+$ T-cell proliferation (37.5%) than in the CD8$^+$ T-cell proliferation (25%). This peptide had a high responder frequency of IL2 production (62.5%) and only a low frequency of IFNγ production (12.5%). In contrast, overlapping FRT3-3/FRT3-4 peptide in MAP2 and its individual peptides induced substantial responder frequency in CD8$^+$ T-cell proliferation (44.4%) but nil-to-moderate frequency in the CD4$^+$ T-cell proliferation (0%-33.3%) (Table 9). MAP2 induced high IL2 production which was slightly higher than IFNγ production. Both FRT3-3 and FRT3-4 induced moderate frequency of IL2 but only FRT3-4 induced moderate frequency of IFNγ with only minimal frequency with FRT3-3.

A total of four peptide epitopes that induced either CD4$^+$ or CD8$^+$ T-cell immunity conferred complete production in 1 of 4 in Group 1 and 2 of 4 with partial protection. Partial protection consisted of a delay in FIV infection, a slower loss of CD4$^+$ T-cell counts, and/or a lower virus load compared to Groups 3 and 4. Group 1 had no immunization with MAP1b (Fp14-1) and less immunizations with MAP1 (Fp4-3/Fp14-1) or and MAP2 (FRT3-3/FRT3-4) than Group 2 which had no protected cats. No protection was observed in Group 3 with a single prototype FIV vaccine immunization and the control Group 4 with PBS placebo.

Although the numbers of animals in each group were small, six major findings were made from this study. First, boosts with MAP vaccination containing four T-cell epitopes can confer partial-to-complete protection (Group 1). Second, including epitopes that induce predominantly CD4$^+$ T-cell proliferation (Fp4-3 and Fp14-1) may not enhance protection but may decrease the efficacy of the protective epitopes. Third, the epitopes that induced CD8$^+$ T-cell responses appeared to be important for protection. Fourth, MAP vaccine can be safely administered in domestic cats. Fifth, this is the first report to demonstrate two epitopes Fp14-3 and FRT3-3 which enhanced in vitro FIV infection. Furthermore, an overlap of the enhancing epitope (FRT3-3) with FIV suppressive epitope (FRT3-4) blocked the FIV-enhancing activity and resulted in FIV-suppressive activity. Sixth, single priming with prototype FIV vaccine conferred no protection but instead enhanced FIV infection. Findings 2 and 3 must be further verified by additional studies which either consist of epitopes that only induce CD8+ T-cell activity (e.g., FRT3-3/FRT3-4) or that only induce CD4+ T-cell activity (e.g., Fp4-3 and Fp14-1). In the MAP Vaccine Study 2 described below, FIV epitopes that induced predominantly CD8+ T-cell activity were formulated into MAPs, and the combined MAP vaccine was immunized in cats and tested for prophylactic efficacy against FIV challenge.

Update on the Ongoing MAP Vaccine Study 2

In the MAP Vaccine Study 2, FIV epitopes with predominant CD8+ T-cell inducing activity were combined together as peptide epitopes of FIV structure/enzyme proteins. Each MAP was separately mixed with adjuvant supplemented with feline IL12 (FeIL12) as performed in pilot MAP study and refrigerated 10-20 hours before combining as a single vaccine for immunization. Seventeen age-matched specific-pathogen-free cats were divided into three groups. Group 1 (n=5) was primed with prototype FIV vaccine and boosted 3× with combined MAP vaccine. Group 2 (n=6) had no priming and was vaccinated 3× with combined MAP vaccine. Group 3 (n=6) were divided equally into two groups and immunized with either PBS or PBS in adjuvant supplemented with FeIL12. The duration of the interval between vaccinations varied between 4-5 wk and the interval between the last vaccination and FIV challenge was 5 wk for Group 1 and 6 wk for Groups 2 and 3. Identical to the pilot MAP vaccine study, the cats were immunized SC and ID. However, the total amount of MAP was different from the previous study. The dose of each vaccination for Groups 1 and 2 are shown in FIG. 12. The ongoing study had more total amount of MAP on the second and third vaccination and more MAP immunogens were present in the ID vaccination than SC vaccination. The reason for the latter is that ID vaccinations generally induce more T-cell immunity in mucosal sites which decrease the possibility of antibody production to MAP backbone containing palmitic acid. In the pilot study, ELISA antibodies to individual FIV peptides in the MAP were not detected but the antibodies to MAP1 was detected as early as second-third boost, while antibodies to MAP2 was detected predominantly after the fourth boost. In the ongoing study, the cats received only three MAP vaccinations to decrease the potential of anti-MAP antibody production. Furthermore, three vaccinations are more feasible for veterinary use than four vaccinations.

As expected, the FIV-specific immunity of the vaccinated cats after second MAP vaccination showed predominantly CD8+ T-cell proliferation and substantial IFNγ production by the PBMC but minimal IL2 production. However, after the third MAP vaccination, substantially higher CD8+ T-cell proliferation and more CD4+ T-cell proliferation were observed. Similar to the results from the previous pilot study, higher responder frequencies were observed with CD8+ T-cell proliferation than CD4+ T-cell proliferation (FIG. 13A vs. 4B; 94 vs. 68 bars of CD8+ vs. CD4+ T-cell responses). MAP4, MAP3, and MAP2/MAP2v were vaccinated 3× (3-times) in Group 1, whereas Group 2 received the MAP3 and MAP2/MAP2v 3× and only 1× with MAP4. The other three MAPs (MAP5, MAP9, MAP11) were vaccinated 2×. Consequently, the lower responses to the 2× vaccinated MAPs and their individual peptides were expected. Remarkably, CD8+ T-cell responses to MAP4 and its individual peptide Fp9-3 were observed even with only 1× vaccination with MAP4. In general, Group 1 had more immune responses to the MAPs and their peptide(s) than Group 2 (FIGS. 13 and 14). Since Group 1 received additional 1× prime with prototype FIV vaccine, this prime along with the 3×MAP boosts constituted four vaccinations and appeared to have greatly enhanced the magnitude and responder frequencies to the MAPs and individual peptide(s). Most notably, IL2 production greatly increased post third vaccination. The magnitude of the IL2 and IFNγ responses were much higher than those observed in the previous pilot study (FIG. 14 compared to FIG. 10). Our goal was to increase the magnitude and responder frequencies of IL2 production and maintain the IFN production below 1000 SFU for the MAPs. Our goal for IL2 production was achieved in Group 1 and for MAP2 in Group 2. However, our goal for IFNγ production was achieved for Group 2 but not for Group 1 with extremely high magnitude of IFNγ production. IFNγ can serve as inflammatory cytokine, and treatment with IFNγ has been shown to enhance in vitro FIV and HIV-1 infection (Tanabe and Yamamoto, 2001; Yamamoto et al., 1986). In the ongoing study, higher CD8+ T cell responses and IL2 production were observed than the pilot study which may aid in blocking the FIV-infection enhancing activity of IFNγ. The results from the challenge efficacy (challenge date on Sep. 23, 2015) will determine if such event have occurred.

Future Studies on HIV-1 Vaccine Development

Table 10 demonstrates that HIV-1 counterpart peptides of the cross-reactive FIV peptide epitopes also stimulate substantial HIV-specific immune responses in the PBMC and T cells from HIV+ subjects. This observation suggests that the cross-reactive FIV epitopes and their counterpart HIV epitopes are relatively conserved. This may also indicate that that the amino acid (aa) of the epitope sequence may not be significantly changed because changes in such sequence will negatively affect the viral fitness of both HIV-1 and FIV. The HIV/FIV counterpart epitopes at the aa residues that bind to the HLA/FLA allotypes may be relatively conserved or have more synonomous aa changes. Our study purposely selected T-cell epitopes on HIV/FIV structural and enzyme proteins since these proteins more likely affect the viral fitness more than the accessory proteins (Vpr, Vpu, Nef). Furthermore, FIV viruses do not have Vpr, Vpu, or Nef, and yet commercial FIV vaccine without these accessory genes was successfully developed (Sidney et al., 2008). Thus, HIV counterpart epitope peptides of the viral structure/enzyme proteins may be useful as immunogens for T-cell based HIV-1 vaccine.

In the MAP Vaccine Studies 1 and 2, the FIV peptides which stimulate HIV/FIV-specific T-cell activities were used instead of counterpart HIV peptides in cats. Although no data are shown on the reactivity of counterpart HIV peptides, both the PBMC and the T cells from FIV-vaccinated cats had either low or no responses to the counterpart HIV peptide pools unlike the high responses to both FIV peptide pool and its individual peptide(s) in the pool. A possible reason for this observation is that the T cells were from vaccinated cats instead from FIV-infected cats. The prototype FIV vaccine is inactivated dual-subtype whole viruses and may not process the vaccine proteins in the similar manner as those that occur during infection. PBMC and T cells from HIV+ human subjects were used since even partially effective HIV-1 vaccine (i.e., vaccine with ≥40% efficacy) is not available. Nevertheless, the use of T cells from HIV+ subjects will be important by providing more direct information regarding the potential of these conserved HIV/FIV epitopes to serve as immunogens for HIV vaccine needed in the immunotherapy of HIV+ subjects. Such T-cell based HIV-1 vaccine is important in the effort to achieve a cure for HIV infection when used in combination with ART and drug(s) (e.g., histone deacetylase (HDAC) inhibitors, cytokines that activate JAK/STAT transducers, and activators of JAK/STAT signaling pathway) for activating latent HIV infection (McIlroy, 2013). Hence, the use of peptide Fp4-3, which enhanced FIV infection, may be useful in activating latent FIV infection. Counterpart HIV peptide of Fp4-3 and other HIV peptides are currently being evaluated for its potential to enhance HIV-1 infection.

Similar to our MAP vaccine studies, counterpart HIV-1 epitope peptides will be first used as immunogens for HIV-1 vaccine in HLA-transgenic mice for immunogenicity and humanized mice for vaccine immunity and efficacy against HIV-1 challenge. The cross-reactive FIV epitope peptides will be considered only if the counterpart HIV peptides induce far less responses than the FIV peptides with the T cells from $HIV^+$ subjects.

Selection of HIV-1 Peptides with Epitopes Inducing T-Cell Activity

The selection procedure of HIV-1 peptides is similar to those used for evaluating FIV peptides. Since our goal is to develop HIV vaccine for human use, the HIV peptides (Table 10) counterpart of the cross-reactive FIV peptides shown in Table 9 were tested with PBMC and T cells from $HIV^+$ subjects. The immune functions analyzed were human IFNγ production by ELISpot, cytolysin/cytotoxin production by ICS, and CFSE-based proliferation of $CD3^+CD4^+$ and $CD3^+CD8^+$ T cells from $HIV^+$ subjects (Table 10, the first set of results). In addition, the Los Alamos National Laboratories (LANL) database was used to identify the HLA allele(s) of the HIV epitope sequence with CTL activity that can exist within the sequence of the conserved counterpart HIV peptide (Table 9, LANL CTL). The bold HLA class-I supertypes and the bold 2-digit alleles are those on the "Optimal $CD8^+$ CTL Epitopes" list and those without bold are alleles for potential CTL epitope. Only HLA-A and HLA-B has been classified into groups called supertypes based on the similarity in the peptides binding to the pockets of the HLA allotypes (Sidney et al., 2008). The HLA class II such as HLA-DRB1 has yet to be fully classified into supertypes, and therefore the 4-digit resolution nomenclatures for the HLA-DRB1 alleles are shown.

The preliminary data shown in Table 10 demonstrate HIV-1 peptides Hp14-1, Hp14-2, Hp14-3, HRT3-3, HRT3-4, and HRT3-5, which are the counterparts of FIV peptides Fp14-1, Fp14-3, Fp14-4, FRT3-3, FT3-4, and FRT3-5, respectively in Table 9. These HIV-1 peptides and counterpart FIV peptides induce $CD8^+$ T-cell proliferation and cytolysin/cytotoxin expression in a high number of $HIV^+$ subjects. These HIV-1 peptides will be further tested for enhancer and suppressor activity in the in vitro HIV-1 infection using uninfected human PBMC with different HLA alleles. Our goals are to complete Table 10, select a large number of HIV-1 peptides from those in Table 10, and to test as vaccine immunogens in the HLA-transgenic mice and humanized mice.

The Use of HLA Analyses to Further Select the Conserved HIV-1 Peptides from Table 10

Since a large majority of these HIV-1 peptides in Table 10 is conserved among many HIV-1 subtypes (subtypes A, B, C, and D) (Tables 11 and 12), there is a strong likelihood of these peptides being useful as vaccine immunogens in highly HIV-1 endemic countries and regions with HIV-1 subtypes A, B, C and D. More importantly, HIV-1 subtype C is the major subtype circulating globally followed by subtypes B and A (Taylor et al., 2008).

The next important aspect of these HIV epitopes is whether the predominant HLA supertypes and alleles of the populations in the HIV endemic regions are the same as or similar to the HLA supertypes or alleles/allotypes which recognize these peptide epitopes (Table 10). The most frequently observed HLA supertypes for HIV counterpart peptides in Table 10 (under CTL in bold) are B27 and A3 followed by B7 and B44. Except for B27, three of these supertypes are highly prevalent in African Americans and Caucasians in U.S. (Table 13). In contrast, supertype B27 ranks 6th-8th position out of 10 positions (Table 13).

Further improvements can be made on these peptides by adding 1-2 aa identical to those on HIV at the amino-end or carboxyl-end to increase its binding potential for those HLA prevalent in the population. For example, isoleucine which is on the amino-end of the viral peptide HPR1 sequence was added in order for the peptide to bind to A3 and A2 (Table 10). In addition, the aa at the sites where the peptide contact peptide-binding pocket of the HLA allotype can be changed to increase affinity and provide more stronger antiviral immune responses. These improvements can be tested using HLA-transgenic mice and humanized mice.

TABLE 9

Selection of T-cell epitopes on FIV proteins using $HIV^+$ human subjects and FIV-vaccinated cats

| | FIV Epitope | $HIV^+$ Human Subjects Functional Immune Analyses[bc] | | | | FIV-Vaccinated Cats Functional Immune Analyses[bc] | | | | In Silico MHC Analyses[def] | | | FIV Test |
|---|---|---|---|---|---|---|---|---|---|---|---|---|---|
| No. | Peptides[a] | IFNγ | $CDC4^+$ T | $CD8^+$ T | Cyto | IFNγ | IL2 | $CDC4^+$ T | $CD8^+$ T | NetMHC | NetCTL | NetMHCII | E/S[c] |
| | Gag-p24 | | | | | | | | | | | | |
| 1 | Fp4-3 | — | — | — | N | ++ | + | ++++ | + | — | A1, B39 | 0101 | ↑ |
| 2 | Fp9-3 | ± | — | ++++ | +++ | ++++ | ++++ | ++ | ++++ | B27, A2, B7 | B27, A2, B8, B7, B62 | — | ↓ |
| 3 | Fp10-2 | — | — | — | — | ++ | ++ | + | ++++ | A24, B58, C14 | A24, A3 | 0101, 1101 | — |
| 4 | Fp10-3 | — | — | — | + | ++ | ++ | + | +++ | — | A3 | 0101 | — |
| *Map6* | Fp10-2/3[at] | N | N | N | N | — | +++ | — | — | A24, C14, B58, A3 | A24, A3 | 0101, 1101 | ↓ |
| 5 | Fp14-1 | ++ | + | ++ | +++ | ++ | ++++ | ++ | + | A3, B44 | A26, A1, B39, B58 | — | — |
| 6 | Fp14-3 | ++ | + | +++ | ++++ | ++ | ++ | ++ | ++ | A24, B27, B44, C14 | A24 | 0101, 1101, 1501 | — |
| 7 | Fp14-4 | ± | ++ | +++ | ++++ | ++ | ± | +++ | +++ | A24, C14 | A24, B8 | 0101, 0701, 0401, 1101 | — |

TABLE 9-continued

Selection of T-cell epitopes on FIV proteins using HIV+ human subjects and FIV-vaccinated cats

| | FIV Epitope | HIV+ Human Subjects Functional Immune Analyses[b,c] | | | | FIV-Vaccinated Cats Functional Immune Analyses[b,c] | | | | In Silico MHC Analyses[d,e,f] | | | FIV Test |
|---|---|---|---|---|---|---|---|---|---|---|---|---|---|
| No. | Peptides[a] | IFNγ | CDC4+ T | CD8+ T | Cyto | IFNγ | IL2 | CDC4+ T | CD8+ T | NetMHC | NetCTL | NetMHCII | E/S[c] |
| Map3 | Fp14-3/4a | N | N | N | N | +++ | ++++ | +++ | +++ | A24, B27, B44, C14 | A24, B8 | 0101, 1101, 0401, 1501 | — |
| | Gag-MA | | | | | | | | | | | | |
| 8 | FMA1 | N | N | N | N | ++++ | — | +++ | ++++ | A3, B58 | — | — | N |
| 9 | FMA2 | N | N | N | N | ++ | ++ | ++++ | ++++ | B44, A3, C12, A1 | B39, A3 | — | N |
| | Gag-NC | | | | | | | | | | | | |
| 10 | FNC1 | N | N | N | N | +++ | — | +++ | +++ | A3 | — | — | N |
| 11 | FNC2 | N | N | N | N | ++++ | ++++ | — | ++++ | A2, B7 | A2, B7, B62 | 0101 | N |
| | Pol-RT | | | | | | | | | | | | |
| 12 | FRT3-3 | ++++ | — | ++++ | ++++ | ± | ++ | ++ | +++ | B27, A3 | B27 | 0101, 0701 | ↑ |
| 13 | FRT3-4 | — | — | ++ | ++++ | ++ | ++ | + | +++ | B27, A3 | A3, B27, B62, B8, B39 | 0101, 0301, 0701 | ↓ |
| Map2 | FRT3-3/4a | N | N | N | N | +++ | ++++ | — | +++ | B27, A3 | A3, B27, B62, B8, B39 | 0101, 0301, 0701, 1501 | ↓ |
| 14 | FRT3-5 | | | | | + | ++ | ± | +++ | — | A3 | 1101 | ↓ |
| | FRT3-4/5[at] | N | N | N | N | — | +++ | — | — | B27, A3 | A3, B27, B39 | 1101 | — |
| 15 | FRT7-1 | — | — | ++ | +++ | ++ | ++++ | ++++ | ++++ | B27, B58, A24 | B27, B58, A24, B7 | 0101 | N |
| 16 | FRT7-2 | — | — | ++ | ++++ | ++ | — | ++++ | ++++ | B7, B58, A1 | B58 | — | N |
| Map5 | FRT7-1/2a | N | N | N | N | +++ | +++ | +++ | +++ | B27, B7, A24, B58 | B27, B58, A24, B7 | 0101 | N |
| | Pol-PR | | | | | | | | | | | | |
| 17 | FPR1 | N | N | N | N | — | — | ++++ | ++++ | B27 | B44, B27, B8 | — | N |
| 18 | FPR2 | N | N | N | N | ++++ | ++++ | ++++ | ++++ | A2 | A2 | 0101, 1302, 0701 | N |
| | Pol-IN | | | | | | | | | | | | |
| 19 | FIN7-1 | — | — | +++ | ++ | ++++ | ++++ | ++++ | ++++ | A2, A24, A3, B44 | A2, B62 | 0101, 0401, 0701 | N |
| | Env-TM | | | | | | | | | | | | |
| 20 | FTM4-3 | — | — | — | N | ++++ | ++++ | ++ | ++ | A3, A24, A2, B58 | B39, A24, A26, A1, A2 | — | N |
| 21 | FTM8(20) | — | ++ | ++++ | N | ++ | — | ++ | ++++ | A2 | A2 | 0404, 0101 | N |
| | Env-SU | | | | | | | | | | | | |
| 22 | FSU4 | — | — | — | N | +++ | — | +++ | +++ | A1, B27 | B62, A3 | — | N |

Table 9 footnotes:
[a]Bold italics peptides used in MAP vaccine study.
[b]Frequency of responders: 0%-1.4%(—), 1.5%-12.4% (±), 12.5%-25% (+), 25.1%-40% (++), 40.1%-54% (+++), >54% (++++).
[c]Abbreviations: CD4+ T-cell (CD4+ T) and CD8+ T-cell (CD8+ T) proliferation, cytolysin/cytotoxin (cyto) production, enhancer/suppressor (E/S) analysis of HIV infection.
[d]Bold HLA supertypes [5] or bold 2- or 4-digit resolution alleles similar to those HLA alleles in cats.
[e]MHC based network for HLA class I (Net MEC), class II (NetMECII), and HLA supertypes for cytotoxic T lymphocyte (NetCTL).
[f]Bold HLA supertypes or 2-digit alleles express HLA proteins (i.e., allotypes) that resemble at the peptide binding pockets to feline leukocyte antigens (FLAs) of the domestic cats.

TABLE 10

Selection of T-cell epitopes on HIV-1 proteins using HIV+ human subjects

| | FIV Epitope | Functional Immune Analyses[b,c] | | | | | | In Silico MHC Analyses[e,f,g] | | | HIV Test |
|---|---|---|---|---|---|---|---|---|---|---|---|
| No. | Peptides[a] | IFNγ | CyCD4 | CyCD7 | CDC4+ T | CD8+ T | LANL CTL[d] | NetMHC | NetCTL | NetMHCII | E/S[c] |
| | Gag-p24 | | | | | | | | | | |
| 1 | Hp4-3 | | | | | | B27, C08, _A2_, C07 | A3, _A2_ | — | — | |
| 2 | Hp9-3(10-3) | ++++ | + | +++ | — | ++++ | B8, A24, A2 | B44, A3, B7 | B8, B44, A26, B39 | — | |
| 3 | Hp10-2(11-2) | | | | | | B27, A2, A3 | A24 | A26 | 1302, 0101, 1501 | |
| 4 | Hp10-3(11-3) | | | | | | B27, _A3_, A2, B62 | — | A3, B62, A1 | 1302 | |

TABLE 10-continued

Selection of T-cell epitopes on HIV-1 proteins using HIV+ human subjects

| No. | FIV Epitope Peptides[a] | Functional Immune Analyses[b,c] | | | | | | In Silico MHC Analyses[e,f,g] | | | HIV Test E/S[c] |
|---|---|---|---|---|---|---|---|---|---|---|---|
| | | IFNγ | CyCD4 | CyCD7 | CDC4+ T | CD8+ T | LANL CTL[d] | NetMHC | NetCTL | NetMHCII | |
| — | Hp10-2/3 (11-2/3) | | | | | | B27, B62, *A3*, A2, B7 | A24 | B62, *A3*, A26, A1 | 1302, 0101, 1501, 1101 | |
| 5 | Hp14-1(15-1) | ++++ | ++++ | ++++ | — | ++++ | B44, B58, C05, B7 | B44, C15, B58 | B58 | — | ↓ |
| 6 | Hp14-2(15-2) | ++ | ++++ | ++++ | — | ++++ | B27 | B44 | A24, A26 | — | ND |
| 7 | Hp14-3(15-3) | ++++ | ++++ | ++++ | — | ++++ | — | B44 | A24 | — | ↓ |
| — | Hp14-2/3 (15-2/3) | | | | | | B27 | B44 | A24, A26 | — | ND |
| Gag-MA | | | | | | | | | | | |
| 8 | HMA1 | | | | | | A3, B27, B7, B35 | A3, A1 | A3, B27 | — | ND |
| 9 | HMA2 | | | | | | A2, B8, *A1*, *B44* | *A1*, A3, B27, A2, B58, *B44* | *A1*, B39, B8, B62, A2 | 0101, 0404, 0405 | |
| Gag-NC | | | | | | | | | | | |
| 10 | HNC1 | | | | | | *A3* | *A3* | — | — | ND |
| 11 | HNC2 | | | | | | — | A3 | B44, B27 | — | ND |
| Pol-RT | | | | | | | | | | | |
| 12 | HRT3-3 | + | ++++ | ++++ | ++ | +++ | — | B27, A3 | — | — | |
| 13 | HRT3-4 | + | ++++ | ++++ | ++ | +++ | A3 | B27, A3 | A3 | — | |
| — | HRT3-3/4 | | | | | | A3 | B27, A3 | A3 | — | |
| 14 | HRT3-5 | — | ++++ | ++++ | +++ | ++++ | — | B27 | B8, B62 | 1101 | ND |
| — | HRT3-4/5 | | | | | | A3 | B27, A3 | A3, B8, B62 | 1101 | ND |
| 15 | HRT7-1 | | | | | | B27 | A24, A1, B27 | B58, A24, B8 | 0404 | ND |
| 16 | HRT7-2 | | | | | | B7 | B7, B27 | A24 | — | ND |
| — | HRT7-1/2 | | | | | | B7, B27 | A24, B27, A1, B7 | A24, B58, B8 | 0404 | ND |
| Pol-PR | | | | | | | | | | | |
| 17 | HPR1 | | | | | | A3, *A2*, A1 | B27, *A2*, A24 | A24, B27 | — | ND |
| 18 | HPR2 | | | | | | *A2* | *A2* | — | — | ND |
| Pol-IN | | | | | | | | | | | |
| 19 | HIN7-1 | — | — | — | | + | A11, B44 | C5 | A3 | 0101 | ND |
| Env-TM | | | | | | | | | | | |
| 20 | HTM4-3 | | | | | | B8, A24, C07 | A2 | — | — | ND |
| 21 | HTM8(20) | — | | | + | ++++ | A3, A1, *A2* | *A2*, A3, B58, C12, A1 | B62, *A2*, A3, B58, B7 | 1101, 0101 | |
| Env-SU | | | | | | | | | | | |
| 22 | HSU4 | — | | | + | + | *B27*? | C14, A24, B44, *B27* | A24, *B27*, A3, B44 | 0701 | ND |

Table 10 footnotes:
[a] Bold italics peptides are the HIV-1 counterpart of the FIV peptides used in MAP vaccine study.
[b] Frequency of responders: 0%-1.4%(—), 1.5%-12.4% (±), 12.5%-25% (+), 25.1%-40% (++), 40.1%-54% (+++), >54% (++++).
[c] Abbreviations: CD4+ T-cell (CD4+ T) and CD8+ T-cell (CD8+ T) proliferation, cytolysin and cytotoxin production of CD4+ (CyCD4) and CD8+ (CyCD8) T cells; enhancer and suppressor (E/S) analysis of HIV infection.
[d] Bold HLA supertypes [5] or bold 2- or 4-digit resolution alleles similar to those HLA alleles in cats.
[e] HLA supertypes [5] or 2- or 4-digit resolution alleles.
[f] MHC based network for HLA class I (Net MEC), class II (NetMECII), and HLA supertypes or 2-digit alleles for cytotoxic T lymphocyte (NetCTL).
[g] Bold HLA supertypes or 2-digit alleles common with bolded ones in LANL CTL; underline/italics common with underline/italics alleles under LANL CTL.

TABLE 11

Sequence conservation in Hp15/Fp14 pools of viral p24 proteins

Subtype-B HIV-1 Hp15 Peptides

| | |
|---|---|
| Hp15-1 | RAEQASQEVKNWMTE |
| Hp15-2 | ASQEVKNWMTETLLV |
| Hp15-3 | VKNWMTETLLVQNAN |

TABLE 11-continued

Sequence conservation in Hp15/Fp14 pools of viral p24 proteins

| Subtypes/ Strains | Hp15/p14 Peptide Pool | Compared to HIV-1(B) Identity | (Similarity) |
|---|---|---|---|
| HIV-1 (B) | RAEQASQEVKNWMTETLLVQNAN<br>*********** ************* | | |
| HIV-1 (A) | RAEQATQEVKGWMTETLLVQNAN<br>******.*.****.****** | 91% | (100%) |
| HIV-1 (C) | RAEQATQDVKNWMTDTLLVQNAN<br>******..*.******.***** | 87% | (100%) |
| HIV-1 (D) | RAEQASQDVKNWMTETLLVQNAN<br>********.*.********* | 96% | (100%) |
| SIV CPZ | RAEQASQEVKTWMTDTLLVQNAN<br>**...**.*.**** | 91% | (100%) |
| SIV Mac251/Mac239 | RAEQTDAAVKNWMTQTLLIQNAN<br>.::::::*.:*** | 74% | (96%) |
| FIV (A, B, D) [FP14] | DQEQNTAEVKTYLKQSLSIANAN<br>.:::::*.:*** | 39% | (65%) |
| FIV (C) | DQEQNTAEVKTYLKQSLSLANAN | 39% | (70%) |

| Subtype-B FIV Fp14 Peptides | |
|---|---|
| Fp14-1 | DQEQNTAEVKLYLK |
| Fp14-2 | EQNTAEVKLYLKQSL |
| Fp14-3 | AEVKLYLKQSLSIA |
| Fp14-4 | KLYLKQSLSIANAN |

Table 11 footnotes:
All Hp15/SP14/Fp14 sequences are compared to HIV-1 subtype B sequence. Counterpart of Hp15 peptide pool is Fp14 on FIV p24 and Sp14 pool on SIV-Mac251 p24. HIV-1 and SIV determined by LANL QuickAlign tool. Symbols: identical aa (*); closely similar aa (:); moderately similar aa (.); and underlined aa residue differs from the corresponding aa on HIV-1 (B).

```
Table 11 sequences:
RAEQASQEVKNWMTE (SEQ ID NO: 90),

ASQEVKNWMTETLLV (SEQ ID NO: 59),

VKNWMTETLLVQNAN (SEQ ID NO: 91),

RAEQASQEVKNWMTETLLVQNAN (SEQ ID NO: 92),

RAEQATQEVKGWMTETLLVQNAN (SEQ ID NO: 93),

RAEQATQDVKNWMTDTLLVQNAN (SEQ ID NO: 94),

RAEQASQDVKNWMTETLLVQNAN (SEQ ID NO: 95),

RAEQASQEVKTWMTDTLLVQNAN (SEQ ID NO: 96),

RAEQTDAAVKNWMTQTLLIQNAN (SEQ ID NO: 97),

DQEQNTAEVKLYLKQSLSIANAN (SEQ ID NO: 98),

DQEQNTAEVKTYLKQSLSLANAN (SEQ ID NO: 99),

DQEQNTAEVKLYLK (SEQ ID NO: 24),

EQNTAEVKLYLKQSL (SEQ ID NO: 75),

AEVKLYLKQSLSIA (SEQ ID NO: 52),

KLYLKQSLSIANAN (SEQ ID NO: 100).
```

TABLE 12

Sequence conservation in HRT3-3/HRT3-4 & FRT3-3/FRT3-4

| Subtype-B HIV-1 RT3 Peptides | |
|---|---|
| HRT3-3 | KKDSTKWRKLVDFRE |
| HRT3-4 | WRKLVDFRELNKR |

| Subtypes/ Strains | Overlap HRT3-3/HRT3-4 and Overlap FRT3-3/FRT3-4 Pools | Compared to UCD1 Identity | (Similarity) |
|---|---|---|---|
| HIV-1 UCD1 (B) | KKKDSTKWRKLVDFRELNKR<br>******************** | | |
| HIV-1 (A) | KKKDSTKWRKLVDFRELNKR<br>******************** | 100% | (100%) |
| HIV-1 (C) | KKKDSTKWRKLVDFRELNKR<br>******************** | 100% | (100%) |
| HIV-1 (D) | KKKDSTKWRKLVDFRELNKR<br>******************** | 100% | (100%) |
| SIV CPZ | KKKDSTKWRKLVDFRELNKR<br>**.*.*.*******: | 100% | (100%) |
| SIV Mac251 | KKKDKNKWRMLDFRELNRV<br>****.*.***.*.******* | 70% | (90%) |

TABLE 12-continued

Sequence conservation in HRT3-3/HRT3-4 & FRT3-3/FRT3-4

| FIV (A, C) | KKK-SGKWRMLIDFRELNKL | 75% | (80%) |
|---|---|---|---|
| | *** * *** *:*** *** | | |
| FIV (B, D) [FRT3-3/3-4] | KKK-SGKWRMLIDFRVLNKL | 70% | (75%) |

Subtype-B FIV FRT3 Peptides

| FRT3-3 | KKK-SGKWRMLIDFRV |
|---|---|
| FRT3-4 | WRMLIDFRVLINKL |

Table 12 footnotes:
Overlapping HRT3-3/HRT3-4 peptide pool counterpart of overlapping FRT3-3/FRT3-4 peptide pool. HIV-1 and SIV determined by LANL QuickAlign tool.
Symbols: identical aa (*); closely similar aa (:); moderately similar aa (.); and underlined aa residue differs from the corresponding aa on HIV-1 (B).

```
Table 12 sequences:
KKKDSTKWRKLVDFRE (SEQ ID NO: 63),

WRKLVDFRELNKR (SEQ ID NO: 64),

KKKDSTKWRKLVDFRELNKR (SEQ ID NO: 29),

KKKDKNKWRMLIDFRELNRV (SEQ ID NO: 62),

KKK-SGKWRMLIDFRELNKL (SEQ ID NO: 89),

KKK-SGKWRMLIDFRVLNKL (SEQ ID NO: 88),

KKK-SGKWRMLIDFRV (SEQ ID NO: 67),

WRMLIDFRVLINKL (SEQ ID NO: 101).
```

TABLE 13

HLA-A and HLA-B supertypes of selected global populations with moderate to high prevalence of people living with HIV

| Continent/Country/Race [Pop. No., 2014] [a] | HIV+ Pop. No. Living (Death; HIVPR) in 2013 [b] | Study Year [c] | Study Population No. (Source) [c] | Prevalence of HLA Class-I Supertypes [% for each locus] [defgh] | | | |
|---|---|---|---|---|---|---|---|
| | | | | 1st | 2nd | 3rd | 4th |
| North America | | | | | | | |
| U.S. African American [318,892,096] | 1,200,000 (17,000; 0.6) | 2013 | 416,581 (BM Registry) | **B7\*\* [40.0] | A3 [32.2] | A1 [27.3] | A2** [25.9] |
| U.S. Caucasian [See above] | See above | 2013 | 1,242,890 (BM Registry) | B44 [31.3] | A2 [31.0] | **B7\*\* [29.9] | A3** [29.0] |
| Sub-Sahara Africa | | | | | | | |
| Kenya Black [45,010,056] | 1,646,000 (57,500; 6.1) | 2002 | 265 (Anthro Study) | A3 [31.7] | **B7\*\* [31.2] | A1 [29.7] | A2** [28.4] |
| Nigeria Black [177,155,760] | 3,426 (239,700; 3.1) [i] | 2009 | 258 (SC Registry) | **B7\*\* [47.8] | A3 [33.2] | A1 [28.7] | A2** [27.0] |
| South Africa Black [48,375,644] | 6,070 (235,100; 17.9) [i] | 2012 | 204 (Anthro Study) | A1 [35.0] | **B7\*\* [29.7] | A2 [29.3] | A3** [24.7] |
| S. Africa Caucasian [See above] | See above | 2012 | 102 (Anthro Study) | A1 [32.4] | A2 [31.4] | **B7\*\* [29.3] | B44** [26.5] |
| Europe | | | | | | | |
| France Caucasian [66,259,012] | 150,000 (1,700; 0.4*) | 2013 | 4,815 (BM Registry) | **B7\*\* [32.1] | B44 [29.9] | A2 [29.2] | A3** [28.9] |
| Poland Caucasian [38,346,280] | 27,000 (200*; 0.1*) | 2013 | 2,907 (BM Registry) | A1 [31.5] | B44 [30.7] | **B7\*\* [29.1] | A2** [28.9] |
| Asia & SE Asia | | | | | | | |
| China Asian [1,355,692,544] | 780,000 (26,000; 0.1*) | 2008 | 101 (Anthro Study) | A3 [50.0] | B62 [46.0] | A2 [25.7] | **B7\*\*** [20.8] |
| Thailand Asian [67,741,400] | 443,100 (20,800; 1.1) | 2008 | 16,807 (SC Registry) | A3 [46.4] | B62 [39.4] | A2 [29.4] | B44 [23.3] |

| Continent/Country/Race [Pop. No., 2014] [a] | Prevalence of HLA Class-I Supertypes [% for each locus] [defgh] | | | | | |
|---|---|---|---|---|---|---|
| | 5th | 6th | 7th | 8th | 9th | 10th |
| North America | | | | | | |
| U.S. African American [318,892,096] | B44 [22.1] | B27\* [15.4] | B58\* [15.1] | A24 [14.7] | B8 [3.9] | B62 [3.5] |
| U.S. Caucasian [See above] | A1 [28.9] | B27\* [12.8] | B8 [11.6] | A24 [11.0] | B62 [9.6] | B58\* [5.0] |

TABLE 13-continued

HLA-A and HLA-B supertypes of selected global populations with moderate to high prevalence of people living with HIV

| | | | | | | |
|---|---|---|---|---|---|---|
| Sub-Sahara Africa | | | | | | |
| Kenya Black | B58* | B27 | B44 | A24 | B8 | B62 |
| [45,010,056] | [24.3] | [22.7] | [16.4] | [10.1] | [3.1] | [1.6] |
| Nigeria Black | B44 | B58* | B27 | A24 | B62 | B8 |
| [177,155,760] | [17.7] | [15.7] | [15.5] | [11.1] | [2.6] | [0.58] |
| South Africa Black | B58* | B27 | B44 | A24 | B8 | B62 |
| [48,375,644] | [23.3] | [19.6] | [18.4] | [11.0] | [6.4] | [2.5] |
| S. Africa Caucasian | A3 | B8 | B62 | B27 | A24 | B58* |
| [See above] | [25.1] | [13.4] | [12.2] | [9.7] | [9.6] | [8.8] |
| Europe | | | | | | |
| France Caucasian | A1 | B27* | A24 | B8 | B58* | B62 |
| [66,259,012] | [28.0] | [17.6] | [13.8] | [8.5] | [6.4] | [5.4] |
| Poland Caucasian | A3 | B27* | A24 | B62 | B8 | B58* |
| [38,346,280] | [27.0] | [13.8] | [12.6] | [11.0] | [10.0] | [5.3] |
| Asia & SE Asia | | | | | | |
| China Asian | B44 | A24 | B27 | A1 | B58* | B8 |
| [1,355,692,544] | [16.4] | [16.3] | [8.5] | [8.0] | [7.4] | [10] |
| Thailand Asian | B7** | A24 | B58* | B27 | A1 | B8 |
| [67,741,400] | [18.3] | [17.5] | [10.1] | [8.7] | [6.7] | [0.5] |

Table 13 footnotes:
[a] Total population number (Pop. No.) of the specific country in 2014.
[b] Populations dead or living with HIV/AIDS and % HIV prevalence rate in adults for year 2013 (HIVPR) from CIA World Factbook using http://www.indexmundi.com/g/.
[c] Allele Frequencies in Worldwide Populations database (www.allelefrequencies.net/hla6006a.asp): USA NMDP European Caucasian, USA NMDP African American, Nigeria (258), Kenya Luo (265), South African Black (204), South African Caucasians (102), France Lyon (4815), Poland pop 3 (2907), China Yunnan Han (101), and Thailand pop 4 (16807) from Bone Marrow (BM) Registry, Stem Cell (SC) Registry, or Anthropology (Anthro) Study.
[d] Supertypes based on [5] and Society for Biomedical Diabetes Research database: www.socbdr.org/rds/authors/unit_tables_conversions_and_genetic_dictionaries/genotype_ serotype_and_supertype_classification/
[e] Bolded supertypes: >20% of a locus.
[f] HLA-A or HLA-B supertypes total to 100% each based on codominant expression at each HLA locus.
[g] Supertype with multiple alleles associated with slow (*) or rapid (**) progression to AIDS.
[h] HLA-A29, B*4415, B48, and B*8201 excluded due to supertype status is unknown.
[i] No reason provided for the sudden large number of death reported in 2013 which appear to compensate for the low numbers in previous years.

TABLE 14

Comparative Analysis of Selected T-Cell Epitopes

| FIV Epitope Peptide | Viral Protein Region | HIV+ Human Subjects | | | | | FIV-Vaccinated Cats | | | | | E/S tMAP | E/S pMAP |
|---|---|---|---|---|---|---|---|---|---|---|---|---|---|
| | | IFNγ | CD4 | CD8 | Cyto | E/S | IFNγ | IL2 | CD4 | CD8 | E/S | | |
| Fp4-3 | p24 | — | — | — | N | N | ++ | + | ++++ | + | ↑ | N | ↑** |
| Fp14-1 | p24 | ++ | + | ++ | +++* | — | ++ | ++++ | ++ | + | | N | ↑** |
| FRT3-3 | RT | ++++ | — | ++++ | ++++* | — | | ++ | ++ | +++ | ↑ | ↓+ | ↓X |
| FRT3-4 | RT | — | — | ++ | ++++* | — | ++ | ++ | + | +++ | ↓ | | |
| FMA1 | MA | LANL | Sep. | Sep. | Sep. | N | ++++ | | +++ | ++++ | N | N | N |
| FMA2 | MA | LANL | Sep. | Sep. | Sep. | Aug. | ++ | ++ | ++++ | ++++ | Prog | Prog++ | Prog+T |
| Fp9-3 | p24 | ± | — | ++++ | +++* | ↓ | ++++ | ++++ | ++ | ++++ | ↓ | ↑X | N+ |
| Fp10-2 | p24 | — | — | — | — | N | ++ | ++ | + | ++++ | — | ↓X | N |
| Fp10-3 | p24 | — | — | — | + | N | ++ | ++ | + | +++ | — | | |
| Fp14-3 | p24 | ++ | + | +++ | ++++ | — | ++ | ++ | ++ | ++ | — | ↓+ | Prog++ |
| Fp14-4 | p24 | ± | ++ | +++ | ++++ | — | ++ | | +++ | ++++ | — | | |
| FNC2 | NC | Sep. | Sep. | Sep. | Sep. | N | ++++ | ++++ | — | ++++ | N | N | N |
| FPR1 | PR | LANL | Sep. | Sep. | Sep. | Aug. | — | — | ++++ | ++++ | Prog | Prog | Prog |
| FPR2 | PR | LANL | Sep. | Sep. | Sep. | N | ++++ | ++++ | ++++ | ++++ | N | N | N |
| FRT3-5 (FRT3-4) | RT | — | — | ++ | +++* | Aug. | + | ++ | | +++ | —X | —X | N |
| FRT7-1 | RT | — | — | ++ | +++* | Aug. | ++ | ++++ | ++++ | ++++ | Prog | Prog+ | Prog++ |
| FRT7-2 | RT | — | — | ++ | ++++* | Aug. | ++ | ± | ++++ | ++++ | | | |
| FIN7-1 | IN | — | — | +++ | ++ | Aug. | ++++ | ++++ | ++++ | ++++ | Prog | ProgX | Prog++ |
| FTM4-3 | TM | — | — | — | N | N | ++++ | ++++ | ++ | ++ | N | N | N |
| FTM8 | TM | — | ++ | ++++ | Sep. | Aug. | ++ | — | ++ | ++++ | Prog | Prog? | Prog? |
| FSU4 | SU | — | — | — | N | N | +++ | — | +++ | +++ | N | N | N |

TABLE 14-continued

Comparative Analysis of Selected T-Cell Epitopes

| FIV Epitope Peptide | Humans & Cats Biologic Score 2.00 | In Silico Analysis | | | MHC Score | Total Score |
|---|---|---|---|---|---|---|
| | | NetMHCl [3.4] | NetCTL [1.2] | NetMHCII [2.2] | | |
| Fp4-3 | 2.00 | — | A1, B39 | 0101 | 0.33 | 6.33 |
| Fp14-1 | 2.35 | A2, A3, B44 | A26, A1, B39, B58 | — | 2.00 | 8.00 |
| FRT3-3 | | A3, B27, A24, A2, C3 | A3, A2, A24, B27, B8 | 0301, 0405, 1501 | 3.67 | 10.72 |
| FRT3-4 | 1.25 | A1, C15 | B39 | — | | |
| FMA1 | 2.00 | A3, B58 | — | — | 1.00 | 4.75 |
| FMA2 | 2.59 | B44, A3, A1 | B39, A3 | — | 2.33 | 8.33 |
| Fp9-3 | 2.20 | B27, A2, C6, C7, B7 | B27, A2, B8, B7, B62 | — | 3.00 | 10.77 |
| Fp10-2 | | A24, C14, B58, A3 | A24, A3 | 0101, 1101 | 2.33 | 8.93 |
| Fp10-3 | 2.18 | | | | | |
| Fp14-3 | | A24, B27, B44, C14 | A24, B8 | 0101, 1101, 0401, 1501, 0701 | 3.00 | 9.54 |
| Fp14-4 | 3.00 | | | | | |
| FNC2 | 2.00 | N | N | N | ? | ? |
| FPR1 | 2.00 | B27 | B44, B27, B8 | — | 2.33 | 8.33 |
| FPR2 | 2.70 | A2, C3, C5 | A2 | 0101, 1302, 0701 | 1.00 | 7.00 |
| FRT3-5 (FRT3-4) | 2.87 | A3, B27 | A3, B27, B8 | 1101, 0301, 0101, 0701 | 2.67 | 10.77 |
| FRT7-1 | | B27, B7, A24, A1, B58 | B27, B58, A24, B7 | 0101 | 3.67 | 12.28 |
| FRT7-2 | 2.00 | | | | | |
| FIN7-1 | 2.29 | A2, A24, A3, B44, C14 | A2, B62 | 0101, 0401, 0701 | 2.67 | 8.67 |
| FTM4-3 | 2.57 | A3, A24, A2, B58, C14 | B39, A24, A26, A1, A2 | — | 2.67 | 9.54 |
| FTM8 | 1.86 | A2 | A2 | 0404, 0101 | 1.00 | 8.71 |
| FSU4 | | A1, B27, C15 | B62, A3 | — | 1.67 | 7.25 |

Table 14 footnotes:
CD8+ T-cell cytotoxins (perforin, GrzA & B) (Cyto); CD4+ T-cell cytotoxins also high (*); MAP(Fp4-3/Fp14-1) (**); Viral enhancement or suppression (E/S); Tat-MAP (tMAP);
Palmitoyled Pam-MAP (pMAP); Los Alamos National Laboratory database (LANL); In progress (Prog); Not done (N); To be completed in September 30 (Sep.) or August 31
(Aug); Frequency of responders: 0%-1.4% (—), 1.5%-12% (±), 12.5%-25% (+), 26%-40% (++), 41%-54% (+++), >54% (++++). Total Score = MHC Score plus 3X Biologic Score.
Bolded HLA alleles have similar peptide binding region or pocket binding pattern with those of FLA alleles. FLA prediction based on FLA/HLA mixed composite analysis by EpiVax
Inc: FLA/HLA-*A3(75%) > B27(53%) > B44(33%) = A24(33%) = B7(33%) > A2(17%) = A1(13%) > B62(7%) = B8(7/0) > A26/B39/B58(0%);
FLA/HLA-
DRB1*0101(40%) > 0301(29%) > 0401/0404/0405(20%) > 1501(13%) > 0801(7%) > 1101(4%).

Materials and Methods for Example 2

Animals and Immunization.

Specific pathogen free (SPF) cats at the age of 8 weeks were purchased from Liberty Laboratories or bred at University of Florida. The SPF cats were distributed into groups as shown in FIG. 6B and acclimated for 3 weeks before the first immunization. All cats received a total of three immunizations with either MAP vaccine (with adjuvant or adjuvant/IL12), FD-1 adjuvant, FD-1 adjuvant/IL12, or PBS at an interval of 6 weeks by subcutaneous or intradermal routes.

CD4$^+$ and CD8$^+$ T-Cell Proliferation.

Carboxyfluorescein diacetate succinimide ester (CFSE)-proliferation analysis was according to the manufacturer's protocol (Invitrogen-Fisher, Carlsbad, Calif.) and processed as previously described (Roff et al. (2015)) using the following modifications: anti-feline CD3 antibody ((clone NZM1), a generous gift from T. Miyazawa (Univ. of Tokyo, Japan)) in combination with APC-conjugated anti-mouse IgG3 (Southern Biotech, Birmingham, Ala.), PE-conjugated anti-feline CD4 antibody (Southern Biotech), and anti-feline CD8 antibody (gift from N. Gengozian, University of Tennessee (Gengozian et al. (1997))) in combination with PE/Cy7-conjugated anti-mouse IgG2b (Southern Biotech) to detect the proliferation of feline CD3$^+$CD4+ T cells and feline CD3$^+$CD4$^+$ T cells. All results shown in the figures (FIGS. 7A-1, 7B-1, 7A-2, 7B-2, 7A-3, 7B-3) are after subtracting the average value of each results from all control cats. The threshold of CFSE proliferation is $\geq 0.5$ CFSE$^{low}$.

IFNγ and IL2 Production Response.

The feline IFNγ and L2 ELISpot analyses of PBMC to FIV MAPs and peptides were performed as previously described (Abbott et al. (2012)) using feline IFNγ modular kit (R&D Systems, Minneapolis, Minn.) and feline IL2 modular kit (R&D Systems). All results shown in the figures (FIGS. 8A-1, 8B-1, 8A-2, 8B-2, 8A-3, 8B-3) are after subtracting the average value of the results from all control cats. The threshold of the IFNγ and IL2 responses is $\geq 50$ spot forming units (SFU) per $10^6$ PBMC.

Cytokine, Cytolysin, and Cytotoxin mRNA Analyses.

Cytokine (IFNγ, IL2, TNFα), cytolysin (perforin), and cytotoxin (granzymes A and B) mRNA analyses were performed using PBMC from all cats as previously described (Aranyos et al. (2016); Omori et al. (2004)). The following modifications were made PCR amplification cycle of 35 for all cytokine mRNAs and perforin mRNA and 45 for granzymes A and B mRNAs. All results shown in the FIGS. 9A and 9B are after subtracting the average value of the results from all control cats. The threshold of $\geq 2\%$ relative density value.

Example 2—Immunogenicity of MAP Trial 2

Introduction

The goals of Multiple Antigenic Peptide (MAP) Trial 2 were to determine: 1) the immunogenicity of the MAP vaccine using four MAPs that provided the best immunogenicity in previous MAP Trial 1 and 2) the route of vaccination that induces the best immunogenicity to the peptide(s) composing the individual MAPs. All specific pathogen free (SPF) cats were vaccinated with MAP vaccine composed of 100 µg of each MAPs resulting in a total amount of 400 µg per vaccine dose, which was much lower than the total amount in the previous MAP Trial 1 by close to half.

The four MAPs used in MAP Trial 2 are shown in the order of most immunogenic on the left to the least immunogenic on the right (FIG. 6A). MAP4 was only slightly more immunogenic than MAP5 followed by MAP3 and then MAP2v. MAP4 and MAP3 consisted of two peptides from FIV p24 (Fp) which is FIV core protein. Whereas, MAP5 and MAP2v were formulated with peptides from FIV reverse transcriptase (FRT) which is a viral enzyme.

MAP consisted of palmitic acid (Pam) on the carboxyl-end of the lysine (K) backbone with two lysine branches on the amino-end of the MAP, and each lysine branch is attached to two identical FIV peptides resulting in four identical FIV peptides per MAP (FIG. 6B). MAP4 was composed of a single 15mer peptide Fp9 found on the central area of FIV p24, while MAP5 was an overlapping peptide (FRT7-1/2) of peptides FRT7-1 and FRT7-2 found in the central region of FIV RT. MAP3 was composed of an overlapping peptide (Fp-14-3/4) of peptides Fp14-3 and Fp14-4 located more towards the carboxyl-end of the FIV p24. Furthermore, MAP2v consisted of an overlapping peptide (FRT3-3/4) of peptides FRT3-3 and FRT3-4 located at the amino-end of the FIV RT.

The vaccination routes tested were subcutaneous (SQ; Vaccine Group 1) and intradermal (ID; Vaccine Group 2) vaccinations (FIG. 6B) with a total of three vaccinations at an interval of 6 weeks. Since most commercial feline vaccines use SQ route of vaccination which is routinely performed without anesthesia, current trial evaluated the immunogenicity of SQ vaccination compared to ID vaccination using the same adjuvant FD-1 as that used in MAP Trial 1. FD-1 adjuvant is composed of oil in water and safely used in commercial inactivated FIV and feline leukemia virus vaccines (Uhl et al. (2002)). Previous MAP Trial 1 also used ID vaccination, and its vaccine was supplemented with feline IL12 (5 µg/dose). In the current Trial 2, MAP vaccine for ID vaccination was also supplemented with feline IL12 (FIG. 6B) in order that the immunogenicity of current Trial 2 can be compared to the immunogenicity of the MAP vaccine from the previous Trial 1.

Vaccine Groups 1 and 2 consisted of seven SPF cats each (n=7, FIG. 6B). The Adjuvant Control Groups 3a and 3b and PBS-immunized Group 3c consisted of three SPF cats each (n=3), while non-immunized Control Group 3d consisted of one SPF cat (n=1). As much as possible, the SPF cats from different cat liters identified by the first two letters of their ID code were distributed evenly among the Vaccine Groups and Control Groups (FIG. 6B). All SPF cats were 10 weeks of age at the time of first immunization.

Immunogenicity Analyses Over Time

Base on previous MAP Trial 1, current Trial 2 evaluated the immunogenicity at 6 weeks post-$2^{nd}$ vaccination (FIGS. 7A-1, 7B-1, 8A-1, 8B-1), 3 weeks post-$3^{rd}$ vaccination (FIGS. 7A-2, 7B-2, 7A-3, 7B-3), and 6 weeks post-$3^{r}$ vaccination (FIGS. 7A-3, 7B-3). Similar immune parameters as Trial 1 were evaluated in Trial 2. The first parameter evaluated was the proliferation responses of CD4$^+$ T cells (FIGS. 7A-1, 7A-2, 7A-3) and CD8$^+$ T cells (FIGS. 7B-1, 7B-2, 7B-3) to individual MAPs and the FIV peptides composing each MAP. The assay consisted of a fluorescence activated cell sorting (FACS)-based carboxyfluorescein diacetate succinimide ester (CFSE)-proliferation analysis used in a combination with individually labeled antibodies to feline CD4, CD8, and CD3 to identify CD3$^+$CD4$^+$ T cells (or CD4$^+$ T cells) and CD3$^+$CD8$^+$ T cells (or CD8$^+$ T cells) (Aranyos et al. (2016)). FIV-specific activation of CD8$^+$ T cells can differentiate subpopulation of CD8$^+$ T cells into CD8$^+$ cytotoxic T lymphocytes (CTLs) which can kill FIV-infected cells in vaccinated cats which are challenged with FIV. Similarly, FIV-specific activation of CD4$^+$ T cells can differentiate subpopulation of CD4$^+$ T cells into CD4$^+$ CTLs which can also kill FIV-infected cells in vaccinated cats upon challenge with FIV (Abbas et al. (2015); Brown et al. (2010)). In addition, such vaccine-induced activation can induce subpopulation of CD4$^+$ T cells to become CD4$^+$ T-helper (Th) cells which can produce cytokines (IFN$\gamma$, IL2, tumor necrosis factor-$\alpha$ [TNF$\alpha$]) that directly or indirectly enhance FIV-specific CD8$^+$ CTL and CD4$^+$ CTL activities in vaccinated cats (Abbas et al. (2015); Brown et al. (2010)).

The second parameter evaluated was the ability of the peripheral blood mononuclear cells (PBMC) from vaccinated and control cats to produce IL2 and interferon-$\gamma$ (IFN$\gamma$) proteins in responses to FIV MAPs and peptides (FIGS. 8A-1, 8A-2, 8A-3, 8B-1, 8B-2, 8B-3) using feline IL2 and IFN$\gamma$ ELISpot assays (Aranyos et al. (2016); Abbott et al. (2012)). IL2 enhances the proliferation of FIV-specific CD4$^+$ T cells and CD8$^+$ T cells. IFN$\gamma$ is known enhance the FIV-specific CTL activities in vaccinated cats (Abbas et al. (2015)).

Lastly, the third parameter evaluated was the ability of PBMC from vaccinated and control cats at 6 weeks post-$3^{rd}$ vaccination/immunization to induce cytokines (IFN$\gamma$, IL2, TNF$\alpha$), cytolysin (perforin [Perf]) and cytotoxins (granzymes A [GrzA] and B [GrzB]) mRNAs in responses to FIV MAPs and peptides (FIGS. 9A-9B) using mRNA analysis system previously described by our laboratory (Aranyos et al. (2016)). FIV-specific CTLs release perforin, GrzA, and GrzB that destroys of FIV-infected cells. Since antibodies to feline perforin, GrzA, and GrzB molecules that can be used detect these proteins in ELISA, ELISpot, and FACS assays are not available for cats, current evaluation measured in place the mRNA levels to Perf, GrzA, and GrzB.

The average result of all control cats was subtracted from each immunogenicity result of the vaccinated cats shown in the figure (FIGS. 7A-1, 7A-2, 7A-3, 7B-1, 7B-2, 7B-3, 8A-1, 8A-2, 8A-3, 8B-1, 8B-2, 8B-3, 9A-9B). Therefore, the results from the control cats were not shown.

Vaccine-Induced CD4$^+$ T-Cell and CD8$^+$ T-Cell Proliferation.

The FIV-specific CD4$^+$ T-cell proliferation responses increased in frequency (total number of MAP and peptide bars) and magnitude (height of each MAP or peptide bar) with additional vaccination (FIGS. 7A-1 vs. 7A-3). Since T-cell responses are based on major histocompatibility complex (MHC) interaction with peptides (Abbas et al. (2015)), inactivated whole FIV virus (IWV) was used as a negative or minimal-response control stimulant, whereas T-cell mitogen concanavalin A (ConA) was used as a positive control. The comparison of the frequency between the FIV-specific responses at 3 weeks post-$3^{rd}$ vaccination and those at 6 weeks post-$3^{rd}$ vaccination in Trial 2 were about the same (FIGS. 7A-2 vs. 7A-3). Furthermore, the CD4$^+$ T cells from SQ MAP-vaccinated cats induced more FIV-specific CD4$^+$ T-cell proliferation responses than those from ID MAP-vaccinated cats (No. of grey bars greater than No. of blue bars; FIGS. 7A-1, 7A-2, 7A-3). The FIV-specific CD4$^+$ T-cell proliferation responses were more frequent and at a higher magnitude than those observed in the previous Trial 1 (data from Trial 1 not shown but provided in previous submission).

In previous Trial 1, the FIV-specific CD8$^+$ T-cell proliferation responses were substantially greater than FIV-specific CD4$^+$ T-cell proliferation responses (data not shown but provided in previous submission). In current Trial 2, CD4$^+$ T-cell proliferation responses were greater than FIV-specific CD8$^+$ T-cell proliferation responses (FIGS. 7A-1 vs. 7B-1; 7A-2 vs. 7B-2, 7A-3 vs. 7B-3). Notably, CD8$^+$ T cells from SQ MAP-vaccinated cats induced less FIV-specific CD4$^+$ T-cell proliferation responses than those from ID MAP-vaccinated cats (No. of blue bars less than No. of grey bars; FIGS. 7B-1, 7B-2, 7B-3), suggesting that SQ vaccination was more immunogenic.

Overall, strong CD4$^+$ T-cell and CD8$^+$ T-cell proliferation responses were observed by the 3$^{rd}$ vaccination in current Trial 2. Importantly, CD4$^+$ T-cell proliferation responses more than CD8$^+$ T-cell proliferation responses were observed in responses to FIV MAPs and peptides.

Vaccine-Induced IL2 and IFNγ Production.

The highest frequency of IL2 responses to FIV MAPs and peptides were observed in PBMC from vaccinated cats at 6 weeks post-2$^{nd}$ vaccination than those from 6 weeks post-3$^{rd}$ vaccination (FIGS. 8A-1 vs. 8A-3). The highest frequency of IL2 responses was observed to peptides FRT3-3, Fp14-4, and FRT7-2 at 6 weeks post-2nd vaccination, whereas the highest frequency of IL2 responses was observed to only peptide FRT3-4 (FIGS. 8A-1 vs. 8A-3). This observation suggested that modulation of epitope responses was occurring over time. In general, the frequency of IL2 production responses was similar between PBMC from SQ MAP-vaccinated cats and those from ID MAP-vaccinated cats (FIGS. 8A-1, 8A-2, 8A-3).

Similar to the time at the highest frequency of IL2 responses above, the highest frequency of IFNγ responses to FIV MAPs and peptides were observed in the PBMC from MAP-vaccinated cats at 6 weeks post-2$^{rd}$ vaccination than those at 6 weeks post-3$^{rd}$ vaccination (FIGS. 8B-1 vs. 8B-3). The most FIV-specific IFNγ responses were observed to FRT7-2 in PBMC from both SQ and ID MAP-vaccinated cats at 6 weeks post-2$^{rd}$ vaccination (rate of 100%), which decreased substantially by 3-6 weeks post-3$^{rd}$ vaccination (rates of 21.4% and 28.6%) (FIGS. 8B-1 vs. 8B-2; 8B-1 vs. 8B-3). In contrast, the IFNγ response rates to peptide FRT3-4 was only 2 of 14 (14.3%) at 6 weeks post-2$^{nd}$ vaccination but increased to 9 of 14 (64.3%) (FIGS. 8B-1 vs. 8B-3). These two observations suggested that modulation of epitope responses was occurring over time. A consistent observation made at all three time point post-vaccination is the more frequent IFNγ responses were observed in PBMC from ID MAP-vaccinated cats than in those from SQ MAP-vaccinated cats (FIGS. 8B-1, 8B-2, 8B-3). The latter observation may be due to the fact that ID vaccine contained IL12 supplementation which was missing in SQ vaccine. IL12 is known to enhance the production of IFNγ from PBMC (Abbas et al. (2015)).

Overall, the most consistent observation is the frequency of IL2 responses from PBMC from SQ vaccinated cats did not substantially differ from those from ID vaccinated cats over the different time(s) post-vaccination. In contrary, IFNγ responses were detected mostly in PBMC from ID vaccinated cats.

Vaccine-Induced mRNA Expressions of Cytokine, Perforin, and Granzymes A and B.

Preliminary cytokine/perforin/granzyme mRNA analyses demonstrate that the combination of peptides FRT3-3, FRT3-4, and overlap FRT3-3/4 induce the most mRNA expression of IFNγ, IL2, TNFα, and GrzA and an extremely low level of perforin in PBMC from one SQ MAP-vaccinated cat (FIG. 9A). The next most frequent mRNA expressions were for IL2, TNFα, and GrzA upon stimulation of PBMC from the same cat with peptide pool consisting of Fp14-3, Fp14-4 and overlap Fp14-3/4. However, no mRNA expression was detected to Fp9-3 stimulation, and only TNFα and IL2 mRNA expressions were detected when stimulated with peptide pool of FRT7-1, FRT7-2 and overlap FRT7-1/2. In the PBMC of ID MAP-vaccinated cats, IFNγ, L2, TNFα, GrzA and GrzB mRNA expressions were clearly detected upon stimulation with a peptide pool of Fp14-3, Fp14-4, and overlap Fp14-3/4 and with peptide pool of FRT3-3, FRT3-4, and FRT3-3/4 which had all except 112 expression (FIG. 9B). These preliminary results demonstrate that cytokine/perf/Grz mRNA expressions can be induced by FIV peptides in the PBMC from MAP-vaccinated cats. The peptide-specific induction of mRNA expression also suggests that CTL activities are also present in the PBMC from MAP-vaccinated cats.

Table 15. Selection of T-cell epitopes on FIV based on anti-lentiviral immunogenicity, feline leukocyte antigen (FLA) interaction, and lentiviral aa sequence conservation.

The immunogenicity results of 22 FIV peptides as determined from over 220 FIV peptides tested are shown in this table. All of these peptides had substantially high aa sequence conservation with counterpart HIV-1 sequence. The list includes those FIV peptides, which generally induced the most CD8$^+$ T-cell proliferation response and a moderate-to-high IFNγ and IL2 production in the T cells or PBMC from 6-10 FIV-vaccinated cats. In addition, these peptides were also analyzed for IFNγ production, CD4$^+$ and CD8$^+$ T-cell proliferation, and cytolysin (perforin) and cytotoxin (granzyme A (GrzA) and GrzB)) mRNA production of PBMC or T cells from 8-30 HIV$^+$ human subjects. The frequency of responders is based on the individual responses of the vaccinated cats or HIV$^+$ human subjects after subtraction of the average of the responses of PBMC or T cells from 6-8 non-vaccinated cats or 8-20 HIV-negative human subjects. Those FIV peptides that are not from p24 or RT have extremely low responses since the HIV$^+$ subjects used were on antiretroviral therapy (ART) which causes lower HIV-specific immune responses.

The threshold for positive IFNγ and IL2 ELISpot responses is ≥50 spot-forming units (SFU) per 10$^6$ PBMC. The threshold for CFSE-based CD4$^+$ and CD8$^+$ T-cell proliferation is ≥2% CD4$^+$ T-cell CFSE$^{low}$ or CD8$^+$ T-cell CFSE$^{low}$. The threshold of FACS-based intracellular cytokine staining (ICS) is ≥0.2%. The frequency of responders is shown as the percentage of the number of responders equal to or above the threshold level over the total tested and as follows: 0%-1.4% (−), 1.5%-12.4% (+), 12.5%-25% (+), 25.1%-40% (++), 40.1%-54% (+++), >54% (++++). The nine FIV peptides in black were used in the current MAP vaccine trial, whereas the 13 peptides in blue were not used. The four FIV peptides (FRT3-3, FRT3-4, Fp4-3, Fp14-1) in red box were used in pilot MAP vaccine study. The MAPs and their corresponding peptide(s) were also tested for their ability to enhance or suppress in vitro FIV infection of feline PBMC (E/S of peptides and E/S of MAP).

The ideal T-cell based FIV vaccine should contain vaccine peptides that induce high levels of CD8$^+$ T-cell proliferation responses along with high levels of cytolysin/cytotoxin mRNAs which include the induction of antiviral CD8$^+$ cytotoxic T lymphocyte (CTL) activity. Those FIV peptides that stimulate high levels of CD4$^+$ T-cell proliferation and IFNγ production in contrast may enhance FIV infection based on the following reasons. Activated CD4+ T cells with higher expression of FIV receptor (CD134 or OX40 is also activation marker) are more susceptible to FIV infection (Weinberg, 2002; Shimojima et al., 2004) Furthermore, IFNγ enhances in vitro FIV infection of PBMC (Tanabe and Yamamoto, 2001). The ideal CD8+ T cell-inducing vaccine peptides should have high sequence conservation with all AIDS lentiviruses at a sequence site where viral fitness is greatly affected with any major mutations.

These FIV peptides were analyzed for reactivity to human major histocompatibility complex (MHC) or human leukocyte antigen (HLA). Previously we have determined that cats' MHC or feline leukocyte antigen (FLA) molecules have binding pockets similar to HLA. The bolded HLA alleles have similar peptide binding pockets as FLA. Net-MHC3.4 server defines peptides that bind to HLA class I allotypes. Net-CTL1.2 defines peptides that have potential to bind to and induce CD8+ CTL activity. Net-MHC2.2 defines peptides that bind to HLA class II (HLA-DRB) allotypes. The in silico analyses indicate that the nine peptides used in current MAP vaccine trial have one or more epitopes with high potential to bind to FLA. Consequently, these peptides have a high potential to be immunogenic based also on the in silico algorithm as well as demonstrated by the biological activity shown under immunogenicity induced by PBMC or T cells from FIV-vaccinated cats.

TABLE 15

| FIV Epitope Peptide | Viral Protein Region | HIV+ Human Subjects | | | | FIV-Vaccinated Cats | | | | | E/S MAP | In Silico Analysis | | |
|---|---|---|---|---|---|---|---|---|---|---|---|---|---|---|
| | | IFNγ | CD4 | CD8 | Cyto | IFNγ | IL2 | CD4 | CD8 | E/S | | Net-MHC3.4 | Net-CTL1.2 | Net-MHC2.2 |
| Fp9-3 | p24 | ± | - | ++++ | +++* | ++++ | ++++ | ++ | ++++ | ↓ | - | B27, A2, B7 | B27, A2, B8 B7, B62 | - |
| Fp-14-3 | p24 | ++ | + | +++ | ++++ | ++ | ++ | ++ | ++ | - | - | A24, B27, B44, C14 | A24 | 0101, 1101, 1501 |
| Fp14-4 | p24 | ± | ++ | ++++ | ++++ | ++ | ± | +++ | ++++ | - | - | A24, C14 | A24, B8 | 0101, 0701, 0401, 1101 |
| FRT3-3 | RT | ++++ | - | ++++ | ++++* | ± | ++ | ++ | +++ | ↑ | ↓ | A3, B8 | B8, A24 | 0701 |
| FRT3-4 | RT | - | - | ++ | ++++* | ++ | ++ | + | +++ | ↓ | | A3, B27 | A3, B27, B39 | 0301, 1101 |
| FRT7-1 | RT | - | - | ++ | +++* | ++ | ++++ | ++++ | ++++ | ↓ | ↓ | B27, B58, A24 | B27, B58, A24, B7 | 0101 |
| FRT7-2 | RT | - | - | ++ | ++++* | ++ | - | ++++ | ++++ | ↓ | | ,B7, B58, A1 | B58 | - |
| FMA2 | MA | ++ | - | - | - | ++ | ++ | ++++ | ++++ | - | - | B44, A2, A3, A1 | B39, A3 | - |
| FTM8 | TM | - | ++ | ++++ | - | ++ | - | ++ | ++++ | - | - | A2 | A2 | 0404, 0101 |
| Fp4-3 | p24 | - | - | - | - | ++ | + | ++++ | + | ↑ | ↑ | - | A1, B39 | 0101 |
| Fp14-1 | p24 | ++ | + | ++ | +++ | ++ | ++++ | ++ | + | - | - | A3, B44 | A26, A1, B39, B58 | - |
| FRT3-5 | RT | - | - | ++ | ++++* | + | ++ | ± | +++ | - | - | - | A3 | 1101 |
| Fp10-2 | p24 | - | - | - | - | ++ | ++ | + | ++++ | -- | ↓ | A24, B58, C14 | A24, A3 | 0101, 1101 |
| Fp10-3 | p24 | - | - | - | + | ++ | ++ | + | +++ | -- | | - | A3 | 0101 |
| FMA1 | MA | + | - | - | - | ++++ | - | +++ | ++++ | N | N | A3, B58 | - | - |
| FNC1 | NC | ± | - | - | - | +++ | - | +++ | +++ | N | N | A3 | - | - |
| FNC2 | NC | ++ | - | - | + | ++++ | ++++ | - | ++++ | N | N | A2, B7 | A2, B7, B62 | 0101 |
| FPR1 | PR | + | - | - | - | - | - | ++++ | ++++ | - | - | B27, A2 | B44, B27, B8 | - |
| FPR2 | PR | - | - | - | - | ++++ | ++++ | ++++ | ++++ | ↓ | ↓ | A2 | A2 | 0101, 1302, 0701 |
| FIN7-1 | IN | - | - | +++ | ++ | ++++ | ++++ | ++++ | ++++ | ↓ | ↓ | A2, A24, A3, B44, C14 | A2, B62 | 0101, 0401, 0701 |
| FTM4-3 | TM | - | - | - | + | ++++ | ++++ | ++ | ++ | - | - | A3, A24, A2, B58, C14 | B39, A24, A26, A1, A2 | - |
| FSU4 | SU | - | - | - | +++ | +++ | - | +++ | +++ | - | N | A1, B27, C15, A2 | B62, A3 | - |

Table 15 notes:
CD8+ T-cell cytolysin/cytotoxins (perforin, GrzA & B) (Cyto);
CD4+ T-cell cytotoxins also high (*);
Note
all peptides that are not from p24 or RT were analyzed using predominantly HIV+ patients on ART and therefore their responses are extremely low;
Viral enhancement or suppression (E/S);
Frequency of responders:
0%-1.4% (−),
1.5%-12.4% (±),
12.5%-25% (+),
25.1%-40% (++),
40.1%-54% (+++),
>54% (++++).
Bolded HLA alleles have similar peptide binding pockets as FLA alleles.

Table 16. Selection of T-cell epitopes on HIV-1 based on anti-lentiviral immunogenicity, human leukocyte antigen (HLA) interaction, and lentiviral aa sequence conservation.

The counterpart HIV-1 peptides of the FIV peptides were also tested for immunogenicity using PBMC and T cells from HIV$^+$ human subjects. All of these HIV-1 peptides had substantially high aa sequence conservation with counterpart FIV sequence. Those HIV-1 peptides that are not from p24 or RT have extremely low responses since these are the results from HIV$^+$ subjects on antiretroviral therapy (ART). HIV$^+$ subject on ART generally have lower HIV-specific peptides in black are the counterpart FIV peptides used in the current MAP vaccine trial, whereas the 13 peptides in blue were not.

Since these HIV-1 peptides are counterpart of the lentivirally conserved FIV peptides from FIG. 2, the HIV peptide sequences based also on aa sequence similarities (selected peptides shown in FIG. 9) are considered to be lentivirally conserved and unlikely to readily mutate.

TABLE 16

| HIV Epitope | Viral Protein | HIV$^+$ | Human Subjects | | | | | In Silico Analysis | | |
|---|---|---|---|---|---|---|---|---|---|---|
| Peptide | Region | IFNγ | CyCD4 | CyCD8 | CD4$^+$ T | CD8$^+$ T | LANL CTL | Net-MHC3.4 | Net-CTL1.2 | Net-MHC2.2 |
| Hp9-3 (10-3) | p24 | ++++ | + | +++ | − | ++++ | B8, A24, A2 | B44, A3, B7 | B8, B44, A26, B39 | — |
| Hp14-3 (15-2) | p24 | ++ | ++++ | ++++ | − | ++++ | B27 | B44 | A24, A26 | — |
| Hp14-4 (15-3) | p24 | ++++ | ++++ | ++++ | − | ++++ | — | B44 | A24 | — |
| HRT3-3 | RT | + | ++++ | ++++ | ++ | +++ | — | B27, A3 | — | — |
| HRT3-4 | RT | + | ++++ | ++++ | ++ | +++ | A3 | B27, A3 | A3 | — |
| HRT7-1 | RT | + | − | − | − | − | B27 | A24, A1, B27 | B58, A24, B8 | 0404 |
| HRT7-2 | RT | ++ | − | − | − | − | B7 | B7, B27 | A24 | — |
| HMA2 | MA | ++ | − | − | − | − | A2, B8, A1, B44 | A1, A3, B27, A2, B58, B44 | A1, B39, B8, B62, A2 | 0101, 0404, 0405 |
| HTM8 | TM | − | − | − | + | ++++ | A3, A1, A2 | A2, A3, B58, C12, A1 | B62, A2, A3, B58, B7 | 1101, 0101 |
| Hp4-3 | p24 | + | − | ++ | − | − | B27, C08, A2, C07 | A3, A2 | — | — |
| Hp14-1 (15-1) | p24 | ++++ | ++++ | ++++ | − | ++++ | B44, B58, C05, B7 | B44, C15, B58 | B58 | — |
| HRT3-5 | RT | − | ++++ | ++++ | +++ | ++++ | — | B27 | B8, B62 | 1101 |
| Hp10-2 (11-2) | p24 | + | − | − | − | − | B27, A2, A3 | A24 | A26 | 1302, 0101, 1501 |
| Hp10-3 (11-3) | p24 | + | ++ | ++ | − | + | B27, A3, A2, B62 | — | A3, B62, A1 | 1302 |
| HMA1 | MA | +++ | − | − | − | − | A3, B27, B7, B35 | A3, A1 | A3, B27 | — |
| HNC1 | NC | ± | − | − | − | − | A3 | A3 | — | — |
| HNC2 | NC | + | − | + | − | − | — | A3 | B44, B27 | — |
| HPR1 | PR | + | + | − | − | + | A3, A2, A1 | B27, A2, A24 | A24, B27 | — |
| HPR2 | PR | ++ | − | − | − | − | A2 | A2 | — | — |
| HIN7-1 | IN | +++ | − | + | − | + | A3, B44 | C5 | A3 | 0101 |
| HTM4-3 | TM | ++ | − | + | − | − | B8, A24, C07 | A2 | — | — |
| HSU4 | SU | − | − | + | + | + | B27 | C14, A24, B44, B27 | A24, B27, A3, B44 | 0701 |

Table 16 notes:

CD4+ and CD8+ T-cell cytolysin/cytotoxins (perforin, GrzA & B) (CyCD4 and CyCD8);

Note all peptides that are not from p24 or RT except for HRT7-1 and HRT7-2 were analyzed using predominantly HIV+ patients on ART and therefore their responses are extremely low;

Frequency of responders:

0%-1.4% (−), 1.5%-12.4% (±), 12.5%-25% (+), 25.1%-40% (++), 40.1%-54% (+++),

>54% (++++).

Bolded LANL HLA alleles common with bolded in silico HLA alleles.

immune responses as previously reported (McIlroy, 2013; Shan et al., 2012) and as shown in this table. The HRT7-1 and HRT7-2 were also tested with cells from HIV$^+$ subjects on ART. The threshold for positive IFNγ ELISpot response is ≥75 spot-forming units (SFU) per $10^6$ PBMC. The threshold for CFSE-based CD4$^+$ (CD4$^+$ T) and CD8$^+$ (CD8$^+$ T) T-cell proliferation is ≥2% CD4$^+$ T-cell CFSE$^{low}$ or CD8$^+$ T-cell CFSE$^{low}$. The threshold of intracellular cytokine staining (ICS) of FACS-based cytolysin (perforin) and cytotoxins (granzymes A and B) in CD4$^+$ T cells (CyCD4) and CD8$^+$ T cells (CyCD8) is ≥0.2%. The frequency of responders is shown as the percentage of the responders equal to or above the threshold level over the total tested and as follows: 0%-1.4% (−), 1.5%-12.4% (±), 12.5%-25% (+), 25.1%-40% (++), 40.1%-54% (+++), >54% (++++). The nine HIV-1

Table 17. Efficacy of the MAP vaccines against pathogenic FIV challenge at 15 median cat infectious dose ($15CID_{50}$).

As of to date at 12 wk post-challenge (wpc), Groups 1 and 2 have protection rates of 60% and 50%, respectively when no protection was observed in control Group 3. At the same challenge dose (15 $CID_{50}$) in the previous pilot MAP vaccine study, the last control cats became infected at 12 wpc which is at the same time as the current MAP Vaccine Trial I. Since the natural FIV transmission dose is 2 $CID_{50}$ (Yamamoto, 2009), the previous and the current challenge dose is 12.5× the natural transmission dose. More important, the challenge $FIV_{FC1}$ virus is a pathogenic strain which is resistant to virus neutralizing antibodies induced by the commercial dual-subtype FIV vaccine (Coleman et al., 2014).

TABLE 17

| Group No. | Immunization | No. of Cats | Number of Protected Cats [% Protection] | | | | | |
|---|---|---|---|---|---|---|---|---|
| | | | 0 wpc[a] | 3 wpc[a] | 6 wpc[a] | 9 wpc[a] | 12 wpc[b] | 15 wpc[c] | 18 wpc[c] |
| G1 | IWV Prime + 3x MAP Boosts | 5 | 5 | 5 [100%] | 3 [60%] | 3 [60%] | 3 [60%] | ND | ND |
| G2 | 3x MAP Vaccinations | 6 | 6 | 6 [100%] | 6 [100%] | 4 [67%] | 3 [50%] | ND | ND |
| G3 | 3x Adjuvant/FelL12 + 3x PBS | 3 + 3 | 6 (3 + 3) | 5 [83%] (3 + 2) | 1 [17%] (1 + 0) | 1 [17%] (1 + 0) | 0 [0%] (0 + 0) | ND | ND |

Table 17 notes:
[a]Virus isolation and FIV immunoblot analyses at 0-9 weeks post-challenge (wpc).
[b]Results of 12 wpc based on FIV immunoblot analysis at 12 wpc and virus isolation still ongoing.
[c]Not done (ND) since currently at 12 wpc.

Table 18. Summary of the total immune responses to vaccine peptides observed with each vaccinated cat.

The total CD8+ T-cell proliferation responses, the total CD4+ T-cell proliferation, and the cumulative CD8+ T-cell/ CD4+ T-cell response ratio to all vaccine peptides have been added and presented (top three rows). The percentages (%) of peptides with CD8+ T-cell proliferation and CD4+ T-cell proliferation are shown followed by the % of peptides with CD8+ T-cell proliferation over the % of peptides with CD4+ T-cell proliferation when the analyses consisted of a total of 11 peptides (middle three rows). The total IFNγ response and the total IL2 response in SFU/$10^6$ PBMC to all vaccine peptides are shown for each vaccinated cat (last two rows). Those cats in Group 1 (DV4, OLM) and Group 2 (DU5, DX1, OLL) in red are infected and the values in red suggest the potential reason for lack of protection of these cats. The two cats from Group 1 that became infected at 6 wpc are cats DVA and OLM. These cats have the highest IFNγ and IL2 productions and the two lowest CD8 T-Cell/CD4 T-cell response ratios. The two cats from Group 2 that became infected at 9 wpc are DU5 and DX1, and one cat OLL became infected at 12 wpc. These cats had the three highest IFNγ and IL2 productions but only DU5 and OLL had the two lowest CD8 T-cell/CD4 T-cell response ratio. Instead cat DX1 had the second highest CD8/CD4 T-cell response ratio but it also had the highest number (45%) of vaccine peptides inducing CD4+ T-cell proliferation. Except for the CD4/CD8 T-cell response ratio in DX1, the current results at 12 wpc indicate that protection are observed in vaccinated cats with high CD8/CD4 T-cell response ratio and low levels of IFNγ and IL2 productions. The protected cats in Group 1 (DU1, DY2, EA4) and Group 2 (BFA, DU4, DX5) will be monitored for additional 6 wk to demonstrate either complete protection or delay in protection. To confirm complete protection, all cats must be negative for FIV infection not only in PBMC but also in thymus, bone marrow, and lymph node cells and all should be negative for infection-induced FIV antibodies.

TABLE 18

| | TOTAL RESPONSES OF VACCINATED CATS AT POST-LAST VACCINATION (−3-0 wpc) | | | | | | | | | |
|---|---|---|---|---|---|---|---|---|---|---|
| | GROUP 2 (3x MAP Vaccinations) | | | | | | GROUP 1 (1x Prime + 3x MAP Vaccinations) | | | |
| IMMUNE PARAMETERS TO PEPTIDES | BFA | DU4 | DU5 | DX1 | DX5 | OLL | DU1 | DV4 | DY2 | EA4 | OLM |
| Total CD8 T-cell Responses | 41 | 26 | 22 | 65 | 46 | 46 | 117 | 54 | 156 | 118 | 81 |
| Total CD4 T-cell Responses | 18 | 6 | 39 | 14 | 12 | 16 | 40 | 23 | 66 | 25 | 92 |
| Cumulative CD8-T/CD4-T Response Ratio | 31 | 25 | 22 | 45 | 42 | 19 | 67 | 17 | 64 | 83 | 27 |
| % of Peptides (11) with CD8 T-cell Response | 41% | 18% | 9% | 45% | 45% | 55% | 82% | 18% | 100% | 82% | 73% |

TABLE 18-continued

| | TOTAL RESPONSES OF VACCINATED CATS AT POST-LAST VACCINATION (−3-0 wpc) | | | | | | | | | |
|---|---|---|---|---|---|---|---|---|---|---|
| | GROUP 2 (3x MAP Vaccinations) | | | | | GROUP 1 (1x Prime + 3x MAP Vaccinations) | | | | |
| IMMUNE PARAMETERS TO PEPTIDES | BFA | DU4 | DU5 | DX1 | DX5 | OLL | DU1 | DV4 | DY2 | EA4 | OLM |
| % of Peptides (11) with CD4 T-cell Response | 27% | 9% | 18% | 45% | 27% | 27% | 27% | 45% | 64% | 55% | 55% |
| % of CD8/CD4 Positive Peptide No. | 167% | 200% | 50% | 100% | 167% | 200% | 300% | 40% | 157% | 150% | 133% |
| Total IFNγ Responses | 157 | 69 | 203 | 201 | 82 | 1087 | 0 | 1954 | 908 | 319 | 9754 |
| Total IL2 Responses | 91 | 59 | 123 | 154 | 113 | 303 | 0 | 2012 | 439 | 350 | 5117 |

Table 19. Vaccine peptides with sequence conservation for FIV subtypes A-E.

Each peptide in the MAPs was analyzed for amino acid (aa) sequence conservation among all five FIV subtypes (A,B,C,D,E). The symbols between two peptide sequences represent: identical aa (*); closely similar aa (:); moderately similar aa (.); and red aa residue has no similarity with the corresponding aa residue on FIV (A,B,C,D,E). Polymerase sequence for FIV subtype E is not available in NCBI GenBank. The p24 peptide Fp9-3 of MAP4 has 100% sequence identity among all five FIV subtypes evaluated and thus an excellent vaccine peptide. The peptide with the next highest aa identity and similarity is FRT7-1/FRT7-2 of MAP5 followed by Fp14-3/Fp14-4 of MAP3 and then FRT3-3/FRT3-4 of MAP2v. In conclusion, all of the FIV peptides in the top four MAPs have high aa identity and similarity which suggest that they are highly conserved and will be an outstanding vaccine peptides.

TABLE 19

| Subtypes/Strains | FIV Peptide or Overlapping FIV Peptides | Similarity (identity) | SEQ ID NO. |
|---|---|---|---|
| FIV (A)[Fp9-3] [MAP4] | FAPARMQCRAWYLEA <br> *************** | 100% (100%) | 20 |
| FIV (B, C, D, E) | FAPARMQCRAWYLEA | 100% (100%) | 20 |
| | | | |
| FIV (B, C, D) [FRT7-1/7-2] [MAP5] | GRRYVWCSLPQGWVLSPLIY <br> ***********:**** | 100% (100%) | 35 |
| FIV (A/UK8/Bang) | GRRYVWCSLPQGWILSPLIY <br> *:*****:**** | 100% (95%) | 39 |
| FIV (A/Pet/Z1/PPR) | GRRFVWCSLPQGWILSPLIY | 100% (90%) | 40 |
| | | | |
| FIV (A, E) [Fp14-3/14-4] [MAP3] | AEVKLYLKQSLSIANA <br> ***************. | 100% (100%) | 26 |
| FIV (B, D) | AEVKLYLKQSLSIANP <br> ** ***:: | 100% (94%) | 41 |
| FIV (C) | AEVKTYLKQSLSLANS | 94% (81%) | 42 |
| | | | |
| FIV (B, D) [FRT3-3/3-4] [MAP2v] | KKKSGKWRLIDFRVLNKL <br> ************* **** | 100% (100%) | 30 |
| FIV (A) | KKKSGKWRLIDFRELNKL <br> *:***** ** | 94% (94%) | 43 |
| FIV (C) | KKKTGKWRLIDFRELNKL | 94% (89%) | 44 |

Table 19 notes:

Fp9-3 peptide pool is the counterpart of HIV p24 Hp10-3 peptide.

Overlapping FRT7-1/FRT7-2 peptide of FIV reverse transcriptase (RT) is the counterpart of HRT7-1/HRT7-2 peptide on HIV-1 RT and SRT7-1/SRT7-2 peptide on SIV-Mac251 RT.

Overlapping Fp14-3/Fp14-4 peptide of FIV p24 is the counterpart of Hp15-2/Hp15-3 peptide on HIV-1 p24 and Sp14-3/Sp14-4 peptide on SIV-Mac251 p24.

Overlapping FRT3-3/FRT3-4 peptide is the counterpart of overlapping HRT3-3/HRT3-4 peptide.

Symbols:

identical aa (*);

closely similar aa (:);

moderately similar aa (.);

and red aa residue has no similarity with the corresponding aa on FIV (A, B, C, D, E).

Polymerase sequence for subtype E is not available in NCBI GenBank.

Tables 20A-20D. The amino acid sequence conservation of the FIV vaccine peptides and corresponding counterpart HIV-1 peptides.

The four best FIV peptides for vaccine against FIV are also recognized by T cells from HIV⁺ human subjects. The two best vaccine peptides from MAP Vaccine Trial I are peptide Fp9-3 (Table 20A) and overlapping peptide FRT7-1/FRT7-2 (Table 20B). Although FIV peptide Fp9-3 have the least similarity (53%) and identity (13%) to counterpart HIV-1 peptide sequence (Table 20A), this peptide is consistently detected at high magnitude by CD8⁺ T cells from HIV⁺ human subjects. The FIV overlapping peptide FRT7-1/FRT7-2 has the next lowest similarity (65%) and identity (55%) to HIV-1 (Table 20B). The other two FIV overlapping peptides Fp14-3/Fp14-4 (Table 20C) and FRT3-3/FRT3-4 (Table 20D) have a substantial aa sequence similarity (75% in Table 20C and 80% in Table 20D) and moderate-to-substantial aa sequence identities (31-37% in Table 20C; 70% in Table 20D) with the counterpart HIV-1 peptide sequences. Such sequence conservation also exists with counterpart SIV peptide sequences. Thus, the sequence conservation suggests that these FIV and counterpart HIV-1 peptide sequences more likely are resistant to mutation due to any major mutation can affect the fitness of the virus, and therefore they may serve as an outstanding vaccine immunogen.

The lentiviral sequence conservation also demonstrates that the sequence conserved sections are difficult to determine by comparing the counterpart HIV-1 and SIV sequences since their sequences are much more similar to each other than to the FIV sequence. Thus, the use of FIV sequences in comparison to the counterpart HIV-1 and SIV sequences more readily determines the evolutionarily conserved or lentivirally conserved sequence sections on the viral proteins.

TABLE 20A

Sequence conservation in Fp9-3 & Hp10-3 peptides of p24

| | | | SEQ ID NO. |
|---|---|---|---|
| Subtype-A FIV Fp9-3 Peptide | | | |
| Fp9-3 | FAPARMQCRAWYLEA | | 20 |
| Subtypes/Strains | Fp9-3/Hp10-3 Peptides Compared to FIV (A-D) | | |
| FIV (A)[Fp9-3] | FAPARMQCRAWYLEA<br>*************** | Similarity (identity) | 20 |
| FIV (B, C, D) | FAPARMQCRAWYLEA<br>:. ..: * * : . | 100% (100%) | 20 |
| HIV-1 (B, D) | IPVGEIYKR-WIILG<br>:. . : * * : . | 60% (13%) | 19 |
| HIV-1 (A, C) | IPVGDIYKR-WIILG<br>.. . : * * : . | 53% (13%) | 45 |
| HIV-1 (C) | VPVGDIYKR-WIILG<br>.. . : * * : . | 53% (13%) | 46 |
| SIV CPZ | VPVGDIYKR-WIILG<br>:. ..: * *   . | 53% (13%) | 46 |
| SIV Mac251/Mac239 | IPVGNIYRR-WIQLG | 53% (13%) | 47 |
| Subtype-B HIV-1 Hp10-3 Peptides | | | |
| Hp10-3 | IPVGEIYKR-WIILG | | 19 |

Table 20A notes:
Fp9-3 peptide pool is the counterpart of HIV p24 Hp10-3 peptide.
HIV-1 and SIV determined by LANL QuickAlign tool.
Symbols:
identical aa (*);
closely similar aa (:);
moderately similar aa (.);
and red aa residue has no similarity with the corresponding aa on FIV (A, B, C, D).

TABLE 20B

Sequence conservation in FRT7-1/FRT7-2 & HRT7-1/HRT7-2 of RT

| | | | SEQ ID NO. |
|---|---|---|---|
| Subtype-B FIV FRT7 Peptides | | | |
| FRT7-1 | GRRYVWCSLPQGWVL | | 48 |
| FRT7-2 | CSLPQGWVLSPLIY | | 66 |
| Subtypes/Strains | Overlap FRT7-1/FRT7-2 and Overlap Fp14-3/Fp14-4 Pools | Compared to FIV(B) | |
| FIV (B, C, D) [FRT7-1/7-2] | GRRYVWCSLPQGWVLSPLIY<br>***********:**** | Similarity (Identity) | 35 |
| FIV (A/UK8/Bang) | GRRYVWCSLPQGWILSPLIY<br>*:*****:**** | 100% (95%) | 39 |
| FIV (A/Pet/Z1/PPR) | GRRFVWCSLPQGWILSPLIY<br>* ** :  *****  ** *: | 100% (90%) | 40 |
| HIV-1 (A, B, C, D) | GIRYQYNVLPQGWKGSPAIF<br>* ** :  *****  ** *: | 65% (55%) | 34 |
| SIV CPZ | GIRYQYNVLPQGWKGSPAIF<br>*:**:: *****  ** *: | 65% (55%) | 34 |
| SIV Mac251/Mac239 | GKRYIYKVLPQGWKGSPAIF | 75% (55%) | 49 |
| Subtype-B HIV-1 HRT7 Peptides | | | |
| HRT7-1 | GIRYQYNVLPQGWKG | | 50 |
| HRT7-2 | NVLPQGWKGSPAIF | | 51 |

Table 20B notes:
Overlapping FRT7-1/FRT7-2 peptide of FIV reverse transcriptase (RT) is the counterpart of HRT7-1/HRT7-2 peptide on HIV-1 RT and SRT7-1/SRT7-2 peptide on SIV-Mac251 RT.
HIV-1 and SIV determined by LANL QuickAlign tool.
Symbols:
identical aa (*);
closely similar aa (:);
moderately similar aa (.);
and red aa residue has no similarity with the corresponding aa on FIV ( ).

TABLE 20C

Sequence conservation in Fp14-3/Fp14-4 & Hp15-2/Hp15-3 of p24

| | | | SEQ ID NO. |
|---|---|---|---|
| Subtype-A FIV Fp14 Peptides | | | |
| Fp14-3 | AEVKLYLKQSLSIA | | 52 |
| Fp14-4 | KLYLKQSLSIANA | | 53 |
| Subtypes/Strains | Overlap Fp14-3/Fp14-4 and Overlap Hp15-2/Hp15-3 Pools | Compared to FIV(A) | |
| FIV (A) [Fp14-3/14-4] | AEVKLYLKQSLSIANA<br>***************. | Similarity (Identity) | 26 |
| FIV (B, D) | AEVKLYLKQSLSIANP<br>** ***:: | 100% (94%) | 41 |
| FIV (C) | AEVKTYLKQSLSLANS<br>*** ::.::* : ** | 94% (81%) | 42 |
| HIV-1 (B) | QEVKNWMTETLLVQNA<br>*** ::.::* : ** | 75% (37%) | 25 |
| HIV-1 (A) | QEVKGWMTETLLVQNA<br>:** ::.::* : ** | 75% (37%) | 54 |

TABLE 20C-continued

Sequence conservation in Fp14-3/Fp14-4 & Hp15-2/Hp15-3 of p24

| | | | SEQ ID NO. |
|---|---|---|---|
| HIV-1 (C) | QDVKNWMTDTLLVQNA<br>:** ::.::* : ** | 75% (31%) | 55 |
| HIV-1 (D) | QDVKNWMTETLLVQNA<br>*** ::.::* : ** | 75% (31%) | 56 |
| SIV CPZ | QEVKTWMTDTLLVQNA<br>* ** ::.*:* * ** | 75% (37%) | 57 |
| SIV Mac251/Mac239 | AAVKNWMTQTLLIQNA<br>* ** ::.*:* * ** | 75% (50%) | 58 |
| Subtype-B HIV-1 Hp15 Peptides | | | |
| Hp15-2 | ASQEVKNWMTETLLV | | 59 |
| Hp15-3 | VKNWMTETLLVQNA | | 60 |

Table 20C notes:
Overlapping Fp14-3/Fp14-4 peptide of FIV p24 is the counterpart of Hp15-2/Hp15-3 peptide on HIV-1 p24 and Sp14-3/Sp14-4 peptide on SIV-Mac251 p24.
HIV-1 and SIV determined by LANL QuickAlign tool.
Symbols:
identical aa (*);
closely similar aa (:);
moderately similar aa (.);
and red aa residue has no similarity with the corresponding aa on FIV (A).

TABLE 20D

Sequence conservation in FRT3-3/FRT3-4 & HRT3-3/HRT3-4 of RT

| | | | SEQ ID NO. |
|---|---|---|---|
| Subtype-B FIV FRT3 Peptides | | | |
| FRT3-3 | KKK-SGKWRL-IDFRV | | 36 |
| FRT3-4 | WRL-IDFRVLINKL | | 61 |

| Subtypes/Strains | Overlap FRT3-3/FRT3-4 and Overlap HRT3-3/HRT3-4 Pools | Compared to FIV(B, D) | |
|---|---|---|---|
| FIV (B, D) [FRT3-3/3-4] | KKK-SGKWR-LIDFRVLNKL<br>*-*-* ** | Similarity (Identity) | 30 |
| FIV (A) | KKK-SGKWR-LIDFRELNKL<br>*-:-* ** | 94% (94%) | 43 |
| FIV (C) | KKK-TGKWR-LIDFRELNKL<br>*** * *** *:*** *** | 94% (89%) | 44 |
| HIV-1 (A, B, C, D) | KKKDSTKWRKLVDFRELNKR<br>*** * *** *:*** *** | 80% (70%) | 29 |
| SIV CPZ | KKKDSTKWRKLVDFRELNKR<br>*** ..*** ***** **:: | 80% (70%) | 29 |
| SIV Mac251/Mac239 | KKKDKNKWRMLIDFRELNRV | 90% (70%) | 62 |

TABLE 20D-continued

Sequence conservation in FRT3-3/FRT3-4 & HRT3-3/HRT3-4 of RT

| | | SEQ ID NO. |
|---|---|---|
| Subtype-B HIV-I RT3 Peptides | | |
| HRT3-3 | KKKDSTKWRKLVDFRE | 63 |
| HRT3-4 | WRKLVDFRELNKR | 64 |

Table 20D notes:
Overlapping FRT3-3/FRT3-4 peptide is the counterpart of overlapping HRT3-3/HRT3-4 peptide.
HIV-1 and SIV determined by LANL QuickAlign tool.
Symbols:
identical aa (*);
closely similar aa (:);
moderately similar aa (.);
and red aa residue has no similarity with the corresponding aa on FIV (B, D).

REFERENCES

U.S. Pat. No. 5,530,101
U.S. Pat. No. 5,585,089
U.S. Pat. No. 5,693,762
U.S. Pat. No. 6,180,370
U.S. Pat. No. 6,407,213
Abbas A K, Lichtman A H, Pillai S (Eds). Cytokines. In: Cellular and molecular Immunology. Philadelphia, Pa.: Saunders Elsevier; 2010, p. 267-301.
Abbas A K, Lichtman A H, Pillai S (Eds). Cellular and Molecular Immunology. $8^{th}$ Ed, Elsevier Saunders, Philadelphia, Pa. 2015; Ch 6, 9-11, pp. 107-136, 199-238.
Abbott J R, Pu R, Coleman J K, Yamamoto J K. 2012. Utilization of feline ELISPOT for mapping vaccine epitopes. Methods Mol. Biol. 792:47-63.
Abbott J R, Sanou M P, Coleman J K, Yamamoto J K. 2011. Evolutionarily conserved T-cell epitopes on FIV for designing an HIV/AIDS vaccine. Vet. Immunol. Immunopathol. 143:246-54.
Ackley, C. D., J. K. Yamamoto, N. B. Levy, N. C. Pedersen, M. D. Cooper (1990) "Immunologic abnormalities in pathogen-free cats experimentally infected with feline immunodeficiency virus," *J. Virol.* 64:5652-5655.
Ali R, Naqvi R A, Kumar S, Bhat A A, Rao D N. 2013. Multiple antigen peptide containing B and T cell epitopes of F1 antigen of Yersinia pestis showed enhanced Th1 immune response in murine model. Scand J Immunol 77:361-371.
Allele Frequency Net Database, allelefrequencies.net/Accessed Oct. 2, 2014.
Almeida, J. R., Price, D. A., Papagno, L., Arkoub, Z. A., Sauce, D., Bornstein, E., Asher, T. E., Samri, A., Schnuriger, A., Theodorou, I., Costagliola, D., Rouzioux, C., Agut, H., Marcelin, A. G., Douek, D., Autran, B., Appay, V., 2007. Superior control of HIV-1 replication by CD8+ T cells is reflected by their avidity, polyfunctionality, and clonal turnover. The Journal of experimental medicine 204, 2473-2485.
Altschul, S. F. et al. (1990) "Basic Local Alignment Search Tool," *J. Mol. Biol.* 215:402-410.
Altschul, S. F. et al. (1997) "Gapped BLAST and PSI-BLAST: A New Generation of Protein Database Search Programs," *Nucl. Acids Res.* 25:3389-3402.
Aranyos A M, Roff S R, Pu R, Owen J L, Coleman J K. An initial examination of the potential role of T-cell immunity in protection against feline immunodeficiency virus (FIV) infection. Vaccine 2016; 14(12):1480-1488, doi: 10.1016/j.vaccine.2016.01.017. Epub 2016 Jan. 21.
Ardito M, Fueyo J, Tassone R, et al. An integrated genomic and immunoinformatic approach to *H. pylori* vaccine design. Immunome Res 2011; 20; 7: 1.
Balla-Jhagjhoorsingh S S, Koopman G, Mooij P, Haaksma T G, Teeuwsen V J, Bontrop R E, Heeney J L. 1999. Conserved CTL epitopes shared between HIV-infected human long-term survivors and chimpanzees. J. Immunol. 162:2308-14.
Barouch D H, O'Brien K L, Simmons N L, et al. Mosaic HIV-1 vaccines expand the breadth and depth of cellular immune responses in rhesus monkeys. Nat Med 2010; 16: 319-23.
Belyakov I M, Ahlers J D. 2012. Mucosal immunity and HIV-1 infection: applications for mucosal AIDS vaccine development. Curr Top Microbiol Immunol 354:157-79.
BenMohamed L, Wechsler S L, Nesburn A B. 2002. Lipopeptide vaccines—yesterday, today, and tomorrow. Lancet Infect Dis 2:425-431.
Betts M R, Krowka J F, Kepler T B, Davidian M, Christopherson C, Kwok S, Louie L, Eron J, Sheppard H, Frelinger J A. 1999. Human immunodeficiency virus type 1-specific cytotoxic T lymphocyte activity is inversely correlated with HIV type 1 viral load in HIV type 1-infected long-term survivors. AIDS Res. Hum. Retroviruses 15:1219-28.
Betts M R, Nason M C, West S M, De Rosa S C, Migueles S A, Abraham J, Lederman M M, Benito J M, Goepfert P A, Connors M, Roederer M, Koup R A. 2006. HIV nonprogressors preferentially maintain highly functional HIV-specific CD8+ T cells. Blood 107: 4781-9.
Bhasin M, Raghava, G P S. Prediction of CTL epitopes using QM, SVM and ANN techniques. Vaccine 2004; 22: 3195-201.
Brown D M. Cytolytic CD4 cells: Direct mediators in infectious disease and malignancy. Cell Immunol. 2010; 262(2):89-95. doi: 10.1016/j.cellimm.2010.02.008. Epub 2010 Feb. 24.
Buchbinder S P, Mehrotra D V, Duerr A, Fitzgerald D W, Mogg R, Li D, Gilbert P B, Lama J R, Marmor M, Del Rio C, McElrath M J, Casimiro D R, Gottesdiener K M, Chodakewitz J A, Corey L, Robertson M N; Step Study Protocol Team. 2008. Efficacy assessment of a cell-mediated immunity HIV-1 vaccine (the Step Study): a double-blind, randomised, placebo-controlled, test-of-concept trial. Lancet 372:1881-93.

Caligiuri M A. Human natural killer cells. 2008. Blood 112:461-9. Review.

Cao H, Kanki P, Sankale J L, et al. Cytotoxic T-lymphocyte cross-reactivity among different human immunodeficiency virus type 1 clades: implications for vaccine development. J Virol 1997; 71: 8615-23.

Carlson, J. M., Listgarten, J., Pfeifer, N., Tan, V., Kadie, C., Walker, B. D., Ndung'u, T., Shapiro, R., Frater, J., Brumme, Z. L., Goulder, P. J., Heckerman, D., 2012. Widespread impact of HLA restriction on immune control and escape pathways of HIV-1. Journal of virology 86, 5230-5243. doi: 10.1128/JVI.06728-11.

Cassidy S A, Cheent K S, Khakoo S I. 2014. Effects of peptide on NK cell-mediated MHC I recognition. Front Immunol 5:133.

Cebere I, Dorrell L, McShane H, et al. Phase I clinical trial safety of DNA- and modified virus Ankara-vectored human immunodeficiency virus type 1 (HIV-1) vaccines administered alone and in a prime-boost regime to healthy HIV-1-uninfected volunteers. Vaccine 2006; 24: 417-25.

Cohen N R, Garg S, Brenner M B. 2009. Antigen Presentation by CD1 Lipids, T Cells, and NKT Cells in Microbial Immunity. Adv Immunol 102:1-94.

Coleman J K, Pu R, Martin M, Sato E, Yamamoto J K. 2005. HIV-1 p24 vaccine protects cats against FIV. AIDS 19:1457-66.

Coleman J K, Pu R, Martin M M, Noon-Song E N, Zwijnenberg R, Yamamoto J K. Feline immunodeficiency virus (FIV) vaccine efficacy and FIV neutralizing antibodies. *Vaccine* 2014; 32:746-54.

Corey L, McElrath M J. 2010. HIV vaccines: mosaic approach to virus diversity. Nat. Med. 16:268-70.

Cruz L J, Cabrales A, Iglesias E, Aguilar J C, Gonzalez L J, Reyes O. 2009. Enhanced immunogenicity and cross-reactivity of HIV-1 V3-peptide and multiple antigen peptides conjugated to distinct carrier proteins. Int immunopharmacol 9:1452-1459.

De Groot A S, Rivera D S, McMurry J A, Buus S, Martin W. Identification of immunogenic HLA-B7 "Achilles' heel" epitopes within highly conserved regions of HIV. Vaccine 2008; 26: 3059-71.

de Souza M S, Ratto-Kim S, Chuenarom W, Schuetz A, Chantakulkij S, Nuntapinit B, Valencia-Micolta A, Thelian D, Nitayaphan S, Pitisuttithum P, Paris R M, Kaewkungwal J, Michael N L, Rerks-Ngarm S, Mathieson B, Marovich M, Currier J R, Kim J H; Ministry of Public Health-Thai AIDS Vaccine Evaluation Group Collaborators. 2012. The Thai phase III trial (RV144) vaccine regimen induces T cell responses that preferentially target epitopes within the V2 region of HIV-1 envelope. J Immunol. 188:5166-76.

Elder J H, Lin Y C, Fink E, Grant C K. 2010. Feline immunodeficiency virus (FIV) as a model for study of lentivirus infections: parallels with HIV. Curr HIV Res 8:73-80.

Felgner, P. L., T. R. Gadek, M. Holm, R. Roman, H. W. Chan, M. Wenz, J. P. Northrop, G. M. Ringold, M. Danielsen (1987) "Lipofection: a highly efficient, lipid-mediated DNA-transfection procedure," Proc. Natl. Acad. Sci. USA 84(21):7413-7417.

Flynn N M, Forthal D N, Harro C D, Judson F N, Mayer K H, Para M F, rgp120 HIV Vaccine Study Group. 2005. Placebo-controlled phase 3 trial of a recombinant glycoprotein 120 vaccine to prevent HIV-1 infection. J. Infect. Dis. 191:654-65.

Fujii S, Motohashi S, Shimizu K, Nakayama T, Yoshiga Y, Taniguchi M. 2010. Adjuvant activity mediated by iNKT cells. Semin Immunol 22:97-102.

Fujita Y, Taguchi H. 2011. Current status of multiple antigen-presenting peptide vaccine systems: Application of organic and inorganic nanoparticles. Chem Cent J 5:48.

Fust G. 1997. Enhancing antibodies in HIV infection. Parasitology 115 Suppl:S127-140.

Galin F S, Chrisman C L, Cook J R, Jr., Xu L, Jackson P L, Noerager B D, Weathington N M, Blalock J E. 2007. Possible therapeutic vaccines for canine myasthenia gravis: implications for the human disease and associated fatigue. Brain Behav Immun 21:323-331.

Gartland, A. J., Li, S., McNevin, J., Tomaras, G. D., Gottardo, R., Janes, H., Fong, Y., Morris, D., Geraghty, D. E., Kijak, G. H., Edlefsen, P. T., Frahm, N., Larsen, B. B., Tovanabutra, S., Sanders-Buell, E., deCamp, A. C., Magaret, C. A., Ahmed, H., Goodridge, J. P., Chen, L., Konopa, P., Nariya, S., Stoddard, J. N., Wong, K., Zhao, H., Deng, W., Maust, B. S., Bose, M., Howell, S., Bates, A., Lazzaro, M., O'Sullivan, A., Lei, E., Bradfield, A., Ibitamuno, G., Assawadarachai, V., O'Connell, R. J., deSouza, M. S., Nitayaphan, S., Rerks-Ngarm, S., Robb, M. L., Sidney, J., Sette, A., Zolla-Pazner, S., Montefiori, D., McElrath, M. J., Mullins, J. I., Kim, J. H., Gilbert, P. B., Hertz, T., 2014. Analysis of HLA A*02 Association with Vaccine Efficacy in the RV144 HIV-1 Vaccine Trial. Journal of virology 88, 8242-8255.

Gengozian N, Reyes L, Pu R, Homer B L, Bova F J, Yamamoto J K. 1997. Fractionation of feline bone marrow with the soybean agglutinin lectin yields populations enriched for erythroid and myeloid elements: transplantation of soybean agglutinin-negative cells into lethally irradiated recipients. Transplantation 64:510-518.

Goepfert P A, Elizaga M L, Seaton K, Tomaras G D, Montefiori D C, Sato A, Hural J, DeRosa S C, Kalams S A, McElrath M J, Keefer M C, Baden L R, Lama J R, Sanchez J, Mulligan M J, Buchbinder S P, Hammer S M, Koblin B A, Pensiero M, Butler C, Moss B, Robinson H L; HVTN 205 Study Group; National Institutes of Allergy and Infectious Diseases HIV Vaccines Trials Network. 2014. Specificity and 6-month durability of immune responses induced by DNA and recombinant modified vaccinia Ankara vaccines expressing HIV-1 virus-like particles. J Infect Dis 210:99-110.

Gonzalez-Galarza, F. F., Christmas, S., Middleton, D., Jones, A. R., 2011. Allele frequency net: a database and online repository for immune gene frequencies in worldwide populations. Nucleic acids research 39, D913-919. doi: 10.1093/nar/gkq1128.

Goonetilleke N, Moore S, Dally L, et al. Induction of multifunctional human immunodeficiency virus type 1 (HIV-1)-specific T cells capable of proliferation in healthy subjects by using a prime-boost regimen of DNA- and modified vaccinia virus Ankara-vectored vaccines expressing HIV-1 Gag coupled to CD8$^+$ T-cell epitopes. J Virol 2006; 80: 4717-28.

Gorse G J, Baden L R, Wecker M, et al. Safety and immunogenicity of cytotoxic T-lymphocyte poly-epitope, DNA plasmid (EP HIV-1090) vaccine in healthy, human immunodeficiency virus type 1 (HIV-1)-uninfected adults. Vaccine 2008; 26: 215-23.

Goulder P J, Watkins D I. 2008. Impact of MHC class I diversity on immune control of immunodeficiency virus replication. Nat. Rev. Immunol. 8:619-30.

Goulder, P. J., Walker, B. D., 2012. HIV and HLA class I: an evolving relationship. Immunity 37, 426-440. doi:10.1016/j.immuni.2012.09.005.

Hanke T, McMichael A J, Dorrell L. 2007. Clinical experience with plasmid DNA- and modified vaccinia virus Ankara-vectored human immunodeficiency virus type 1 clade A vaccine focusing on T-cell induction. J. Gen. Virol. 8:1-12.

Haynes B F, Gilbert P B, McElrath M J, Zolla-Pazner S, Tomaras G D, Alam S M, Evans D T, Montefiori D C, Karnasuta C, Sutthent R, Liao H X, DeVico A L, Lewis G K, Williams C, Pinter A, Fong Y, Janes H, DeCamp A, Huang Y, Rao M, Billings E, Karasavvas N, Robb M L, Ngauy V, de Souza M S, Paris R, Ferrari G, Bailer R T, Soderberg K A, Andrews C, Berman P W, Frahm N, De Rosa S C, Alpert M D, Yates N L, Shen X, Koup R A, Pitisuttithum P, Kaewkungwal J, Nitayaphan S, Rerks-Ngarm S, Michael N L, Kim J H. 2012. Immune-correlates analysis of an HIV-1 vaccine efficacy trial. N Engl J Med 366:1275-1286.

Heegaard P M H, Boas U, Sorensen N S. 2010. Dendrimers for vaccine and immunostimulatory uses. A review. Bioconjug Chem 21:405-418.

Horton H., E. P. Thomas, J. A. Stucky, I. Frank, Z. Moodie, Y. Huang, Y. Chiu, M. J. McElrath and S. C. De Rosa. 2007. Optimization and validation of an 8-color intracellular cytokine staining (ICS) assay to quantify antigen-specific T cells induced by vaccination. J Immunol. 323: 39-54.

Hosie, M. J., O. Jarrett (1990) "Serological responses of cats to feline immunodeficiency virus," AIDS 4:215-220.

Ipp H, Zemlin A. The paradox of the immune response in HIV infection: when inflammation becomes harmful. Clin Chim Acta 2013; 416:96-9.

Jacobs E S, Persad D, Ran L, Danesh A, Heitman J W, Deng X, Cameron M J, Kelvin D J, Norris P J. 2014. A CD4+ T cell antagonist epitope down-regulates activating signaling proteins, up-regulates inhibitory signaling proteins and abrogates HIV-specific T cell function. Retrovirology 11:57.

Jaoko W, Nakwagala F N, Anzala O, et al. Safety and immunogenicity of recombinant low-dosage HIV-1 A vaccine candidates vectored by plasmid pTHr DNA or modified vaccinia virus Ankara (MVA) in humans in East Africa. Vaccine 2008; 26: 2788-95.

Jenner E. An inquiry into the causes and effects of the Variolae Vaccinae, a disease discovered in some of the western counties of England, particularly Gloucestershire, and known by the name of the cow-pox. London: Sampson Low, 1798.

Johnson R P, Trocha A, Yang L, et al. HIV-1 gag-specific cytotoxic T lymphocytes recognize multiple highly conserved epitopes. Fine specificity of the gag-specific response defined by using unstimulated peripheral blood mononuclear cells and cloned effector cells. J Immunol 1991; 147: 1512-21.

Kakinuma, S., K. Motokawa, T. Hohdatsu, J. K. Yamamoto, H. Koyama, H. Hashimoto (1995) "Nucleotide Sequence of Feline Immunodeficiency Virus: Classification of Japanese Isolates into Two Subtypes Which Are Distinct from Non-Japanese Subtypes," J. Virol. 69(6):3639-3646.

Karlin, S. and Altschul, S. F. (1990) "Methods for Assessing the Statistical Significance of Molecular Sequence Features by Using General Scoring Schemes," Proc. Natl. Acad. Sci. USA 87:2264-2268.

Karlin, S. and Altschul, S. F. (1993) "Applications and Statistics for Multiple High-Scoring Segments in Molecular Sequences," Proc. Natl. Acad. Sci. USA 90:5873-5877.

Kiepiela P, Kholiswa N, Thobakgale C, et al. CD8+ T-cell responses to different HIV proteins have discordant associations with viral load. Nature Med 2007; 13: 46-53.

Kim J H, Rerks-Ngarm S, Excler J L, Michael N L. 2010. HIV vaccines: lessons learned and the way forward. Curr Opin HIV AIDS 5:428-434.

Klenerman P, Rowland-Jones S, McAdam S, Edwards J, Daenke S, Lalloo D, Koppe B, Rosenberg W, Boyd D, Edwards A, Giangrande P, Phillips R E, McMichael A J. 1994. Cytotoxic T-cell activity antagonized by naturally occurring HIV-1 Gag variants. Nature 369:403-407.

Koff W C. 2010. HIV vaccine development: Challenges and opportunities towards solving the HIV vaccine-neutralizing antibody problem. Vaccine 30:4310-5.

Kohler, G., C. Milstein (1975) "Continuous cultures of fused cells secreting antibody of predefined specificity" Nature 256(5517):495-497.

Korber B T, Letvin N L, Haynes B F. T-cell vaccine strategies for human immunodeficiency virus, the virus with a thousand faces. J Virol 2009; 83: 8300-14.

Kotterman M A, Schaffer D V. Engineering adeno-associated viruses for clinical gene therapy. Nat Rev Gene 2014; 15:445-51. Review.

Kowalczyk W, de la Torre B G, Andreu D. 2010. Strategies and limitations in dendrimeric immunogen synthesis. The influenza virus M2e epitope as a case study. Bioconjug Chem 21:102-110.

Kowalczyk W, Monsó M, de la Torre B G, Andreu D. Synthesis of multiple antigenic peptides (MAPs)—strategies and limitations. J. Pept. Sci., 2011, 17:247-251 (published online 30 Nov. 2010).

La Cava A. 2010. Modulation of autoimmunity with artificial peptides. Autoimmun Rev 10:18-21.

Lane H C. Pathogenesis of HIV infection: total CD4+ T-cell pool, immune activation, and inflammation. Top HIV Med 2010; 18:2-6.

Larsen M V, Lundegaard C, Lamberth K, Buus S, Lund O, Nielsen M. Large-scale validation of methods for cytotoxic T-lymphocyte epitope prediction. BMC Bioinform 2007; 8:424.

Leeansyah E, Malone DFG, Anthony D D, Sandberg J K. 2013. Soluble biomarkers of HIV transmission, disease progression and comorbidities. Curr Opin HIV AIDS 8:117-124.

Leslie A J, Pfafferott K J, Chetty P, Draenert R, Addo M M, Feeney M, Tang Y, Holmes E C, Allen T, Prado J G, Altfeld M, Brander C, Dixon C, Ramduth D, Jeena P, Thomas S A, St John A, Roach T A, Kupfer B, Luzzi G, Edwards A, Taylor G, Lyall H, Tudor-Williams G, Novelli V, Martinez-Picado J, Kiepiela P, 494 Walker B D, Goulder P J. 2004. HIV evolution: CTL escape mutation and reversion after transmission. Nat. Med. 10:282-9.

Leslie, A., Matthews, P. C., Listgarten, J., Carlson, J. M., Kadie, C., Ndung'u, T., Brander, C., Coovadia, H., Walker, B. D., Heckerman, D., Goulder, P. J., 2010. Additive contribution of HLA class I alleles in the immune control of HIV-1 infection. Journal of virology 84, 9879-9888. doi: 10.1128/JVI.00320-10.

Lettau M, Schmidt H, Kabelitz D, Janssen O. 2007. Secretory lysosomes and their cargo in T and N K cells. Immunol Lett 108:10-19.

Levy J A (Ed). Intracelllular control of HIV replication. In: HIV and the Pathogenesis of AIDS. 3rd Ed. Chapter 5, ASM Press, Washington D. C., USA, pp. 109-131, 2007.

Li F, Finnefrock A C, Dubey S A, Korber B T, Szinger J, Cole S, McElrath M J, Shiver J W, Casimiro D R, Corey L, Self S G. 2011. Mapping HIV-1 vaccine induced T-cell responses: bias towards less-conserved regions and potential impact on vaccine efficacy in the Step study. PloS One. 6:e20479. doi:10.1371/journal.pone.0020479.

Li F, Horton H, Gilbert P B, McElrath J M, Corey L, Self S G. HIV-1 CTL-based vaccine immunogen selection: antigen diversity and cellular response features. Curr HIV Res 2007; 5: 97-107.

Lichterfeld M, Kaufmann D E, Yu X G, Mui S K, Addo M M, Johnston M N, Cohen D, Robbins G K, Pae E, Alter G, Wurcel A, Stone D, Rosenberg E S, Walker B D, Altfeld M. 2004. Loss of HIV-1-specific CD8+ T cell proliferation after acute HIV-1 infection and restoration by vaccine-induced HIV-1-specific CD4+ T cells. J. Exp. Med. 200:701-12.

Liu, C., Carrington, M., Kaslow, R. A., Gao, X., Rinaldo, C. R., Jacobson, L. P., Margolick, J. B., Phair, J., O'Brien, S. J., Detels, R., 2003. Association of polymorphisms in human leukocyte antigen class I and transporter associated with antigen processing genes with resistance to human immunodeficiency virus type 1 infection. The Journal of infectious diseases 187, 1404-1410.

Llano A, Frahm N, Brander C. 2009. How to optimally define optimal cytotoxic T lymphocyte epitopes in HIV infection? In Yusim K (ed), HIV Molecular Immunology 2009. Los Alamos National Laboratory, Los Alamos, N. Mex.

Los Alamos National Laboratory. HIV molecular immunology database: Best-defined CTL/CD8 Epitope Summary: (hiv.lanl.gov/content/immunology/tables/optimal ctl summary.html)

Louwagie, J., F. E. McCutchan, M. Peeters, T. P. Brennan, E. Sanders-Buell, G. A. Eddy, G. van den Grosen, K. Fransen, G. M. Gershy-Damet, R. Deleys, D. S. Burke (1993) "Phylogenetic analysis of gag genes from 70 international HIV-1 isolates provides evidence for multiple genotypes," AIDS 7:769-780.

Lu J, Higashimoto Y, Appella E, Celis E. 2004. Mu4tiepitope Trojan antigen peptide vaccines for the induction of antitumor CTL and Th immune responses. J Immunol 172:4575-4582.

Lu J, Wettstein P J, Higashimoto Y, Appella E, Celis E. 2001. TAP-independent presentation of CTL epitopes by Trojan antigens. J Immunol 166:7063-7071.

Lundegaard C, Lamberth K, Harndahl M, Buus S, Lund O, Nielsen M. NetMHC-3.0: Accurate web accessible predictions of Human, Mouse, and Monkey MHC class I affinities for peptides of length 8-11. NAR 2008; 36: 50912.

MacDonald, K. S., Embree, J. E., Nagelkerke, N. J., Castillo, J., Ramhadin, S., Njenga, S., Oyug, J., Ndinya-Achola, J., Barber, B. H., Bwayo, J. J., Plummer, F. A., 2001. The HLA A2/6802 supertype is associated with reduced risk of perinatal human immunodeficiency virus type 1 transmission. The Journal of infectious diseases 183, 503-506.

MacDonald, K. S., Matukas, L., Embree, J. E., Fowke, K., Kimani, J., Nagelkerke, N. J., Oyugi, J., Kiama, P., Kaul, R., Luscher, M. A., Rowland-Jones, S., Ndinya-Achola, J., Ngugi, E., Bwayo, J. J., Plummer, F. A., 2001. Human leucocyte antigen supertypes and immune susceptibility to HIV-1, implications for vaccine design. Immunology letters 79, 151-157.

Mahajan B, Berzofsky J A, Boykins R A, Majam V, Zheng H, Chattopadhyay R, de la Vega P, Moch J K, Haynes J D, Belyakov I M, Nakhasi H L, Kumar S. 2010. Multiple antigen peptide vaccines against *Plasmodium falciparum* malaria. Infect Immun 78:4613-4624.

Marsh S. G., Parham P., Barber L. D. 2000. The HLA Class I and Class II Loci. In Marsh S. G., Parham P., Barber L. D. (eds), The HLA Facts Book. London: Academy Press; p. 93-272.

Marsh S G, Parham P, Barber L D. 2000. HLA polymorphism, peptide-binding motifs and T-cell epitopes. pp. 61-72. In The HLA Facts Book. Academy Press, London, UK.

McDermott A B, Koup R A. 2012. CD8+ T cells in preventing HIV infection and disease. AIDS 26:1281-92.

McKinnon L R, Kaul R, Kimani J, Nagelkerke N J, Wachihi C, Fowke K R, Ball T B, Plummer F A. 2012. HIV-specific CD8+ T-cell proliferation is prospectively associated with delayed disease progression. Immunol. Cell Biol. 90:346-51.

McIlroy D. Do HIV-specific CTL continue to have an antiviral function during antiretroviral therapy? If not, why not, and what can be done about it? Front. Immunol. Vol. 4, article 52, online on March 2013, DOI: 10.3389/fimmu.2013.00052.

Moss S F, Moise L, Lee D S, et al. HelicoVax: epitope-based therapeutic *Helicobacter pylori* vaccination in a mouse model. Vaccine 2011; 29:2085-91.

Mothe B, Liano A, Ibarrondo J, Daniels M, Miranda C, Zamarreño J, Bach V, Zuniga R, Pérez-Álvarez S, Berger C T, Puertas M C, Martinez-Picado J, Rolland M, Farfan M, Szinger J J, Hildebrand W H, Yang O O, Sanchez-Merino V, Brumme C J, Brumme Z L, Heckerman D, Allen T M, Mullins J I, Gómez G, Goulder P J, Walker B D, Gatell J M, Clotet B, Korber B T, Sanchez J, Brander C. 2011. Definition of the viral targets of protective HIV-1-specific T cell responses. J. Transl. Med. 9:208.

Murphy, F., D. W. Kingsbury (1990) "Virus Taxonomy," In Fields Virology, 2nd Ed., B.N. Fields, D. M. Knipe et al., eds, Raven Press, New York, Chapter 2, pp. 9-36.

Mwau M I, Cebere J, Sutton P, et al. A human immunodeficiency virus 1 (HIV-1) clade A vaccine in clinical trials: stimulation of HIV-specific T-cell responses by DNA and recombinant modified vaccinia virus Ankara (MVA) vaccines in humans. J Gen Virol 2004; 85: 911-9.

Nakayama K. Furin: a mammalian subtilisin/Kex2p-like endoprotease involved in processing of a wide variety of precursor proteins. *Biochem J* 1997; 327:625-35.

Nardelli B, Tam J P. 1993. Cellular immune-responses Induced by in-vivo priming with a lipid-conjugated multimeric antigen peptide. Immunology 79:355-361.

Nishimura Y, Shimojima M, Sato E, Izumiya Y, Tohya Y, Mikami T, Miyazawa T. 2004. Down-modulation of CD3epsilon expression in CD8alpha+beta-T cells of feline immunodeficiency virus-infected cats. J Gen Virol 85:2585-2589.

Ogg G S, Jin X, Bonhoeffer S, Dunbar P R, Nowak M A, Monard S, Segal J P, Cao Y, Rowland-Jones S L, Cerundolo V, Hurley A, Markowitz M, Ho D D, Nixon D F, McMichael A J. 1998. Quantitation of HIV-1-specific cytotoxic T lymphocytes and plasma load of viral RNA. Science 279:2103-6.

Oka Y, Tsuboi A, Fujiki F, Li Z Y, Nakajima H, Hosen N, Shirakata T, Nishida S, Oji Y, Kawase I, Sugiyama H. 2009. WT1 Peptide Vaccine as a Paradigm for "Cancer Antigen-Derived Peptide"-Based Immunotherapy for Malignancies: Successful Induction of Anti-Cancer Effect by Vaccination with a Single Kind of WT1 Peptide. Anti-Cancer Agent Med Chem 9:787-797.

Olmsted, R. A., A. K. Barnes, J. K. Yamamoto, V. M. Hirsch, R. H. Purcell, P. R. Johnson (1989a) "Molecular cloning of feline immunodeficiency virus," *Proc. Nat. Acad. Sci. USA* 86:2448-2452.

Olmsted, R. A., V. M. Hirsch, R. H. Purcell, P. R. Johnson (1989b) "Nucleotide sequence analysis of feline immunodeficiency virus: Genome organization and relationship to other lentivirus," *Proc. Natl. Acad. Sci. USA* 86:8088-8092.

Omori M, Pu R, Tanabe T, Hou W, Coleman J K, Arai M, Yamamoto J K. 2004. Cellular immune responses to feline immunodeficiency virus (FIV) induced by dual-subtype FIV vaccine. Vaccine 23:386-398.

Pattacini, L., Mize, G. J., Graham, J. B., Fluharty, T. R., Graham, T. M., Lingnau, K., Wizel, B., Perdiguero, B., Esteban, M., Pantaleo, G., Shen, M., Spies, G. A., McElrath, M. J., Lund, J. M., 2012. A novel HIV vaccine adjuvanted by IC31 induces robust and persistent humoral and cellular immunity. PloS one 7, e42163. doi: 10.1371/journal.pone.0042163.

Pedersen, N. C., E. W. Ho, M. L. Brown, J. K. Yamamoto (1987) "Isolation of a T-lymphotropic virus from domestic cats with an immunodeficiency-like syndrome," *Science* 235:790-793.

Pitisuttithum P, Gilbert P, Gurwith M, Heyward W, Martin M, van Griensven F,5 Hu D, Tappero J W, Choopanya K, Bangkok Vaccine Evaluation Group. 2006. Randomized, double-blind, placebo-controlled efficacy trial of a bivalent recombinant glycoprotein 120 HIV-1 vaccine among injection drug users in Bangkok, Thailand. J. Infect. Dis. 194:1661-71.

Plotkin S A. 2008. Vaccines: correlates of vaccine-induced immunity. Clin. Infect. Dis. 47:401-09.

Posnett, D. N. et al. (1988) "A Novel Method for Producing Anti-peptide Antibodies," *J. Biol. Chem.* 263(4):1719-1725.

Pu R, Coleman J, Omori M, Arai M, Hohdatsu T, Huang C, Tanabe T, Yamamoto J K. 2001. Dual-subtype FIV vaccine protects cats against in vivo swarms of both homologous and heterologous subtype FIV isolates. AIDS 15:1225-1237.

Pu R, Okada S, Little E R, Xu B, Stoffs W V, Yamamoto J K. 1995. Protection of neonatal kittens against feline immunodeficiency virus infection with passive maternal antiviral antibodies. AIDS 9:235-242.

Pu R, Omori M, Okada S, Rine S L, Lewis B A, Lipton E, Yamamoto J K. 1999. MHC-restricted protection of cats against FIV infection by adoptive transfer of immune cells from FIV-vaccinated donors. Cell Immunol 198:30-43.

Rerks-Ngarm S, Pitisuttithum P, Nitayaphan S, Kaewkungwal J, Chiu J, Paris R, Premsri N, Namwat C, de Souza M, Adams E, Benenson M, Gurunathan S, Tartaglia J, McNeil J G, Francis D P, Stablein D, Birx D L, Chunsuttiwat S, Khamboonruang C, Thongcharoen P, Robb M L, Michael N L, Kunasol P, Kim J H, MOPH-TAVEG Investigators. 2009. Vaccination with ALVAC and AIDS-VAX to prevent HIV-1 infection in Thailand. N. Engl. J. Med. 361:2209-20.

Richmond M, McKinnon L R, Kiazyk S A, Wachihi C, Kimani M, Kimani J, Plummer F A, Ball T B. 2011. Epitope mapping of HIV-specific CD8+ T cell responses by multiple immunological readouts reveals distinct specificities defined by function. J Virol. 85:1275-86.

Rigby, M. A., E. C. Holmes, M. Pistello, A. Mackay, A. J. Leigh-Brown, J. C. Neil (1993) "Evolution of structural proteins of feline immunodeficiency virus: molecular epidemiology and evidence of selection for change," *J. Gen. Virol.* 74:425-436.

Roff S R, Noon-Song E N, Yamamoto J K. The significance of interferon-γ in HIV-1 pathogenesis, therapy, and prophylaxis. Front. Immunol. Vol. 4, article 498, online on Jan. 13, 2014; DOI: 10.3389/fimmu.2013.00498.

Roff S R, Sanou M P, Rathore M H, Levy J A, Yamamoto J K. Conserved epitopes on HIV-1, FIV and SIV p24 proteins are recognized by HIV-1-infected subjects. Hum Vac Immunother, 2015, 11(6):1540-1556.

Rolland M, Nickle D C, Mullins J I. 2007. HIV-1 Group M Conserved Elements Vaccine. PLoS Pathog. 3:e157. doi: 10.1371/journal.ppat.0030157.

Rowland-Jones S L, Dong T, Fowke K R, et al. Cytotoxic T cell responses to multiple conserved HIV epitopes in HIV-resistant prostitutes in Nairobi. J Clin Invest 1998; 102: 1758-65.

Rowland-Jones, S., J. Sutton, K. Ariyoshi, T. Dong, F. Gotch, S. McAdam, et al. (1995) "HIV-specific cytotoxic T-cells in HIV-exposed but uninfected Gambian women," *Nat. Med.* 1:59-64.

Salmon-Ceron D, Durier C, Desaint C. Cuzin L, Surenaud M, Hamouda N B, Lelievre J D, Bonnet B, Pialoux G, Poizot-Martin I, Aboulker J P, Levy Y, Launay O, ANRS VAC18 trial group. 2010. Immunogenicity and safety of an HIV-1 lipopeptide vaccine in healthy adults: a phase 2 placebo-controlled ANRS trial. AIDS 24:2211-23.

Sanou M P, De Groot A S, Murphy-Corb M, Levy J A, Yamamoto J K. 2012a. HIV-1 Vaccine Trials: Evolving Concepts and Designs. Open AIDS J. 6:246-260.

Sanou, M. P., De Groot, A. S., Murphey-Corb, M., Levy, J. A., Yamamoto, J. K., 2012b. HIV-1 Vaccine Trials: Evolving Concepts and Designs. The open AIDS journal 6, 274-288.

Sanou, M. P., Roff, S. R., Mennella, A., Sleasman, J. W., Rathore, M. H., Yamamoto, J. K., Levy, J. A., 2013. Evolutionarily conserved epitopes on human immunodeficiency virus type 1 (HIV-1) and feline immunodeficiency virus reverse transcriptases detected by HIV-1-infected subjects. Journal of Virology, 87(17):10004-10015.

Santra S, Liao H X, Zhang R, et al. Mosaic vaccines elicit $CD8^+$ T lymphocyte responses that confer enhanced immune coverage of diverse HIV strains in monkeys. Nat Med 2010; 16: 324-8.

Santra S, Muldoon M, Watson S, Buzby A, Balachandran H, Carlson K R, Mach L, Kong W P, McKee K, Yang Z Y, Rao S S, Mascola J R, Nabel G J, Korber B T, Letvin N L. 2012. Breadth of cellular and humoral immune responses elicited in rhesus monkeys by multi-valent mosaic and consensus immunogens. Virology 428:121-7.

Saunders K O, Rudicell R S, Nabel G J. 2012. The design and evaluation of HIV-1 vaccines. AIDS 26:1293-1302.

Shan L, Deng K, Shroff N S, Durand C M, Rabi S A, Yang H-C, Zhang H, Margolick J B, Blankson J N, Siliciano R F. Stimulation of HIV-1-specific cytolytic T lymphocytes facilitates elimination of latent viral reservoir after virus reactivation. Immunity. 36:491-501, 2012.

Shimojima M, Miyazawa T, Ikeda Y, McMonagle E L, Haining H, Akashi H, Takeuchi Y, Hosie M J, Willett B J. Use of CD134 as a primary receptor by the feline immunodeficiency virus. Science. 303:1192-5, 2004.

Sidney J, Peters B, Frahm N, Brander C, Sette A. HLA class I supertypes: a revised and updated classification. BMC Immunol. 2008 Jan. 22; 9:1. doi: 10.1186/1471-2172-9-1.

Smith S M. HIV CTL escape: at what cost? Retrovirology 2004; 1: 8.

Sodora, D. L., E. G. Shpaer, B. E. Kitchell, S. W. Dow, E. A. Hoover, J. I. Mullins (1994) "Identification of three feline immunodeficiency virus (FIV) env gene subtype and comparison of the FIV and human immunodeficiency virus type 1 evolutionary patterns," *J. Virol.* 68:2230-2238.

Soghoian D Z, Jessen H, Flanders M, Sierra-Davidson K, Cutler S, Pertel T, Ranasinghe S, Lindqvist M, Davis I, Lane K, Rychert J, Rosenberg E S, Piechocka-Trocha A, Brass A L, Brenchley J M, Walker B D, Streeck H. 2012. HIV-specific cytolytic CD4 T cell responses during acute HIV infection predict disease outcome. Sci. Transl. Med. 4:123ra25. doi: 10.1126/scitranslmed.3003165.

Spearman P, Kalams S, Elizaga M, Metch B, Chiu Y L, et al. Safety and immunogenicity of a CTL multiepitope peptide vaccine for HIV with or without G M-CSF in a phase I trial. Vaccine 2009; 27: 243-9.

Spina, C. A., Prince, H. E., Richman, D. D., 1997. Preferential replication of HIV-1 in the CD45RO memory cell subset of primary CD4 lymphocytes in vitro. The Journal of clinical investigation 99, 1774-1785.

Stamatatos L. 2012. HIV vaccine design: the neutralizing antibody conundrum. Curr. Opin. Immunol. 24:316-23.

Stevenson, M., Stanwick, T. L., Dempsey, M. P., Lamonica, C. A., 1990. HIV-1 replication is controlled at the level of T cell activation and proviral integration. The EMBO journal 9, 1551-1560.

Stranzl T, Larsen M V, Lundegaard C, Nielsen M. NetCTL-pan: pan-specific MHC class I pathway epitope predictions. Immunogenetics 2010; 62: 357-68.

Talbott, R. L., E. E. Sparger, K. M. Lovelace, W. M. Fitch, N. C. Pedersen, P. A. Luciw, J. H. Elder (1989) "Nucleotide sequence and genomic organization of feline immunodeficiency virus," *Proc. Natl. Acad. Sci. USA* 86:5743-5747.

Tam, J. P. (1988) "Synthetic Peptide Vaccine Design: Synthesis and Properties of a High-Density Multiple Antigenic Peptide System," *Proc. Nat. Acad. Sci. USA* 85(15): 5409-5413.

Tanabe T, Yamamoto J K. Feline immunodeficiency virus lacks sensitivity to the antiviral activity of feline IFN-gamma. *J Interferon Cytokine Res* 2001; 21:1039-46.

Tang, J., Cormier, E., Gilmour, J., Price, M. A., Prentice, H. A., Song, W., Kamali, A., Karita, E., Lakhi, S., Sanders, E. J., Anzala, O., Amornkul, P. N., Allen, S., Hunter, E., Kaslow, R. A., Network, I.A.H.R., 2011. Human leukocyte antigen variants B*44 and B*57 are consistently favorable during two distinct phases of primary HIV-1 infection in sub-Saharan Africans with several viral subtypes. Journal of virology 85, 8894-8902. doi: 10.1128/JVI.00439-11.

Taylor B S, Sobieszczyk M E, McCutchan F E, Hammer S M. The challenge of HIV-1 subtype diversity. N Engl J Med. 2008 Apr. 10; 358(15):1590-602. doi: 10.1056/NEJMra0706737.

Tellier M C, Pu R, Pollock D, Vitsky A, Tartaglia J, Paoletti E, Yamamoto J K. 1998. Efficacy evaluation of prime-boost protocol: canarypoxvirus-based feline immunodeficiency virus (FIV) vaccine and inactivated FIV-infected cell vaccine against heterologous FIV challenge in cats. AIDS 12:11-18.

Troyer R M, McNevin J, Liu Y, Zhang S C, Krizan R W, Abraha A, Tebit D M, Zhao H, Avila S, Lobritz M A, McElrath M J, Le Gall S, Mullins J I, Arts E J. 2009. Variable fitness impact of HIV-1 escape mutations to cytotoxic T lymphocyte (CTL) response. PLoS Pathog. 5:e1000365. doi:10.1371/journal.ppat.1000365.

Uhl E W, Heaton-Jones T G, Pu R, Yamamoto J K. FIV vaccine development and its importance to veterinary and human medicine: a review FIV vaccine 2002 update and review. Vet Immunol Immunopathol. 2002; 90(3-4): 113-32.

Uhl E W, Martin M, Coleman J K, Yamamoto J K. 2008. Advances in FIV vaccine technology. Vet Immunol Immunopathol 123:65-80.

Vaccari M, Poonam P, Franchini G. 2010. Phase III HIV vaccine trial in Thailand: a step toward a protective vaccine for HIV. Expert Rev Vaccines 9:997-1005.

Vogel T U, Beer B E, zur Megede J, Ihlenfeldt H G, Jung G, Holzammer S, Watkins D I, Altman J D, Kurth R, Norley S. 2002. Induction of anti-simian immunodeficiency virus cellular and humoral immune responses in rhesus macaques by peptide immunogens: correlation of CTL activity and reduction of cell-associated but not plasma virus load following challenge. J Gen Virol 83:81-91.

Voronin Y, Manrique A, Bernstein A. 2010. The future of HIV vaccine research and the role of the Global HIV Vaccine Enterprise. Curr Opin HIV AIDS 5:414-420.

Walker B D, Flexner C, Paradis T J, Fuller T C, Hirsch M S, Schooley R T, Moss B. 1988. HIV-1 reverse transcriptase is a target for cytotoxic T lymphocytes in infected individuals. Science 240:64-6.

Walther-Jallow L, Nilsson C, Soderlund J, ten Haaft P, Makitalo B, Biberfeld P, Bottiger P, Heeney J, Biberfeld G, Thorstensson R. 2001. Cross-protection against mucosal simian immunodeficiency virus (SIVsm) challenge in human immunodeficiency virus type 2-vaccinated cynomolgus monkeys. J. Gen. Virol. 82:1601-12.

Wang G Z, Tang X D, Lu M H, Gao J H, Liang G P, Li N, Li C Z, Wu Y Y, Chen L, Cao Y L, Fang D C, Yang S M. 2011. Multiple Antigenic Peptides of Human Heparanase Elicit a Much More Potent Immune Response against Tumors. Cancer Prev Res 4:1285-1295.

Wang Y E, Li B, Carlson J M. Protective HLA class I alleles that restrict acute-phase CD8 T-cell responses are associated with viral escape mutations located in highly conserved regions of human immunodeficiency virus type-1. J Virol 2009; 83: 1845-55.

Weinberg A D. OX40: targeted immunotherapy—implications for tempering autoimmunity and enhancing vaccines. Trends Immunol. 23:102-109, 2002.

Yamamoto J K, Okuda T, Ackley C D, Louie H, Pembroke E, Zochlinski H, Munn R J, Gardner M B. 1991. Experimental vaccine protection against feline immunodeficiency virus. AIDS Res Hum Retroviruses 7:911-922.

Yamamoto J K, Pu R, Sato E, Hohdatsu T. Feline immunodeficiency virus pathogenesis and development of a dual-subtype feline-immunodeficiency-virus vaccine. AIDS 2007; 21: 547-63.

Yamamoto J K, Sanou M P, Abbott J R, Coleman J K. Feline immunodeficiency virus model for designing HIV/AIDS vaccines. Curr HIV Res 2010; 8:14-25.

Yamamoto J K. Bovine and feline immunodeficiency viruses. In: Encyclopedia of Virology. 3rd Ed. B. Hahy and M Van Regenmortel (Eds), Elsevier Ltd, Oxford, U K, pp. 347-354, 2008.

Yamamoto J K. Evolving perspectives on FIV vaccines. Practitioner's Update: Feline Retrovirus Disease. 1:4-7, 2009.

Yamamoto, J. K., B. A. Torres, R. Pu (2002) "Development of the dual-subtype FIV vaccine," *AIDScience* April 2002, 2(8), website at aidscience.org/Articles/AIDScience020.asp/Accessed 25 Dec. 2004.

Yamamoto, J. K., Barre-Sinoussi, F., Bolton, V., Pedersen, N. C., Gardner, M. B., 1986. Human alpha- and beta-interferon but not gamma-suppress the in vitro replication of LAV, HTLV-III, and ARV-2. Journal of interferon research 6, 143-152.

Yamamoto, J. K., E. Sparger, E. W. Ho, P. H. Andersen, T. P. O'Connor, C. P. Mandell, L. Lowenstine, N. C. Pedersen (1988b) "Pathogenesis of experimentally induced feline immunodeficiency virus infection in cats," *Am. J. Vet. Res.* 49:1246-1258.

Yamamoto, J. K., N. C. Pedersen, E. W. Ho, T. Okuda, G. H. Theilen (1988a) "Feline immunodeficiency syndrome—a comparison between feline T-lymphotropic lentivirus and feline leukemia virus," *Leukemia*, December Supplement 2:204S-215S.

Yongqun H, Rappuoli R, De Groot A S, Chen R T. Emerging Vaccine Informatics. J Biomed Biotechnol 2010; 2010: 218590.

Yusim K, Kesmir C, Gaschen B, et al. Clustering patterns of cytotoxic T-lymphocyte epitopes in human immunodeficiency virus type 1 (HIV-1) proteins reveal imprints of immune evasion on HIV-1 global variation. J Virol 2002; 76:8757-68.

Zhang, X., Huang, X., Xia, W., Li, W., Zhang, T., Wu, H., Xu, X., Yan, H., 2013. HLA-B*44 is associated with a lower viral set point and slow CD4 decline in a cohort of Chinese homosexual men acutely infected with HIV-1. Clinical and vaccine immunology: CVI 20, 1048-1054. doi: 10.1128/CVI.00015-13.

Zorko M, Langel U. 2005. Cell-penetrating peptides: mechanism and kinetics of cargo delivery. Adv Drug Deliv Rev 57:529-545.

1. Kim J H, Rerks-Ngarm S, Excler J L, Michael N L. 2010. HIV vaccines: lessons learned and the way forward. Curr Opin HIV AIDS 5:428-434.
2. Voronin Y, Manrique A, Bernstein A. 2010. The future of HIV vaccine research and the role of the Global HIV Vaccine Enterprise. Curr Opin HIV AIDS 5:414-420.
3. Vaccari M, Poonam P, Franchini G. 2010. Phase III HIV vaccine trial in Thailand: a step toward a protective vaccine for HIV. Expert Rev Vaccines 9:997-1005.
4. Rerks-Ngarm S, Pitisuttithum P, Nitayaphan S, Kaewkungwal J, Chiu J, Paris R, Premsri N, Namwat C, de Souza M, Adams E, Benenson M, Gurunathan S, Tartaglia J, McNeil J G, Francis D P, Stablein D, Birx D L, Chunsuttiwat S, Khamboonruang C, Thongcharoen P, Robb M L, Michael N L, Kunasol P, Kim J H, Investigators M-T. 2009. Vaccination with ALVAC and AIDSVAX to prevent HIV-1 infection in Thailand. N Engl J Med 361:2209-2220.
5. Haynes B F, Gilbert P B, McElrath M J, Zolla-Pazner S, Tomaras G D, Alam S M, Evans D T, Montefiori D C, Karnasuta C, Sutthent R, Liao H X, DeVico A L, Lewis G K, Williams C, Pinter A, Fong Y, Janes H, DeCamp A, Huang Y, Rao M, Billings E, Karasavvas N, Robb M L, Ngauy V, de Souza M S, Paris R, Ferrari G, Bailer R T, Soderberg K A, Andrews C, Berman P W, Frahm N, De Rosa S C, Alpert M D, Yates N L, Shen X, Koup R A, Pitisuttithum P, Kaewkungwal J, Nitayaphan S, Rerks-Ngarm S, Michael N L, Kim J H. 2012. Immune-correlates analysis of an HIV-1 vaccine efficacy trial. N Engl J Med 366:1275-1286.
6. de Souza M S, Ratto-Kim S, Chuenarom W, Schuetz A, Chantakulkij S, Nuntapinit B, Valencia-Micolta A, Thelian D, Nitayaphan S, Pitisuttithum P, Paris R M, Kaewkungwal J, Michael N L, Rerks-Ngarm S, Mathieson B, Marovich M, Currier J R, Kim J H. 2012. The Thai phase III trial (RV144) vaccine regimen induces T cell responses that preferentially target epitopes within the V2 region of HIV-1 envelope. J Immunol 188:5166-5176.
7. Flynn N M, Forthal D N, Harro C D, Judson F N, Mayer K H, Para M F, rgp HIVVSG. 2005. Placebo-controlled phase 3 trial of a recombinant glycoprotein 120 vaccine to prevent HIV-1 infection. J Infect Dis 191:654-665.
8. Pitisuttithum P, Gilbert P, Gurwith M, Heyward W, Martin M, van Griensven F, Hu D, Tappero J W, Choopanya K, Bangkok Vaccine Evaluation G. 2006. Randomized, double-blind, placebo-controlled efficacy trial of a bivalent recombinant glycoprotein 120 HIV-1 vaccine among injection drug users in Bangkok, Thailand. J Infect Dis 194:1661-1671.
9. Saunders K O, Rudicell R S, Nabel G J. 2012. The design and evaluation of HIV-1 vaccines. AIDS 26:1293-1302.
10. Goepfert P A, Elizaga M L, Seaton K, Tomaras G D, Montefiori D C, Sato A, Hural J, DeRosa S C, Kalams S A, McElrath M J, Keefer M C, Baden L R, *Lama* J R, Sanchez J, Mulligan M J, Buchbinder S P, Hammer S M, Koblin B A, Pensiero M, Butler C, Moss B, Robinson H L; HVTN 205 Study Group; National Institutes of Allergy and Infectious Diseases HIV Vaccines Trials Network. 2014. Specificity and 6-month durability of immune responses induced by DNA and recombinant modified vaccinia Ankara vaccines expressing HIV-1 virus-like particles. J Infect Dis 210:99-110.
11. Sanou M P, Roff S R, Mennella A, Sleasman J W, Rathore M H, Yamamoto J K, Levy J A. 2013. Evolutionarily conserved epitopes on human immunodeficiency virus type 1 (HIV-1) and feline immunodeficiency virus reverse transcriptases detected by HIV-1-infected subjects. J Virol 87:10004-10015.
12. Roff S R, Sanou M P, Rathore M H, Levy J A, Yamamoto J K. 2015. Conserved epitopes on HIV-1, FIV and SIV p24 proteins are recognized by HIV-1 infected subjects. Hum Vaccin Immunother 11:6 (In press).
13. Coleman J K, Pu R, Martin M M, Noon-Song E N, Zwijnenberg R, Yamamoto J K. 2014. Feline immunodeficiency virus (FIV) vaccine efficacy and FIV neutralizing antibodies. Vaccine 32:746-754.
14. Elder J H, Lin Y C, Fink E, Grant C K. 2010. Feline immunodeficiency virus (FIV) as a model for study of lentivirus infections: parallels with HIV. Curr HIV Res 8:73-80.
15. Uhl E W, Martin M, Coleman J K, Yamamoto J K. 2008. Advances in FIV vaccine technology. Vet Immunol Immunopathol 123:65-80.
16. Omori M, Pu R, Tanabe T, Hou W, Coleman J K, Arai M, Yamamoto J K. 2004. Cellular immune responses to feline immunodeficiency virus (FIV) induced by dual-subtype FIV vaccine. Vaccine 23:386-398.
17. Fujita Y, Taguchi H. 2011. Current status of multiple antigen-presenting peptide vaccine systems: Application of organic and inorganic nanoparticles. Chem Cent J 5:48.
18. Jacobs E S, Persad D, Ran L, Danesh A, Heitman J W, Deng X, Cameron M J, Kelvin D J, Norris P J. 2014. A CD4+ T cell antagonist epitope down-regulates activating signaling proteins, up-regulates inhibitory signaling proteins and abrogates HIV-specific T cell function. Retrovirology 11:57.
19. Klenerman P, Rowland-Jones S, McAdam S, Edwards J, Daenke S, Lalloo D, Koppe B, Rosenberg W, Boyd D, Edwards A, Giangrande P, Phillips R E, McMichael A J.

19. 1994. Cytotoxic T-cell activity antagonized by naturally occurring HIV-1 Gag variants. Nature 369:403-407.
20. Fust G. 1997. Enhancing antibodies in HIV infection. Parasitology 115 Suppl:S127-140.
21. Wang G Z, Tang X D, Lu M H, Gao J H, Liang G P, Li N, Li C Z, Wu Y Y, Chen L, Cao Y L, Fang D C, Yang S M. 2011. Multiple Antigenic Peptides of Human Heparanase Elicit a Much More Potent Immune Response against Tumors. Cancer Prev Res 4:1285-1295.
22. Oka Y, Tsuboi A, Fujiki F, Li Z Y, Nakajima H, Hosen N, Shirakata T, Nishida S, Oji Y, Kawase I, Sugiyama H. 2009. WT1 Peptide Vaccine as a Paradigm for "Cancer Antigen-Derived Peptide"-Based Immunotherapy for Malignancies: Successful Induction of Anti-Cancer Effect by Vaccination with a Single Kind of WT1 Peptide. Anti-Cancer Agent Med Chem 9:787-797.
23. Kowalczyk W, de la Torre B G, Andreu D. 2010. Strategies and limitations in dendrimeric immunogen synthesis. The influenza virus M2e epitope as a case study. Bioconjug Chem 21:102-110.
24. Mahajan B, Berzofsky J A, Boykins R A, Majam V, Zheng H, Chattopadhyay R, de la Vega P, Moch J K, Haynes J D, Belyakov I M, Nakhasi H L, Kumar S. 2010. Multiple antigen peptide vaccines against Plasmodium falciparum malaria. Infect Immun 78:4613-4624.
25. Galin F S, Chrisman C L, Cook J R, Jr., Xu L, Jackson P L, Noerager B D, Weathington N M, Blalock J E. 2007. Possible therapeutic vaccines for canine myasthenia gravis: implications for the human disease and associated fatigue. Brain Behav Immun 21:323-331.
26. La Cava A. 2010. Modulation of autoimmunity with artificial peptides. Autoimmun Rev 10:18-21.
27. Cruz L J, Cabrales A, Iglesias E, Aguilar J C, Gonzalez L J, Reyes O. 2009. Enhanced immunogenicity and cross-reactivity of HIV-1 V3-peptide and multiple antigen peptides conjugated to distinct carrier proteins. Int immunopharmacol 9:1452-1459.
28. Vogel T U, Beer B E, zur Megede J, Ihlenfeldt H G, Jung G, Holzammer S, Watkins D I, Altman J D, Kurth R, Norley S. 2002. Induction of anti-simian immunodeficiency virus cellular and humoral immune responses in rhesus macaques by peptide immunogens: correlation of CTL activity and reduction of cell-associated but not plasma virus load following challenge. J Gen Virol 83:81-91.
29. Nakayama K. 1997. Furin: a mammalian subtilisin/Kex2p-like endoprotease involved in processing of a wide variety of precursor proteins. Biochem J 327 (Pt 3):625-635.
30. Lu J, Wettstein P J, Higashimoto Y, Appella E, Celis E. 2001. TAP-independent presentation of CTL epitopes by Trojan antigens. J Immunol 166:7063-7071.
31. Abbott J R, Pu R, Coleman J K, Yamamoto J K. 2012. Utilization of feline ELISPOT for mapping vaccine epitopes. Methods Mol Biol 792:47-63.
32. Nishimura Y, Shimojima M, Sato E, Izumiya Y, Tohya Y, Mikami T, Miyazawa T. 2004. Downmodulation of CD3epsilon expression in CD8alpha+beta-T cells of feline immunodeficiency virus-infected cats. J Gen Virol 85:2585-2589.
33. Gengozian N, Reyes L, Pu R, Homer B L, Bova F J, Yamamoto J K. 1997. Fractionation of feline bone marrow with the soybean agglutinin lectin yields populations enriched for erythroid and myeloid elements: transplantation of soybean agglutinin-negative cells into lethally irradiated recipients. Transplantation 64:510-518.
34. Pu R, Coleman J, Omori M, Arai M, Hohdatsu T, Huang C, Tanabe T, Yamamoto J K. 2001. Dual-subtype FIV vaccine protects cats against in vivo swarms of both homologous and heterologous subtype FIV isolates. AIDS 15:1225-1237.
35. Pu R, Omori M, Okada S, Rine S L, Lewis B A, Lipton E, Yamamoto J K. 1999. MHC-restricted protection of cats against FIV infection by adoptive transfer of immune cells from FIV-vaccinated donors. Cell Immunol 198:30-43.
36. Pu R, Okada S, Little E R, Xu B, Stoffs W V, Yamamoto J K. 1995. Protection of neonatal kittens against feline immunodeficiency virus infection with passive maternal antiviral antibodies. AIDS 9:235-242.
37. Tanabe T, Yamamoto J K. 2001. Feline immunodeficiency virus lacks sensitivity to the antiviral activity of feline IFN-gamma. J interferon Cytokine Res 21:1039-1046.
38. Marsh S G, Parham P, Barber L D. 2000. HLA polymorphism, peptide-binding motifs and T-cell epitopes. pp. 61-72. In The HLA Facts Book. Academy Press, London, UK.
39. Cohen N R, Garg S, Brenner M B. 2009. Antigen Presentation by CD1 Lipids, T Cells, and NKT Cells in Microbial Immunity. Adv Immunol 102:1-94.
40. Fujii S, Motohashi S, Shimizu K, Nakayama T, Yoshiga Y, Taniguchi M. 2010. Adjuvant activity mediated by iNKT cells. Semin Immunol 22:97-102.
41. Zorko M, Langel U. 2005. Cell-penetrating peptides: mechanism and kinetics of cargo delivery. Adv Drug Deliv Rev 57:529-545.
42. Tellier M C, Pu R, Pollock D, Vitsky A, Tartaglia J, Paoletti E, Yamamoto J K. 1998. Efficacy evaluation of prime-boost protocol: canarypoxvirus-based feline immunodeficiency virus (FIV) vaccine and inactivated FIV-infected cell vaccine against heterologous FIV challenge in cats. AIDS 12:11-18.
43. Yamamoto J K, Okuda T, Ackley C D, Louie H, Pembroke E, Zochlinski H, Munn R J, Gardner M B. 1991. Experimental vaccine protection against feline immunodeficiency virus. AIDS Res Hum Retroviruses 7:911-922.
44. Cassidy S A, Cheent K S, Khakoo S I. 2014. Effects of peptide on N K cell-mediated MHC I recognition. Front Immunol 5:133.
45. Soghoian D Z, Jessen H, Flanders M, Sierra-Davidson K, Cutler S, Pertel T, Ranasinghe S, Lindqvist M, Davis I, Lane K, Rychert J, Rosenberg E S, Piechocka-Trocha A, Brass A L, Brenchley J M, Walker B D, Streeck H. 2012. HIV-specific cytolytic CD4 T cell responses during acute HIV infection predict disease outcome. Sci Transl Med 4:123ra125.
46. Lettau M, Schmidt H, Kabelitz D, Janssen O. 2007. Secretory lysosomes and their cargo in T and N K cells. Immunol Lett 108:10-19.
47. Leeansyah E, Malone DFG, Anthony D D, Sandberg J K. 2013. Soluble biomarkers of HIV transmission, disease progression and comorbidities. Curr Opin HIV AIDS 8:117-124.
48. Ipp H, Zemlin A. 2013. The paradox of the immune response in HIV infection: when inflammation becomes harmful. Clin Chim Acta 416:96-99.
49. Yamamoto J K, Barre-Sinoussi F, Bolton V, Pedersen N C, Gardner M B. 1986. Human alpha- and beta-interferon but not gamma-suppress the in vitro replication of LAV, HTLV-III, and ARV-2. J interferon Res 6:143-152.

50. Ali R, Naqvi R A, Kumar S, Bhat A A, Rao D N. 2013. Multiple antigen peptide containing B and T cell epitopes of F1 antigen of *Yersinia pestis* showed enhanced Th1 immune response in murine model. Scand J Immunol 77:361-371.
51. Heegaard P M H, Boas U, Sorensen N S. 2010. Dendrimers for vaccine and immunostimulatory uses. A review. Bioconjug Chem 21:405-418.
52. Nardelli B, Tam J P. 1993. Cellular immune-responses Induced by in-vivo priming with a lipid-conjugated multimeric antigen peptide. Immunology 79:355-361.
53. BenMohamed L, Wechsler S L, Nesburn A B. 2002. Lipopeptide vaccines—yesterday, today, and tomorrow. Lancet Infect Dis 2:425-431.
54. Sanou M P, De Groot A S, Murphey-Corb M, Levy J A, Yamamoto J K. 2012. HIV-1 Vaccine Trials: Evolving Concepts and Designs. Open AIDS J 6:274-288.
55. Lu J, Higashimoto Y, Appella E, Celis E. 2004. Mu4tiepitope Trojan antigen peptide vaccines for the induction of antitumor CTL and Th immune responses. J Immunol 172:4575-4582.

I claim:

1. A method for inducing an immune response in a person or animal against an immunodeficiency virus, comprising administering one or more antigens and/or immunogens to the person or animal, wherein said one or more antigens and/or immunogens comprise one or more evolutionarily conserved epitopes, wherein said epitopes are conserved between two or more different immunodeficiency viruses, and wherein said epitopes independently consist of the amino acid sequence of any of SEQ ID NOs: 1 to 37 or SEQ ID NOs:39 to 102.

2. The method according to claim 1, wherein said epitopes are conserved between HIV and FIV, or are conserved between HIV, SIV, and FIV.

3. The method according to claim 1, wherein at least one of said epitopes is a T-cell epitope.

4. The method according to claim 3, wherein said T cell epitope induces one or more T cell responses.

5. The method according to claim 4, wherein said T cell response is production and/or release of cytotoxins, cytolysins, and/or cytokines.

6. The method according to claim 1, wherein said induced immune response is a CTL-associated immune response and/or a T helper (Th) immune response.

7. The method according to claim 1, wherein said induced immune response comprises induction of a CD4+ and/or CD8+ T cell response.

8. The method according to claim 4, wherein said one or more antigens and/or immunogens are administered to said person or animal subcutaneously or intradermally.

9. The method according to claim 5, wherein said cytotoxins, cytolysins, and/or cytokines are one or more of IL2, IFNγ, tumor necrosis factor α (TNFα), perforin, or granzyme A or B.

10. The method according to claim 1, wherein said immune response is a protective immune response that provides protection against infection by said immunodeficiency virus.

11. The method according to claim 1, wherein said epitopes independently consist of the amino acid sequence of any of SEQ ID NOs:26, 30, 35, or 88.

12. The method according to claim 1, wherein said animal is a feline animal.

13. The method according to claim 1, wherein said immunodeficiency virus is HIV or FIV.

14. The method according to claim 1, wherein said epitopes are provided in a multiple antigenic peptide (MAP) construct.

15. The method according to claim 1, wherein said antigens and/or immunogens are administered as a vaccine composition.

16. The method according to claim 15, wherein said vaccine composition comprises a pharmaceutically-acceptable carrier, diluent, or adjuvant.

17. The method according to claim 16, wherein said adjuvant is threonyl muramyl dipeptide (MDP), RIBI adjuvant system components including the cell wall skeleton (CWS) component, Freund's complete adjuvant, Freund's incomplete adjuvant, bacterial lipopolysaccharide (LPS), a cytokine, a lymphokine, or an interleukin, or any combination thereof.

18. The method according to claim 17, wherein said cytokine is γ-IFN, GM-CSF, or CSF or said interleukin is IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, or IL-22.

19. The method according to claim 1, wherein said epitopes independently consist of two or more of any of SEQ ID NOs: 1 to 37 or SEQ ID NOs: 39 to 102.

20. The method according claim 1, wherein said epitopes independently consist of the amino acid sequence of any of SEQ ID NOs: 1, 3, 4, 5, 6, 8, 10, 12, 14, 15, 16, 17, 19, 20, 21, 22, 23, 26, 29, 30, 31, 32, 33, 34, 35, 36, 37, 52, 53, or 66.

* * * * *

UNITED STATES PATENT AND TRADEMARK OFFICE
CERTIFICATE OF CORRECTION

PATENT NO. : 10,758,609 B2
APPLICATION NO. : 15/762108
DATED : September 1, 2020
INVENTOR(S) : Janet K. Yamamoto It is certified that error appears in the above-identified patent and that said Letters Patent is hereby corrected as shown below:

In the Specification

Column 2
Line 37, "USCAlemyO1" should read --USCAlemy01--

Column 6
Line 51, "MAP5" should read --MAPS--

Column 7
Line 5, "3'" should read --3$^{rd}$--
Line 7, "3'" should read --3$^{rd}$--
Line 11, "3'" should read --3$^{rd}$--

Column 18
Line 15, "(11-18)" should read --(IL-18)--
Lines 19-20, "11-12 and IL-15, or IL-15 and 11-18, or IL-12 and IL-18, or 11-12, 11-15, and 11-18" should read --IL-12 and IL-15, or IL-15 and IL-18, or IL-12 and IL-18, or IL-12, IL-15, and IL-18--

Column 34
Line 21, "p2$^{4}$" should read --p24--

Column 49
Table 10, Footnote d, "Bold HLA supertypes [5] or bold 2- or 4-digit resolution alleles similar to those HLA alleles in cats." should read --Bold supertypes or 2-digit alleles under LANL CTL are from LANL's optimal CTL list; underline/italics are common with those determined by NetMHC and/or NetCTL--
Table 10, Footnote f, "(Net MEC), class II (NetMECII)" should read --(Net MHC), class II (NetMHCII)--

Signed and Sealed this
Twelfth Day of January, 2021

Andrei Iancu
*Director of the United States Patent and Trademark Office*

Column 56
Table 13, row "China Asian", last column,
"B8           --B8
[10]" should read   [1.0]--

Columns 55-56
Table 14, Row "FRT3-3", Column "IFNγ", [blank] should read -- ± --
Table 14, Row "FMA1", Column "IL2", [blank] should read -- – --
Table 14, Row "FRT3-5", Column "CD4", [blank] should read -- ± --
Table 14, Row "FRT7-2", Column "IL2", "±" should read -- – --

Column 57
Table 14, Column "Humans & Cats Biologic Score",

" 
| FIV Epitope Peptide | Humans & Cats Biologic Score |
|---|---|
| Fp4-3 | 2.00 |
| Fp14-1 | 2.35 |
| FRT3-3 | |
| FRT3-4 | 1.25 |
| FMA1 | 2.00 |
| FMA2 | 2.59 |
| Fp9-3 | 2.20 |
| Fp10-2 | |
| Fp10-3 | 2.18 |
| Fp14-3 | |
| Fp14-4 | 3.00 |
| FNC2 | 2.00 |
| FPR1 | 2.00 |
| FPR2 | 2.70 |
| FRT3-5 (FRT3-4) | 2.87 |
| FRT7-1 | |
| FRT7-2 | 2.00 |
| FIN7-1 | 2.29 |
| FTM4-3 | 2.57 |
| FTM8 | 1.86 |
| FSU4 | |

" should read --

| FIV Epitope Peptide | Humans & Cats Biologic Score |
|---|---|
| Fp4-3 | 2.00 |
| Fp14-1 | 2.00 |
| FRT3-3 | 2.35 |
| FRT3-4 | |
| FMA1 | 1.25 |
| FMA2 | 2.00 |
| Fp9-3 | 2.59 |
| Fp10-2 | 2.20 |
| Fp10-3 | |
| Fp14-3 | 2.18 |
| Fp14-4 | |
| FNC2 | 3.00 |
| FPR1 | 2.00 |
| FPR2 | 2.00 |
| FRT3-5 (FRT3-4) | 2.70 |
| FRT7-1 | 2.87 |
| FRT7-2 | |
| FIN7-1 | 2.00 |
| FTM4-3 | 2.29 |
| FTM8 | 2.57 |
| FSU4 | 1.86 |

--

Column 58
Line 35 (Table 14 footnotes), "B62(7%)=B8(7/0)" should read --B62(7%)=B8(7%)--
Line 39, "L2 ELISpot" should read --IL2 ELISpot--

Column 62
Line 15, "112" should read --IL2--

Column 64
Table 15, Row "FNC2", Column "E/S", "N" should read -- – --

SEQUENCE LISTING

```
<160> NUMBER OF SEQ ID NOS: 114

<210> SEQ ID NO 1
<211> LENGTH: 12
<212> TYPE: PRT
<213> ORGANISM: Human immunodeficiency virus

<400> SEQUENCE: 1

Lys Ile Arg Leu Arg Pro Gly Gly Lys Lys Lys Tyr
1               5                   10

<210> SEQ ID NO 2
<211> LENGTH: 13
<212> TYPE: PRT
<213> ORGANISM: Feline immunodeficiency virus

<400> SEQUENCE: 2

Asn Val Ala Val Gly Val Gly Gly Lys Ser Lys Lys Phe
1               5                   10

<210> SEQ ID NO 3
<211> LENGTH: 15
<212> TYPE: PRT
<213> ORGANISM: Human immunodeficiency virus

<400> SEQUENCE: 3

Gly Ser Glu Glu Leu Arg Ser Leu Tyr Asn Thr Val Ala Thr Leu
1               5                   10                  15

<210> SEQ ID NO 4
<211> LENGTH: 15
<212> TYPE: PRT
<213> ORGANISM: Feline immunodeficiency virus

<400> SEQUENCE: 4

Gly Ser Ser Lys Glu Ile Asp Met Ala Ile Val Thr Leu Lys Val
1               5                   10                  15

<210> SEQ ID NO 5
<211> LENGTH: 16
<212> TYPE: PRT
<213> ORGANISM: Human immunodeficiency virus

<400> SEQUENCE: 5

Thr Ala Pro Pro Glu Glu Ser Phe Arg Ser Gly Val Glu Thr Thr Thr
1               5                   10                  15

<210> SEQ ID NO 6
<211> LENGTH: 16
<212> TYPE: PRT
<213> ORGANISM: Feline immunodeficiency virus

<400> SEQUENCE: 6
```

```
Ala Ala Ala Pro Val Asn Gln Met Gln Gln Ala Val Met Pro Ser Ala
1               5                   10                  15
```

<210> SEQ ID NO 7
<211> LENGTH: 15
<212> TYPE: PRT
<213> ORGANISM: Human immunodeficiency virus

<400> SEQUENCE: 7

```
Gly Glu Arg Ile Val Asp Ile Ile Ala Thr Asp Ile Gln Thr Lys
1               5                   10                  15
```

<210> SEQ ID NO 8
<211> LENGTH: 15
<212> TYPE: PRT
<213> ORGANISM: Feline immunodeficiency virus

<400> SEQUENCE: 8

```
Tyr Glu Leu Tyr Met Gln Gln Glu Ser Leu Arg Ile Gln Asp Arg
1               5                   10                  15
```

<210> SEQ ID NO 9
<211> LENGTH: 14
<212> TYPE: PRT
<213> ORGANISM: Human immunodeficiency virus

<400> SEQUENCE: 9

```
Thr Leu Trp Gln Arg Pro Leu Val Thr Ile Lys Ile Gly Gly
1               5                   10
```

<210> SEQ ID NO 10
<211> LENGTH: 14
<212> TYPE: PRT
<213> ORGANISM: Feline immunodeficiency virus

<400> SEQUENCE: 10

```
Thr Leu Glu Lys Arg Pro Glu Ile Leu Ile Phe Val Asn Gly
1               5                   10
```

<210> SEQ ID NO 11
<211> LENGTH: 14
<212> TYPE: PRT
<213> ORGANISM: Human immunodeficiency virus

<400> SEQUENCE: 11

```
Glu Ala Leu Leu Asp Thr Gly Ala Asp Asp Thr Val Leu Glu
1               5                   10
```

<210> SEQ ID NO 12
<211> LENGTH: 14
<212> TYPE: PRT
<213> ORGANISM: Feline immunodeficiency virus

<400> SEQUENCE: 12

```
Lys Phe Leu Leu Asp Thr Gly Ala Asp Ile Thr Ile Leu Asn
1               5                   10
```

<210> SEQ ID NO 13
<211> LENGTH: 13
<212> TYPE: PRT
<213> ORGANISM: Human immunodeficiency virus

<400> SEQUENCE: 13

```
Tyr Leu Lys Asp Gln Gln Leu Leu Gly Ile Trp Gly Cys
```

<210> SEQ ID NO 14
<211> LENGTH: 13
<212> TYPE: PRT
<213> ORGANISM: Feline immunodeficiency virus

<400> SEQUENCE: 14

Lys Phe Leu Tyr Thr Ala Phe Ala Met Gln Glu Leu Arg
1               5                   10

<210> SEQ ID NO 15
<211> LENGTH: 16
<212> TYPE: PRT
<213> ORGANISM: Human immunodeficiency virus

<400> SEQUENCE: 15

Leu Arg Ile Val Phe Ala Val Leu Ser Ile Val Asn Arg Val Arg Gln
1               5                   10                  15

<210> SEQ ID NO 16
<211> LENGTH: 16
<212> TYPE: PRT
<213> ORGANISM: Feline immunodeficiency virus

<400> SEQUENCE: 16

Leu Leu Leu Ile Leu Cys Leu Pro Thr Leu Val Asp Cys Ile Arg Asn
1               5                   10                  15

<210> SEQ ID NO 17
<211> LENGTH: 15
<212> TYPE: PRT
<213> ORGANISM: Human immunodeficiency virus

<400> SEQUENCE: 17

Asp Asn Trp Arg Ser Glu Leu Tyr Lys Tyr Lys Val Val Lys Ile
1               5                   10                  15

<210> SEQ ID NO 18
<211> LENGTH: 15
<212> TYPE: PRT
<213> ORGANISM: Feline immunodeficiency virus

<400> SEQUENCE: 18

Ala Gly Leu Arg Gln Ser Leu Glu Gln Tyr Gln Val Val Lys Gln
1               5                   10                  15

<210> SEQ ID NO 19
<211> LENGTH: 14
<212> TYPE: PRT
<213> ORGANISM: Human immunodeficiency virus

<400> SEQUENCE: 19

Ile Pro Val Gly Glu Ile Tyr Lys Arg Trp Ile Ile Leu Gly
1               5                   10

<210> SEQ ID NO 20
<211> LENGTH: 15
<212> TYPE: PRT
<213> ORGANISM: Feline immunodeficiency virus

<400> SEQUENCE: 20

Phe Ala Pro Ala Arg Met Gln Cys Arg Ala Trp Tyr Leu Glu Ala
1               5                   10                  15

```
<210> SEQ ID NO 21
<211> LENGTH: 14
<212> TYPE: PRT
<213> ORGANISM: Human immunodeficiency virus

<400> SEQUENCE: 21

Arg Trp Ile Ile Leu Gly Leu Asn Lys Ile Val Arg Met Tyr
1               5                   10

<210> SEQ ID NO 22
<211> LENGTH: 17
<212> TYPE: PRT
<213> ORGANISM: Feline immunodeficiency virus

<400> SEQUENCE: 22

Arg Ala Trp Tyr Leu Glu Ala Leu Gly Lys Leu Ala Ala Ile Lys Ala
1               5                   10                  15

Lys

<210> SEQ ID NO 23
<211> LENGTH: 14
<212> TYPE: PRT
<213> ORGANISM: Human immunodeficiency virus

<400> SEQUENCE: 23

Arg Ala Glu Gln Ala Ser Gln Glu Val Lys Asn Trp Met Thr
1               5                   10

<210> SEQ ID NO 24
<211> LENGTH: 14
<212> TYPE: PRT
<213> ORGANISM: Feline immunodeficiency virus

<400> SEQUENCE: 24

Asp Gln Glu Gln Asn Thr Ala Glu Val Lys Leu Tyr Leu Lys
1               5                   10

<210> SEQ ID NO 25
<211> LENGTH: 16
<212> TYPE: PRT
<213> ORGANISM: Human immunodeficiency virus

<400> SEQUENCE: 25

Gln Glu Val Lys Asn Trp Met Thr Glu Thr Leu Leu Val Gln Asn Ala
1               5                   10                  15

<210> SEQ ID NO 26
<211> LENGTH: 16
<212> TYPE: PRT
<213> ORGANISM: Feline immunodeficiency virus

<400> SEQUENCE: 26

Ala Glu Val Lys Leu Tyr Leu Lys Gln Ser Leu Ser Ile Ala Asn Ala
1               5                   10                  15

<210> SEQ ID NO 27
<211> LENGTH: 15
<212> TYPE: PRT
<213> ORGANISM: Human immunodeficiency virus

<400> SEQUENCE: 27

Pro Gln Asp Leu Asn Thr Met Leu Asn Thr Val Gly Gly His Gln
1               5                   10                  15
```

```
<210> SEQ ID NO 28
<211> LENGTH: 15
<212> TYPE: PRT
<213> ORGANISM: Feline immunodeficiency virus

<400> SEQUENCE: 28

Pro Thr Asp Met Ala Thr Leu Ile Met Ala Ala Pro Gly Cys Ala
1               5                   10                  15

<210> SEQ ID NO 29
<211> LENGTH: 20
<212> TYPE: PRT
<213> ORGANISM: Human immunodeficiency virus

<400> SEQUENCE: 29

Lys Lys Lys Asp Ser Thr Lys Trp Arg Lys Leu Val Asp Phe Arg Glu
1               5                   10                  15

Leu Asn Lys Arg
            20

<210> SEQ ID NO 30
<211> LENGTH: 18
<212> TYPE: PRT
<213> ORGANISM: Feline immunodeficiency virus

<400> SEQUENCE: 30

Lys Lys Lys Ser Gly Lys Trp Arg Leu Ile Asp Phe Arg Val Leu Asn
1               5                   10                  15

Lys Leu

<210> SEQ ID NO 31
<211> LENGTH: 19
<212> TYPE: PRT
<213> ORGANISM: Feline immunodeficiency virus

<400> SEQUENCE: 31

Lys Lys Lys Ser Gly Lys Trp Arg Leu Leu Ile Asp Phe Arg Val Leu
1               5                   10                  15

Asn Lys Leu

<210> SEQ ID NO 32
<211> LENGTH: 18
<212> TYPE: PRT
<213> ORGANISM: Human immunodeficiency virus

<400> SEQUENCE: 32

Trp Arg Lys Leu Val Asp Phe Arg Glu Leu Asn Lys Arg Thr Gln Asp
1               5                   10                  15

Phe Trp

<210> SEQ ID NO 33
<211> LENGTH: 18
<212> TYPE: PRT
<213> ORGANISM: Feline immunodeficiency virus

<400> SEQUENCE: 33

Trp Arg Met Leu Ile Asp Phe Arg Val Leu Asn Lys Leu Thr Asp Lys
1               5                   10                  15

Gly Ala

<210> SEQ ID NO 34
```

```
<211> LENGTH: 20
<212> TYPE: PRT
<213> ORGANISM: Human immunodeficiency virus

<400> SEQUENCE: 34

Gly Ile Arg Tyr Gln Tyr Asn Val Leu Pro Gln Gly Trp Lys Gly Ser
1               5                   10                  15

Pro Ala Ile Phe
            20

<210> SEQ ID NO 35
<211> LENGTH: 20
<212> TYPE: PRT
<213> ORGANISM: Feline immunodeficiency virus

<400> SEQUENCE: 35

Gly Arg Arg Tyr Val Trp Cys Ser Leu Pro Gln Gly Trp Val Leu Ser
1               5                   10                  15

Pro Leu Ile Tyr
            20

<210> SEQ ID NO 36
<211> LENGTH: 14
<212> TYPE: PRT
<213> ORGANISM: Feline immunodeficiency virus

<400> SEQUENCE: 36

Lys Lys Lys Ser Gly Lys Trp Arg Leu Ile Asp Phe Arg Val
1               5                   10

<210> SEQ ID NO 37
<211> LENGTH: 12
<212> TYPE: PRT
<213> ORGANISM: Feline immunodeficiency virus

<400> SEQUENCE: 37

Trp Arg Leu Ile Asp Phe Arg Val Leu Asn Lys Leu
1               5                   10

<210> SEQ ID NO 38
<211> LENGTH: 4
<212> TYPE: PRT
<213> ORGANISM: Feline immunodeficiency virus

<400> SEQUENCE: 38

Arg Val Lys Arg
1

<210> SEQ ID NO 39
<211> LENGTH: 20
<212> TYPE: PRT
<213> ORGANISM: Feline immunodeficiency virus

<400> SEQUENCE: 39

Gly Arg Arg Tyr Val Trp Cys Ser Leu Pro Gln Gly Trp Ile Leu Ser
1               5                   10                  15

Pro Leu Ile Tyr
            20

<210> SEQ ID NO 40
<211> LENGTH: 20
<212> TYPE: PRT
<213> ORGANISM: Feline immunodeficiency virus
```

```
<400> SEQUENCE: 40

Gly Arg Arg Phe Val Trp Cys Ser Leu Pro Gln Gly Trp Ile Leu Ser
1               5                   10                  15

Pro Leu Ile Tyr
            20

<210> SEQ ID NO 41
<211> LENGTH: 16
<212> TYPE: PRT
<213> ORGANISM: Feline immunodeficiency virus

<400> SEQUENCE: 41

Ala Glu Val Lys Leu Tyr Leu Lys Gln Ser Leu Ser Ile Ala Asn Pro
1               5                   10                  15

<210> SEQ ID NO 42
<211> LENGTH: 16
<212> TYPE: PRT
<213> ORGANISM: Feline immunodeficiency virus

<400> SEQUENCE: 42

Ala Glu Val Lys Thr Tyr Leu Lys Gln Ser Leu Ser Leu Ala Asn Ser
1               5                   10                  15

<210> SEQ ID NO 43
<211> LENGTH: 18
<212> TYPE: PRT
<213> ORGANISM: Feline immunodeficiency virus

<400> SEQUENCE: 43

Lys Lys Lys Ser Gly Lys Trp Arg Leu Ile Asp Phe Arg Glu Leu Asn
1               5                   10                  15

Lys Leu

<210> SEQ ID NO 44
<211> LENGTH: 18
<212> TYPE: PRT
<213> ORGANISM: Feline immunodeficiency virus

<400> SEQUENCE: 44

Lys Lys Lys Thr Gly Lys Trp Arg Leu Ile Asp Phe Arg Glu Leu Asn
1               5                   10                  15

Lys Leu

<210> SEQ ID NO 45
<211> LENGTH: 14
<212> TYPE: PRT
<213> ORGANISM: Human immunodeficiency virus

<400> SEQUENCE: 45

Ile Pro Val Gly Asp Ile Tyr Lys Arg Trp Ile Ile Leu Gly
1               5                   10

<210> SEQ ID NO 46
<211> LENGTH: 14
<212> TYPE: PRT
<213> ORGANISM: Human immunodeficiency virus

<400> SEQUENCE: 46

Val Pro Val Gly Asp Ile Tyr Lys Arg Trp Ile Ile Leu Gly
1               5                   10
```

```
<210> SEQ ID NO 47
<211> LENGTH: 14
<212> TYPE: PRT
<213> ORGANISM: Human immunodeficiency virus

<400> SEQUENCE: 47

Ile Pro Val Gly Asn Ile Tyr Arg Arg Trp Ile Gln Leu Gly
1               5                   10

<210> SEQ ID NO 48
<211> LENGTH: 15
<212> TYPE: PRT
<213> ORGANISM: Feline immunodeficiency virus

<400> SEQUENCE: 48

Gly Arg Arg Tyr Val Trp Cys Ser Leu Pro Gln Gly Trp Val Leu
1               5                   10                  15

<210> SEQ ID NO 49
<211> LENGTH: 20
<212> TYPE: PRT
<213> ORGANISM: Human immunodeficiency virus

<400> SEQUENCE: 49

Gly Lys Arg Tyr Ile Tyr Lys Val Leu Pro Gln Gly Trp Lys Gly Ser
1               5                   10                  15

Pro Ala Ile Phe
            20

<210> SEQ ID NO 50
<211> LENGTH: 15
<212> TYPE: PRT
<213> ORGANISM: Human immunodeficiency virus

<400> SEQUENCE: 50

Gly Ile Arg Tyr Gln Tyr Asn Val Leu Pro Gln Gly Trp Lys Gly
1               5                   10                  15

<210> SEQ ID NO 51
<211> LENGTH: 14
<212> TYPE: PRT
<213> ORGANISM: Human immunodeficiency virus

<400> SEQUENCE: 51

Asn Val Leu Pro Gln Gly Trp Lys Gly Ser Pro Ala Ile Phe
1               5                   10

<210> SEQ ID NO 52
<211> LENGTH: 14
<212> TYPE: PRT
<213> ORGANISM: Feline immunodeficiency virus

<400> SEQUENCE: 52

Ala Glu Val Lys Leu Tyr Leu Lys Gln Ser Leu Ser Ile Ala
1               5                   10

<210> SEQ ID NO 53
<211> LENGTH: 13
<212> TYPE: PRT
<213> ORGANISM: Feline immunodeficiency virus

<400> SEQUENCE: 53

Lys Leu Tyr Leu Lys Gln Ser Leu Ser Ile Ala Asn Ala
1               5                   10
```

<210> SEQ ID NO 54
<211> LENGTH: 16
<212> TYPE: PRT
<213> ORGANISM: Human immunodeficiency virus

<400> SEQUENCE: 54

Gln Glu Val Lys Gly Trp Met Thr Glu Thr Leu Leu Val Gln Asn Ala
1               5                   10                  15

<210> SEQ ID NO 55
<211> LENGTH: 16
<212> TYPE: PRT
<213> ORGANISM: Human immunodeficiency virus

<400> SEQUENCE: 55

Gln Asp Val Lys Asn Trp Met Thr Asp Thr Leu Leu Val Gln Asn Ala
1               5                   10                  15

<210> SEQ ID NO 56
<211> LENGTH: 16
<212> TYPE: PRT
<213> ORGANISM: Human immunodeficiency virus

<400> SEQUENCE: 56

Gln Asp Val Lys Asn Trp Met Thr Glu Thr Leu Leu Val Gln Asn Ala
1               5                   10                  15

<210> SEQ ID NO 57
<211> LENGTH: 16
<212> TYPE: PRT
<213> ORGANISM: Human immunodeficiency virus

<400> SEQUENCE: 57

Gln Glu Val Lys Thr Trp Met Thr Asp Thr Leu Leu Val Gln Asn Ala
1               5                   10                  15

<210> SEQ ID NO 58
<211> LENGTH: 16
<212> TYPE: PRT
<213> ORGANISM: Human immunodeficiency virus

<400> SEQUENCE: 58

Ala Ala Val Lys Asn Trp Met Thr Gln Thr Leu Leu Ile Gln Asn Ala
1               5                   10                  15

<210> SEQ ID NO 59
<211> LENGTH: 15
<212> TYPE: PRT
<213> ORGANISM: Human immunodeficiency virus

<400> SEQUENCE: 59

Ala Ser Gln Glu Val Lys Asn Trp Met Thr Glu Thr Leu Leu Val
1               5                   10                  15

<210> SEQ ID NO 60
<211> LENGTH: 14
<212> TYPE: PRT
<213> ORGANISM: Human immunodeficiency virus

<400> SEQUENCE: 60

Val Lys Asn Trp Met Thr Glu Thr Leu Leu Val Gln Asn Ala
1               5                   10

<210> SEQ ID NO 61

-continued

```
<211> LENGTH: 13
<212> TYPE: PRT
<213> ORGANISM: Feline immunodeficiency virus

<400> SEQUENCE: 61

Trp Arg Leu Ile Asp Phe Arg Val Leu Ile Asn Lys Leu
1               5                   10

<210> SEQ ID NO 62
<211> LENGTH: 20
<212> TYPE: PRT
<213> ORGANISM: Human immunodeficiency virus

<400> SEQUENCE: 62

Lys Lys Lys Asp Lys Asn Lys Trp Arg Met Leu Ile Asp Phe Arg Glu
1               5                   10                  15

Leu Asn Arg Val
            20

<210> SEQ ID NO 63
<211> LENGTH: 16
<212> TYPE: PRT
<213> ORGANISM: Human immunodeficiency virus

<400> SEQUENCE: 63

Lys Lys Lys Asp Ser Thr Lys Trp Arg Lys Leu Val Asp Phe Arg Glu
1               5                   10                  15

<210> SEQ ID NO 64
<211> LENGTH: 13
<212> TYPE: PRT
<213> ORGANISM: Human immunodeficiency virus

<400> SEQUENCE: 64

Trp Arg Lys Leu Val Asp Phe Arg Glu Leu Asn Lys Arg
1               5                   10

<210> SEQ ID NO 65
<211> LENGTH: 16
<212> TYPE: PRT
<213> ORGANISM: Feline immunodeficiency virus

<400> SEQUENCE: 65

Gly Ser Ser Lys Glu Ile Asp Met Ala Ile Val Thr Leu Lys Val Arg
1               5                   10                  15

<210> SEQ ID NO 66
<211> LENGTH: 14
<212> TYPE: PRT
<213> ORGANISM: Feline immunodeficiency virus

<400> SEQUENCE: 66

Cys Ser Leu Pro Gln Gly Trp Val Leu Ser Pro Leu Ile Tyr
1               5                   10

<210> SEQ ID NO 67
<211> LENGTH: 15
<212> TYPE: PRT
<213> ORGANISM: Feline immunodeficiency virus

<400> SEQUENCE: 67

Lys Lys Lys Ser Gly Lys Trp Arg Met Leu Ile Asp Phe Arg Val
1               5                   10                  15
```

```
<210> SEQ ID NO 68
<211> LENGTH: 12
<212> TYPE: PRT
<213> ORGANISM: Artificial
<220> FEATURE:
<223> OTHER INFORMATION: transmembrane peptide

<400> SEQUENCE: 68

Gln Glu Leu Gly Cys Asn Gln Asn Gln Phe Phe Cys
1               5                   10

<210> SEQ ID NO 69
<211> LENGTH: 10
<212> TYPE: PRT
<213> ORGANISM: Artificial
<220> FEATURE:
<223> OTHER INFORMATION: p24 agonist peptide

<400> SEQUENCE: 69

Lys Arg Trp Ile Ile Met Gly Leu Asn Lys
1               5                   10

<210> SEQ ID NO 70
<211> LENGTH: 10
<212> TYPE: PRT
<213> ORGANISM: Artificial
<220> FEATURE:
<223> OTHER INFORMATION: p24 antagonist peptide

<400> SEQUENCE: 70

Lys Arg Trp Ile Ile Leu Gly Leu Asn Lys
1               5                   10

<210> SEQ ID NO 71
<211> LENGTH: 16
<212> TYPE: PRT
<213> ORGANISM: Artificial
<220> FEATURE:
<223> OTHER INFORMATION: p24 agonist peptide

<400> SEQUENCE: 71

Pro Glu Val Ile Pro Met Phe Ser Ala Leu Ser Glu Gly Ala Thr Pro
1               5                   10                  15

<210> SEQ ID NO 72
<211> LENGTH: 13
<212> TYPE: PRT
<213> ORGANISM: Artificial
<220> FEATURE:
<223> OTHER INFORMATION: p24 antagonist peptide

<400> SEQUENCE: 72

Pro Glu Val Ile Pro Met Phe Ser Ala Leu Ser Glu Gly
1               5                   10

<210> SEQ ID NO 73
<211> LENGTH: 15
<212> TYPE: PRT
<213> ORGANISM: Feline immunodeficiency virus

<400> SEQUENCE: 73

Ala Phe Ser Ala Asn Leu Thr Pro Thr Asp Met Ala Thr Leu Ile
1               5                   10                  15

<210> SEQ ID NO 74
<211> LENGTH: 14
<212> TYPE: PRT
```

```
<213> ORGANISM: Feline immunodeficiency virus

<400> SEQUENCE: 74

Asn Leu Thr Pro Thr Asp Met Ala Thr Leu Ile Met Ala Ala
1               5                   10

<210> SEQ ID NO 75
<211> LENGTH: 15
<212> TYPE: PRT
<213> ORGANISM: Feline immunodeficiency virus

<400> SEQUENCE: 75

Glu Gln Asn Thr Ala Glu Val Lys Leu Tyr Leu Lys Gln Ser Leu
1               5                   10                  15

<210> SEQ ID NO 76
<211> LENGTH: 13
<212> TYPE: PRT
<213> ORGANISM: Feline immunodeficiency virus

<400> SEQUENCE: 76

Asn Pro Trp Asn Thr Pro Val Phe Ala Ile Lys Lys Lys
1               5                   10

<210> SEQ ID NO 77
<211> LENGTH: 15
<212> TYPE: PRT
<213> ORGANISM: Feline immunodeficiency virus

<400> SEQUENCE: 77

Thr Pro Val Phe Ala Ile Lys Lys Lys Ser Gly Lys Trp Arg Met
1               5                   10                  15

<210> SEQ ID NO 78
<211> LENGTH: 13
<212> TYPE: PRT
<213> ORGANISM: Feline immunodeficiency virus

<400> SEQUENCE: 78

Trp Arg Met Leu Ile Asp Phe Arg Val Leu Asn Lys Leu
1               5                   10

<210> SEQ ID NO 79
<211> LENGTH: 14
<212> TYPE: PRT
<213> ORGANISM: Feline immunodeficiency virus

<400> SEQUENCE: 79

Ile Asp Phe Arg Val Leu Asn Lys Leu Thr Asp Lys Gly Ala
1               5                   10

<210> SEQ ID NO 80
<211> LENGTH: 15
<212> TYPE: PRT
<213> ORGANISM: Feline immunodeficiency virus

<400> SEQUENCE: 80

Ser Thr Asp Met Ala Thr Leu Ile Met Ser Ala Pro Gly Cys Ala
1               5                   10                  15

<210> SEQ ID NO 81
<211> LENGTH: 15
<212> TYPE: PRT
<213> ORGANISM: Human immunodeficiency virus
```

<400> SEQUENCE: 81

Pro Gln Asp Leu Asn Met Met Leu Asn Ile Val Gly Gly His Gln
1               5                   10                  15

<210> SEQ ID NO 82
<211> LENGTH: 15
<212> TYPE: PRT
<213> ORGANISM: Human immunodeficiency virus

<400> SEQUENCE: 82

Pro Tyr Asp Ile Asn Gln Met Leu Asn Cys Val Gly Asp His Gln
1               5                   10                  15

<210> SEQ ID NO 83
<211> LENGTH: 14
<212> TYPE: PRT
<213> ORGANISM: Feline immunodeficiency virus

<400> SEQUENCE: 83

Asp Gln Glu Gln Asn Thr Ala Glu Val Lys Thr Tyr Leu Lys
1               5                   10

<210> SEQ ID NO 84
<211> LENGTH: 14
<212> TYPE: PRT
<213> ORGANISM: Human immunodeficiency virus

<400> SEQUENCE: 84

Arg Ala Glu Gln Ala Thr Gln Glu Val Lys Gly Trp Met Thr
1               5                   10

<210> SEQ ID NO 85
<211> LENGTH: 14
<212> TYPE: PRT
<213> ORGANISM: Human immunodeficiency virus

<400> SEQUENCE: 85

Arg Ala Glu Gln Ala Thr Gln Asp Val Lys Asn Trp Met Thr
1               5                   10

<210> SEQ ID NO 86
<211> LENGTH: 14
<212> TYPE: PRT
<213> ORGANISM: Human immunodeficiency virus

<400> SEQUENCE: 86

Arg Ala Glu Gln Ala Ser Gln Asp Val Lys Asn Trp Met Thr
1               5                   10

<210> SEQ ID NO 87
<211> LENGTH: 14
<212> TYPE: PRT
<213> ORGANISM: Human immunodeficiency virus

<400> SEQUENCE: 87

Arg Ala Glu Gln Thr Asp Ala Ala Val Lys Asn Trp Met Thr
1               5                   10

<210> SEQ ID NO 88
<211> LENGTH: 19
<212> TYPE: PRT
<213> ORGANISM: Feline immunodeficiency virus

<400> SEQUENCE: 88

```
Lys Lys Lys Ser Gly Lys Trp Arg Met Leu Ile Asp Phe Arg Val Leu
1               5                   10                  15

Asn Lys Leu

<210> SEQ ID NO 89
<211> LENGTH: 19
<212> TYPE: PRT
<213> ORGANISM: Feline immunodeficiency virus

<400> SEQUENCE: 89

Lys Lys Lys Ser Gly Lys Trp Arg Met Leu Ile Asp Phe Arg Glu Leu
1               5                   10                  15

Asn Lys Leu

<210> SEQ ID NO 90
<211> LENGTH: 15
<212> TYPE: PRT
<213> ORGANISM: Human immunodeficiency virus

<400> SEQUENCE: 90

Arg Ala Glu Gln Ala Ser Gln Glu Val Lys Asn Trp Met Thr Glu
1               5                   10                  15

<210> SEQ ID NO 91
<211> LENGTH: 15
<212> TYPE: PRT
<213> ORGANISM: Human immunodeficiency virus

<400> SEQUENCE: 91

Val Lys Asn Trp Met Thr Glu Thr Leu Leu Val Gln Asn Ala Asn
1               5                   10                  15

<210> SEQ ID NO 92
<211> LENGTH: 23
<212> TYPE: PRT
<213> ORGANISM: Human immunodeficiency virus

<400> SEQUENCE: 92

Arg Ala Glu Gln Ala Ser Gln Glu Val Lys Asn Trp Met Thr Glu Thr
1               5                   10                  15

Leu Leu Val Gln Asn Ala Asn
            20

<210> SEQ ID NO 93
<211> LENGTH: 23
<212> TYPE: PRT
<213> ORGANISM: Human immunodeficiency virus

<400> SEQUENCE: 93

Arg Ala Glu Gln Ala Thr Gln Glu Val Lys Gly Trp Met Thr Glu Thr
1               5                   10                  15

Leu Leu Val Gln Asn Ala Asn
            20

<210> SEQ ID NO 94
<211> LENGTH: 23
<212> TYPE: PRT
<213> ORGANISM: Human immunodeficiency virus

<400> SEQUENCE: 94

Arg Ala Glu Gln Ala Thr Gln Asp Val Lys Asn Trp Met Thr Asp Thr
1               5                   10                  15
```

Leu Leu Val Gln Asn Ala Asn
            20

<210> SEQ ID NO 95
<211> LENGTH: 23
<212> TYPE: PRT
<213> ORGANISM: Human immunodeficiency virus

<400> SEQUENCE: 95

Arg Ala Glu Gln Ala Ser Gln Asp Val Lys Asn Trp Met Thr Glu Thr
1               5                   10                  15

Leu Leu Val Gln Asn Ala Asn
            20

<210> SEQ ID NO 96
<211> LENGTH: 23
<212> TYPE: PRT
<213> ORGANISM: Human immunodeficiency virus

<400> SEQUENCE: 96

Arg Ala Glu Gln Ala Ser Gln Glu Val Lys Thr Trp Met Thr Asp Thr
1               5                   10                  15

Leu Leu Val Gln Asn Ala Asn
            20

<210> SEQ ID NO 97
<211> LENGTH: 23
<212> TYPE: PRT
<213> ORGANISM: Human immunodeficiency virus

<400> SEQUENCE: 97

Arg Ala Glu Gln Thr Asp Ala Ala Val Lys Asn Trp Met Thr Gln Thr
1               5                   10                  15

Leu Leu Ile Gln Asn Ala Asn
            20

<210> SEQ ID NO 98
<211> LENGTH: 23
<212> TYPE: PRT
<213> ORGANISM: Feline immunodeficiency virus

<400> SEQUENCE: 98

Asp Gln Glu Gln Asn Thr Ala Glu Val Lys Leu Tyr Leu Lys Gln Ser
1               5                   10                  15

Leu Ser Ile Ala Asn Ala Asn
            20

<210> SEQ ID NO 99
<211> LENGTH: 23
<212> TYPE: PRT
<213> ORGANISM: Feline immunodeficiency virus

<400> SEQUENCE: 99

Asp Gln Glu Gln Asn Thr Ala Glu Val Lys Thr Tyr Leu Lys Gln Ser
1               5                   10                  15

Leu Ser Leu Ala Asn Ala Asn
            20

<210> SEQ ID NO 100
<211> LENGTH: 14
<212> TYPE: PRT
<213> ORGANISM: Feline immunodeficiency virus

```
<400> SEQUENCE: 100

Lys Leu Tyr Leu Lys Gln Ser Leu Ser Ile Ala Asn Ala Asn
1               5                   10

<210> SEQ ID NO 101
<211> LENGTH: 14
<212> TYPE: PRT
<213> ORGANISM: Feline immunodeficiency virus

<400> SEQUENCE: 101

Trp Arg Met Leu Ile Asp Phe Arg Val Leu Ile Asn Lys Leu
1               5                   10

<210> SEQ ID NO 102
<211> LENGTH: 33
<212> TYPE: PRT
<213> ORGANISM: Feline immunodeficiency virus

<400> SEQUENCE: 102

Pro Thr Asp Leu Ala Thr Leu Ile Leu Ala Ala Pro Gly Ser Ala Arg
1               5                   10                  15

Val Lys Arg Asp Gln Glu Gln Asn Thr Ala Glu Val Lys Leu Tyr Leu
            20                  25                  30

Lys

<210> SEQ ID NO 103
<211> LENGTH: 20
<212> TYPE: DNA
<213> ORGANISM: Artificial Sequence
<220> FEATURE:
<223> OTHER INFORMATION: Forward primer

<400> SEQUENCE: 103
atggtgggtc gcttttcgta                                            20

<210> SEQ ID NO 104
<211> LENGTH: 23
<212> TYPE: DNA
<213> ORGANISM: Artificial Sequence
<220> FEATURE:
<223> OTHER INFORMATION: Reverse primer

<400> SEQUENCE: 104
gcagatcatt cacagggatt tga                                        23

<210> SEQ ID NO 105
<211> LENGTH: 20
<212> TYPE: DNA
<213> ORGANISM: Artificial Sequence
<220> FEATURE:
<223> OTHER INFORMATION: Forward primer

<400> SEQUENCE: 105
ccaagaaggc cacagaattg                                            20

<210> SEQ ID NO 106
<211> LENGTH: 20
<212> TYPE: DNA
<213> ORGANISM: Artificial Sequence
<220> FEATURE:
<223> OTHER INFORMATION: Reverse primer

<400> SEQUENCE: 106
gtcagcgttg agaagatgct                                            20
```

<210> SEQ ID NO 107
<211> LENGTH: 20
<212> TYPE: DNA
<213> ORGANISM: Artificial Sequence
<220> FEATURE:
<223> OTHER INFORMATION: Forward primer

<400> SEQUENCE: 107
tgccacaacg tcctgaaaca                                              20

<210> SEQ ID NO 108
<211> LENGTH: 21
<212> TYPE: DNA
<213> ORGANISM: Artificial Sequence
<220> FEATURE:
<223> OTHER INFORMATION: Reverse primer

<400> SEQUENCE: 108
taccaggtga gagctgtaga a                                            21

<210> SEQ ID NO 109
<211> LENGTH: 20
<212> TYPE: DNA
<213> ORGANISM: Artificial Sequence
<220> FEATURE:
<223> OTHER INFORMATION: Forward primer

<400> SEQUENCE: 109
ccaagaacga gccagaaaag                                              20

<210> SEQ ID NO 110
<211> LENGTH: 20
<212> TYPE: DNA
<213> ORGANISM: Artificial Sequence
<220> FEATURE:
<223> OTHER INFORMATION: Reverse primer

<400> SEQUENCE: 110
ccagaatctc cattgcacga                                              20

<210> SEQ ID NO 111
<211> LENGTH: 20
<212> TYPE: DNA
<213> ORGANISM: Artificial Sequence
<220> FEATURE:
<223> OTHER INFORMATION: Forward primer

<400> SEQUENCE: 111
gcccacaaca tcaagaagca                                              20

<210> SEQ ID NO 112
<211> LENGTH: 20
<212> TYPE: DNA
<213> ORGANISM: Artificial Sequence
<220> FEATURE:
<223> OTHER INFORMATION: Reverse primer

<400> SEQUENCE: 112
cagagtcccc ctgaaaggaa                                              20

<210> SEQ ID NO 113
<211> LENGTH: 20
<212> TYPE: DNA
<213> ORGANISM: Artificial Sequence
<220> FEATURE:

```
<223> OTHER INFORMATION: Forward primer

<400> SEQUENCE: 113
tgctgtctct gtacgcttct                                                    20

<210> SEQ ID NO 114
<211> LENGTH: 20
<212> TYPE: DNA
<213> ORGANISM: Artificial Sequence
<220> FEATURE:
<223> OTHER INFORMATION: Reverse primer

<400> SEQUENCE: 114
caggactcca tacccaggaa                                                    20
```